(12) United States Patent
Kawaguchi et al.

(10) Patent No.: US 7,514,449 B2
(45) Date of Patent: Apr. 7, 2009

(54) FUSED FURAN COMPOUND

(75) Inventors: Takayuki Kawaguchi, Tokyo-to (JP); Hidenori Akatsuka, Toda (JP); Toru Iijima, Toda (JP); Tatsuya Watanabe, Koganei (JP); Jun Murakami, Saitama (JP); Takashi Mitsui, Nishitokyo (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 583 days.

(21) Appl. No.: 10/540,878

(22) PCT Filed: Jan. 8, 2004

(86) PCT No.: PCT/JP2004/000074

§ 371 (c)(1),
(2), (4) Date: Jun. 27, 2005

(87) PCT Pub. No.: WO2004/063202

PCT Pub. Date: Jul. 29, 2004

(65) Prior Publication Data

US 2006/0094724 A1    May 4, 2006

(30) Foreign Application Priority Data

Jan. 9, 2003   (JP) ............................. 2003-003536
Sep. 26, 2003  (JP) ............................. 2003-334598

(51) Int. Cl.
    *A61K 31/444*   (2006.01)
    *C07D 491/048*  (2006.01)
(52) U.S. Cl. ...................................... 514/302; 546/115
(58) Field of Classification Search ................. 546/115; 514/302
    See application file for complete search history.

(56) References Cited

U.S. PATENT DOCUMENTS

| 5,753,670 A | 5/1998 | Ono et al. |
| 2003/0203909 A1 | 10/2003 | Ushio et al. |

FOREIGN PATENT DOCUMENTS

| EP | 1 277 738 A1 | 1/2003 |
| WO | WO-94/17075 A1 | 8/1994 |
| WO | WO-95/33720 A1 | 12/1995 |
| WO | WO-96/22992 A1 | 8/1996 |
| WO | WO-99/42439 | 8/1999 |
| WO | WO-01/83456 A1 | 8/2001 |
| WO | WO-02/12189 A1 | 2/2002 |
| WO | WO-03/082847 A1 | 10/2003 |
| WO | WO-2004/012671 A2 | 2/2004 |
| WO | WO-2005/039506 A2 | 5/2005 |

OTHER PUBLICATIONS

Attia et al., Egypt. J. Chem., vol. 28, No. 5, pp. 427-432 (1985).

Srinivas et al., Indian Journal of Chemistry, vol. 42B, pp. 605-610, Mar. 2003.
Harwalkar, G.S. et al., "Synthesis and Reactions of 2-Substituted-4H-Benzofuro[3,2-d]-m-Oxazin-4-Ones," Indian Journal of Heterocyclic Chemistry, vol. 3, Apr.-Jun. 1994, pp. 247-252.
Sogorinsho 41:2913-2918, 1992 and English short summary.
Freedman, Michael D., "Oral Anticoagulants: Pharmacodynamics, Clinical Indications and Adverse Effects," J. Clin. Pharmacol. 1992;32:196-209.
Hirsh, Jack, "Oral Anticoagulant Drugs," The New England Journal of Medicine, vol. 324, No. 26, Jun. 1991; pp. 1865-1875.
Sixma, Jan J. et al., "The Ideal Anti-Thrombotic Drug," Thrombosis Research, 1992, vol. 68, pp. 507-512.
Matsuo, O. ed., "t-PA and Pro-UK," Gakusaikikaku, 1986, pp. 5-40.
Kaiser, Brigitte et al., "Pharmacological Characterization of a New Highly Effective Synthetic Thrombin Inhibitor," Biomed. Biochim. Acta 44 (1985) 7/8, pp. 1201-1210.
Tidwell et al., Thrombosis Research, 19; 339-349, 1980.
Gewald et al., "Journal F. prakt. Chem. Band" vol. 318 No. 2, 1976, XP009019038, pp. 313-320.
Attia et al., "Synthesis of some furopyridine derivatives" XP002446231, Database accession, No. 1989: 75349.
Wagner et al., pp. 250-253, XP002446225, (1993) Pharmazie, vol. 48, No. 4.

(Continued)

*Primary Examiner*—Rebecca L Anderson
(74) *Attorney, Agent, or Firm*—Birch, Stewart, Kolasch & Birch, LLP.

(57) ABSTRACT

The present invention provides a condensed furan compound of the formula (I):

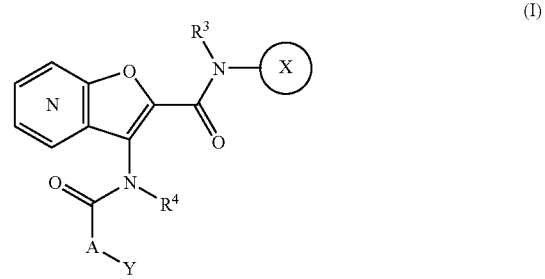

(I)

wherein Ring X is benzene, pyridine, or the like; Y is an optionally substituted amino, an optionally substituted cycloalkyl, an optionally substituted aryl, an optionally substituted saturated heterocyclic group, an optionally substituted unsaturated heterocyclic group; A is a single bond, lower alkylene, lower alkenylidene, lower alkenylene or an oxygen atom; $R^3$ is hydrogen or the like; and, $R^4$ is hydrogen, or the like, or pharmaceutically acceptable salts thereof, which is useful as a medicament, particularly, as an activated blood coagulation factor X inhibitor.

20 Claims, No Drawings

OTHER PUBLICATIONS

Narsaiah et al., "Journal of Fluorine Chemistry", vol. 69, 1994, pp. 139-143, XP00246226.

Khattab et al., "Sulfur Letters" vol. 19, No. 1, 1995 pp. 23-28, XP009054957.

Dunn et al., J. prakt. Chem., vol. 338, pp. 663-666, 1996, XP002446227.

Srinivas et al., "A facile synthesis of 4-oxo-1,2,3,4-tetrahydropyridofuropyridines" XP-002446232, Database accession No. 2003: 243614.

Mohamed et al., "Journal of the Chemical Society of Pakistan" ISSN: 0253-5106, 1985, XP-002446233.

Chandra Sheker Reddy et al., "Journal of Flourine Chemistry" vol. 74, 1995, pp. 1-7, XP004020503.

Wagner et al., pp. 213-214, XP002446224, (1990), , Pharmazie, vol. 45, No. 3.

FUSED FURAN COMPOUND

This application is a 371 of PCT/JP04/00074 filed Jan. 8, 2004.

TECHNICAL FIELD

The present invention relates to a condensed furan compound useful as a medicament, particularly as an inhibitor of activated blood coagulation factor X, or pharmaceutically acceptable salts thereof.

BACKGROUND ART

In late years, as the westernization of living habit and the aging of populations, thromboembolic diseases such as myocardial infarction, cerebral infarction and peripheral arterial thrombosis have increased year by year, and social importance of treatment thereof has risen more and more.

Among therapies of thromboembolic diseases, anticoagulant therapy, as well as fibrinolytic therapy and antiplatelet therapy, takes part in medical therapy for treatment and prevention of thrombosis (Sogorinsho 41: 2141-2145, 1989). In particular, the safety sustainable to chronic administration as well as the reliable and appropriate expression of anticoagulant activity are essential in the prevention of thrombosis. A coumarin derivative, especially warfarin potassium, has often been used all over the world as only anticoagulant available orally. However, owing to the characteristics arisen from the mechanism of action, it requires a long time until the drug efficacy manifests and has very long half-life in blood, although the concentration range for expression of drug efficacy is relatively narrow, and also shows significant differences in the effective dose among individuals. For these reasons, the anticoagulant ability can hardly be controlled (Journal of Clinical Pharmacology, 1992, vol. 32, pp. 196-209; NEW ENGLAND JOURNAL OF MEDICINE, 1991, vol. 324, no. 26, pp. 1865-1875). In addition, there may be adverse drug reactions such as risk of bleeding, nausea, vomiting, diarrhea, depilation, etc., and therefore the clinical application thereof is very difficult and the development of anticoagulants that are useful and easy to handle has been demanded.

Besides, enhancement of blood clotting ability is one of significant causative factors of unstable angina, cerebral infarction, cerebral embolism, myocardial infarction, pulmonary infarction, pulmonary embolism, Buerger's disease, deep vein thrombosis, disseminated intravascular coagulation, thrombogenesis after artificial heart valve displacement, reocclusion after blood circulation reconstruction and thrombogenesis during extracorporeal circulation, etc. Therefore, a distinguished anticoagulant that shows good dose response and lower risk of hemorrhage with few side-effects, and can exert sufficient effects upon oral administration has been desired (Thrombosis Research, 1992, vol. 68, pp. 507-512).

Thrombin participates not only in the conversion of fibrinogen to fibrin, which is the final stage of the coagulation cascade, but also deeply in the activation and aggregation of blood platelets (Matsuo, O., "t-PA and Pro-UK", Gakusaikikaku, 1986, pp. 5-40), and an inhibitor thereof has long been the center of the research in anticoagulants as a target of development of new drugs. However, a thrombin inhibitor shows low bioavailability upon oral administration and also has drawbacks in regard to safety such as bleeding tendency as one of side effects (Biomedica Biochimica Acta, 1985, Vol. 44, p. 1201-1210), and there have been no thrombin inhibitors marketed so far, which can be orally administered.

The activated blood coagulation factor X is a key enzyme located in the position of the common pathway of both extrinsic and intrinsic coagulation cascade reactions. The factor Xa is located upstream from thrombin in the coagulation cascade. Therefore, the inhibition of the factor Xa is possibly more effective and specific in the inhibition of coagulation system compared to the inhibition of thrombin (Thrombosis Research, 1980, Vol. 19, pp. 339-349).

Thus, a substance, which inhibits blood coagulation factor Xa and shows distinguished enzyme selectivity and high bioavailability, is expected to undergo control of its anticoagulant activity for a long period of time and can express superior therapeutic effect upon oral administration compared to the existing anticoagulants. Accordingly, the development of a novel inhibitor of activated blood coagulation factor X (FXa inhibitor) that can be administered orally has been earnestly demanded.

Examples of known compounds having inhibitory effect on activated blood coagulation factor X include thiobenzamide compounds that are useful in prevention or treatment of thrombosis (WO99/42439).

The following benzofuran compounds have also been known (Indian Journal of Heterocyclic Chemistry, 1994, Vol. 3, pp. 3247-3252), but said literature does not mention about the inhibitory effect of the compounds on activated blood coagulation factor X.

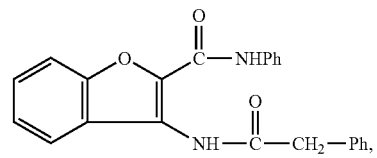

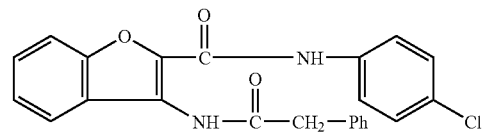

Condensed bicyclic amide compounds of the formula:

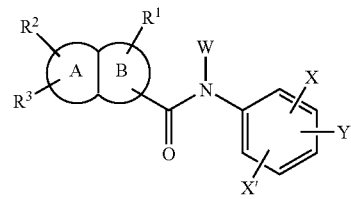

which have an activity of suppressing the growth of activated lymphocytes and are useful as a drug for preventing or treating autoimmune diseases are also known (WO02/12189). However, the WO02/12189 does not mention about the inhibitory effect on activated blood coagulation factor X either. In the pamphlet, compounds having a condensed ring of pyridine and furan to which ring an amide and a carbamoyl groups are di-substituted are disclosed; however, those compounds all have a benzene ring on the nitrogen atom of the carbamoyl group, which benzene ring is substituted by X and Y simultaneously.

DISCLOSURE OF INVENTION

The present invention provides novel condensed furan compounds having excellent inhibitory effect on activated blood coagulation factor X, or pharmaceutically acceptable salts thereof.

The present inventors have intensively studied and have found that a condensed furan compound of the formula below has excellent inhibitory effect on activated blood coagulation factor X and have accomplished the present invention.

That is, the present invention is as follows:

1. A condensed furan compound of the formula (I):

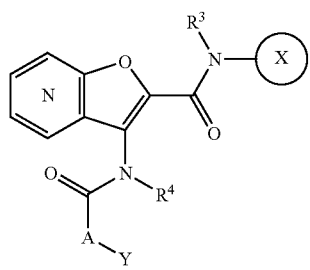
(I)

wherein, Ring:

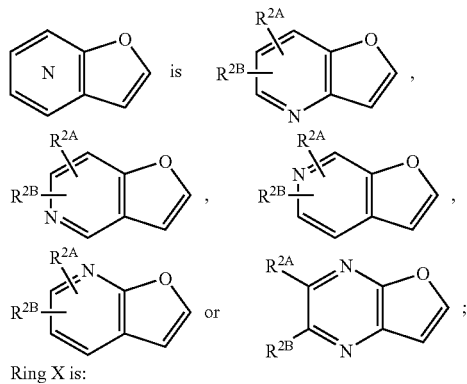

Ring X is:

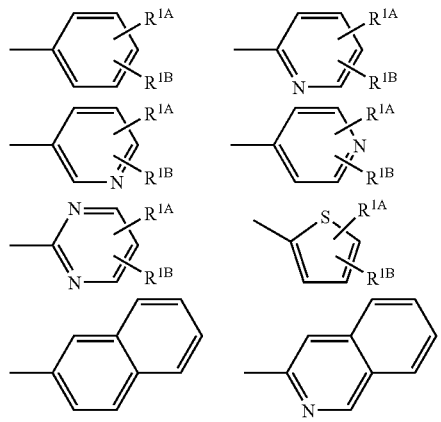

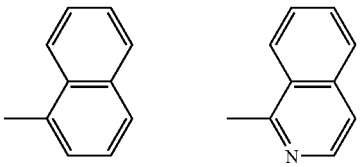

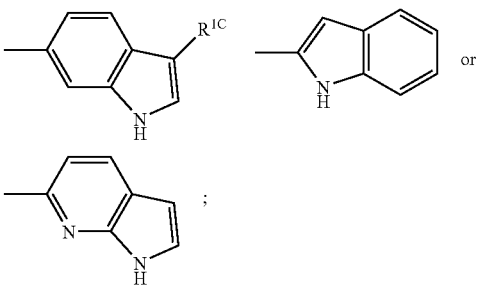

Y is an optionally substituted amino; an optionally substituted cycloalkyl; an optional substituted aryl; an optionally substituted saturated heterocyclic group; or an optionally substituted unsaturated heterocyclic group;

A is a single bond; an alkylene optionally substituted by oxo; an alkenylene; an alkenylidene; or an oxygen atom;

$R^{1A}$, $R^{1B}$ are the same or different and each is hydrogen; a halogen; an alkyl; a haloalkyl; an alkoxy; cyano; nitro; or an optionally substituted amino;

$R^{1C}$ is hydrogen, an alkyl or a halogen;

$R^{2A}$, $R^{2B}$ are the same or different and each is hydrogen; a halogen; an optionally substituted alkyl; an optionally substituted alkoxy; an optionally substituted amino; nitro; cyano; hydroxy; carboxy; an optionally substituted alkoxycarbonyl; an optionally substituted carbamoyl; a carbonyl substituted by an optionally substituted saturated heterocyclic group; an optionally substituted saturated heterocyclic group; aryl; or an optionally substituted unsaturated heterocyclic group;

$R^3$ is hydrogen or an alkyl; and $R^4$ is hydrogen or an alkyl, or a pharmaceutically acceptable salt thereof.

2. The condensed furan compound according to 1, wherein Ring:

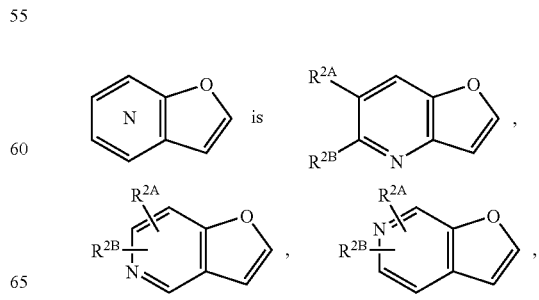

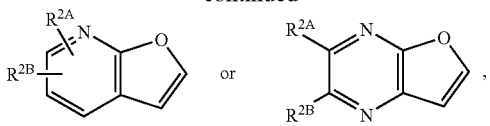

wherein the symbols are the same as defined in 1 above, or a pharmaceutically acceptable salt thereof.

3. The condensed furan compound according to 1 or 2, wherein Ring:

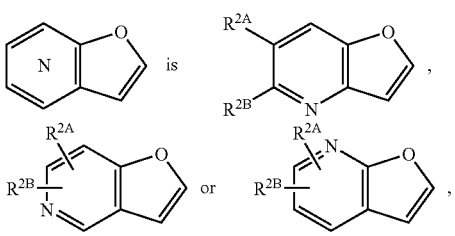

wherein the symbols are the same as defined in 1 above, or a pharmaceutically acceptable salt thereof.

4. The condensed furan compound according to any one of 1 to 3, wherein Y is an optionally substituted cycloalkyl or an optionally substituted saturated heterocyclic group, or a pharmaceutically acceptable salt thereof.

5. The condensed furan compound according to any one of 1 to 4 above, wherein the substituent in the definition of "optionally substituted cycloalkyl" for Y is a group selected from an optionally substituted alkyl; an optionally substituted carbamoyl; a carbonyl substituted by an optionally substituted saturated heterocyclic group; an optionally substituted amino; and an optionally substituted saturated heterocyclic group, or a pharmaceutically acceptable salt thereof.

6. The condensed furan compound according to any one of 1 to 5 above, wherein the substituent in the definition of "optionally substituted cycloalkyl" for Y is a group selected from: (1) an amino optionally substituted by a group selected from an optionally substituted acyl, an alkoxycarbonyl and an optionally substituted alkyl; (2) an aminoalkyl optionally substituted by a group selected from an optionally substituted acyl and an optionally substituted alkyl; (3) a carbamoyl optionally substituted by an optionally substituted alkyl; (4) a carbonyl substituted by a saturated heterocyclic group; and (5) an optionally substituted saturated heterocyclic group, or a pharmaceutically acceptable salt thereof.

7. The condensed furan compound according to 5 or 6 above, wherein the saturated heterocyclic group is a 4- to 7-membered saturated heterocyclic group containing 1 to 4 hetero atoms selected from the group consisting of nitrogen atom, oxygen atom and sulfur atom, or a pharmaceutically acceptable salt thereof.

8. The condensed furan compound according to any one of 5 to 7, wherein the saturated heterocyclic group is a group selected from imidazolidinyl, pyrazolidinyl, piperidyl, piperidino, piperazinyl, morpholinyl, morpholino, thiomorpholinyl, thiomorpholino, homopiperazinyl, homopiperidyl, homopiperidino and pyrrolidinyl, or a pharmaceutically acceptable salt thereof.

9. The condensed furan compound according to any one of 1 to 6 above, wherein the substituent in the definition of "optionally substituted cycloalkyl" for Y is: (1) an amino optionally substituted by a group selected from acyl, alkoxycarbonyl, alkyl, aminoalkyl, alkyl-substituted aminoalkyl, alkoxycarbonylaminoalkyl and acylaminoalkyl; (2) an alkyl substituted by amino optionally substituted by alkyl; (3) a carbamoyl optionally mono- or di-substituted by alkyl or aminoalkyl which may be substituted by alkyl; (4) a group selected from pyrrolidinylcarbonyl, piperidylcarbonyl, piperazinylcarbonyl, morpholinocarbonyl, homopiperidinylcarbonyl and homopiperazinylcarbonyl; or (5) a saturated heterocyclic group selected from pyrrolidinyl optionally substituted by oxo, piperidyl optionally substituted by oxo, piperazinyl optionally substituted by oxo, morpholino optionally substituted by oxo, homopiperidinyl optionally substituted by oxo, and homopiperazinyl optionally substituted by oxo, or a pharmaceutically acceptable salt thereof.

10. The condensed furan compound according to any one of 1 to 6 above, wherein the substituent in the definition of "optionally substituted cycloalkyl" for Y is pyrrolidinyl optionally substituted by oxo; morpholino optionally substituted by oxo; dialkylcarbamoyl; pyrrolidinylcarbonyl; amino that is di-substituted by alkyl and acylaminoalkyl; or dialkylamino, or a pharmaceutically acceptable salt thereof.

11. The condensed furan compound according to any one of 1 to 3 above, wherein Y is an aryl or unsaturated heterocyclic group substituted by an optionally substituted carbamoyl, or a phrmaceutically acceptable salt thereof.

12. The condensed furan compound according to any one of 1 to 11 above, wherein A is a single bond or methylene, or a pharmaceutically acceptable salt thereof.

13. The condensed furan compound according to any one of 1 to 4 above, wherein A is a single bond or methylene, and Y is an unsaturated heterocyclic group or a saturated heterocyclic group optionally substituted by alkyl, or a pharmaceutically acceptable salt thereof.

14. The condensed furan compound according to any one of 1 to 3 above, wherein A is tetramethylene, and Y is an optionally substituted saturated heterocyclic group, or a pharmaceutically acceptable salt thereof.

15. The condensed furan compound according to any one of 1 to 14 above, wherein $R^{1A}$, $R^{1B}$ are the same or different and each is hydrogen, a halogen, or an alkyl, or a pharmaceutically acceptable salt thereof.

16. The condensed furan compound according to any one of 1 to 15 above, wherein $R^{2A}$, $R^{2B}$ are the same or different and each is hydrogen; a halogen; an optionally substituted alkyl; an optionally substituted alkoxy; an optionally substituted amino; cyano; carboxy; an alkoxycarbonyl; an optionally substituted carbamoyl; a carbonyl substituted by saturated heterocyclic group; or a saturated heterocyclic group, or a pharmaceutically acceptable salt thereof.

17. The condensed furan compound according to 16 above, wherein the saturated heterocyclic group is a 4- to 7-membered saturated heterocyclic group containing 1 to 4 hetero atoms selected from the group consisting of nitrogen atom, oxygen atom and sulfur atom, or a pharmaceutically acceptable salt thereof.

18. The condensed furan compound according to any one of 1 to 17 above, wherein $R^{2A}$, $R^{2B}$ are the same or different and each is hydrogen, fluoro, chloro, bromo, methyl, hydroxymethyl, methoxy, amino, methylsulfonylamino, acetylamino, t-butoxycarbonylamino, dimethylamino, cyano, carboxy, methoxycarbonyl, ethoxycarbonyl, methoxy, ethoxy, isopropoxy, methoxyethoxy, dimethylcarbamoyl, N-methyl-N-(2-methoxyethyl)carbamoyl, pyrrolidinyl, pyrrolidinylcarbonyl, morpholinocarbonyl or morpholino, or a pharmaceutically acceptable salt thereof.

19. The condensed furan compound according to any one of 1 to 18 above, wherein $R^3$ is hydrogen, or a pharmaceutically acceptable salt thereof.

20. The condensed furan compound according to any one of 1 to 19 above, wherein $R^4$ is hydrogen, or a pharmaceutically acceptable salt thereof.

21. The condensed furan compound according to any one of 1 to 20 above, wherein Ring X is

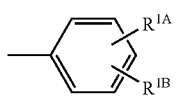 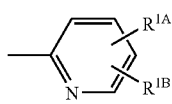

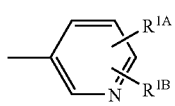 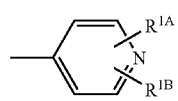

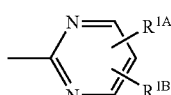 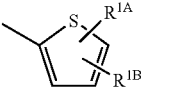

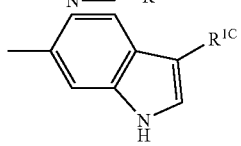 or 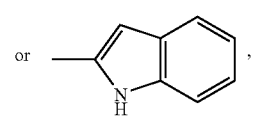, wherein the symbols are as defined in 1 above, or a pharmaceutically acceptable salt thereof.

22. The condensed furan compound according to 21 above, wherein Ring X is

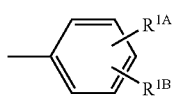 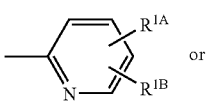 or

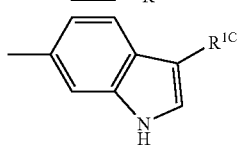, wherein the symbols are as defined in 1 above, or a pharmaceutically acceptable salt thereof.

23. The condensed furan compound according to any one of 1-22 above, which is selected from the following compounds:

(1) 5-amino-N-(5-chloropyridin-2-yl)-3-{[(trans-4-pyrrolidin-1-ylcyclohexyl)carbonyl]amino}furo[3,2-b]pyridine-2-carboxamide, (2) 6-amino-N-(5-chloropyridin-2-yl)-3-({[trans-4-(3-oxomorpholin-4-yl)cyclohexyl]carbonyl}amino)furo[3,2-b]pyridine-2-carboxamide, (3) N-(4-chlorophenyl)-3-{[(trans-4-pyrrolidin-1-ylcyclohexyl)carbonyl]amino}furo[3,2-b]pyridine-2-carboxamide, (4) N-(5-chloropyridin-2-yl)-5-[(methylsulfonyl)amino]-3-{[(trans-4-pyrrolidin-1-ylcyclohexyl)carbonyl]amino}furo[3,2-b]pyridine-2-carboxamide, (5) 2-{[(5-chloropyridin-2-yl)amino]carbonyl}-3-{[(trans-4-pyrrolidin-1-ylcyclohexyl)carbonyl]amino}furo[3,2-b]pyridine-5-carboxylic acid, (6) N-(5-chloropyridin-2-yl)-3-{[(trans-4-pyrrolidin-1-ylcyclohexyl)carbonyl]amino}furo[3,2-c]pyridine-2-carboxamide, (7) N-(5-chloropyridin-2-yl)-5-(hydroxymethyl)-3-({[trans-4-(3-oxomorpholin-4-yl)cyclohexyl]carbonyl}amino)furo[3,2-b]pyridine-2-carboxamide, (8) N-(5-chloropyridin-2-yl)-5-methoxy-3-({[trans-4-(3-oxomorpholin-4-yl)cyclohexyl]carbonyl}amino)furo[3,2-b]pyridine-2-carboxamide, (9) N-(5-chloropyridin-2-yl)-3-{[(trans-4-pyrrolidin-1-ylcyclohexyl)carbonyl]amino}furo[3,2-b]pyridine-2-carboxamide,

(10) N-(5-chloropyridin-2-yl)-5-methoxy-3-{[(trans-4-pyrrolidin-1-ylcyclohexyl)carbonyl]amino}furo[3,2-b]pyridine-2-carboxamide,

(11) N-(4-chlorophenyl)-3-({[trans-4-(3-oxomorpholin-4-yl)cyclohexyl]carbonyl}amino)furo[3,2-b]pyridine-2-carboxamide,

(12) 5-amino-N-(5-chloropyridin-2-yl)-3-({[trans-4-(3-oxomorpholin-4-yl)cyclohexyl]carbonyl}amino)furo[3,2-b]pyridine-2-carboxamide,

(13) 5-(acetylamino)-N-(5-chloropyridin-2-yl)-3-{[(trans-4-pyrrolidin-1-ylcyclohexyl)carbonyl]amino}furo[3,2-b]pyridine-2-carboxamide,

(14) N-(5-chloropyridin-2-yl)-5-fluoro-3-({[trans-4-(3-oxomorpholin-4-yl)cyclohexyl]carbonyl}amino)furo[3,2-b]pyridine-2-carboxamide,

(15) 5-chloro-N-(5-chloropyridin-2-yl)-3-{[(trans-4-pyrrolidin-1-ylcyclohexyl)carbonyl]amino}furo[3,2-b]pyridine-2-carboxamide,

(16) N-(5-chloropyridin-2-yl)-5-methyl-3-{[(trans-4-pyrrolidin-1-ylcyclohexyl)carbonyl]amino}furo[3,2-b]pyridine-2-carboxamide,

(17) $N^2$-(5-chloropyridin-2-yl)-$N^5$,$N^5$-dimethyl-3-{[(trans-4-pyrrolidin-1-ylcyclohexyl)carbonyl]amino}furo[3,2-b]pyridine-2,5-dicarboxamide,

(18) 5-(acetylamino)-N-(5-chloropyridin-2-yl)-3-({[trans-4-(3-oxomorpholin-4-yl)cyclohexyl]carbonyl}amino)furo[3,2-b]pyridine-2-carboxamide,

(19) t-butyl (2-{[(5-chloropyridin-2-yl)amino]carbonyl}-3-{[(trans-4-pyrrolidin-1-ylcyclohexyl)carbonyl]amino}furo[3,2-b]pyridin-6-yl)-carbamate,

(20) N-(5-chloropyridin-2-yl)-5-[(methylsulfonyl)amino]-3-({[trans-4-(3-oxomorpholin-4-yl)cyclohexyl]carbonyl}amino)furo[3,2-b]pyridine-2-carboxamide,

(21) N-(4-chlorophenyl)-3-({[trans-4-(2-oxopyrrolidin-1-yl)cyclohexyl]carbonyl}amino)furo[3,2-b]pyridine-2-carboxamide,
(22) N-(5-chloropyridin-2-yl)-3-{[(1-pyridin-4-ylpiperidin-4-yl)carbonyl]amino}furo[3,2-b]pyridine-2-carboxamide,
(23) N-(5-chloropyridin-2-yl)-3-({[trans-4-(3-oxomorpholin-4-yl)cyclohexyl]carbonyl}amino)furo[3,2-b]pyridine-2-carboxamide,
(24) t-butyl [2-{[(5-chloropyridin-2-yl)amino]carbonyl}-3-({[trans-4-(3-oxomorpholin-4-yl)cyclohexyl]carbonyl}amino)furo[3,2-b]pyridin-6-yl]carbamate,
(25) 6-amino-N-(5-chloropyridin-2-yl)-3-({[trans-4-(2-oxopyrrolidin-1-yl)cyclohexyl]carbonyl}amino)furo[3,2-b]pyridine-2-carboxamide,
(26) 6-amino-N-(5-chloropyridin-2-yl)-3-{[(trans-4-pyrrolidin-1-ylcyclohexyl)carbonyl]amino}furo[3,2-b]pyridine-2-carboxamide,
(27) 2-{[(5-chloropyridin-2-yl)amino]carbonyl}-3-({[trans-4-(3-oxomorpholin-4-yl)cyclohexyl]carbonyl}amino)furo[3,2-b]pyridine-5-carboxylic acid,
(28) $N^2$-(5-chloropyridin-2-yl)-$N^5$,$N^5$-dimethyl-3-({[trans-4-(3-oxomorpholin-4-yl)cyclohexyl]carbonyl}amino)furo[3,2-b]pyridine-2,5-dicarboxamide,
(29) N-(5-chloropyridin-2-yl)-5-(morpholin-4-ylcarbonyl)-3-{[(trans-4-pyrrolidin-1-ylcyclohexyl)carbonyl]amino}furo[3,2-b]pyridine-2-carboxamide,
(30) t-butyl (2-{[(5-chloropyridin-2-yl)amino]carbonyl}-3-{[(trans-4-pyrrolidin-1-ylcyclohexyl)carbonyl]amino}furo[3,2-b]pyridin-5-yl)carbamate,
(31) N-(5-chloropyridin-2-yl)-5-methyl-3-({[trans-4-(3-oxomorpholin-4-yl)cyclohexyl]carbonyl}amino)furo[3,2-b]pyridine-2-carboxamide,
(32) methyl 2-{[(5-chloropyridin-2-yl)amino]carbonyl}-3-{[(trans-4-pyrrolidin-1-ylcyclohexyl)carbonyl]amino}furo[3,2-b]pyridine-5-carboxylate,
(33) 5-bromo-N-(5-chloropyridin-2-yl)-3-{[(trans-4-pyrrolidin-1-ylcyclohexyl)carbonyl]amino}furo[3,2-b]pyridine-2-carboxamide,
(34) N-(5-chloropyridin-2-yl)-5-[(methylsulfonyl)amino]-3-({[trans-4-(2-oxopyrrolidin-1-yl)cyclohexyl]carbonyl}amino)furo[3,2-b]pyridine-2-carboxamide,
(35) N-(4-chlorophenyl)-3-({[trans-4-(dimethylamino)cyclohexyl]-carbonyl}amino)furo[3,2-b]pyridine-2-carboxamide,
(36) N-(5-chloropyridin-2-yl)-5-cyano-3-{[(trans-4-pyrrolidin-1-ylcyclohexyl)carbonyl]amino}furo[3,2-b]pyridine-2-carboxamide,
(37) N-(5-chloropyridin-2-yl)-5-fluoro-3-{[(trans-4-pyrrolidin-1-ylcyclohexyl)carbonyl]amino}furo[3,2-b]pyridine-2-carboxamide,
(38) $N^2$-(5-chloropyridin-2-yl)-$N^5$-(2-methoxyethyl)-$N^5$-methyl-3-({[trans-4-(3-oxomorpholin-4-yl)cyclohexyl]carbonyl}amino)furo[3,2-b]pyridine-2,5-dicarboxamide,
(39) N-(5-chloropyridin-2-yl)-3-({[trans-4-(dimethylamino)-cyclohexyl]carbonyl}amino)furo[3,2-b]pyridine-2-carboxamide,
(40) N-(5-chloropyridin-2-yl)-3-({[trans-4-(3-oxomorpholin-4-yl)cyclohexyl]carbonyl}amino)-5-(pyrrolidin-1-ylcarbonyl)furo[3,2-b]pyridine-2-carboxamide,
(41) t-butyl [2-{[(5-chloropyridin-2-yl)amino]carbonyl}-3-({[trans-4-(3-oxomorpholin-4-yl)cyclohexyl]carbonyl}amino)furo[3,2-b]pyridin-5-yl]carbamate,
(42) 5-bromo-N-(5-chloropyridin-2-yl)-3-({[trans-4-(3-oxomorpholin-4-yl)cyclohexyl]carbonyl}amino)furo[3,2-b]pyridine-2-carboxamide,
(43) N-(5-chloropyridin-2-yl)-5-(morpholin-4-ylcarbonyl)-3-({[trans-4-(3-oxomorpholin-4-yl)cyclohexyl]carbonyl}amino)furo[3,2-b]pyridine-2-carboxamide,
(44) N-(5-chloropyridin-2-yl)-3-({[trans-4-(dimethylamino)cyclohexyl]carbonyl}amino)-5-methoxyfuro[3,2-b]pyridine-2-carboxamide,
(45) 5-chloro-N-(5-chloropyridin-2-yl)-3-({[trans-4-(3-oxomorpholin-4-yl)cyclohexyl]carbonyl}amino)furo[3,2-b]pyridine-2-carboxamide,
(46) 2-{[(5-chloropyridin-2-yl)amino]carbonyl}-3-({[trans-4-(2-oxopyrrolidin-1-yl)cyclohexyl]carbonyl}amino)furo[3,2-b]pyridine-5-carboxylic acid,
(47) N-(5-chloropyridin-2-yl)-5-cyano-3-({[trans-4-(2-oxopyrrolidin-1-yl)cyclohexyl]carbonyl}amino)furo[3,2-b]pyridine-2-carboxamide,
(48) N-(5-chloropyridin-2-yl)-5-cyano-3-({[trans-4-(3-oxomorpholin-4-yl)cyclohexyl]carbonyl}amino)furo[3,2-b]pyridine-2-carboxamide,
(49) N-(5-chloropyridin-2-yl)-5-(hydroxymethyl)-3-({[trans-4-(2-oxopyrrolidin-1-yl)cyclohexyl]carbonyl}amino)furo[3,2-b]pyridine-2-carboxamide,
(50) N-(5-chloropyridin-2-yl)-5-methoxy-3-({[trans-4-(2-oxopyrrolidin-1-yl)cyclohexyl]carbonyl}amino)furo[3,2-b]pyridine-2-carboxamide,
(51) N-(5-chloropyridin-2-yl)-3-({[trans-4-(2-oxopyrrolidin-1-yl)cyclohexyl]carbonyl}amino)-5-(pyrrolidin-1-ylcarbonyl)furo[3,2-b]pyridine-2-carboxamide,
(52) N-(5-chloropyridin-2-yl)-5-methyl-3-({[trans-4-(2-oxopyrrolidin-1-yl)cyclohexyl]carbonyl}amino)furo[3,2-b]pyridine-2-carboxamide,
(53) N-(5-chloropyridin-2-yl)-3-({[trans-4-(dimethylamino)cyclohexyl]carbonyl}amino)-5-methylfuro[3,2-b]pyridine-2-carboxamide,
(54) 5-chloro-N-(5-chloropyridin-2-yl)-3-({[trans-4-(dimethylamino)cyclohexyl]carbonyl}amino)furo[3,2-b]pyridine-2-carboxamide,
(55) $N^2$-(5-chloropyridin-2-yl)-3-({[trans-4-(dimethylamino)cyclohexyl]carbonyl}amino)-$N^5$,$N^5$-dimethylfuro[3,2-b]pyridine-2,5-dicarboxamide,
(56) methyl 2-{[(5-chloropyridin-2-yl)amino]carbonyl}-3-({[trans-4-(3-oxomorpholin-4-yl)cyclohexyl]carbonyl}amino)furo[3,2-b]pyridine-5-carboxylate,
(57) N-(5-chloropyridin-2-yl)-3-({[trans-4-(2-oxopyrrolidin-1-yl)cyclohexyl]carbonyl}amino)furo[3,2-b]pyridine-2-carboxamide,
(58) 5-amino-N-(5-chloropyridin-2-yl)-3-({[trans-4-(2-oxopyrrolidin-1-yl)cyclohexyl]carbonyl}amino)furo[3,2-b]pyridine-2-carboxamide,
(59) N-(5-chloropyridin-2-yl)-3-({[trans-4-(2-oxopyrrolidin-1-yl)cyclohexyl]carbonyl}amino)furo[3,2-b]pyridine-2-carboxamide,
(60) 2-{[(5-chloropyridin-2-yl)amino]carbonyl}-3-{[5-(3-oxomorpholin-4-yl)pentanoyl]amino}furo[3,2-b]pyridine-5-carboxylic acid,
(61) N-(5-chloropyridin-2-yl)-3-({[trans-4-(dimethylamino)cyclohexyl]carbonyl}amino)furo[3,2-b]pyridine-2-carboxamide,
(62) 6-chloro-N-(5-chloropyridin-2-yl)-3-{[(trans-4-pyrrolidin-1-ylcyclohexyl)carbonyl]amino}furo[3,2-b]pyridine-2-carboxamide,
(63) 5-chloro-N-(5-chloropyridin-2-yl)-3-({[trans-4-(2-oxopyrrolidin-1-yl)cyclohexyl]carbonyl}amino)furo[3,2-b]pyridine-2-carboxamide,

(64) N²-(5-chloropyridin-2-yl)-N⁵,N⁵-dimethyl-3-({[trans-4-(2-oxopyrrolidin-1-yl)cyclohexyl]carbonyl}amino)furo[3,2-b]pyridine-2,5-dicarboxamide,

(65) 6-(acetylamino)-N-(5-chloropyridin-2-yl)-3-({[trans-4-(pyrrolidin-1-ylcyclohexyl)carbonyl]amino}furo[3,2-b]pyridine-2-carboxamide,

(66) t-butyl [2-{[(5-chloropyridin-2-yl)amino]carbonyl}-3-({[trans-4-(2-oxopyrrolidin-1-yl)cyclohexyl]carbonyl}amino)furo[3,2-b]pyridin-6-yl]carbamate,

(67) 6-chloro-N-(5-chloropyridin-2-yl)-3-({[trans-4-(3-oxomorpholin-4-yl)cyclohexyl]carbonyl}amino)furo[3,2-b]pyridine-2-carboxamide,

(68) N-(4-methylphenyl)-3-({[trans-4-(3-oxomorpholin-4-yl)cyclohexyl]carbonyl}amino)furo[3,2-b]pyridine-2-carboxamide,

(69) 2-{[(5-chloropyridin-2-yl)amino]carbonyl}-3-{[(trans-4-pyrrolidin-1-ylcyclohexyl)carbonyl]amino}furo[3,2-b]pyridine-6-carboxylic acid,

(70) N-(5-chloropyridin-2-yl)-3-{[5-(3-oxomorpholin-4-yl)pentanoyl]amino}furo[3,2-b]pyridine-2-carboxamide,

(71) 5-(acetylamino)-N-(5-chloropyridin-2-yl)-3-({[trans-4-(2-oxopyrrolidin-1-yl)cyclohexyl]carbonyl}amino)furo[3,2-b]pyridine-2-carboxamide,

(72) N-(4-chlorophenyl)-3-{[(trans-4-morpholin-4-ylcyclohexyl)carbonyl]amino}furo[3,2-b]pyridine-2-carboxamide,

(73) 5-bromo-N-(5-chloropyridin-2-yl)-3-({[trans-4-(dimethylamino)cyclohexyl]carbonyl}amino)furo[3,2-b]pyridine-2-carboxamide,

(74) N-(5-chloropyridin-2-yl)-3-({[trans-4-(dimethylamino)cyclohexyl]carbonyl}amino)furo[2,3-b]pyridine-2-carboxamide,

(75) 3-[({trans-4-[[3-(acetylamino)propyl](methyl)amino]-cyclohexyl}carbonyl)amino]-N-(5-chloropyridin-2-yl)furo[3,2-b]pyridine-2-carboxamide,

(76) trans-N'-(2-{[(5-chloropyridin-2-yl)amino]carbonyl}furo[3,2-b]pyridin-3-yl)-N,N-dimethylcyclohexane-1,4-dicarboxamide,

(77) N-(5-chloropyridin-2-yl)-3-({[trans-4-(pyrrolidin-1-ylcarbonyl)cyclohexyl]carbonyl}amino)furo[3,2-b]pyridine-2-carboxamide,

(78) 2-{[(5-chloropyridin-2-yl)amino]carbonyl}-3-[({trans-4-[(dimethylamino)carbonyl]cyclohexyl}carbonyl)amino]furo[3,2-b]-pyridine-5-carboxylic acid,

(79) methyl 2-{[(5-chloropyridin-2-yl)amino]carbonyl}-3-({[trans-4-(pyrrolidin-1-ylcarbonyl)cyclohexyl]carbonyl}amino)furo[3,2-b]-pyridine-5-carboxylate,

(80) methyl 2-{[(5-chloropyridin-2-yl)amino]carbonyl}-3-[({trans-4-[(dimethylamino)carbonyl]cyclohexyl}carbonyl)amino]furo[3,2-b]pyridine-5-carboxylate,

(81) 2-{[(5-chloropyridin-2-yl)amino]carbonyl}-3-({[trans-4-(pyrrolidin-1-ylcarbonyl)cyclohexyl]carbonyl}amino) furo[3,2-b]pyridine-5-carboxylic acid,

(82) N²-5-chloropyridin-2-yl)-3-[({trans-4-[(dimethylamino)carbonyl]cyclohexyl}carbonyl)amino]-N⁵-(2-methoxyethyl)-N⁵-methylfuro[3,2-b]pyridine-2,5-dicarboxamide,

(83) N²-(5-chloropyridin-2-yl)-N⁵-(2-methoxyethyl)-N⁵-methyl-3-({[trans-4-(pyrrolidin-1-ylcyclohexyl)cyclohexyl]carbonyl}amino)furo[3,2-b]pyridine-2,5-dicarboxamide,

(84) N-(5-chloropyridin-2-yl)-5-pyrrolidin-1-yl-3-{[(trans-4-pyrrolidin-1-ylcyclohexyl)carbonyl]amino}furo[3,2-b]pyridine-2-carboxamide,

(85) N-(5-chloropyridin-2-yl)-5-morpholin-4-yl-3-{[(trans-4-pyrrolidin-1-ylcyclohexyl)carbonyl]amino}furo[3,2-b]pyridine-2-carboxamide,

(86) N-(5-chloropyridin-2-yl)-3-({[trans-4-(3-oxomorpholin-4-yl)cyclohexyl]carbonyl}amino)-5-pyrrolidin-1-ylfuro[3,2-b]pyridine-2-carboxamide,

(87) N-(5-chloropyridin-2-yl)-5-(dimethylamino)-3-({[trans-4-(3-oxomorpholin-4-yl)cyclohexyl]carbonyl}amino)furo[3,2-b]pyridine-2-carboxamide,

(88) N-(5-chloropyridin-2-yl)-5-morpholin-4-yl-3-({[trans-4-(3-oxomorpholin-4-yl)cyclohexyl]carbonyl}amino)furo[3,2-b]pyridine-2-carboxamide,

(89) N-(5-chloropyridin-2-yl)-4-(2-methoxyethoxy)-3-{[(trans-4-pyrrolidin-1-ylcyclohexyl)carbonyl]amino}furo[3,2-c]pyridine-2-carboxamide,

(90) N-(5-chloropyridin-2-yl)-5-(2-methoxyethoxy)-3-({[trans-4-(3-oxomorpholin-4-yl)cyclohexyl]carbonyl}amino)furo[3,2-b]pyridine-2-carboxamide,

(91) N-(5-chloropyridin-2-yl)-5-(pyrrolidin-1-ylcarbonyl)-3-{[(trans-4-pyrrolidin-1-ylcyclohexyl)carbonyl]amino}furo[3,2-b]pyridine-2-carboxamide,

(92) N-(5-chloropyridin-2-yl)-4-(2-methoxyethoxy)-3-({[trans-4-(3-oxomorpholin-4-yl)cyclohexyl]carbonyl}amino)furo[3,2-c]pyridine-2-carboxamide,

(93) N-(5-chloropyridin-2-yl)-4-methoxy-3-{[(trans-4-pyrrolidin-1-ylcyclohexyl)carbonyl]amino}furo[3,2-c]pyridine-2-carboxamide,

(94) N-(5-chloropyridin-2-yl)-3-({[trans-4-(dimethylamino)cyclohexyl]carbonyl}amino)-5-pyrrolidin-1-ylfuro[3,2-b]pyridine-2-carboxamide,

(95) N²-(5-chloropyridin-2-yl)-N⁵-(2-methoxyethyl)-N⁵-methyl-3-{[(trans-4-pyrrolidin-1-ylcyclohexyl)carbonyl]amino}furo[3,2-b]pyridine-2,5-dicarboxamide,

(96) N-(5-chloropyridin-2-yl)-3-({[trans-4-(3-oxomorpholin-4-yl)cyclohexyl]carbonyl}amino)furo[3,2-c]pyridine-2-carboxamide,

(97) N-(5-chloropyridin-2-yl)-5-(dimethylamino)-3-{[(trans-4-pyrrolidin-1-ylcyclohexyl)carbonyl]amino}furo[3,2-b]pyridine-2-carboxamide,

(98) N-1H-indol-6-yl-3-({[trans-4-(3-oxomorpholin-4-yl)cyclohexyl]carbonyl}amino)furo[3,2-b]pyridine-2-carboxamide,

(99) N-(5-chloropyridin-2-yl)-4-methoxy-3-({[trans-4-(3-oxomorpholin-4-yl)cyclohexyl]carbonyl}amino)furo[3,2-c]pyridine-2-carboxamide, (100) N-(5-chloropyridin-2-yl)-3-({[trans-4-(2-oxopyrrolidin-1-yl)cyclohexyl]carbonyl}amino)-5-pyrrolidin-1-ylfuro[3,2-b]pyridine-2-carboxamide, (101) N-(5-chloropyridin-2-yl)-5-isopropoxy-3-{[(trans-4-pyrrolidin-1-ylcyclohexyl)carbonyl]amino}furo[3,2-b]pyridine-2-carboxamide, (102) N-(5-chloropyridin-2-yl)-5-isopropoxy-3-({[trans-4-(3-oxomorpholin-4-yl)cyclohexyl]carbonyl}amino)furo[3,2-b]pyridine-2-carboxamide, (103) N-(5-chloropyridin-2-yl)-3-({[trans-4-(dimethylamino)cyclohexyl]carbonyl}amino)-5-(2-methoxyethoxy)furo[3,2-b]pyridine-2-carboxamide, (104) N-(5-chloropyridin-2-yl)-5-morpholin-4-yl-3-({[trans-4-(2-oxopyrrolidin-1-yl)cyclohexyl]carbonyl}amino)furo[3,2-b]pyridine-2-carboxamide, (105) N-(5-chloropyridin-2-yl)-3-({[trans-4-(2-oxopyrrolidin-1-yl)cyclohexyl]carbonyl}amino)furo[3,2-b]pyridine-2-carboxamide, (106) N-(5-chloropyridin-2-yl)-3-({[trans-4-(dimethylamino)cyclohexyl]carbonyl}amino)-5-morpholin-4-ylfuro[3,2-b]pyridine-2-carboxamide, (107) N-(5-chloropyridin-2-yl)-5-(2-methoxyethoxy)-3-({[trans-4-(2-oxopyrrolidin-1-yl)cyclohexyl]carbonyl}amino)furo[3,2-b]pyridine-2-carboxamide, (108) N-(5-chloropyridin-2-yl)-5-(dimethylamino)-3-({[trans-4-(dimethylamino)cyclohexyl]carbonyl}amino)furo[3,2-b]pyridine-2-carboxamide, (109) N-(5-chloropyridin-2-yl)-3-({[trans-4-(dimethylamino)cyclohexyl]carbonyl}amino)-5-isopropoxyfuro[3,2-b]pyridine-2-carboxamide, (110) N-1H-indol-6-yl-3-{[(trans-4-pyrrolidin-1-ylcyclohexyl)carbonyl]amino}furo[3,2-b]pyridine-2-carboxamide, (111) N-(5-chloropyridin-2-yl)-4-cyano-3-{[(trans-4-pyrrolidin-1-ylcyclohexyl)carbonyl]amino}furo[3,2-c]pyridine-2-carboxamide, (112) N-(5-chloropyridin-2-yl)-4-methyl-3-({[trans-4-(3-oxomorpholin-4-yl)cyclohexyl]carbonyl}amino)furo[3,2-c]pyridine-2-carboxamide, (113) N-(5-chloropyridin-2-yl)-4-cyano-3-({[trans-4-(3-oxomorpholin-4-yl)cyclohexyl]carbonyl}amino)furo[3,2-c]pyridine-2-carboxamide, (114) N-(5-chloropyridin-2-yl)-4-methyl-3-({[trans-4-(2-oxopyrrolidin-1-yl)cyclohyexyl]carbonyl}amino)furo[3,2-c]pyridine-2-carboxamide, (115) 4-chloro-N-(5-chloropyridin-2-yl)-3-({[trans-4-(3-oxomorpholin-4-yl)cyclohexyl]carbonyl}amino)furo[3,2-c]pyridine-2-carboxamide, and (116) N-(5-chloropyridin-2-yl)-4-methyl-3-{[(trans-4-pyrrolidin-1-ylcyclohexyl)carbonyl]amino}furo[3,2-c]pyridine-2-carboxamide or a pharmaceutically acceptable salt thereof.

24. A compound of the formula (II):

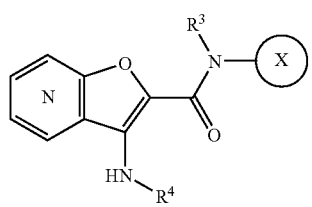

(II)

wherein the symbols are as defined in 1 above, or a salt thereof.

25. A compound of the formula (VI):

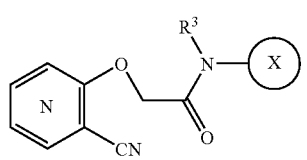

(VI)

wherein the symbols are as defined in 1 above, or a salt thereof.

26. A compound of the formula (IV):

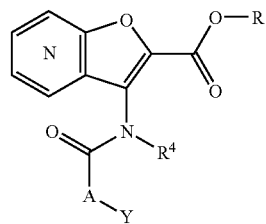

(IV)

wherein R is hydrogen, $C_{1-4}$ alkyl or a carboxy-protecting group, and the other symbols are as defined in 1 above, or a salt thereof.

27. A compound of the formula (IX):

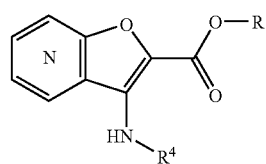

(IX)

wherein R is hydrogen, $C_{1-4}$ alkyl or a carboxy-protecting group, and the other symbols are as defined in 1 above, or a salt thereof.

The present invention also encompasses the following inventions.

28. A medicament comprising a compound of the formula (I) or a pharmaceutically acceptable salt thereof.

29. An inhibitor of activated blood coagulation factor X, which comprises as an active ingredient a compound of the formula (I) or a pharmaceutically acceptable salt thereof.

30. The inhibitor of activated blood coagulation factor X according to 29 above, which is a medicament for prevention or treatment of disorder caused by thrombus and/or embolus.

31. The inhibitor of activated blood coagulation factor X according to 30 above, wherein the disorder caused by thrombus and/or embolus is selected from stable angina pectoris, unstable angina pectoris, cerebral thrombosis, cerebral infarction, cerebral embolism, transient ischemic attack (TIA), ischemic cerebrovascular disease such as cerebrovascular spasm after subarachnoid hemorrhage, ischemic heart disease caused by coronary artery thrombogenesis, congestive chronic heart failure, myocardial infarction, acute myocardial infarction, pulmonary infarction, pulmonary embolism, pulmonary vascular disorders, economy-class syndrome, kidney disease (diabetic renal disease, chronic glomerulonephritis, IgA nephropathy, etc.), thrombogenesis with atherosclerosis, peripheral arterial occlusion, peripheral venous occlusion, Buerger's disease, deep vein thrombosis, disseminated intravascular coagulation (DIC), thrombogenesis after implantation of a synthetic vascular prosthesis or replacement of artificial heart valve or joint, intermittent claudication, thrombogenesis and reocclusion after blood circulation reconstruction such as percutaneous transluminal coronary angioplasty (PTCA) or percutaneous transluminal coronary recanalization (PTCR), systemic inflammatory response syndrome (SIRS), multiple organ dysfunction syndrome (MODS), thrombogenesis in extracorporeal circulation, blood coagulation in case of blood drawing, diabetic circulatory disturbance, graft rejection, organ protection and improvement of function in case of transplantation.

32. A pharmaceutical composition, which comprises a compound of the formula (I) or a pharmaceutically acceptable salt thereof, and a pharmaceutically acceptable carrier therefor.

The substituents represented by respective symbols used in the present specification and claims will be hereinafter described.

(1) Examples of substituent in the definition of "optionally substituted amino" for Y include an optionally substituted alkyl, an optionally substituted saturated heterocyclic group, acyl, and the like. Among them, alkyl, piperidyl optionally substituted by alkyl, or acyl is preferred.

In this context, the term "alkyl" means, for example, a straight chain or branched chain alkyl group having 1 to 6 carbon atoms, specifically, methyl, ethyl, propyl, isopropyl, butyl, isobutyl, tert-butyl, pentyl, hexyl, and the like. Among them, $C_{1-4}$ alkyl is preferred.

Examples of "piperidyl optionally substituted by alkyl" include piperidyl optionally substituted by a straight chain or branched chain alkyl group having 1 to 6 carbon atoms, preferably, 1 to 4 carbon atoms, specifically, piperidin-4-yl, 1-methylpiperidin-4-yl, 1-ethylpiperidin-4-yl, 1-isopropylpiperidin-4-yl, and the like.

Examples of "acyl" include alkanoyl, alkylthiocarbonyl and alkylsulfonyl. The term "alkanoyl" means, for example, a straight chain or branched chain alkanoyl group having 1 to 6 carbon atoms, specifically, formyl, acetyl, propionyl, butyryl, and the like. The term "alkylthiocarbonyl" means, for example, a straight chain or branched chain alkylthiocarbonyl group having 2 to 6 carbon atoms, specifically, thioacetyl, thiopropionyl, and the like. The term "alkylsulfonyl" means, for example, a straight chain or branched chain alkylsulfonyl group having 1 to 6 carbon atoms, specifically, methylsulfonyl, ethylsulfonyl, and the like.

(2) Examples of "optionally substituted cycloalkyl" for Y include a cycloalkyl group that may have a substituent(s) such as: (a) an optionally substituted alkyl, (b) an optionally substituted carbamoyl, (c) a carbonyl substituted by an optionally substituted saturated heterocyclic group, (d) an optionally substituted amino, (e) an optionally substituted saturated heterocyclic group, or the like. Examples of "cycloalkyl" include a $C_{3-7}$ cycloalkyl group, specifically, cyclopropyl, cyclobutyl, cyclopentyl, cyclohexyl, cycloheptyl, and the like, and cyclohexyl is preferred.

(a) In this context, the term "optionally substituted alkyl" means an alkyl group optionally substituted by amino that may have one or two substituents selected from acyl and alkyl. The term "alkyl" means, for example, a straight chain or branched chain alkyl group having 1 to 6 carbon atoms, specifically, methyl, ethyl, propyl, isopropyl, butyl, isobutyl, tert-butyl, pentyl, hexyl, and the like.

Examples of "acyl", as a substituent, include alkanoyl, alkylthiocarbonyl and alkylsulfonyl. The term "alkanoyl" means, for example, a straight chain or branched chain alkanoyl group having 1 to 6 carbon atoms, specifically, formyl, acetyl, propionyl, butyryl, and the like. The term "alkylthiocarbonyl" means, for example, a straight chain or branched chain alkylthiocarbonyl group having 2 to 6 carbon atoms, specifically, thioacetyl, thiopropionyl, and the like.

The term "alkylsulfonyl" means, for example, a straight chain or branched chain alkylsulfonyl group having 1 to 6 carbon atoms, specifically, methylsulfonyl, ethylsulfonyl, and the like.

Examples of "alkyl", as a substituent, include a straight chain or branched chain alkyl group having 1 to 6 carbon atoms, specifically, methyl, ethyl, propyl, isopropyl, butyl, isobutyl, tert-butyl, pentyl, hexyl, and the like.

Among the "optionally substituted alkyl", an aminoalkyl optionally substituted by a group selected from an optionally substituted acyl and an optionally substituted alkyl is preferred, and aminoalkyl substituted by alkyl is more preferred.

Specific examples of "optionally substituted alkyl" include aminomethyl, methylaminomethyl, dimethylaminomethyl, ethylaminomethyl, diethylaminomethyl, diethylaminoethyl, acetylaminomethyl, propionylaminomethyl, N-acetyl-N-methylaminomethyl, and the like.

(b) The term "optionally substituted carbamoyl" means a carbamoyl group that may have, as a substituent, an optionally substituted alkyl.

Examples of "alkyl", as a substituent, include a straight chain or branched chain alkyl group having 1 to 6 carbon atoms, specifically, methyl, ethyl, propyl, isopropyl, butyl, isobutyl, tert-butyl, pentyl, hexyl, and the like, and methyl and ethyl are especially preferred. The alkyl group may be substituted by amino that is optionally mono- or di-substituted by a $C_{1-4}$ alkyl; hydroxy; or a $C_{1-4}$ alkoxy, for example, amino, methylamino, dimethylamino, diethylamino, hydroxy group, methoxy, ethoxy, or the like. Specific examples of substituted alkyl include aminoethyl, methylaminoethyl, dimethylaminoethyl, hydroxyethyl, hydroxypropyl, methoxyethyl, ethoxyethyl, methoxypropyl, and the like.

Specific examples of "optionally substituted carbamoyl" include carbamoyl, dimethylcarbamoyl, diethylcarbamoyl, N-ethyl-N-methylcarbamoyl, N-methyl-N-(2-hydroxyethyl) carbamoyl, N-methyl-N-(2-methoxyethyl)carbamoyl, N-methyl-N-(2-dimethylaminoethyl)carbamoyl, N-ethyl-N-(2-dimethylaminoethyl)carbamoyl, and the like.

(c) The term "carbonyl substituted by an optionally substituted saturated heterocyclic group" means, for example, a carbonyl group that is substituted by an optionally substituted 5- to 7-membered saturated heterocyclic group containing 1 to 4, preferably 1 or 2 hetero atoms selected from the group consisting of nitrogen atom, oxygen atom and sulfur atom, specifically, imidazolidinylcarbonyl, pyrazolidinylcarbonyl, piperidylcarbonyl, piperidinocarbonyl, piperazinylcarbonyl, morpholinylcarbonyl, morpholinocarbonyl, thiomorpholinylcarbonyl, thiomorpholinocarbonyl, homopiperazinylcarbonyl, homopiperidylcarbonyl, homopiperidinocarbonyl, pyrrolidinylcarbonyl, and the like. Preferred examples include pyrrolidinylcarbonyl, piperidylcarbonyl, piperidinocarbonyl, piperazinylcarbonyl, morpholinocarbonyl, homopiperidinocarbonyl, homopiperazinylcarbonyl, and the like. The saturated heterocyclic group may be substituted by an optionally substituted $C_{1-4}$ alkyl (substituents for the $C_{1-4}$ alkyl: amino optionally mono- or di-substituted by $C_{1-4}$ alkyl; $C_{1-4}$ alkoxy; hydroxy, etc.), an amino that may be mono- or di-substituted by $C_{1-4}$ alkyl, a $C_{1-4}$ alkoxy, hydroxy, oxo, or the like.

(d) The term "optionally substituted amino" means an amino group that may have a substituent(s) such as (i) an optionally substituted acyl, (ii) an alkoxycarbonyl, or (iii) an optionally substituted alkyl, and the like.

In this context, (i) examples of "optionally substituted acyl", as a substituent, include alkanoyl, alkylthiocarbonyl and alkylsulfonyl. The term "alkanoyl" means, for example, a straight chain or branched chain alkanoyl group having 1 to 6 carbon atoms, specifically, formyl, acetyl, propionyl, butyryl, and the like. The term "alkylthiocarbonyl" means, for example, a straight chain or branched chain alkylthiocarbonyl group having 2 to 6 carbon atoms, specifically, thioacetyl, thiopropionyl, and the like. The term "alkylsulfonyl" means, for example, a straight chain or branched chain alkylsulfonyl group having 1 to 6 carbon atoms, specifically, methylsulfonyl, ethylsulfonyl, and the like. The acyl group may be substituted by a saturated heterocyclic group (pyrrolidino, piperidino, morpholino, piperazin-1-yl, etc.), an amino optionally substituted by $C_{1-6}$ acyl or $C_{1-6}$ alkyl, or the like.

(ii) Examples of "alkoxycarbonyl", as a substituent, include a straight or branched chain alkoxycarbonyl group having 2 to 7 carbon atoms, specifically, methoxycarbonyl, ethoxycarbonyl, propoxycarbonyl, isopropyloxycarbonyl, butoxycarbonyl, and the like.

(iii) Examples of "optionally substituted alkyl", as a substituent, include a straight chain or branched chain alkyl group having 1 to 6 carbon atoms, specifically, methyl, ethyl, propyl, isopropyl, butyl, isobutyl, tert-butyl, pentyl, hexyl, and the like. The alkyl group may have a substituent(s) selected from hydroxy, an optionally substituted amino, an alkoxycarbonyl, a cyano and a saturated heterocyclic group. Among these substituents, "optionally substituted amino" means an amino that may have 1 or 2 substituents selected from $C_{1-6}$ alkyl, $C_{1-6}$ acyl and $C_{2-7}$ alkoxycarbonyl, and specific examples thereof include amino, methylamino, dimethylamino, diethylamino, formylamino, acetylamino, N-acetyl-N-methylamino, N-formyl-N-methylamino, N-acetyl-N-ethylamino, methoxycarbonylamino, tert-butoxycarbonylamino, and the like. The term "alkoxycarbonyl" means an alkoxycarbonyl group having 2 to 7 carbon atoms, and specific examples thereof include methoxycarbonyl, ethoxycarbonyl, and the like. The term "saturated heterocyclic group" means an optionally substituted 5- or 6-membered saturated heterocyclic group containing 1 or 2 hetero atoms selected from the group consisting of nitrogen atom, oxygen atom and sulfur atom, and specific examples thereof include an optionally substituted pyrrolidinyl, piperidyl, morpholinyl, piperazinyl, and the like.

Among the substituents for the optionally substituted amino, an optionally substituted acyl, an alkoxycarbonyl and an optionally substituted alkyl are preferred, and acyl, alkoxycarbonyl, alkyl, aminoalkyl, alkoxycarbonylaminoalkyl and acylaminoalkyl are more preferred.

Specific examples of "optionally substituted amino" include amino, methylamino, dimethylamino, N-acetyl-N-methylamino, N-formyl-N-methylamino, N-tert-butoxycarbonyl-N-methylamino, N-(3-(tert-butoxycarbonylamino)propyl)-N-methylamino, N-(3-aminopropyl)-N-methylamino, N-(3-(acetylamino)propyl)-N-methylamino, N-acetylamino, methoxycarbonylmethylamino, cyanomethylamino, methoxycarbonylamino, and the like.

(e) The term "optionally substituted saturated heterocyclic group" means, for example, 4- to 7-membered saturated heterocyclic group containing 1 to 4, preferably 1 or 2 hetero atoms selected from the group consisting of nitrogen atom, oxygen atom and sulfur atom, which may have a substituent(s) such as alkoxycarbonyl, acyl, alkyl, oxo, and the like, and can form a condensed ring. Specific examples include pyrrolidinyl, 2-oxopyrrolidinyl, imidazolidinyl, pyrazolidinyl, 2-oxo-oxazolidinyl, 4-oxo-oxazolidinyl, 4-oxo-tetrahydrooxazinyl, 1,1-dioxo-tetrahydroisothiazolyl, piperidyl, piperidino, piperazinyl, 2-oxopiperazinyl, 4-methyl-2-oxopiperazinyl, 4-acetyl-2-oxopiperazinyl, morpholinyl, morpholino, 3-oxomorpholino, thiomorpholinyl, thiomorpholino, homopiperazinyl, homopiperidyl, homopiperidino, and the like, preferably, pyrrolidinyl, 2-oxopyrrolidinyl, piperidyl, piperidino, piperazinyl, morpholino, 3-oxomorpholino, homopiperidino, homopiperazinyl, 2-oxo-oxazolidinyl, 4-oxo-oxazolidinyl, 4-oxo-tetrahydrooxazinyl, 1,1-dioxo-tetrahydroisothiazolyl, 2-oxopiperazinyl, 4-methyl-2-oxopiperazinyl and 4-acetyl-2-oxopiperazinyl.

(3) Examples of "optionally substituted aryl" for Y include an aryl group that may have a substituent(s) such as an optionally substituted alkyl, an optionally substituted carbamoyl, a carbonyl substituted by an optionally substituted saturated heterocyclic group, an optionally substituted amino, an optionally substituted saturated heterocyclic group, and the like. Examples of "aryl" include an aromatic hydrocarbon group having 6 to 14 carbon atoms, specifically, phenyl, naphthyl, and the like, and phenyl is preferred.

In this context, the substituent(s) on aryl is the same as the substituent(s) on the "optionally substituted cycloalkyl" for Y. Above all, an optionally substituted carbamoyl is preferred.

(4) The term "optionally substituted saturated heterocyclic group" for Y means, for example, an optionally substituted 5- to 7-membered saturated heterocyclic group containing 1 to 4, preferably 1 or 2 hetero atoms selected from the group consisting of nitrogen atom, oxygen atom and sulfur atom, which may form a condensed ring. Specific examples include imidazolidinyl, pyrazolidinyl, piperidyl, piperidino, piperazinyl, morpholinyl, morpholino, thiomorpholinyl, thiomorpholino, homopiperazinyl, homopiperidyl, homopiperidino, pyrrolidinyl, and the like, and preferably, pyrrolidinyl, piperidyl, piperidino, piperazinyl, morpholino, homopiperidino and homopiperazinyl. Examples of a substituent(s) for the saturated heterocyclic group include (a) an optionally substituted alkyl, (b) an optionally substituted saturated heterocyclic group, (c) an optionally substituted acyl, (d) an optionally substituted unsaturated heterocyclic group, (e) oxo, and the like.

In this context, (a) examples of "alkyl", as a substituent, include a straight chain or branched chain alkyl group having 1 to 6 carbon atoms, specifically, methyl, ethyl, propyl, isopropyl, butyl, isobutyl, tert-butyl, pentyl, hexyl, and the like. The alkyl group may have a substituent(s) such as an unsaturated heterocyclic group (pyridyl, etc.), an amino group optionally substituted by $C_{1-6}$ alkyl, or the like.

(b) Examples of "optionally substituted saturated heterocyclic group", as a substituent, means, for example, 5- or 6-membered saturated heterocyclic group containing 1 or 2 hetero atoms selected from the group consisting of nitrogen atom, oxygen atom and sulfur atom, which may have a substituent(s) such as oxo, specifically, piperidyl, pyrrolidinyl, 2-oxopyrrolidinyl, and the like. The saturated heterocyclic group may have, as a substitutents(s), $C_{1-6}$ alkyl, $C_{1-6}$ acyl, and the like.

(c) Examples of "acyl", as a substituent, include alkanoyl, alkylthiocarbonyl and alkylsulfonyl. The term "alkanoyl" means, for example, a straight chain or branched chain alkanoyl group having 1 to 6 carbon atoms, specifically, formyl, acetyl, propionyl, butyryl, and the like. The term "alkylthiocarbonyl" means, for example, a straight chain or branched chain alkylthiocarbonyl group having 2 to 6 carbon atoms, specifically, thioacetyl, thiopropionyl, and the like.

The term "alkylsulfonyl" means, for example, a straight chain or branched chain alkylsulfonyl group having 1 to 6 carbon atoms, specifically, methylsulfonyl, ethylsulfonyl, and the like. The acyl group may be substituted by an optionally substituted amino, pyridyl, and the like.

(d) Examples of "optionally substituted unsaturated heterocyclic group", as a substituent, include, for example, a 5- or 6-membered unsaturated heterocyclic group containing 1 or 2 hetero atoms selected from the group consisting of nitrogen atom, oxygen atom and sulfur atom, specifically, pyridyl, pyrimidyl, thiazolyl, oxazolinyl, and the like.

Examples of "substituted saturated heterocyclic group" include 3-oxomorpholino, 2-oxopyrrolidinyl, 1-isopropylpiperidyl, 1-dimethylcarbamoylpiperidyl, and the like.

(5) Examples of "optionally substituted unsaturated heterocyclic group" for Y means, for example, an optionally substituted 5- to 7-membered unsaturated heterocyclic group containing 1 to 4, preferably, 1 or 2 hetero atoms selected from the group consisting of nitrogen atom, oxygen atom and sulfur atom, which may form a condensed ring. Specific examples include pyridyl, pyrimidinyl, pyrazinyl, furyl, thienyl, pyrrolyl, imidazolyl, pyrazolyl, oxazolyl, isoxazolyl, thiazolyl, isothiazolyl, and the like. Preferred examples include pyridyl, pyrimidinyl, pyrazinyl, thienyl, oxazolyl and thiazolyl. The unsaturated heterocyclic group may have a substituent(s) such as (a) an optionally substituted amino, (b) an optionally substituted aminoalkyl, (c) an optionally substituted saturated heterocyclic group, (d) an optionally substituted carbamoyl, and the like.

(a) Examples of a substituent of "optionally substituted amino", as a substituent, include a $C_{1-6}$ alkyl group substituted by amino that may be substituted by $C_{1-6}$ alkyl.

(b) Examples of "aminoalkyl", as a substituent, include an aminoalkyl group containing a $C_{1-6}$ alkyl group, which may have a substituent(s) such as $C_{1-6}$ alkyl, unsaturated heterocyclic group (oxazolidinyl, etc.), and the like.

(c) Examples of "optionally substituted saturated heterocyclic group", as a substituent, include a saturated 5- to 7-membered heterocyclic group containing 1 or 2 hetero atoms selected from the group consisting of nitrogen atom, oxygen atom and sulfur atom, and specific examples include homopiperazinyl, and the like.

(d) Examples of "optionally substituted carbamoyl", as a substituent, are the same as those defined in the substituent of "cycloalkyl" for Y.

Examples of "alkylene" for A include a straight- or branched-chain alkylene group having 1 to 6 carbon atoms, specifically, methylene, ethylene, trimethylene, tetramethylene, pentamethylene, hexamethylene, and the like. Among them, alkylenes having 1 to 5 carbon atoms are preferred, and methylene and tetramethylene are particularly preferred. The alkylene may be substituted by oxo, and specific examples include propionyl, butyryl, pentanoyl, and the like.

Examples of "alkenylene" for A include a straight- or branched-chain alkenylene having 2 to 6 carbon atoms, specifically, vinylene, propenylene, butenylene, pentenylene, and the like. Among them, an alkenylene having 2 to 5 carbon atoms is preferred.

Examples of "alkenylidene" for A include an alkenylidene having 2 to 6 carbon atoms, specifically, vinylidene, propenylidene, butenylidene, pentenylidene, and the like.

Examples of "halogen" for $R^{1A}$, $R^{1B}$ include fluoro, chloro, bromo, iodo, and the like.

Examples of "alkyl" for $R^{1A}$, $R^{1B}$ include a straight chain or branched chain alkyl group having 1 to 6, preferably 1 to 4 carbon atoms, specifically, methyl, ethyl, propyl, isopropyl, butyl, isobutyl, tert-butyl, pentyl, hexyl, and the like. Above all, methyl is especially preferred.

Examples of "haloalkyl" for $R^{1A}$, $R^{1B}$ include a straight chain or branched chain alkyl group having 1 to 6, preferably 1 to 4 carbon atoms that is substituted by a halogen(s), specifically, chloromethyl, dichloromethyl, fluoromethyl, difluoromethyl, trifluoromethyl, 2,2,2-trifluoroethyl, and the like.

Examples of "alkoxy" for $R^{1A}$, $R^{1B}$ include a straight chain or branched chain alkoxy group having 1 to 6, preferably 1 to 4 carbon atoms, specifically, methoxy, ethoxy, propoxy, isopropoxy, butoxy, tert-butoxy, pentyloxy, hexyloxy, and the like. Above all, methoxy is especially preferred.

Examples of substituent of "optionally substituted amino" for $R^{1A}$, $R^{1B}$ include a straight chain or branched chain alkyl group having 1 to 6, preferably 1 to 4 carbon atoms, specifically, methyl, ethyl, propyl, isopropyl, butyl, isobutyl, tert-butyl, pentyl, hexyl, and the like. Above all, methyl is especially preferred.

Preferred substituent for $R^{1A}$, $R^{1B}$ is halogen and alkyl, and chloro and methyl are especially preferred.

Examples of "alkyl" and "halogen" for $R^{1C}$ are the same as those defined in "alkyl" and "halogen" for $R^{1A}$, $R^{1B}$. Preferred substituent for $R^{1C}$ is hydrogen.

Examples of "halogen" for $R^{2A}$, $R^{2B}$ include fluoro, chloro, bromo, iodo, and the like, and fluoro, chloro and bromo are preferred.

Examples of "optionally substituted alkyl" for $R^{2A}$, $R^{2B}$ include a straight chain or branched chain alkyl group having 1 to 6, preferably, 1 to 4 carbon atoms, specifically, methyl, ethyl, propyl, isopropyl, butyl, isobutyl, tert-butyl, pentyl, hexyl, and the like, and methyl and ethyl are especially preferred. The alkyl may have a substituent(s) such as an amino that may be substituted by $C_{1-6}$ alkyl, hydroxy, a $C_{1-6}$ alkoxy, carboxy, a $C_{2-7}$ alkoxycarbonyl, an optionally substituted carbamoyl, and the like. Specific examples of substituted alkyl include aminomethyl, methylaminomethyl, dimethylaminomethyl, hydroxymethyl, 2-hydroxyethyl, methoxymethyl, carboxymethyl, methoxycarbonylmethyl, dimethylcarbamoylmethyl, and the like, and hydroxymethyl is especially preferred.

Examples of "optionally substituted alkoxy" for $R^{2A}$, $R^{2B}$ include a straight chain or branched chain alkoxy group having 1 to 6, preferably 1 to 4 carbon atoms, specifically, methoxy, ethoxy, propoxy, isopropoxy, butoxy, tert-butoxy, pentyloxy, hexyloxy, and the like. Above all, methoxy, ethoxy, isopropoxy are especially preferred. The alkoxy may have a substituent(s) such as an amino that may be substituted by $C_{1-6}$ alkyl, hydroxy, a $C_{1-6}$ alkoxy, and the like. Specific examples of substituted alkoxy include aminoethoxy, dimethylaminoetoxy, hydroxyethoxy, methoxyethoxy, and the like, and methoxyethoxy is preferred.

Examples of substituent of "optionally substituted amino" for $R^{2A}$, $R^{2B}$ include $C_{1-6}$ alkyl, $C_{1-6}$ acyl (e.g., alkanoyl, alkylthiocarbonyl, alkylsulfonyl), $C_{2-7}$ alkoxycarbonyl, and the like, specifically, amino, methylamino, dimethylamino, ethylamino, formylamino, acetylamino, N-acetyl-N-methylamino, N-methylsulfonylamino, N-methyl-N-methylsulfonylamino, methoxycarbonylamino, tert-butoxycarbonylamino, and the like, and amino, dimethylamino, acetylamino, methylsulfonylamino and tert-butoxycarbonylamino are especially preferred.

Examples of "optionally substituted alkoxycarbonyl" for $R^{2A}$, $R^{2B}$ include a straight chain or branched chain alkoxycarbonyl group having 2 to 7 carbon atoms, specifically, methoxycarbonyl, ethoxycarbonyl, propoxycarbonyl, butoxycarbonyl, and the like. The alkoxycarbonyl may have a substituent(s) such as hydroxy, a $C_{1-6}$ alkoxy, an optionally substituted amino, and the like.

Examples of substituent of "optionally substituted carbamoyl" for $R^{2A}$, $R^{2B}$ include an optionally substituted alkyl group having 1 to 6 carbon atoms, and the like. The alkyl may be substituted by an amino that may be mono- or di-substituted by $C_{1-6}$ alkyl or $C_{1-6}$ acyl, or a $C_{1-6}$ alkoxy.

Specific Examples of the carbamoyl include carbamoyl, N-methylcarbamoyl, N,N-dimethylcarbamoyl, N-(2-methoxyethyl)carbamoyl, N-methyl-N-methoxyethylcarbamoyl, N-(N,N-dimethylaminoethyl)carbamoyl, N-(N,N-dimethylaminoethyl)-N-methylcarbamoyl, and the like. Above all, N,N-dimethylcarbamoyl, N-methyl-N-methoxyethylcarbamoyl and N-(N,N-dimethylaminoethyl)-N-methylcarbamoyl are preferred.

The term "carbonyl substituted by an optionally substituted saturated heterocyclic group" for $R^{2A}$, $R^{2B}$ means, for example, a carbonyl substituted by an optionally substituted 5- to 7-membered saturated heterocyclic group containing 1 to 4, preferably 1 or 2 hetero atoms selected from the group consisting of nitrogen atom, oxygen atom and sulfur atom. Specific examples include imidazolidinylcarbonyl, pyrazolidinylcarbonyl, piperidylcarbonyl, piperidinocarbonyl, piperazinylcarbonyl, morpholinylcarbonyl, morpholinocarbonyl, thiomorpholinylcarbonyl, thiomorpholinocarbonyl, homopiperazinylcarbonyl, homopiperidylcarbonyl, homopiperidinocarbonyl, pyrrolidinylcarbonyl, and the like preferably, pyrrolidinylcarbonyl, piperidylcarbonyl, piperidinocarbonyl, piperazinylcarbonyl, morpholinocarbonyl, homopiperidinocarbonyl, homopiperazinylcarbonyl, and the like. The saturated heterocyclic group may be substituted by an oxo and the like.

The term "optionally substituted saturated heterocyclic group" for $R^{2A}$, $R^{2B}$ means, for example, a 5- to 7-membered saturated heterocyclic group containing 1 to 4, preferably 1 or 2 hetero atoms selected from the group consisting of nitrogen atom, oxygen atom and sulfur atom, which may have a substituent(s) and can form a condensed ring. Specific examples include imidazolidinyl, pyrazolidinyl, piperidyl, piperidino, piperazinyl, morpholinyl, morpholino, thiomorpholinyl, thiomorpholino, homopiperazinyl, homopiperidyl, homopiperidino, pyrrolidinyl, and the like, and preferably, pyrrolidinyl, piperidyl, piperidino, piperazinyl, morpholino, homopiperidino and homopiperazinyl. Examples of a substituent(s) for said saturated heterocyclic group include an optionally substituted alkyl, an optionally substituted saturated heterocyclic group, an optionally substituted acyl, an optionally substituted unsaturated heterocyclic group, oxo, and the like, and these substituents are the same as those defined in "optionally substituted saturated heterocyclic group" for Y.

Examples of "aryl" for $R^{2A}$, $R^{2B}$ include an aromatic hydrocarbon group having 6 to 14 carbon atoms, specifically, phenyl, naphthyl, and the like.

The term "optionally substituted unsaturated heterocyclic group" for $R^{2A}$, $R^{2B}$ means, for example, a 5- to 7-membered unsaturated heterocyclic group containing 1 to 4, preferably, 1 or 2 hetero atoms selected from the group consisting of nitrogen atom, oxygen atom and sulfur atom which may have a substitutent(s), specifically, pyridyl, pyrimidinyl, pyrazinyl, furyl, thienyl, pyrrolyl, imidazolyl, pyrazolyl, oxazolyl, isoxazolyl, thiazolyl, isothiazolyl, and the like. The unsaturated heterocyclic group may have a substituent(s) such as an optionally di- or mono substituted amino (substituent: $C_{1-4}$ alkyl, $C_{1-4}$ alkanoyl, etc.), an optionally substituted alkyl (substituent: amino that is mono- or di-substituted by $C_{1-4}$ alkyl, $C_{1-4}$ alkanoyl, etc.), or the like.

Preferred examples of a substituent for $R^{2A}$, $R^{2B}$ include hydrogen, halogen, an optionally substituted alkyl, an optionally substituted alkoxy, an optionally substituted amino, cyano, carboxy, alkoxycarbonyl, an optionally substituted carbamoyl or a carbonyl substituted by an optionally substituted saturated heterocyclic group. Above all, hydrogen, fluoro, chloro, bromo, methyl, hydroxymethyl, methoxy, isopropoxy, amino, dimethylamino, methylsulfonylamino, acetylamino, tert-butoxycarbonylamino, cyano, carboxy, methoxycarbonyl, ethoxycarbonyl, dimethylcarbamoyl, N-methyl-N-methoxyethylcarbamoyl, morpholinocarbonyl and pyrrolidinylcarbonyl are preferred.

Examples of "Ring X" include the following groups:

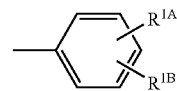

(a)

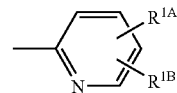

(b)

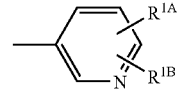

(c)

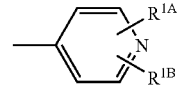

(d)

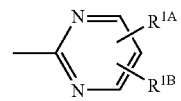

(e)

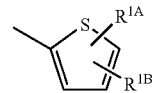

(f)

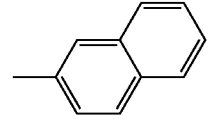

(g)

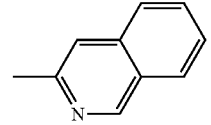

(h)

-continued

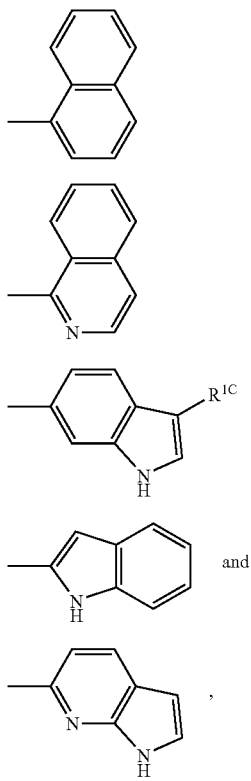

(i)

(j)

(k)

(l)

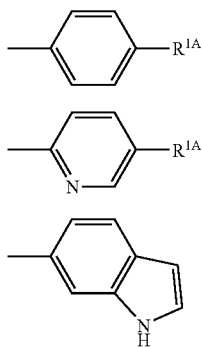

(m)

wherein (a) to (f), (k) and (l) are preferred and (a), (b) and (k) are especially preferred. The following groups are particularly preferred.

(a')

(b')

(k')

The term "alkyl" for $R^3$ means, for example, a straight chain or branched chain alkyl group having 1 to 6, preferably 1 to 4 carbon atoms, specifically, methyl, ethyl, propyl, isopropyl, butyl, isobutyl, tert-butyl, pentyl, hexyl, and the like. Hydrogen is especially preferred for $R^3$.

The term "alkyl" for $R^4$ means, for example, a straight chain or branched chain alkyl group having 1 to 6, preferably 1 to 4 carbon atoms, specifically, methyl, ethyl, propyl, isopropyl, butyl, isobutyl, tert-butyl, pentyl, hexyl, and the like. Hydrogen is especially preferred for $R^4$.

In the present specification, "saturated heterocyclic group" is preferably an optionally substituted 5- to 7-membered saturated heterocyclic group containing at least one nitrogen atom, especially preferred are the said saturated heterocyclic groups having a bond on nitrogen atom.

Ring:

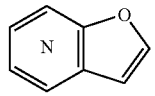

is preferably:

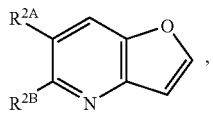 , 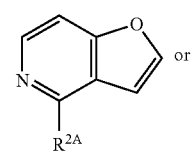 or

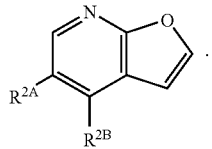 .

Among the compounds of the present invention, the above-mentioned compounds (1) to (110) are preferred.

The pharmaceutically acceptable salt of the compound (I) includes a salt with an inorganic acid such as hydrochloric acid, hydrobromic acid, hydroiodic acid, sulfuric acid, nitric acid, phosphoric acid, etc.; a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; salt with an acidic amino acid such as aspartic acid, glutamic acid, etc.; salt with a metal such as sodium, potassium, lithium, magnesium, calcium, alminum, etc.; salt with an amine such as ammonia, methylamine, ethylamine, ethanolamine, etc.; or a salt with a basic amino acid such as lysine, ornithine, etc.

The compound (I) of the present invention can be in the form of quaternary salt and such a quaternary salt falls within the scope of the present compound (I).

Further, the compound (I) of the present invention includes a intramolecular salt. hydrate, solvate, and the like. Besides, when the compound (I) has an asymmetric carbon atom(s), it can exist as an optical isomer, and the present invention encompasses one of, or a mixture of the isomers. Moreover, when the compound (I) has a double bond(s) or a cycloalkylene group having two or more substituents on the ring, it may exist in the form of cis, trans or meso, and, when the compound (I) has an unsaturated bond such as carbonyl, it may exist in the from of a tautomerism. The present compound (I) encompasses one of, or a mixture of these isomers.

Additionally, the compound (I) of the present invention encompasses a prodrug of a compound as mentioned above. Examples of a prodrug include those prepared by protecting a functional group such as an amino or carboxy group of a compound (I) with a conventional protecting group.

BEST MODE FOR CARRYING OUT THE INVENTION

The compound of the present invention may be prepared according to the following processes.

PROCESS 1: The compound (I) of the present invention can be prepared in the following manner.

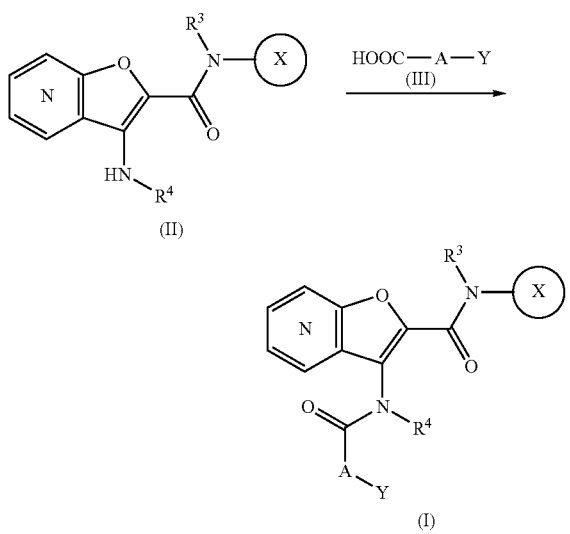

wherein the symbols are as defined above.

The compound (I) can be prepared by subjecting a compound (II) and a compound (III) to condensation reaction.

The condensation of the compound (II) with the compound (III) can be carried out by subjecting these compounds to a conventional condensation reaction using a condensing agent, or converting the compound (III) into a reactive derivative (an acid halide, a mixed anhydride, a reactive ester, etc.), and reacting with the compound (II).

(1) In cases where the compound (II) and the compound (III) are subjected to a conventional condensation reaction, the reaction can be carried out in an appropriate solvent. The condensing agent usable in the reaction includes N,N-dicyclohexylcarbodiimide (DCC), 1-ethyl-3-(3-dimethylaminopropyl)carbodiimide (EDC) or a hydrochloride thereof, carbonyldiimidazole (CDI), diphenylphosphorylazide (DPPA), diethyl cyanophosphonate (DEPC), and the like. Above all, DCC, EDC or a hydrochloride thereof is preferred.

The present reaction is generally carried out at a temperature of 0° C. to 100° C.; however, a higher or a lower temperature can be selected appropriately, if necessary. The reaction time for the present reaction is generally between 30 minutes and 24 hours; however, a longer or a shorter reaction time can be selected appropriately, if necessary.

(2) In cases where a reactive derivative of the compound (III) is used, the compound (III) is converted into a reactive derivative in a conventional manner such as, for example, into an acid halide using a halogenating agent (thionyl chloride, thionyl bromide, oxalyl chloride, etc.), a mixed acid anhydride using a chlorocarbonate ester (methyl chlorocarbonate, ethylchlorocarbonate, isobutyl chlorocarbonate, etc.) or an acid chloride (2,4,6-trichlorobenzoyl chloride, etc.), a reactive ester using 1-hydroxysuccinimide, 1-hydroxybenzotriazole or p-nitrophenol, etc., or a lower alcohol ester (methyl ester, ethyl ester, etc.). The resulting reactive derivative is then subjected to condensation reaction with the compound (II) in an appropriate solvent or without solvent in the presence of an acid scavenger, when needed.

The process wherein the compound (III) is converted into an acid halide is preferred for the present condensation reaction.

When the reaction involves the conversion into acid halide, the reaction can be accelerated by adding, as a catalyst, dimethylformamide or the like.

Furthermore, in the above-mentioned condensation reaction, the reaction can be facilitated or accelerated by adding 4-dimethylaminopyridine or the like.

The acid scavenger that is used when needed includes, for example, inorganic or organic bases. Examples of inorganic bases include alkali metal carbonates (sodium carbonate, potassium carbonate, cesium carbonate, etc.), alkali metal hydrogen carbonates (sodium hydrogen carbonate, potassium hydrogen carbonate, etc.) and alkali metal hydroxides (sodium hydroxide, potassium hydroxide, lithium hydroxide, etc.). Examples of organic bases include linear tri-lower alkylamines (triethylamine, tributylamine, diisopropylethylamine, etc.), cyclic tertiary-amines (1,4-diazabicyclo[2.2.2]octane, 1,5-diazabicyclo[4.3.0]non-5-ene, 1,8-diazabicyclo[5.4.0]undec-7-ene, etc.), aromatic tertiary amines (N,N-dimethylaniline, N,N-diethylaniline, etc.), pyridine, lutidine, collidine, etc. Above all, triethylamine, diisopropylethylamine and pyridine are preferred for the present reaction. If an acid scavenger is used in the present reaction, said acid scavenger may serve as a solvent.

The present reaction is generally carried out at a temperature of −20° C. to the reflux temperature of the solvent; however, a lower temperature can be selected appropriately, if necessary. The reaction time is generally between 30 minutes and 24 hours; however, a longer or shorter reaction time can be selected appropriately, if necessary.

In cases where a solvent is used in the condensation reaction above, any inert solvent which does not disturb the reaction can be used, for example, halogenated solvents (chloroform, dichloromethane, dichloroethane, etc.), aromatic hydrocarbons (benzene, toluene, xylene, etc.), ethers (diethyl ether, diisopropyl ether, tetrahydrofuran, dioxane, 1,2-dimethoxyethane, etc.), esters (ethyl acetate, etc.), amides (N,N-dimethylformamide, N,N-dimethylacetamide, 1,3-dimethyl-2-imidazolidinone, etc.), nitriles (acetonitrile, etc.), dimethyl sulfoxide, pyridine, 2,6-lutidine, water, and the like. A mixed solvent comprising two or more of these solvents is also available. Among the solvents, dichloromethane, chloroform, toluene, xylene, tetrahydrofuran, dioxane, N,N-dimethylformamide, N,N-dimethylacetamide, 1,3-dimethyl-2-imidazolidinone and pyridine are preferred, and dichloromethane, chloroform, N,N-dimethylformamide, pyridine, and a mixed solvent thereof are especially preferred.

PROCESS 2: Among the compounds (I), compounds wherein Y is cycloalkyl substituted by —N(G)R$^5$, —NHR$^5$ and —N(R$^5$)CH$_2$R$^6$, i.e., the compounds (I-a), (I-b) and (I-c), respectively, can be prepared in the following manner.

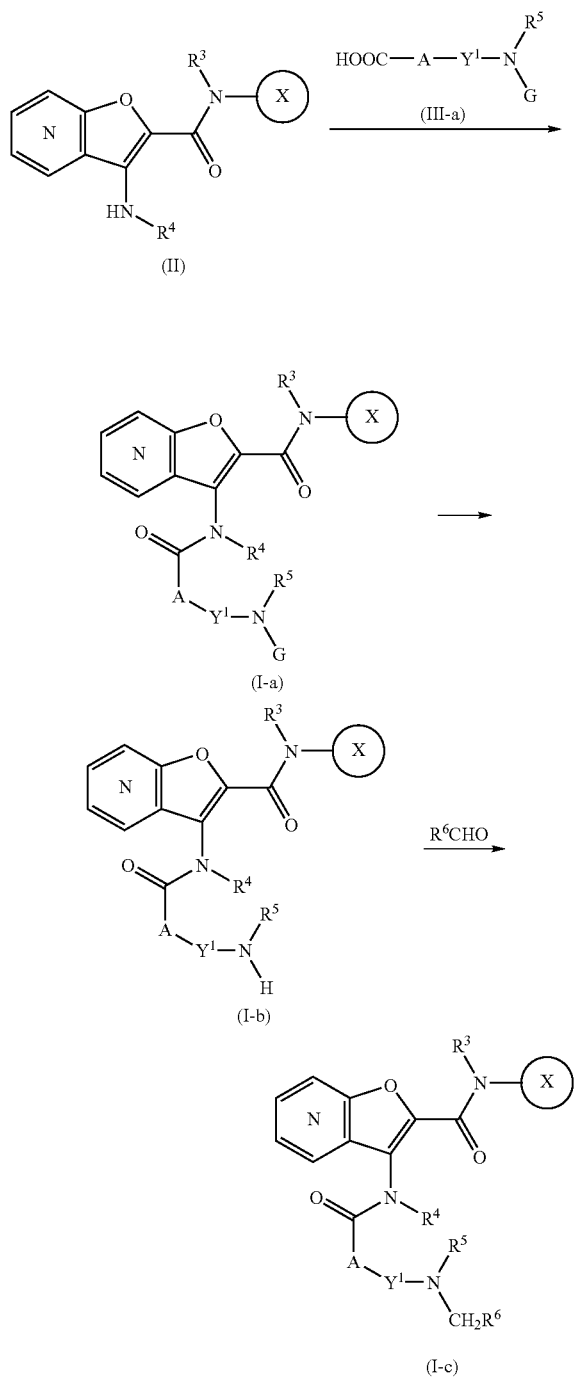

wherein $Y^1$ is cycloalkylene, $R^5$ is hydrogen, alkyl, acyl, alkoxycarbonyl or an unsaturated heterocyclic group, $R^6$ is an optionally substituted alkyl or an unsaturated heterocyclic group, G is an amino-protecting group such as tert-butoxycarbonyl, benzyloxycarbonyl, etc., and the other symbols are the same as defined above.

The compound (I-b) can be prepared by condensing a compound (II) with a compound (III-a) to give a compound (I-a), and removing the amino-protecting group. Subsequently, the compound (I-c) can be prepared by subjecting the compound (I-b) to reductive alkylation using an aldehyde of the formula: $R^6CHO$.

The condensation between the compound (II) and the compound (III-a) can be carried out under similar conditions to those described in PROCESS 1.

The deprotection of compound (I-a) can be carried out by a method generally used in the field of synthetic organic chemistry. For instance, when G of the compound (1-a) is tert-butoxycarbonyl, the said compound can be treated with an acid (e.g., hydrochloric acid, trifluoroacetic acid, methanesulfonic acid, etc.) in an appropriate solvent (dioxane, tetrahydrofuran, ethyl acetate, dichloromethane, chloroform, methanol, ethanol, etc.) to give the compound (1-b).

The reductive alkylation of compound (I-b) can be carried out by reacting the compound (I-b) with an aldehyde ($R^6CHO$) in an appropriate solvent in the presence of a reducing agent.

In the reductive alkylation, any reducing agents that do not affect the amide bond etc. can be used, and examples thereof include metal reducing agents such as sodium borohydride, sodium triacetoxy borohydride, sodium cyano borohydride, etc.

In the reductive alkylation, any inert solvent which does not disturb the reaction can be used, for example, halogenated solvents (chloroform, dichloromethane, dichloroethane, etc.), ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), nitriles (acetonitrile, etc.), aromatic hydrocarbons (benzene, toluene, xylene, etc.), alcohols (methanol, ethanol, propanol, etc.), water, and the like. A mixed solvent comprising two or more of these solvents is also available, when needed. Above all, dichloromethane, dichloroethane, tetrahydrofuran, 1,2-dimethoxyethane, methanol, ethanol, propanol, and the like are preferred.

The reductive alkylation is generally carried out at a temperature of −10° C. to the reflux temperature of the solvent, preferably at a temperature of under ice-cooling to room temperature. The reaction time is generally between 30 minutes and 24 hours; however, a longer or a shorter reaction time can be selected appropriately, if necessary.

The present reaction can also be conducted by catalytic hydrogenation using hydrogen under a metal catalyst (palladium-carbon, platinum-carbon, platinum oxide, Raney Nickel, etc.) in place of the above-mentioned reducing agents.

In the present reaction, any inert solvent which does not disturb the reaction can be used, for example, ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), esters (ethyl acetate, etc.), aromatic hydrocarbons (benzene, toluene, xylene, etc.), alcohols (methanol, ethanol, propanol, etc.), water, and the like. A mixed solvent comprising two or more of these solvents is also available, if appropriate. Above all, tetrahydrofuran, N,N-dimethylformamide, methanol and ethanol are preferred.

The present reaction is generally carried out at a temperature of −10° C. to the reflux temperature of the solvent, preferably at a temperature of under ice-cooling to room temperature. The reaction time is generally between 30 minutes and 24 hours; however, a longer or a shorter reaction time can be selected appropriately, if necessary.

Further, an organic acid such as acetic acid, or a mineral acid such as hydrochloric acid can also be added in order to facilitate the reductive alkylation.

PROCESS 3: The compound (I) of the present invention can also be prepared in the following manner.

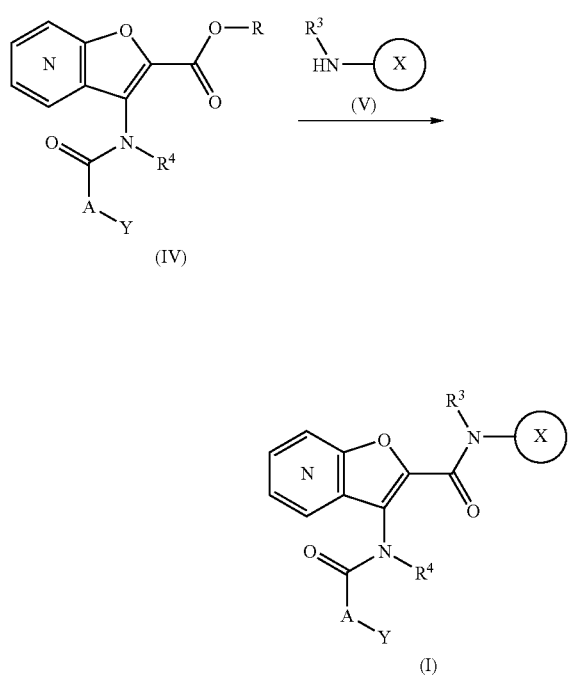

wherein R is hydrogen, $C_{1-4}$ alkyl, or a carboxy-protecting group, and the other symbols are as defined above.

The compound (I) can be prepared by subjecting a compound (IV) and a compound (V) to condensation reaction.

The condensation reaction of the compound (IV) with the compound (V) can be carried by heating the compounds without solvent, or by converting the compound (V) into a corresponding alminum amide compound in the presence of tri-lower alkyl alminum (trimethylalminum), sodium diethyldihydroaluminate, or the like in an appropriate solvent, and reacting with a compound (IV).

In the reaction, any inert solvent which does not disturb the reaction can be used, for example, halogenated solvents (chloroform, dichloromethane, dichloroethane, etc.), aromatic hydrocarbons (benzene, toluene, xylene, etc.), ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), hydrocarbons (hexane, etc.), dimethyl sulfoxide, pyridine, 2,6-lutidine, water, and the like, and a mixed solvent comprising two or more of these solvents. Above all, dichloromethane, chloroform, toluene, xylene and hexane are especially preferred.

The present reaction can be carried out in a wide range of temperature from under cooling to under heating, for example, from −10° C. to the boiling point of the solvent, and especially preferably from a temperature under ice-cooling to 60° C. The reaction time varies depending on the solvent used; however, it is generally between 1 and 24 hours, preferably between 2 and 8 hours.

Process 4:

Among the compounds (II), a compound wherein $R^4$ is hydrogen and Ring:

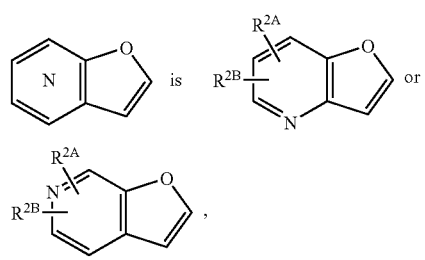

wherein the symbols are as defined above, that is, a compound of the formula (II-a):

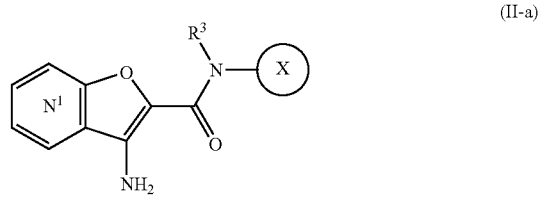

wherein Ring:

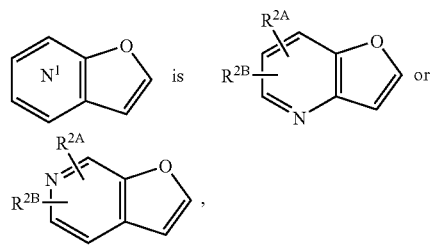

and the other symbols are as defined above, can be prepared in the following manner.

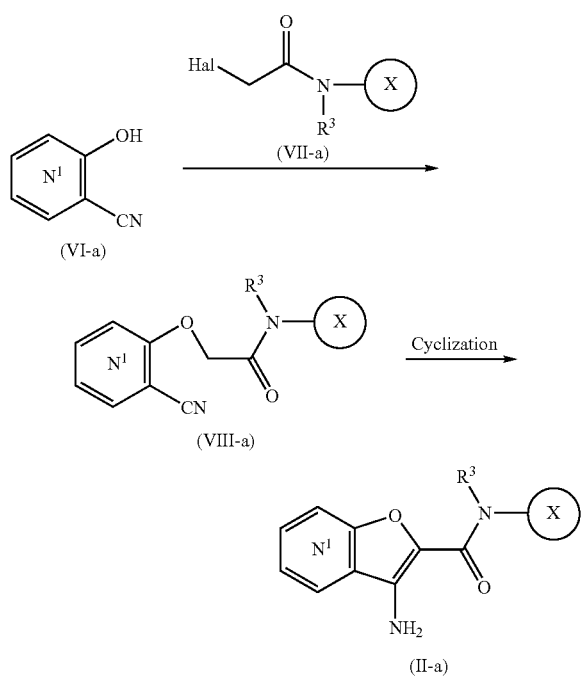

wherein Hal is a halogen such as chloro, bromo, or the like, and the other symbols are as defined above.

(1) The O-alkylation reaction of a compound (VI-a) can be carried out in the presence of a base in an appropriate solvent, if necessary.

The base usable in the O-alkylation includes, for example, inorganic and organic bases. Examples of inorganic base include alkali metal carbonates (sodium carbonate, potassium carbonate, cesium carbonate, etc.), alkali metal hydrogen carbonates (sodium hydrogen carbonate, potassium hydrogen carbonate, etc.), alkali metal hydroxides (sodium hydroxide, potassium hydroxide, lithium hydroxide, etc.), and the like. In the O-alkylation, a halide (sodium iodide, lithium iodide, potassium iodide, lithium bromide, etc.), preferably, an iodide ((sodium iodide, lithium iodide, potassium iodide, etc.) is used together with a base.

Examples of organic bases include linear tri-lower alkylamines (triethylamine, tributylamine, diisopropylethylamine, etc.), cyclic tertiary-amines (1,4-diazabicyclo[2.2.2]octane, 1,5-diazabicyclo[4.3.0]-non-5-ene, 1,8-diazabicyclo[5.4.0]undec-7-ene, etc.), aromatic tertiary amines (N,N-dimethylaniline, N,N-diethylaniline, 4-dimethylaminopyridine, etc.), pyridine, lutidine, collidine, etc. Besides, a base such as alkali metal alkoxides (sodium methoxide, potassium butoxide, etc.) is also available. An alkali metal carbonate is especially preferred for the present reaction. These bases can also serve as a solvent in the present reaction.

In the O-alkylation, any inert solvent which does not disturb the reaction can be used, for example, ketones (acetone, methylethyl ketone, etc.), aromatic hydrocarbons (benzene, toluene, xylene, etc.), ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), nitriles (acetonitrile, etc.), dimethyl sulfoxide, pyridine, 2,6-lutidine, and the like. A mixed solvent comprising two or more of these solvents is also available. Above all, ketones and amides are preferred.

The present reaction is generally carried out at a temperature of under ice-cooling to the reflux temperature of the solvent. The reaction time is generally between 30 minutes and 24 hours; however, a longer or a shorter reaction time can be selected appropriately, if necessary.

(2) The cyclization reaction of the compound (VIII-a) can be carried out by treating with a base in an appropriate solvent, if necessary.

The cyclization can be carried out using a similar base to that described in regard to O-alkylation above, preferably, a base of alkali metal carbonates, potassium t-butoxide or cyclic tertiary-amines.

In cases where a solvent is used in the cyclization, any inert solvent which does not disturb the reaction can be used, for example, ketones (acetone, methylethyl ketone, etc.), aromatic hydrocarbons (benzene, toluene, xylene, etc.), ethers (diethyl ether, diisopropyl ether, tetrahydrofuran, dioxane, 1,2-dimethoxyethane, etc.), amides (N,N-dimethylformamide, N,N-dimethylacetamide, 1,3-dimethyl-2-imidazolidinone, etc.), nitrites (acetonitrile, etc.), alcohols (methanol, ethanol, propanol, 2-butanol, t-butanol, etc.), dimethyl sulfoxide, pyridine, 2,6-lutidine, and the like. A mixed solvent comprising two or more of these solvents is also available. Above all, ketones, amides and alcohols are preferred, and N,N-dimethylacetamide, 1,3-dimethyl-2-imidazolidinone and t-butanol are especially preferred.

The present reaction is generally carried out at a temperature of under ice-cooling to the reflux temperature of the solvent. The reaction time for the cyclization is generally between 30 minutes and 24 hours; however, a longer or a shorter reaction time can be selected appropriately, if necessary.

Process 5:

Among the compounds (II), a compound wherein $R^4$ is hydrogen and Ring:

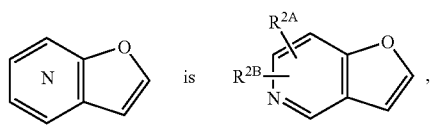

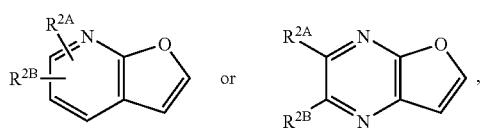

wherein the symbols are as defined above, that is, a compound of the formula (II-b):

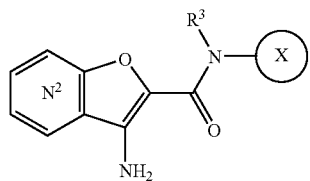

wherein Ring:

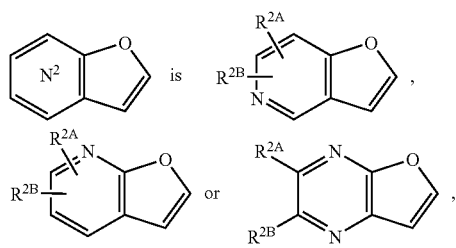

and the other symbols are as defined above, can be prepared in the following manner.

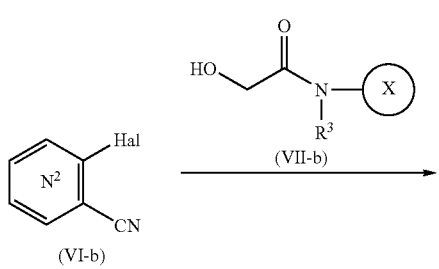

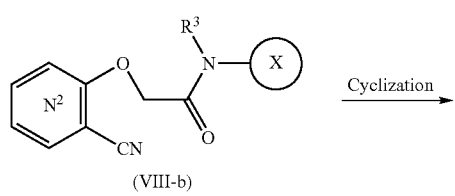

wherein the symbols are as defined above.

(1) The reaction between a compound (VI-b) and a compound (VII-b) can be carried out in the presence of a base in an appropriate solvent, if necessary. Examples of the base usable in the present reaction include alkali metal carbonates (sodium carbonate, potassium carbonate, cesium carbonate, etc.), alkali metal hydrides (sodium hydride, etc.) and alkali metal alkoxides (sodium methoxide, potassium tert-butoxide, etc.). Above all, sodium hydride is particularly preferred. The solvents include amides (N,N-dimethylformamide, N,N-dimethylacetamide, 1,3-dimethyl-2-imidazolidinone, etc.) and ethers (diethyl ether, diisopropyl ether, tetrahydrofuran, dioxane, 1,2-dimethoxyethane, etc.). Above all, N,N-dimethylformamide, N,N-dimethylacetamide, 1,3-dimethyl-2-imidazolidinone, and the like are preferred.

(2) The cyclization reaction of the compound (VIII-b) can be carried out under similar conditions to those used in the cyclization reaction described in PROCESS 3.

Process 6:

The compound (IV) can be prepared in the following manner.

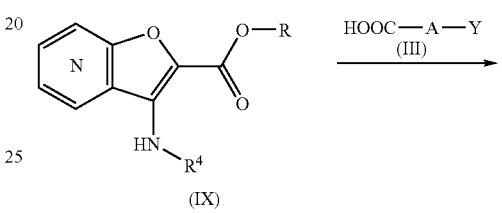

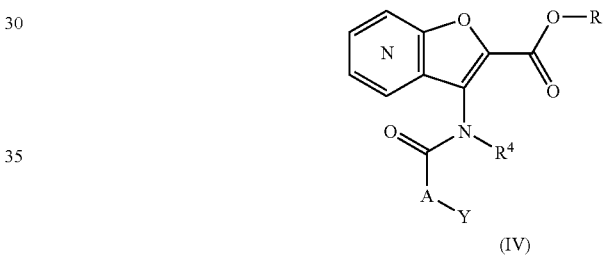

wherein the symbols are as defined above.

The compound (IV) can be prepared by subjecting a compound (IX) and a compound (III) to condensation reaction. The condensation reaction can be carried out under similar conditions to those described in PROCESS 1.

Process 7:

Among the compounds (IX), a compound wherein $R^4$ is hydrogen can be prepared in the following manner.

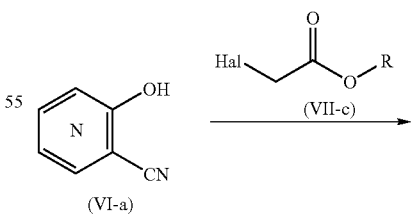

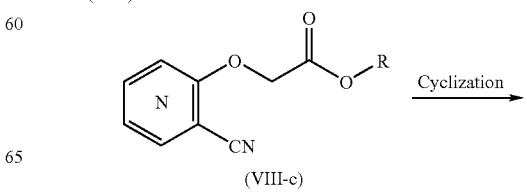

-continued

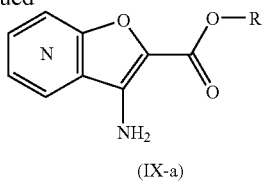

(IX-a)

wherein the symbols are as defined above.

The compound (IX-a) can be prepared by subjecting a compound (VI-a) and a compound (VII-c) to O-alkylation in the presence of a base, and cyclizing the resulting compound VIII-c. The respective reactions for O-alkylation and cyclization can be carried out under similar conditions to those described in PROCESS 4.

Process 8:

The compound (VII-a) can be prepared in the following manner.

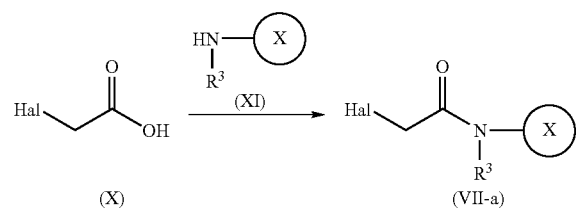

wherein the symbols are as defined above.

The compound (VII-a) can be prepared by subjecting a compound (X) and a compound (XI) to a conventional condensation reaction using a condensing agent, or by converting the compound (X) into a reactive derivative (an acid halide, a mixed anhydride, a reactive ester, etc.), and reacting with the compound (XI).

The present reaction can be carried out under the similar conditions to those described in PROCESS 1. The process wherein a reactive derivative (acid halide) of compound (x) is used is particularly preferred.

Process 9:

The compound (VII-b) can be prepared in the following manner.

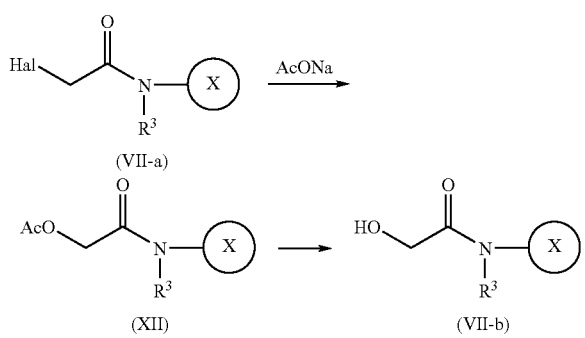

wherein Ac is acetyl and other symbols are as defined above.

The compound (VII-b) can be prepared by reacting a compound (VII-a) with sodium acetate in an appropriate solvent in accordance with a conventional method for converting a halide into a hydroxyl group, and subjecting the resulting compound (XII) to solvolysis or hydrolysis.

In the present reaction, any inert solvent which does not disturb the reaction can be used, and amides (N,N-dimethylformamide, N,N-dimethylacetamide, 1,3-dimethyl-2-imidazolidinone, etc.) are preferred.

The present reaction is generally carried out at a temperature of 0° C. to 100° C.; however, a higher or a lower temperature can be selected appropriately, if necessary. The reaction time is generally between 30 minutes and 24 hours; however, a longer or a shorter reaction time can be selected appropriately, if necessary.

The compound (VII-b) can be prepared by treating the compound (XII) with an inorganic base or the like in a solvent such as alcohol (methanol, ethanol, etc.), water or the like, or with an alkali metal alkoxide or an inorganic base in an inert solvent. The inorganic base usable in the present reaction includes alkali metal carbonates (sodium carbonate, potassium carbonate, etc.), alkali metal hydroxides (sodium hydroxide, potassium hydroxide, lithium hydroxide, etc.), and alkali metal carbonates are especially preferred.

The alkali metal alkoxide usable in the present reaction includes sodium methoxide, potassium tert-butoxide, and the like.

In the present reaction, any inert solvent which does not disturb the reaction can be used, for example, alcohols (methanol, ethanol, propanol, 2-butanol, etc.), water, amides (N,N-dimethylformamide, N,N-dimethylacetamide, 1,3-dimethyl-2-imidazolidinone, etc.), ethers (diethyl ether, diisopropyl ether, tetrahydrofuran, dioxane, 1,2-dimethoxyethane, etc.), and the like. A mixed solvent comprising two or more of these solvents is also available. Above all, methanol and water are preferred.

Process 10:

Among the compounds (III-a), a compound wherein $R^5$ is hydrogen can be prepared in the following manner.

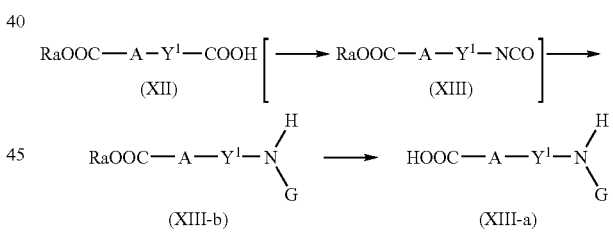

wherein $R^a$ is alkyl such as methyl, and the other symbols are as defined above.

The compound (XIII-b) can be prepared by converting the compound (XII) into a compound (XIII) through Curtius Rearrangement reaction, wherein the compound (XII) is treated with an azide compound in an appropriate solvent in the presence of a base and, if necessary, an activating agent, and treating with an alcohol. The compound (XIII-a) can be prepared by hydrolyzing the compound (XIII-b).

Examples of the base usable in the Curtius Rearrangement reaction include triethylamine, diisopropyl-ethylamine, and the like.

The activating agent usable in the Curtius Rearrangement reaction, when needed, includes methyl chlorocarbonate, ethyl chlorocarbonate, isopropyl chlorocarbonate, isobutyl chlorocarbonate, phenyl chlorocarbonate, and the like.

The azide compound usable in the Curtius Rearrangement reaction includes sodium azide, diphenylphosphorylazide, and the like.

Examples of the solvent usable in the Curtius Rearrangement reaction include toluene, xylene, benzene, tetrahydrofuran, dioxane, ethylene glycol dimethyl ether, dimethylformamide, chloroform, dichloroethane, ethyl acetate, acetonitrile, tert-butyl alcohol, and the like. When tert-butyl alcohol is used as a solvent, the alcohol treatment below is not necessarily required and the compound (XIII-b) can be obtained only through the above-mentioned treatment.

The Curtius Rearrangement reaction is generally carried out at a temperature of −20° C. to 150° C.; however, a higher or a lower temperature can be selected, if necessary.

The reaction time for the Curtius Rearrangement reaction is generally between 30 minutes and 10 hours; however, a longer or shorter reaction time can be selected, if necessary.

Examples of alcohol usable in the preparation of the compound (XIII-b) include straight chain or branched chain $C_{1-4}$ alcohols that may have phenyl, specifically, methanol, ethanol, tert-butyl alcohol, benzyl alcohol, and the like.

The reaction for obtaining the compound (XIII-b) is generally carried out at a temperature of −20° C. to the reflux temperature of the solvent; however, a higher or a lower temperature can be selected, if necessary.

The reaction time for obtaining the compound (XIII-b) is generally between 30 minutes and 24 hours; however, a longer or a shorter reaction time can be selected appropriately, if necessary.

The resulting compound (XIII-b) can be converted into the compound (XIII-a) by subjecting the compound (XXX-b) to a known reaction for hydrolysis generally used in the field of synthetic organic chemistry.

Process 11:

When a compound of the present invention has an amino group, it can be N-alkylated or N-acylated by a method known in the field of synthetic organic chemistry. When a compound of the present invention has a carbamoyl group or an amide group, it can be N-alkylated by a method known in the field of synthetic organic chemistry. When a compound of the present invention has a carboxyl group, it can be esterified or amidated by a method known in the field of synthetic organic chemistry. When a compound of the present invention has an ester or an amide, it can be converted into corresponding carboxylic acid, alcohol and amine through hydrolysis or reduction by a method known in the field of synthetic organic chemistry.

When a compound of the present invention has a halogen on aryl or unsaturated heterocyclic group, it can be converted into corresponding aryl, unsaturated heterocyclic group, optionally substituted amino and alkoxy by a method known in the field of organic synthetic chemistry such as coupling reaction using palladium or nickel catalyst. When the aforementioned coupling reaction is carried out under carbon monoxide atmosphere, it can be converted into corresponding alkoxycarbonyl or an optionally substituted carbamoyl.

The resulting compounds of the present invention thus produced can be isolated and purified by a procedure well known in the field of synthetic organic chemistry such as recrystallization, column chromatography, and the like.

The present compound (I) or a pharmaceutically acceptable salt thereof has an excellent inhibitory effect on activated blood coagulation factor X, and hence is useful in the prevention and treatment of various disorders caused by thrombi and emboli in a mammal (e.g., human, monkey, rabbit, dog, cat, pig, horse, bull, mouse, rat, guinea pig, etc.), which disorders include, for example, stable angina pectoris, unstable angina pectoris, cerebral thrombosis, cerebral infarction, cerebral embolism, transient ischemic attack (TIA), ischemic cerebrovascular disease such as cerebrovascular spasm after subarachnoid hemorrhage, ischemic heart disease caused by coronary artery thrombogenesis, congestive chronic heart failure, myocardial infarction, acute myocardial infarction, pulmonary infarction, pulmonary embolism, pulmonary vascular disorders, economy-class syndrome, kidney disease (diabetic renal disease, chronic glomerulonephritis, IgA nephropathy, etc.), thrombogenesis with atherosclerosis, peripheral arterial occlusion, peripheral venous occlusion, Buerger's disease, deep vein thrombosis, disseminated intravascular coagulation (DIC), thrombogenesis after implantation of a synthetic vascular prosthesis or replacement of artificial heart valve or joint, intermittent claudication, thrombogenesis and reocclusion after blood circulation reconstruction such as percutaneous transluminal coronary angioplasty (PTCA) or percutaneous transluminal coronary recanalization (PTCR), systemic inflammatory response syndrome (SIRS), multiple organ dysfunction syndrome (MODS), thrombogenesis in extracorporeal circulation, blood coagulation in case of blood drawing, diabetic circulatory disturbance, graft rejection, organ protection and improvement of function in case of transplantation, etc.

The present compound is characterized in that it shows excellent inhibitory effect on activated blood coagulation factor X, decreased toxicity, and causes few side effects (bleeding, etc.) that are seen in the existing anticoagulants.

The present compound (I) or a pharmaceutically acceptable salt thereof can be formulated into a pharmaceutical composition comprising a therapeutically effective amount of the compound (I) and a pharmaceutically acceptable carrier therefor. The pharmaceutically acceptable carriers include diluents, binders (e.g., syrup, gum arabic, gelatine, sorbit, tragacanth, polyvinylpyrrolidone), excipients (e.g., lactose, sucrose, corn starch, potassium phosphate, sorbit, glycine), lubricants (e.g., magnesium stearate, talc, polyethylene glycol, silica), disintegrants (e.g., potato starch) and wetting agents (e.g., sodium lauryl sulfate), and the like.

The compound (I) of the present invention or a pharmaceutically acceptable salt thereof can be administered orally or parenterally, and be used as an appropriate pharmaceutical preparation. Examples of an appropriate preparation for oral administration include solid preparations (tablets, granules, capsules, powders, etc.), solutions, suspensions and emulsions. Examples of an appropriate preparation for parenteral administration include suppository, injections or preparation for continuous infusion prepared using distilled water for injection, physiological saline or aqueous glucose solution, etc., or inhalant.

The dose of the compound (I) or a pharmaceutically acceptable salt thereof of the present invention may vary depending on the administration routes, and the age, weight and condition of the patient, or the kind or severity of the disease, it is usually in the range of about 0.1 to 50 mg/kg/day, preferably about 0.1 to 30 mg/kg/day.

EXAMPLES

The present invention will be illustrated in detail by Examples and Reference Examples, but should not be construed to be limited thereto.

Example 1

N-(5-Chloropyridin-2-yl)-3-({[trans-4-(2-oxo-pyrrolidin-1-yl)cyclohexyl]carbonyl}amino)furo[3,2-b]pyridine-2-carboxamide

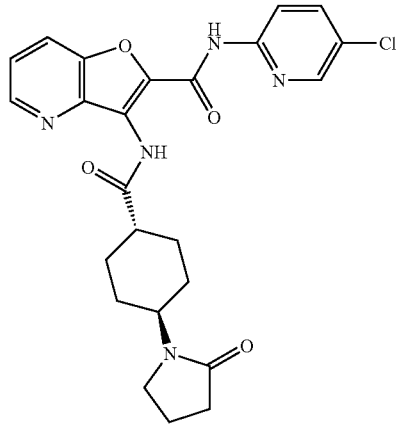

Trans-4-(2-oxopyrrolidin-1-yl)cyclohexanecarboxylic acid (22.0 g) obtained in Reference Example 2 is dissolved in thionyl chloride (150 ml), and the mixture is stirred at room temperature for 6 hours. The reaction solution is concentrated under reduced pressure, and the residue is suspended in chloroform (500 ml). To the suspension is added in small portions 3-amino-N-(5-chloropyridin-2-yl)furo[3,2-b]pyridine-2-carboxamide (20.0 g) obtained in Reference Example 24 under ice-cooling. Pyridine (56 ml) is added dropwise thereto, and the reaction solution is warmed to room temperature and stirred for 15 hours. To the reaction solution is poured saturated aqueous sodium hydrogen carbonate solution under ice-cooling, and the mixture is extracted with chloroform. The organic layer is washed successively with water and saturated brine, dried over sodium sulfate, and the solvent is evaporated under reduced pressure. The resulting residue is purified by NH-silica gel column chromatography (eluent: ethyl acetate/methanol=10/1, followed by chloroform). The resulting residue is suspended in ethyl acetate under warming. The precipitates are collected by filtration and dried to give the title compound (32.2 g).

APCI-MS M/Z: 482/484[M+H]$^+$.

The title compound is further treated with methanesulfonic acid, benzenesulfonic acid, sulfuric acid and hydrochloric acid in a conventional manner to give the corresponding salts of the title compound.

Methanesulfonate: APCI-MS M/Z: 482/484[M+H]$^+$
Di-methanesulfonate: APCI-MS M/Z: 482/484[M+H]$^+$
Benzenesulfonate: APCI-MS M/Z: 482/484[M+H]$^+$
Di-benzenesulfonate: APCI-MS M/Z: 482/484[M+H]$^+$
Sulfate: APCI-MS M/Z: 482/484[M+H]$^+$
Hydrochloride: APCI-MS M/Z: 482/484[M+H]$^+$ Example 2

N-(5-Chloropyridin-2-yl)-3-({[trans-4-(3-oxomorpholin-4-yl)cyclohexyl]carbonyl}amino)furo[3,2-b]pyridine-2-carboxamide

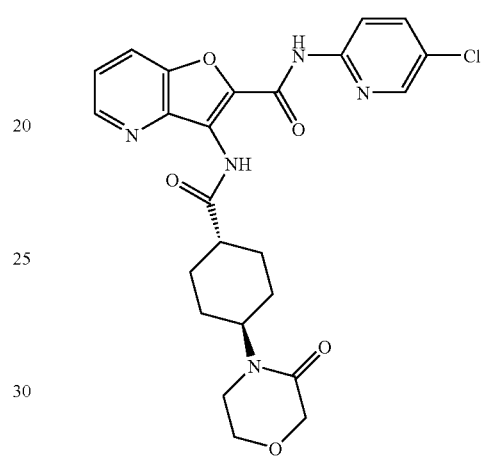

Trans-4-(3-oxomorpholin-4-yl)cyclohexanecarboxylic acid (118 mg) obtained in Reference Example 4 is dissolved in thionyl chloride (3 ml), and the mixture stirred at room temperature for 12 hours. The reaction solution is concentrated under reduced pressure, and the residue is dissolved in chloroform (5 ml). To the solution is added 3-amino-N-(5-chloropyridin-2-yl)furo[3,2-b]pyridine-2-carboxamide (100 mg) obtained in Reference Example 24 under ice-cooling. Pyridine (280 µl) is added thereto, and the reaction solution is warmed to room temperature and stirred for 12 hours. To the reaction solution is poured saturated aqueous sodium hydrogen carbonate solution, and the mixture is extracted with chloroform. The organic layer is washed successively with water and saturated brine, dried over sodium sulfate, and the solvent is evaporated under reduced pressure. The resulting residue is purified by NH-silica gel column chromatography (eluent: ethyl acetate followed by ethyl acetate/methanol=10/1). The resulting solid is suspended in ethyl acetate-diethyl ether. The precipitates are collected by filtration to give the title compound (120 mg).

APCI-MS M/Z: 498/500[M+H]$^+$

Examples 3-78

The corresponding amino compounds and carboxylic acid compounds are treated in a similar manner to Example 2 to give the following compounds.

TABLE 1
| Ex. No. | Structure | Physicochemical Properties |
|---|---|---|
| 3 | 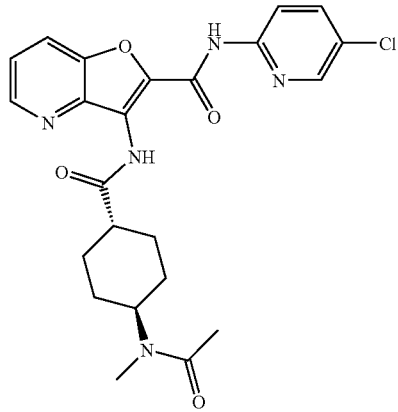 | APCI-MS M/Z: 470/472 [M + H]+ |
| 4 | 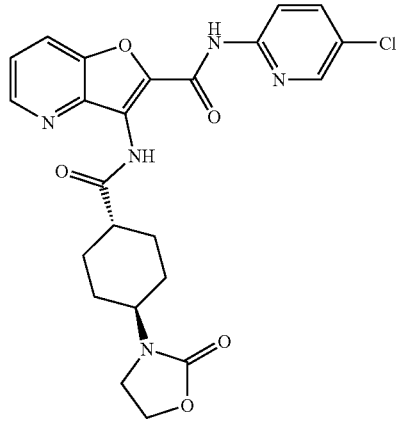 | APCI-MS M/Z: 484/486 [M + H]+ |
| 5 | 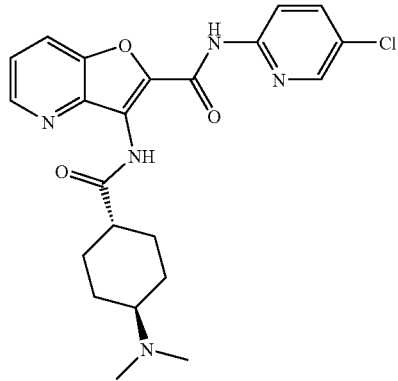 | APCI-MS M/Z: 442/444 [M + H]+ |

TABLE 1-continued

| Ex. No. | Structure | Physicochemical Properties |
|---|---|---|
| 6 | 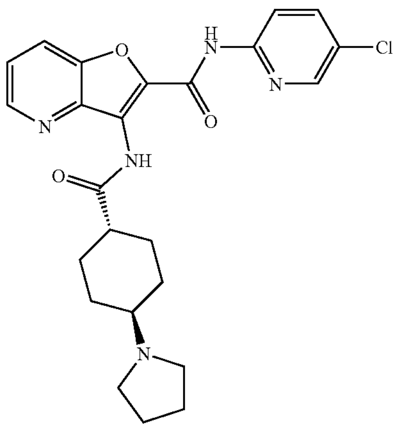 | APCI-MS M/Z: 468/470 [M + H]+ |

TABLE 2

| Ex. No. | Structure | Physicochemical Properties |
|---|---|---|
| 7 | 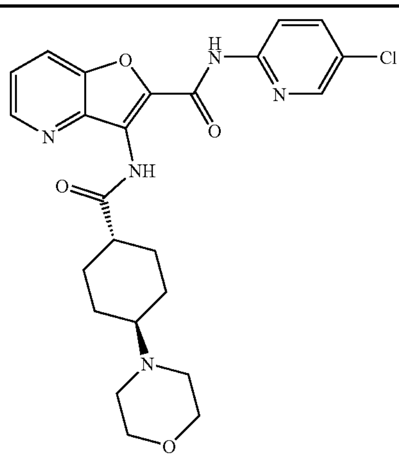 | APCI-MS M/Z: 484/486 [M + H]+ |
| 8 | 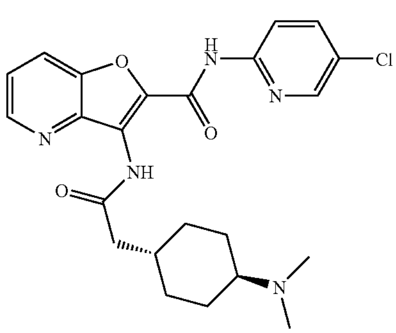 | APCI-MS M/Z: 456/458 [M + H]+ |

TABLE 2-continued

| Ex. No. | Structure | Physicochemical Properties |
|---|---|---|
| 9 | 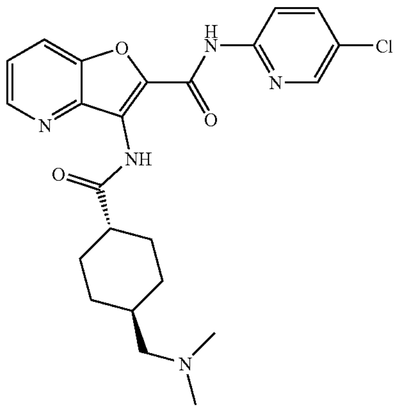 | APCI-MS M/Z: 456/458 [M + H]+ |
| 10 | 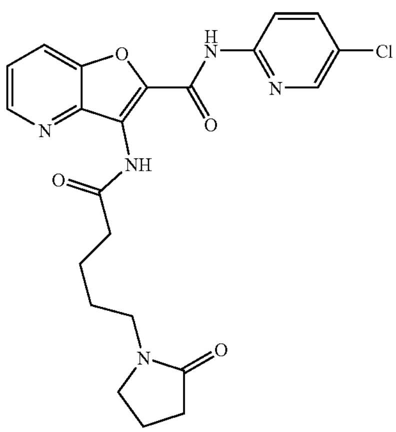 | APCI-MS M/Z: 456/458 [M + H]+ |

TABLE 3

| Ex. No. | Structure | Physicochemical Properties |
|---|---|---|
| 11 | 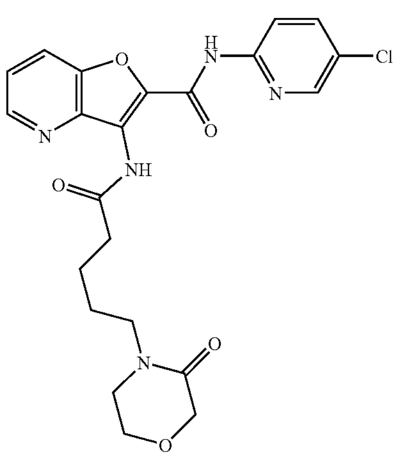 | APCI-MS M/Z: 472/474 [M + H]+ |

TABLE 3-continued

| Ex. No. | Structure | Physicochemical Properties |
|---|---|---|
| 12 | 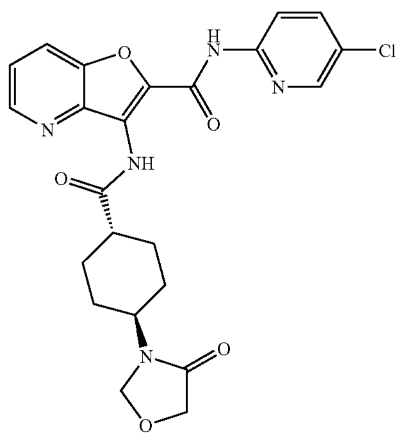 | APCI-MS M/Z: 484/486 [M + H]+ |
| 13 | 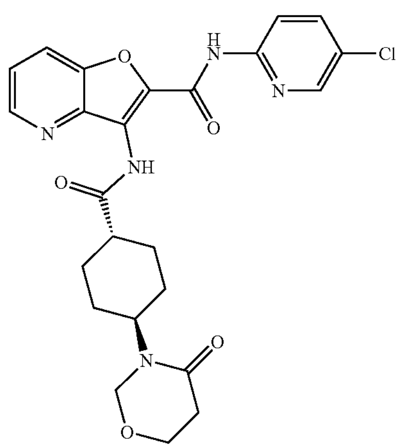 | APCI-MS M/Z: 498/500 [M + H]+ |
| 14 | 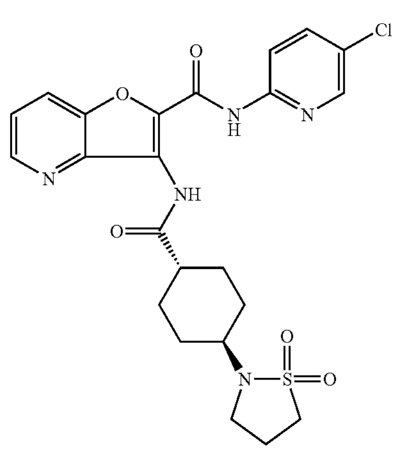 | APCI-MS M/Z: 518/520 [M + H]+ |

TABLE 4

| Ex. No. | Structure | Physicochemical Properties |
|---|---|---|
| 15 | 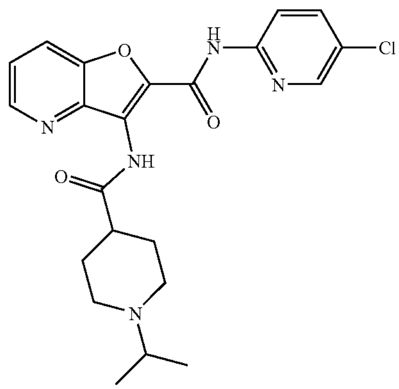 | APCI-MS M/Z: 442/444 [M + H]+ |
| 16 | 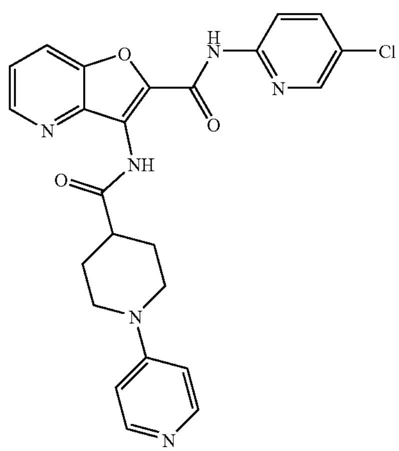 | ESI-MS M/Z: 477/479 [M + H]+ |
| 17 | 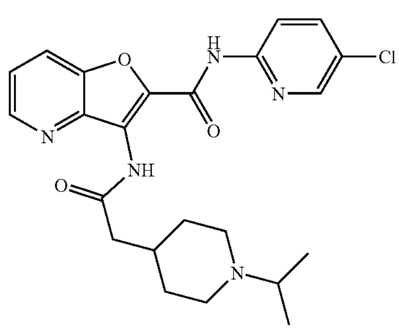 | APCI-MS M/Z: 456/458 [M + H]+ |

TABLE 4-continued

| Ex. No. | Structure | Physicochemical Properties |
|---|---|---|
| 18 | 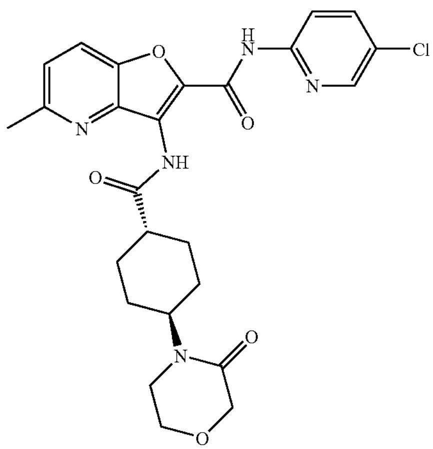 | APCI-MS M/Z: 512/514 [M + H]+ |

TABLE 5

| Ex. No. | Structure | Physicochemical Properties |
|---|---|---|
| 19 | 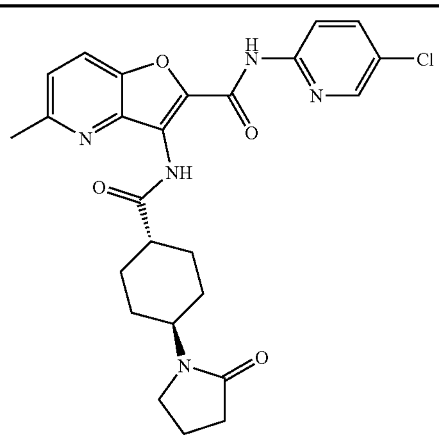 | APCI-MS M/Z: 496/498 [M + H]+ |
| 20 | 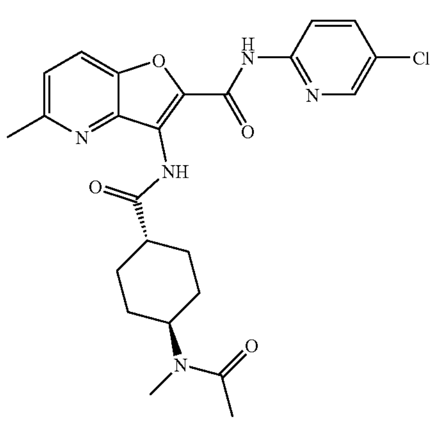 | APCI-MS M/Z: 484/486 [M + H]+ |

TABLE 5-continued

| Ex. No. | Structure | Physicochemical Properties |
|---|---|---|
| 21 | 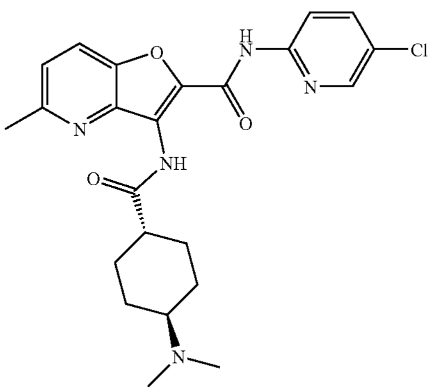 | APCI-MS M/Z: 456/458 [M + H]+ |
| 22 | 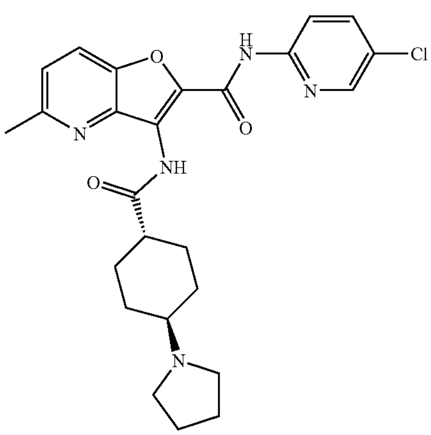 | APCI-MS M/Z: 482/484 [M + H]+ |

TABLE 6

| Ex. No. | Structure | Physicochemical Properties |
|---|---|---|
| 23 | 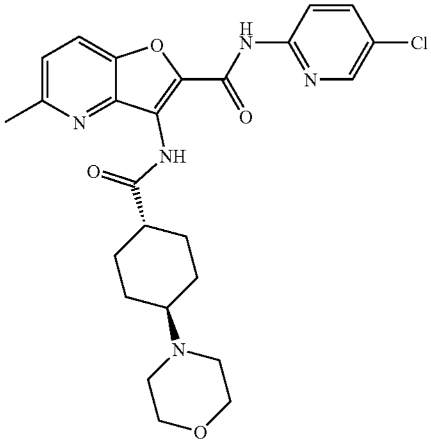 | APCI-MS M/Z: 498/500 [M + H]+ |

TABLE 6-continued

| Ex. No. | Structure | Physicochemical Properties |
|---|---|---|
| 24 | 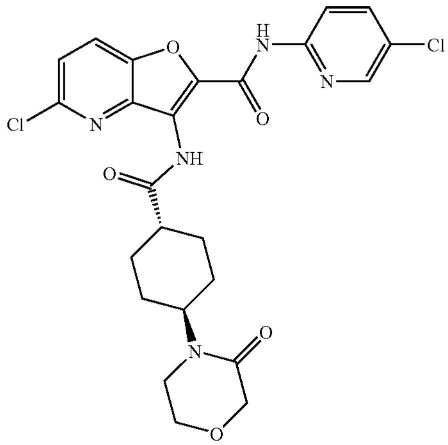 | APCI-MS M/Z: 532/534 [M + H]+ |
| 25 | 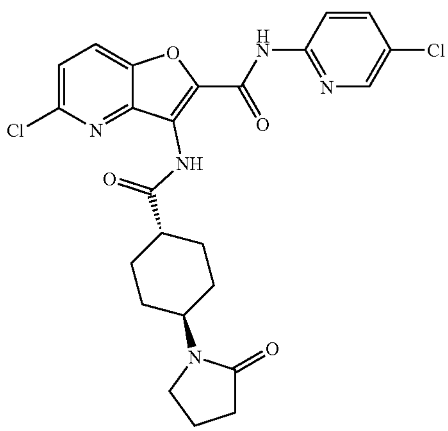 | APCI-MS M/Z: 516/518 [M + H]+ |
| 26 | 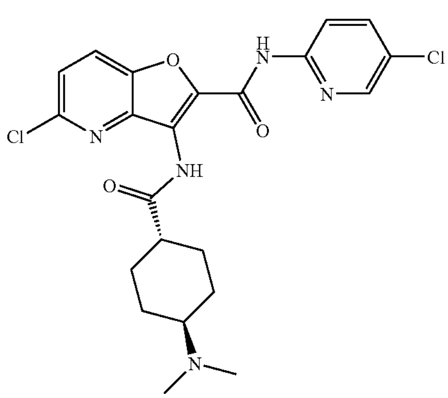 | APCI-MS M/Z: 476/478 [M + H]+ |

TABLE 7
| Ex. No. | Structure | Physicochemical Properties |
|---|---|---|
| 27 | 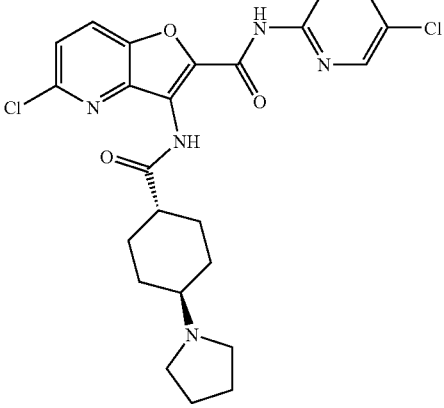 | APCI-MS M/Z: 502/504 [M + H]+ |
| 28 | 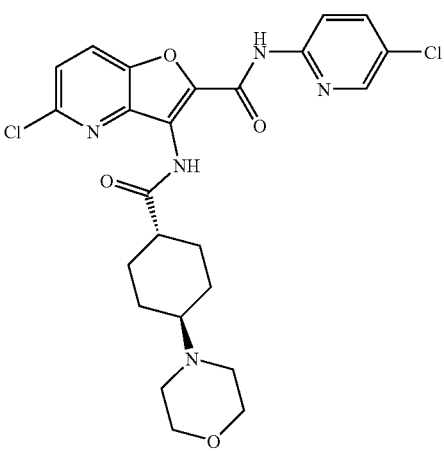 | APCI-MS M/Z: 518/520 [M + H]+ |
| 29 | 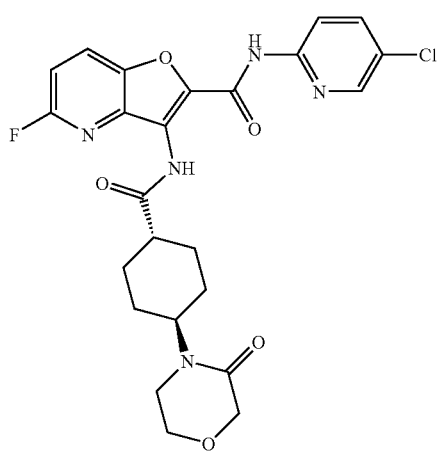 | APCI-MS M/Z: 516/518 [M + H]+ |

TABLE 7-continued

| Ex. No. | Structure | Physicochemical Properties |
|---|---|---|
| 30 | 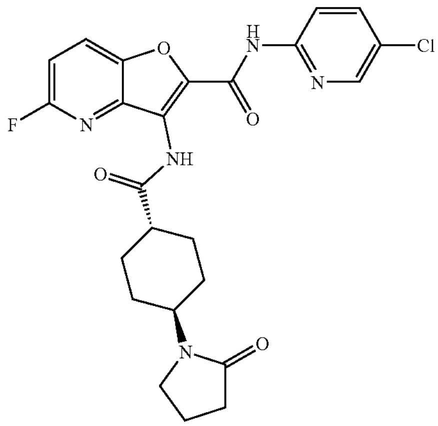 | APCI-MS M/Z: 500/502 [M + H]+ |

TABLE 8

| Ex. No. | Structure | Physicochemical Properties |
|---|---|---|
| 31 | 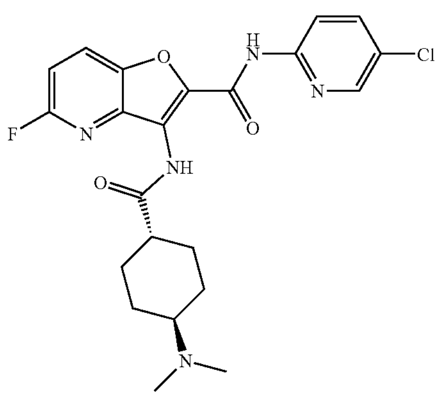 | APCI-MS M/Z: 460/462 [M + H]+ |
| 32 | 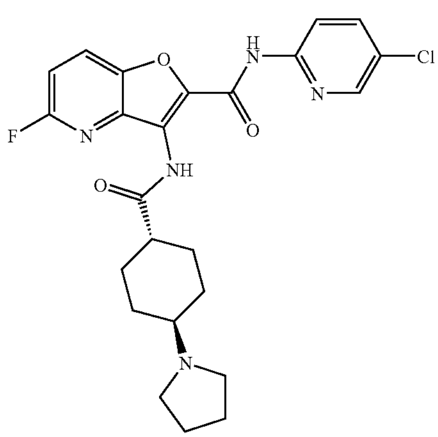 | APCI-MS M/Z: 486/488 [M + H]+ |

TABLE 8-continued

| Ex. No. | Structure | Physicochemical Properties |
|---|---|---|
| 33 | 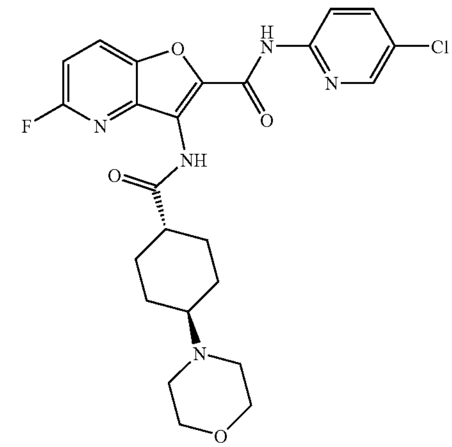 | APCI-MS M/Z: 502/504 [M + H]+ |
| 34 | 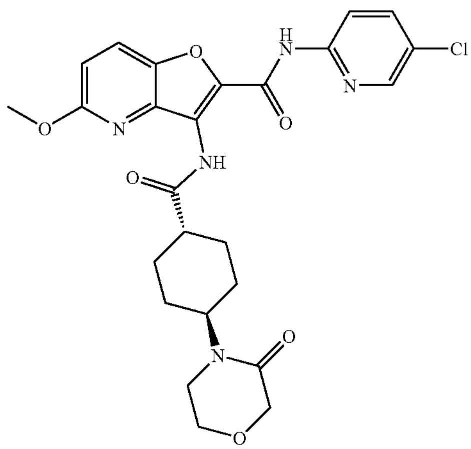 | APCI-MS M/Z: 528/530 [M + H]+ |

TABLE 9

| Ex. No. | Structure | Physicochemical Properties |
|---|---|---|
| 35 | 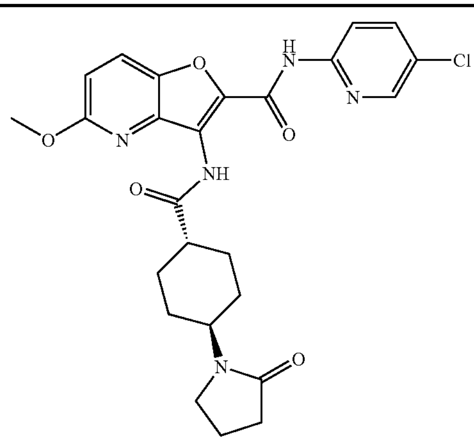 | APCI-MS M/Z: 512/514 [M + H]+ |

TABLE 9-continued

| Ex. No. | Structure | Physicochemical Properties |
|---|---|---|
| 36 | 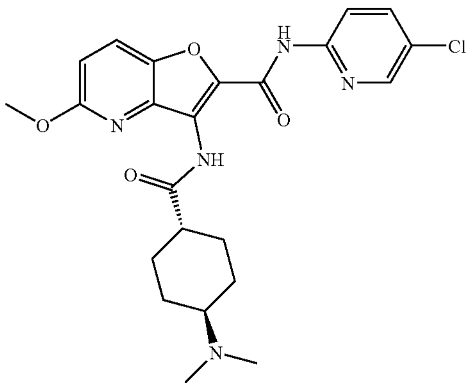 | APCI-MS M/Z: 472/474 [M + H]+ |
| 37 | 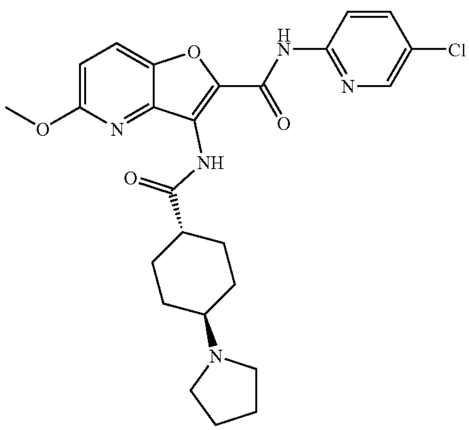 | APCI-MS M/Z: 498/500 [M + H]+ |
| 38 | 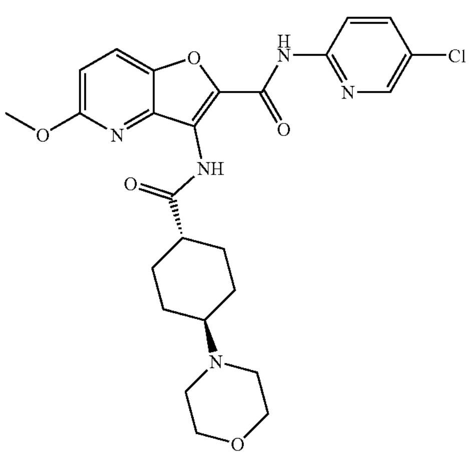 | APCI-MS M/Z: 514/516 [M + H]+ |

TABLE 10

| Ex. No. | Structure | Physicochemical Properties |
|---|---|---|
| 39 | 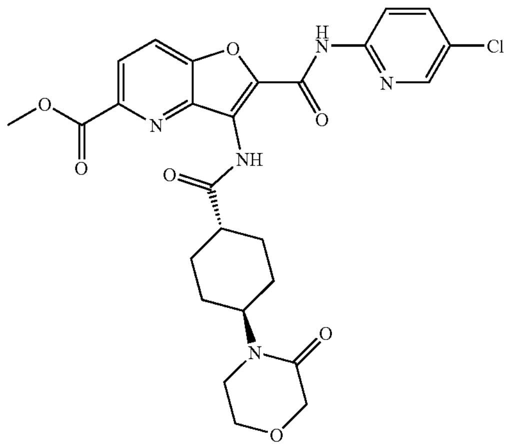 | APCI-MS M/Z: 556/558 [M + H]+ |
| 40 | 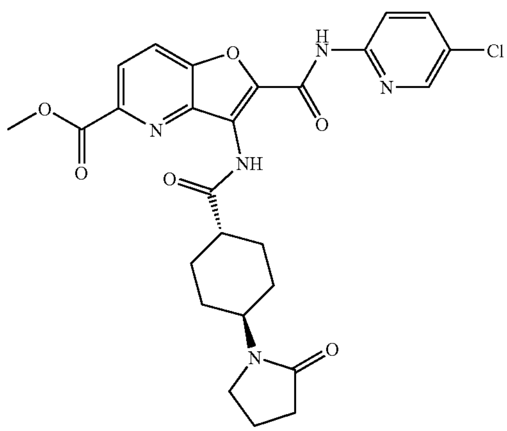 | APCI-MS M/Z: 540/542 [M + H]+ |
| 41 | 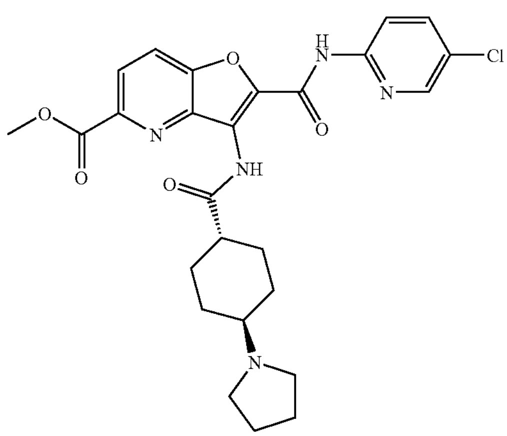 | APCI-MS M/Z: 526/528 [M + H]+ |

TABLE 10-continued

| Ex. No. | Structure | Physicochemical Properties |
|---|---|---|
| 42 | 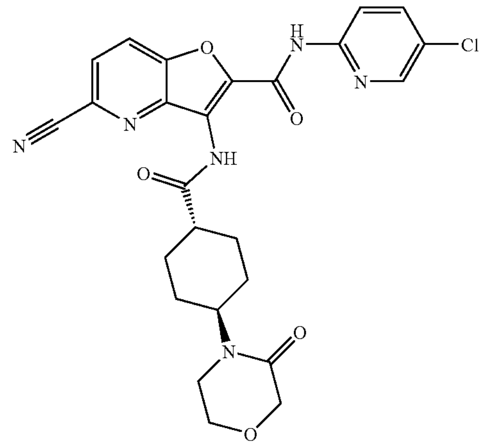 | APCI-MS M/Z: 523/525 [M + H]+ |

TABLE 11

| Ex. No. | Structure | Physicochemical Properties |
|---|---|---|
| 43 | 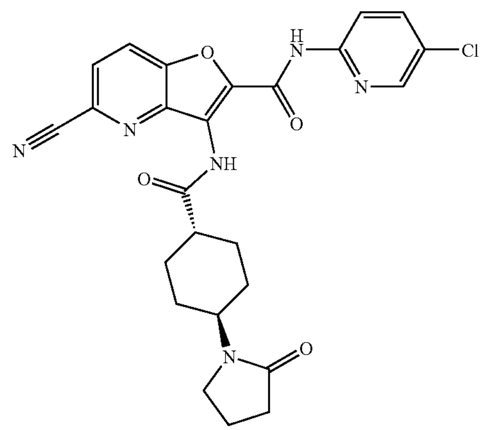 | APCI-MS M/Z: 507/509 [M + H]+ |
| 44 | 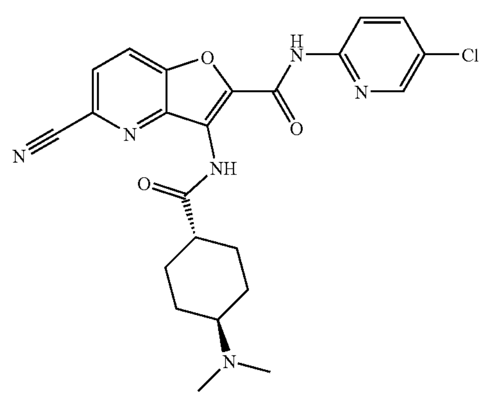 | APCI-MS M/Z: 467/469 [M + H]+ |

TABLE 11-continued

| Ex. No. | Structure | Physicochemical Properties |
|---|---|---|
| 45 | 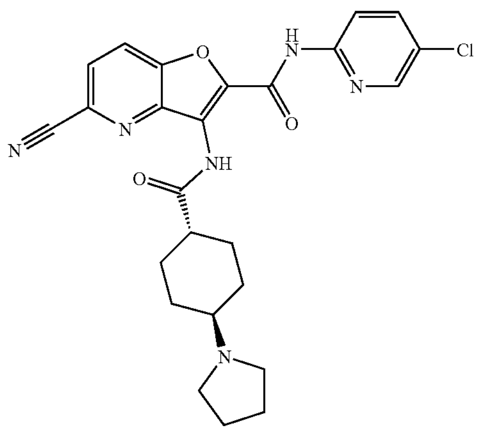 | APCI-MS M/Z: 493/495 [M + H]+ |
| 46 | 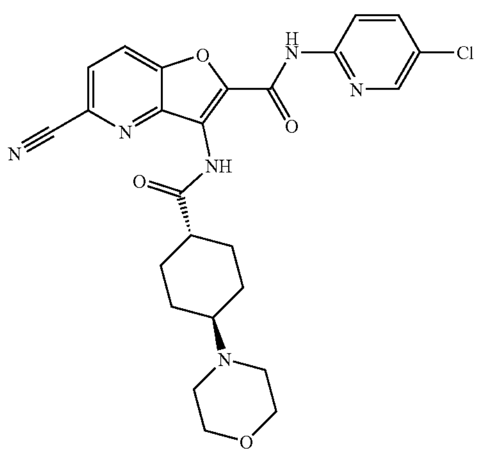 | APCI-MS M/Z: 509/511 [M + H]+ |

TABLE 12

| Ex. No. | Structure | Physicochemical Properties |
|---|---|---|
| 47 | 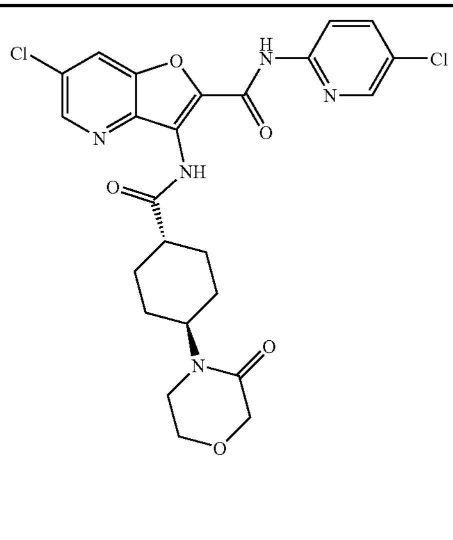 | APCI-MS M/Z: 532/534 [M + H]+ |

TABLE 12-continued

| Ex. No. | Structure | Physicochemical Properties |
|---|---|---|
| 48 | 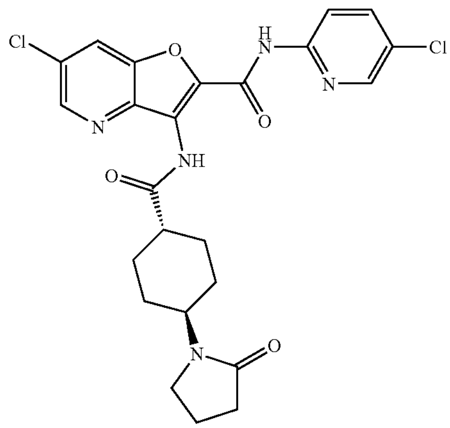 | APCI-MS M/Z: 516/518 [M + H]+ |
| 49 | 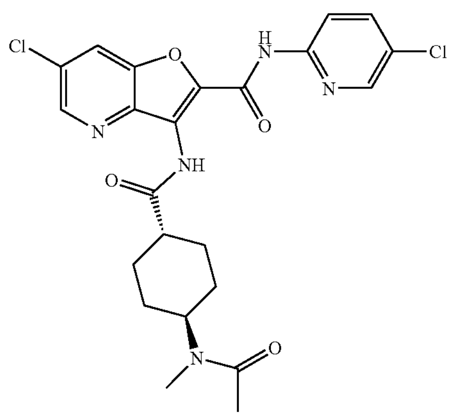 | APCI-MS M/Z: 504/506 [M + H]+ |
| 50 | 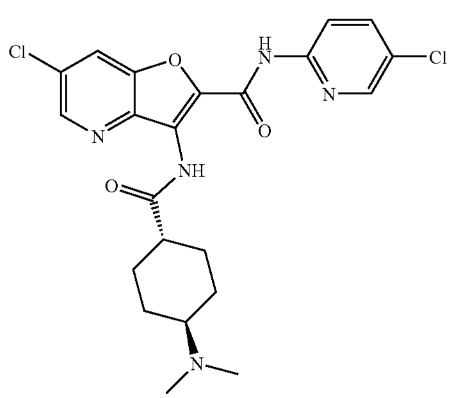 | APCI-MS M/Z: 476/478 [M + H]+ |

TABLE 13
| Ex. No. | Structure | Physicochemical Properties |
|---|---|---|
| 51 | 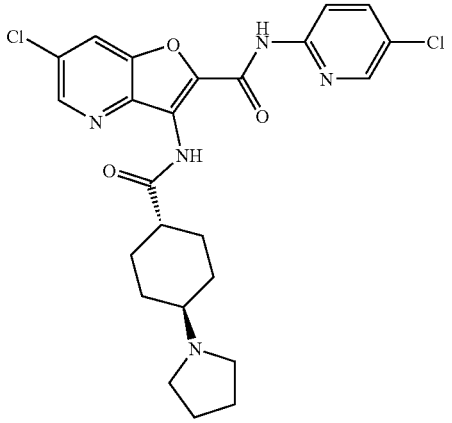 | APCI-MS M/Z: 502/504 [M + H]+ |
| 52 | 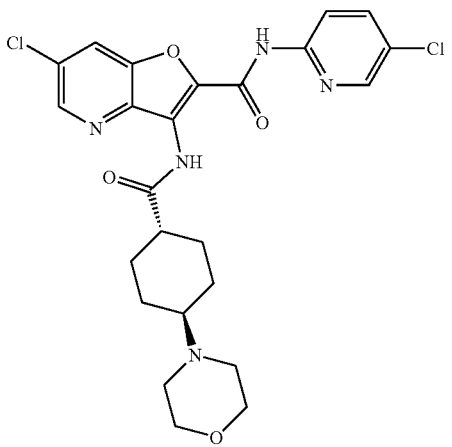 | APCI-MS M/Z: 518/520 [M + H]+ |
| 53 | 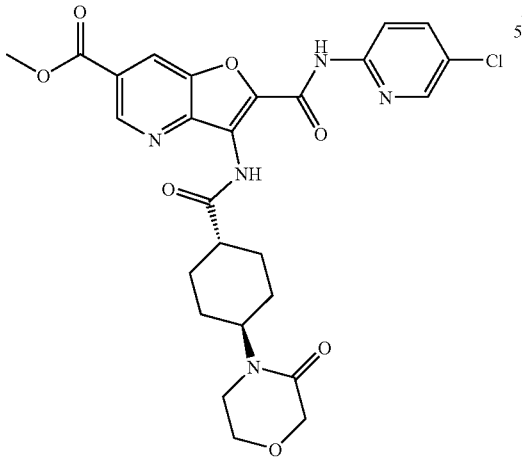 | APCI-MS M/Z: 556/558 [M + H]+ |

TABLE 13-continued

| Ex. No. | Structure | Physicochemical Properties |
|---|---|---|
| 54 | 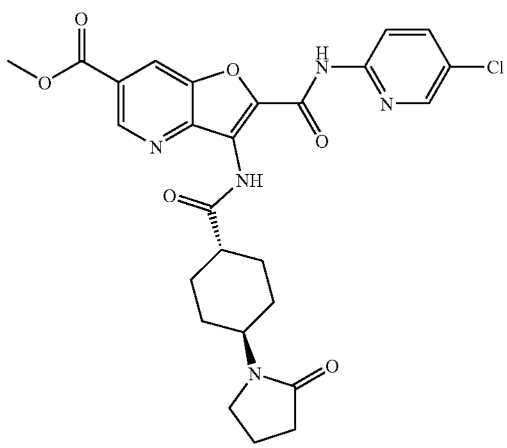 | APCI-MS M/Z: 540/542 [M + H]+ |

TABLE 14

| Ex. No. | Structure | Physicochemical Properties |
|---|---|---|
| 55 | 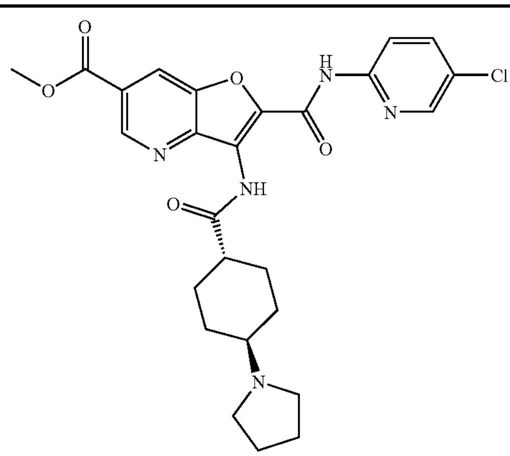 | APCI-MS M/Z: 526/528 [M + H]+ |
| 56 | 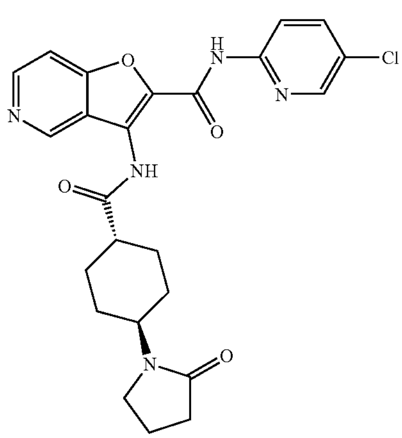 | APCI-MS M/Z: 482/484 [M + H]+ |

TABLE 14-continued

| Ex. No. | Structure | Physicochemical Properties |
|---|---|---|
| 57 | 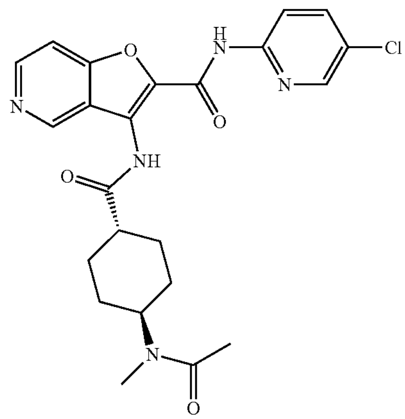 | APCI-MS M/Z: 470/472 [M + H]+ |
| 58 | 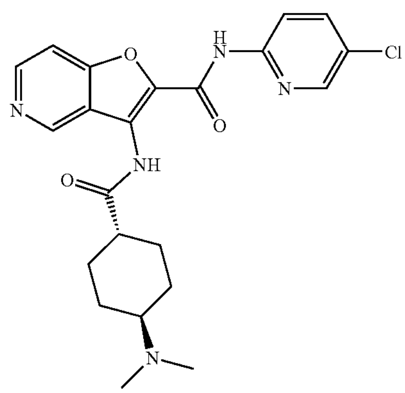 | APCI-MS M/Z: 442/444 [M + H]+ |

TABLE 15

| Ex. No. | Structure | Physicochemical Properties |
|---|---|---|
| 59 | 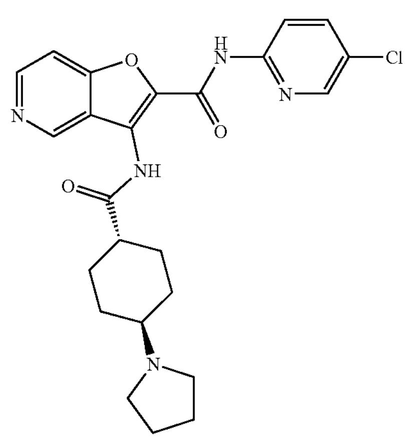 | APCI-MS M/Z: 468/470 [M + H]+ |

TABLE 15-continued

| Ex. No. | Structure | Physicochemical Properties |
|---|---|---|
| 60 | 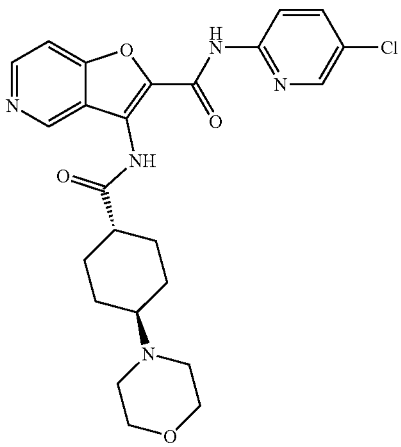 | APCI-MS M/Z: 484/486 [M + H]+ |
| 61 | 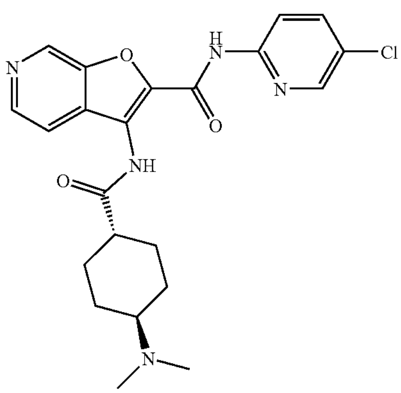 | APCI-MS M/Z: 442/444 [M + H]+ |
| 62 | 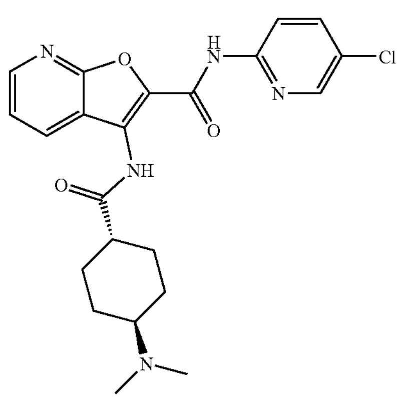 | APCI-MS M/Z: 442/444 [M + H]+ |

TABLE 16

| Ex. No. | Structure | Physicochemical Properties |
|---|---|---|
| 63 | 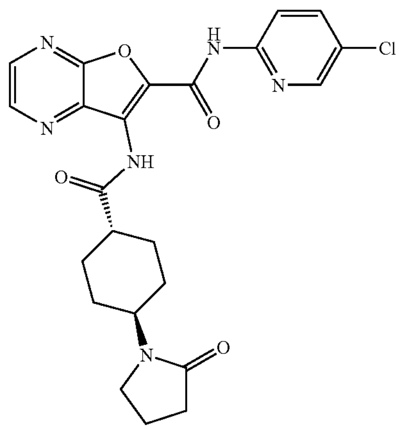 | APCI-MS M/Z: 483/485 [M + H]+ |
| 64 | 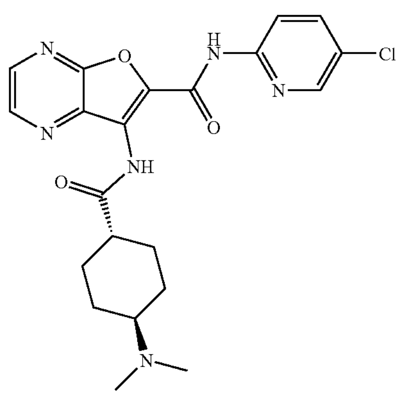 | APCI-MS M/Z: 443/445 [M + H]+ |
| 65 | 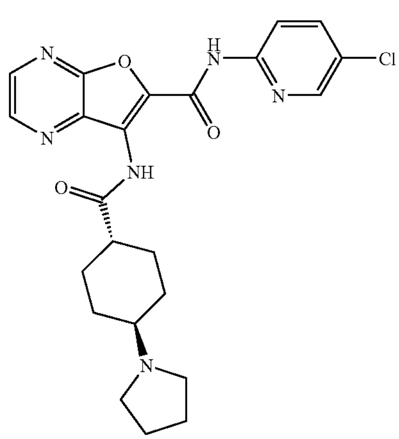 | APCI-MS M/Z: 469/471 [M + H]+ |

TABLE 16-continued
| Ex. No. | Structure | Physicochemical Properties |
|---|---|---|
| 66 | 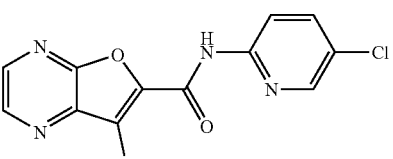 | APCI-MS M/Z: 485/487 [M + H]⁺ |
TABLE 17
| Ex. No. | Structure | Physicochemical Properties |
|---|---|---|
| 67 | 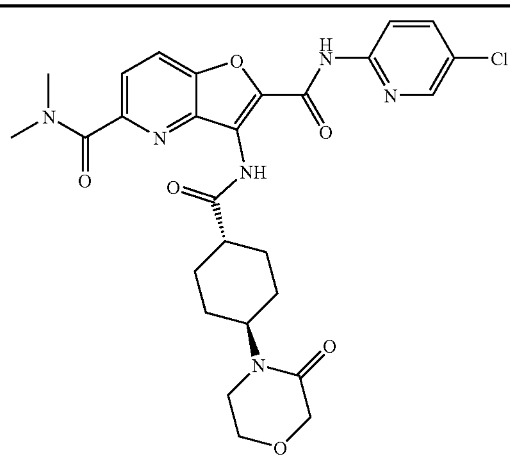 | APCI-MS M/Z: 569/571 [M + H]⁺ |
| 68 | 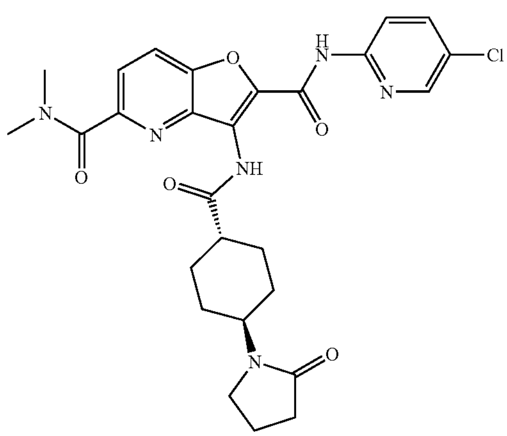 | APCI-MS M/Z: 553/555 [M + H]⁺ |

TABLE 17-continued

| Ex. No. | Structure | Physicochemical Properties |
|---|---|---|
| 69 | 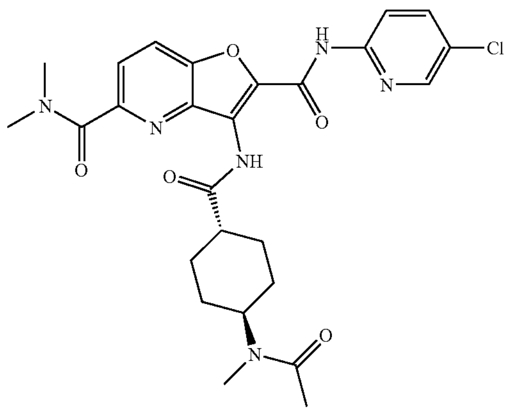 | APCI-MS M/Z: 541/543 [M + H]+ |
| 70 | 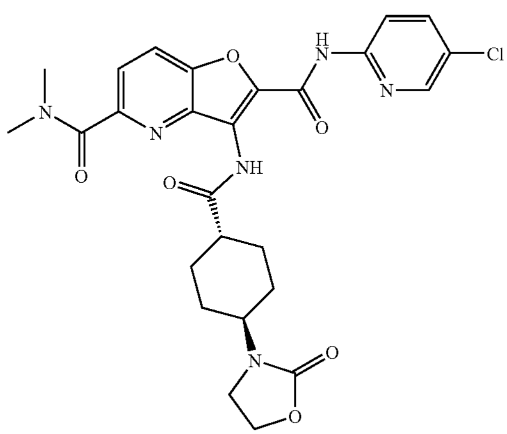 | APCI-MS M/Z: 555/557 [M + H]+ |

TABLE 18

| Ex. No. | Structure | Physicochemical Properties |
|---|---|---|
| 71 | 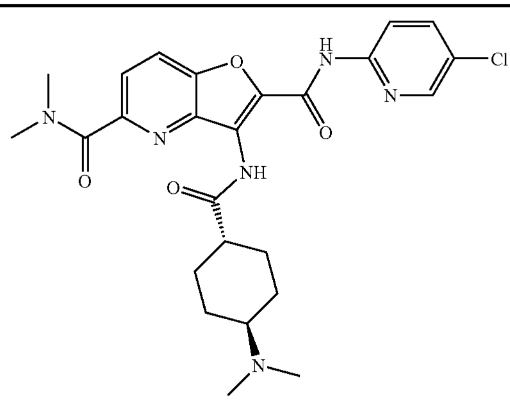 | APCI-MS M/Z: 513/515 [M + H]+ |

TABLE 18-continued

| Ex. No. | Structure | Physicochemical Properties |
|---|---|---|
| 72 | 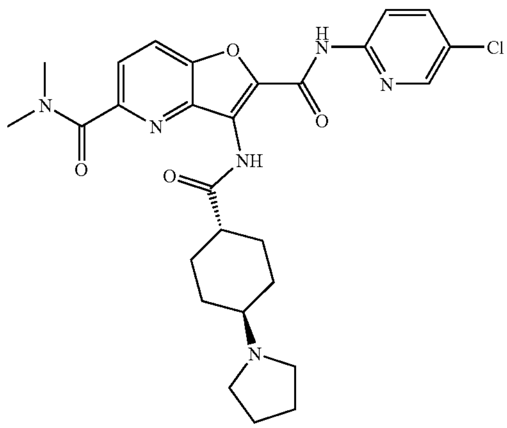 | APCI-MS M/Z: 539/541 [M + H]+ |
| 73 | 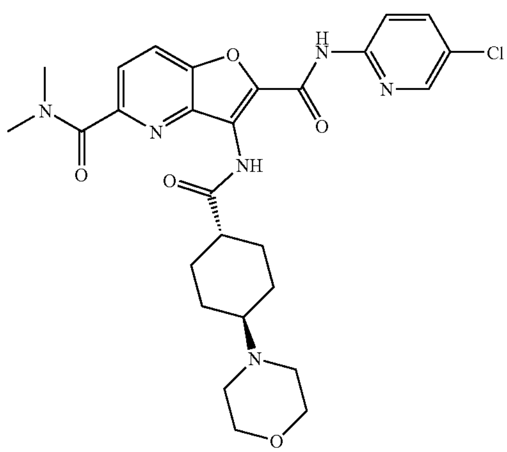 | APCI-MS M/Z: 555/557 [M + H]+ |
| 74 | 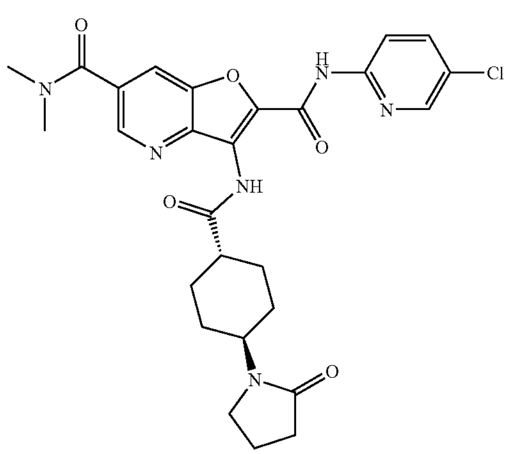 | APCI-MS M/Z: 553/555 [M + H]+ |

TABLE 19
| Ex. No. | Structure | Pysicochemical Properties |
|---|---|---|
| 75 | 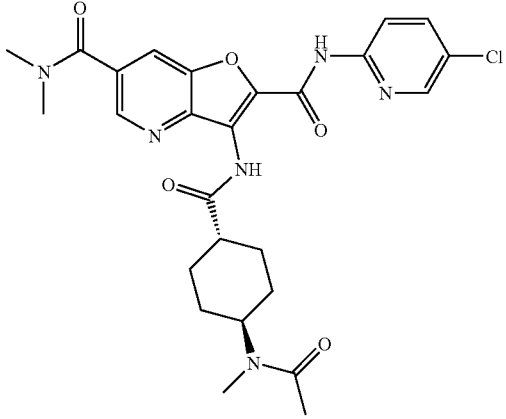 | APCI-MS M/Z: 541/543 [M + H]+ |
| 76 | 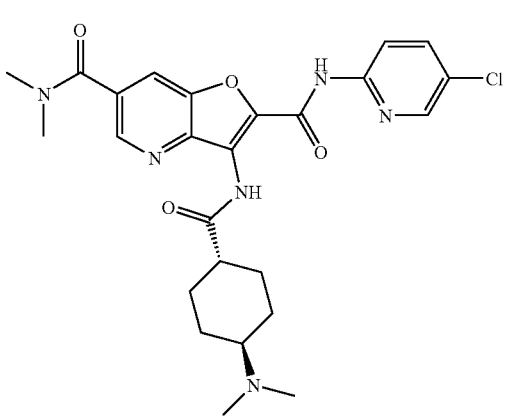 | APCI-MS M/Z: 513/515 [M + H]+ |

TABLE 19-continued
| Ex. No. | Structure | Pysicochemical Properties |
|---|---|---|
| 77 | 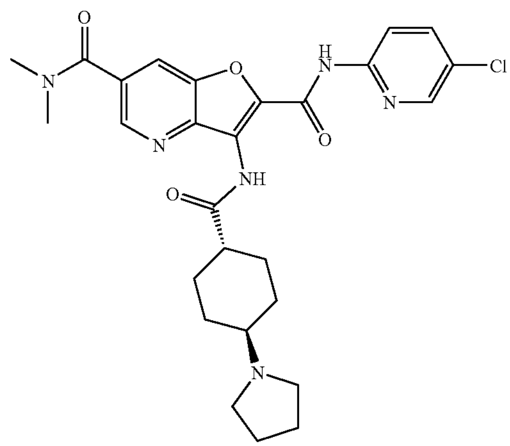 | APCI-MS M/Z: 539/541 [M + H]+ |
| 78 | 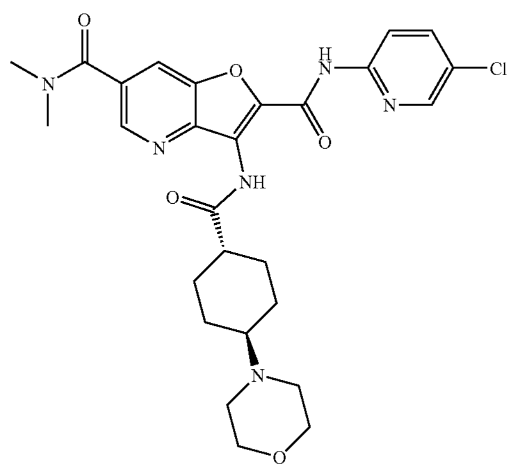 | APCI-MS M/Z: 555/557 [M + H]+ |
Example 79
2-{[(5-Chloropyridin-2-yl)amino]carbonyl}-3-({ [trans-4-(3-oxomorpholin-4-yl)cyclohexyl] carbonyl}amino)furo[3,2-b]pyridine-5-carboxylic acid
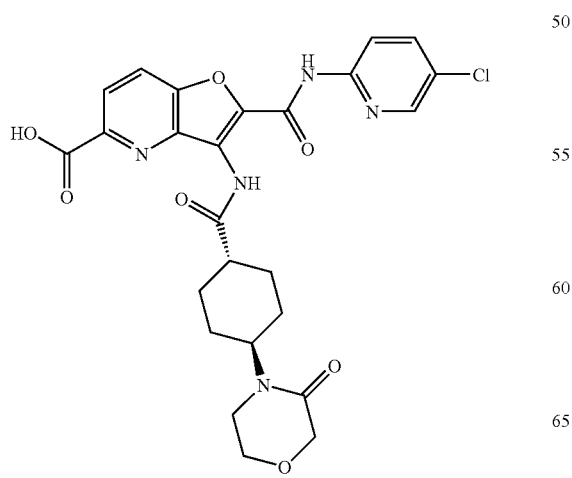

Methyl 2-{[(5-Chloropyridin-2-yl)amino]carbonyl}-3-({[trans-4-(3-oxomorpholin-4-yl)cyclohexyl]carbonyl}amino)furo[3,2-b]pyridine-5-carboxylate (9.40 g) obtained in Example 39 is suspended in tetrahydrofuran (135 ml), and thereto is added 1 N aqueous sodium hydroxide solution (34 ml) under ice-cooling. The mixture is warmed to room temperature, and stirred for 3 hours. To the reaction solution is poured 2N hydrochloric acid (17 ml) under ice-cooling, and the reaction solution is concentrated under reduced pressure. The residue is suspended in water and the precipitates are collected by filtration. The resulting solid is washed with water and diethyl ether to give the title compound (7.83 g).

ESI-MS M/Z: 540/542[M−H]⁻

Examples: 80-84

The corresponding starting compounds are treated in a similar manner to Example 79 to give the following compounds.

TABLE 20

| Ex. No. | Structure | Physicochemical Properties |
|---|---|---|
| 80 | 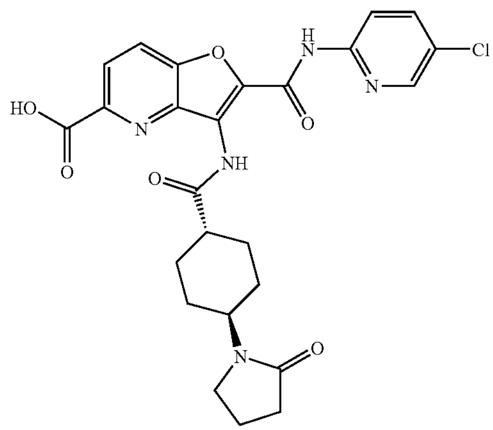 | ESI-MS M/Z: 524/526 [M − H]⁻ |
| 81 | 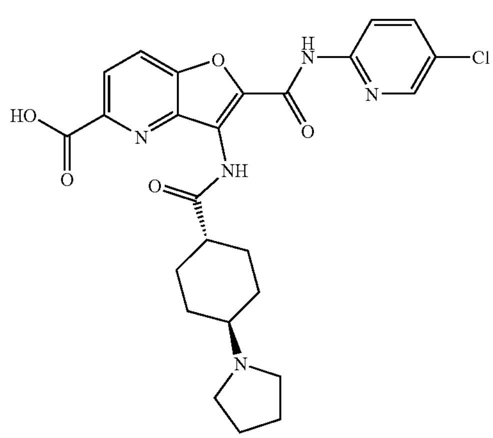 | ESI-MS M/Z: 510/512 [M − H]⁻ |

TABLE 20-continued

| Ex. No. | Structure | Physicochemical Properties |
|---|---|---|
| 82 | 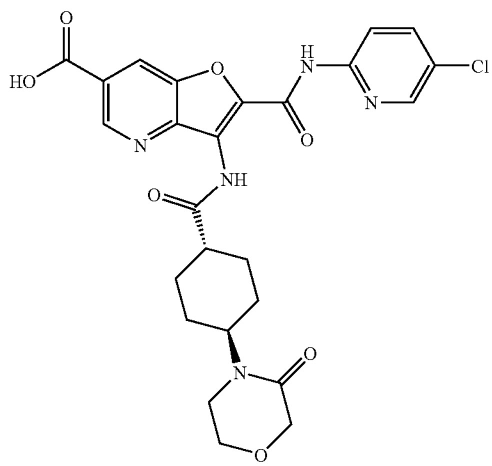 | ESI-MS M/Z: 540/542 [M − H]⁻ |
| 83 | 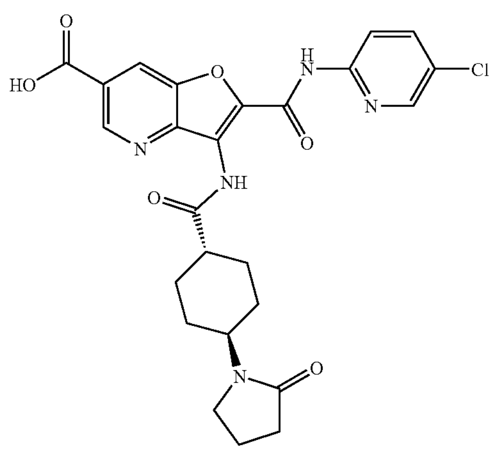 | ESI-MS M/Z: 524/526 [M − H]⁻ |

TABLE 21

| Ex. No. | Structure | Physicochemical Properties |
|---|---|---|
| 84 | 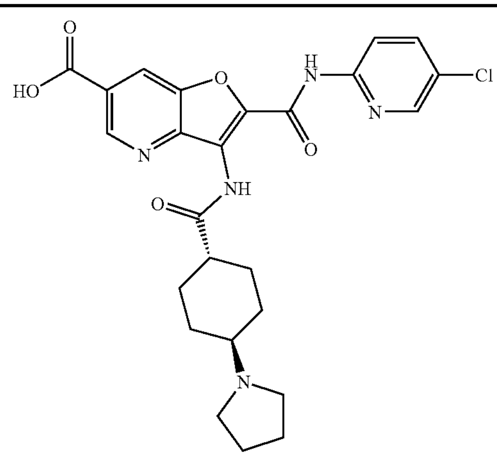 | ESI-MS M/Z: 510/512 [M − H]⁻ |

Example 85

N-(5-Chloropyridin-2-yl)-5-(morpholin-4-ylcarbonyl)-3-({[trans-4-(3-oxomorpholin-4-yl)cyclohexyl]carbonyl}amino)furo[3,2-b]pyridine-2-carboxamide

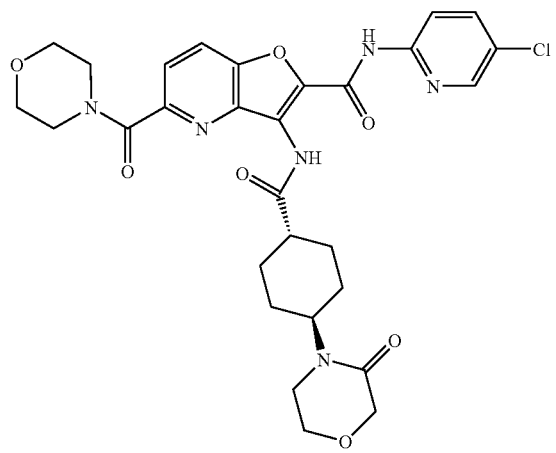

2-{[(5-Chloropyridin-2-yl)amino]carbonyl}-3-({[trans-4-(3-oxomorpholin-4-yl)cyclohexyl]carbonyl}amino)furo[3,2-b]pyridine-5-carboxylic acid (100 mg) obtained in Example 79 is dissolved in N,N-dimethylformamide (3 ml), and thereto are added successively morpholine (32 μl), 1-hydroxybenzotriazole (50 mg) and 1-ethyl-3-(3-dimethylaminopropyl)carbodiimide hydrochloride (71 mg), and the mixture is stirred at room temperature for 15 hours. The reaction solution is diluted with ethyl acetate-tetrahydrofuran, and the solution is washed successively with saturated aqueous sodium hydrogen carbonate solution, water and saturated brine, dried over sodium sulfate. The solvent is evaporated under reduced pressure and the resulting residue is suspended in ethyl acetate-diethyl ether. The solid precipitates are collected by filtration to give the title compound (109 mg).

APCI-MS M/Z: 611/613[M+H]$^+$

Examples 86-93

The corresponding starting compounds are treated in a similar manner to Example 85 to give the following compounds.

TABLE 22

| Ex. No. | Structure | Physicochemical Properties |
|---|---|---|
| 86 | 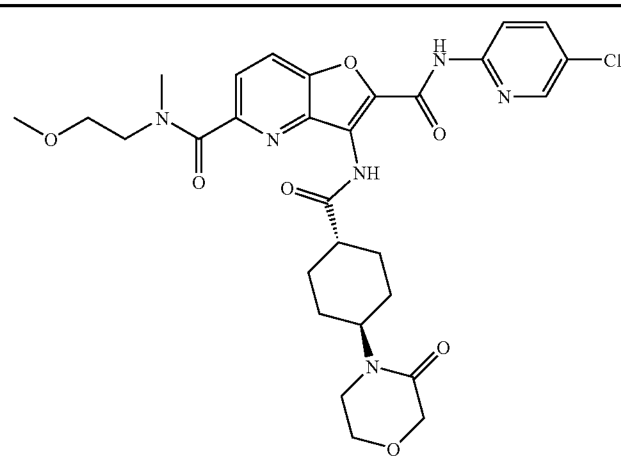 | APCI-MS M/Z: 613/615 [M + H]$^+$ |
| 87 | 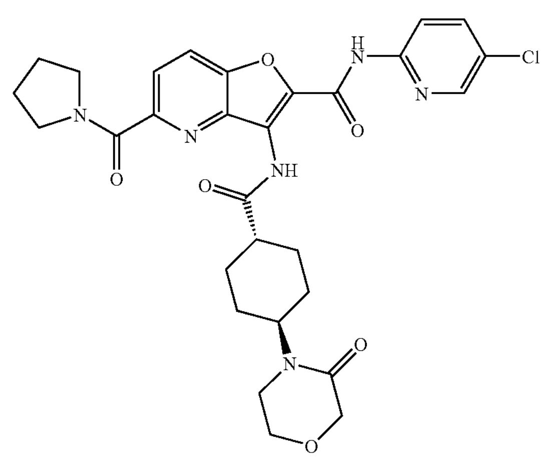 | APCI-MS M/Z: 595/597 [M + H]$^+$ |

TABLE 22-continued

| Ex. No. | Structure | Physicochemical Properties |
|---|---|---|
| 88 | 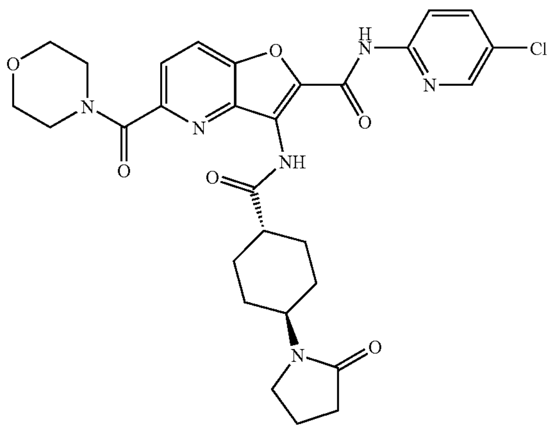 | APCI-MS M/Z: 595/597 [M + H]+ |
| 89 | 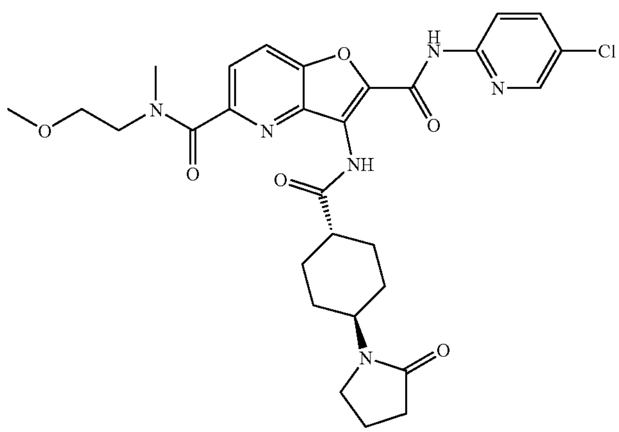 | APCI-MS M/Z: 597/599 [M + H]+ |

TABLE 23

| Ex. No. | Structure | Physicochemical Properties |
|---|---|---|
| 90 | 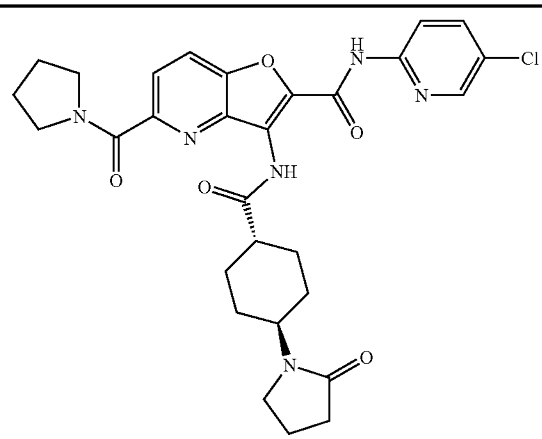 | APCI-MS M/Z: 579/581 [M + H]+ |

TABLE 23-continued

| Ex. No. | Structure | Physicochemical Properties |
| --- | --- | --- |
| 91 | 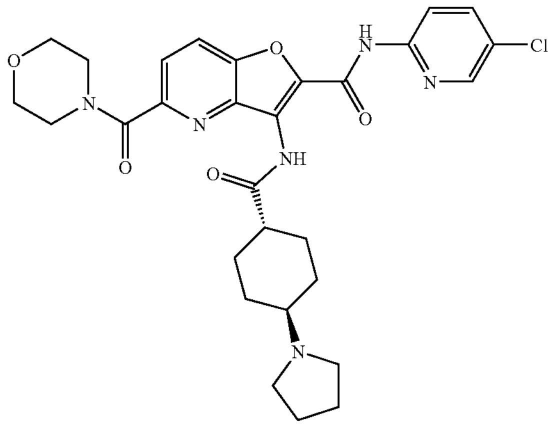 | APCI-MS M/Z: 581/583 [M + H]⁺ |
| 92 | 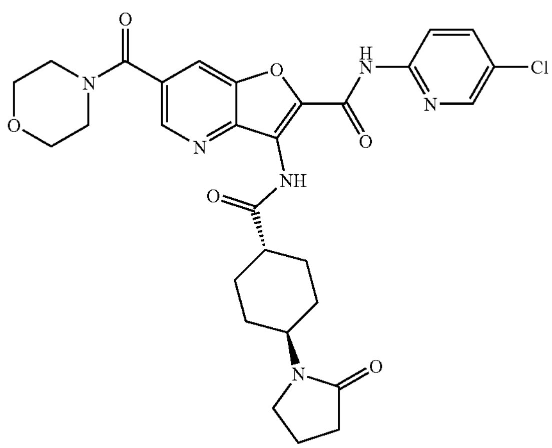 | APCI-MS M/Z: 595/597 [M + H]⁺ |
| 93 | 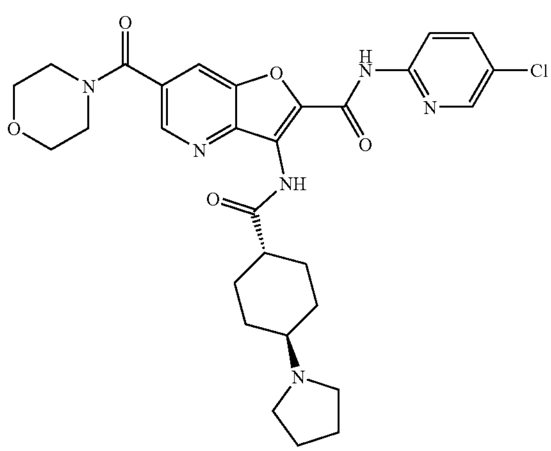 | APCI-MS M/Z: 581/583 [M + H]⁺ |

Example 94 t-Butyl [2-{[(5-chloropyridin-2-yl)amino]carbonyl}-3-({[trans-4-(3-oxomorpholin-4-yl)cyclohexyl]carbonyl}amino)furo[3,2-b]pyridin-5-yl]carbamate

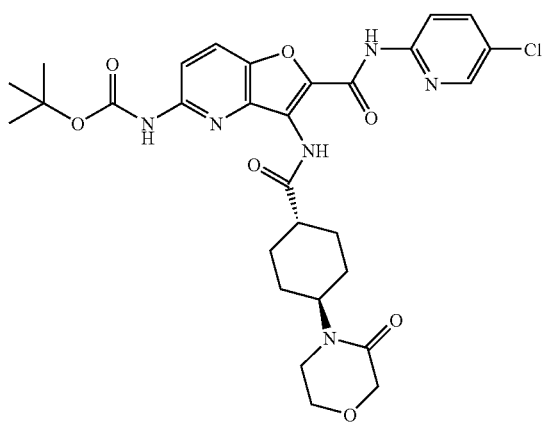

2-{[(5-Chloropyridin-2-yl)amino]carbonyl}-3-({[trans-4-(3-oxomorpholin-4-yl)cyclohexyl]carbonyl}amino)furo[3,2-b]pyridine-5-carboxylic acid (6.80 g) obtained in Example 79 is suspended in t-butanol (300 ml). To the suspension are added triethylamine (3.48 ml) and diphenylphosphoryl azide (5.39 ml) at room temperature, and the mixture is stirred at 100° C. for 15 hours. The reaction solution is concentrated under reduced pressure. The residue is diluted with chloroform, and washed with water and saturated brine. The organic layer is dried over sodium sulfate, and the solvent is evaporated under reduced pressure. The resulting residue is purified by silica gel column chromatography (eluent: chloroform/methanol=100/1 followed by 20/1) to give the title compound (5.64 g).

APCI-MS M/Z: 613/615[M+H]$^+$

Examples 95-99

The corresponding starting compounds are treated in a similar manner to Example 94 to give the following compounds.

TABLE 24

| Ex. No. | Structure | Physicochemical Properties |
|---|---|---|
| 95 | 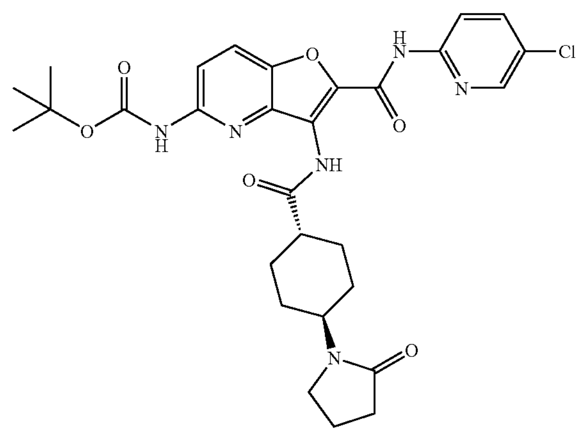 | APCI-MS M/Z: 597/599 [M + H]$^+$ |
| 96 | 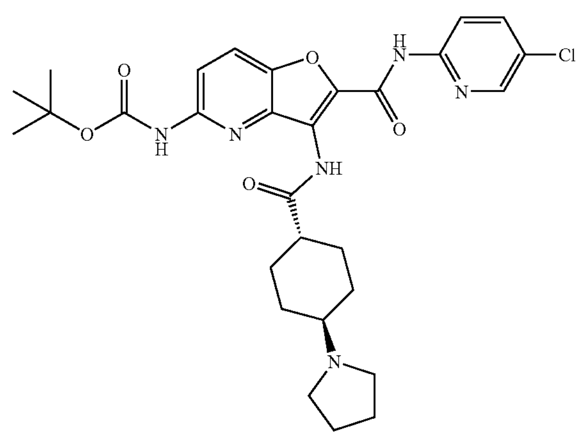 | APCI-MS M/Z: 583/585 [M + H]$^+$ |

TABLE 24-continued

| Ex. No. | Structure | Physicochemical Properties |
|---|---|---|
| 97 | 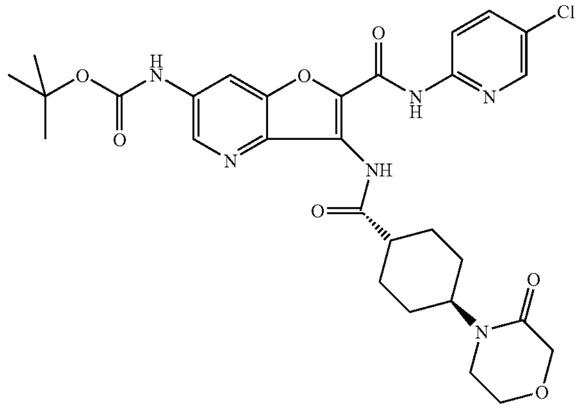 | APCI-MS M/Z: 613/615 [M + H]+ |
| 98 | 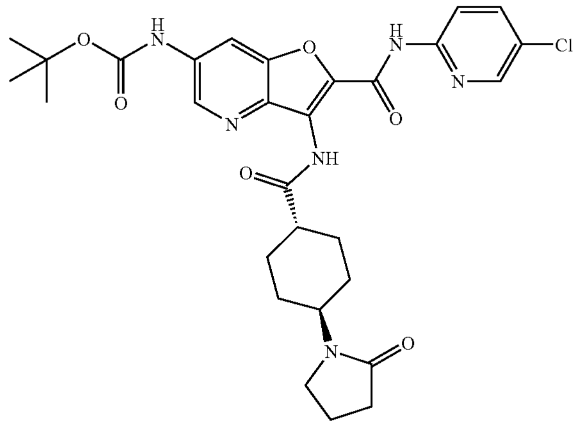 | APCI-MS M/Z: 597/599 [M + H]+ |

TABLE 25

| Ex. No. | Structure | Physicochemical Properties |
|---|---|---|
| 99 | 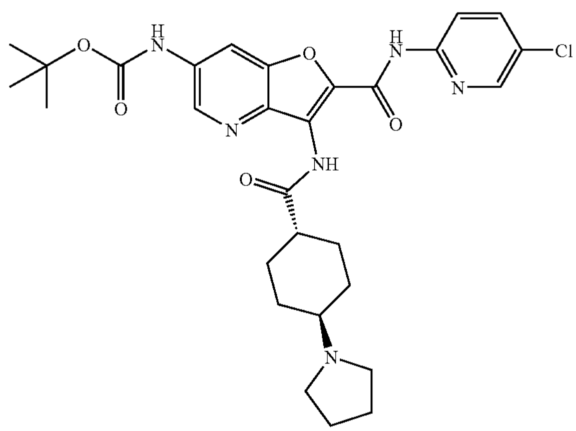 | APCI-MS M/Z: 583/585 [M + H]+ |

Example 100

5-Amino-N-(5-chloropyridin-2-yl)-3-({[trans-4-(3-oxomorpholin-4-yl)cyclohexyl]carbonyl}amino)furo[3,2-b]pyridine-2-carboxamide hydrochloride

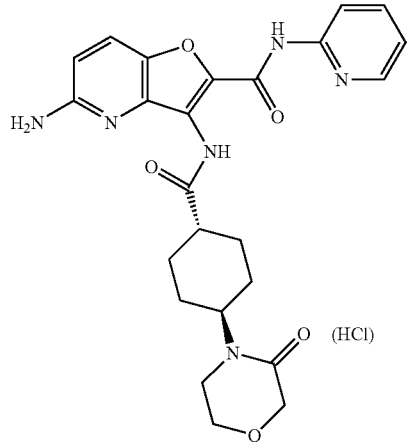

t-Butyl [2-{[(5-Chloropyridin-2-yl)amino]carbonyl}-3-({[trans-4-(3-oxomorpholin-4-yl)cyclohexyl]carbonyl}amino)furo[3,2-b]pyridin-5-yl]carbamate (5.55 g) obtained in Example 94 is suspended in methanol (20 ml), and thereto is added 4N hydrogen chloride-dioxane solution (50 ml) under ice-cooling. The mixture is stirred at room temperature for 8 hours. The reaction solution is concentrated under reduced pressure and the resulting residue is suspended in diethyl ether. The precipitates are collected by filtration to give the title compound (4.67 g).

APCI-MS M/Z: 513/515[M+H]$^+$

Example 101

5-Amino-N-(5-chloropyridin-2-yl)-3-{[[(trans-4-pyrrolidin-1-ylcyclohexyl)carbonyl]amino}furo[3,2-b]pyridine-2-carboxamide

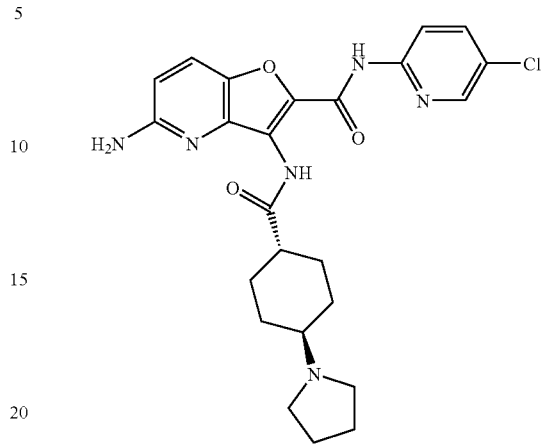

t-Butyl (2-{[(5-chloropyridin-2-yl)amino]carbonyl}-3-{[(trans-4-pyrrolidin-1-ylcyclohexyl)carbonyl]amino}furo[3,2-b]pyridin-5-yl)carbamate (280 mg) obtained in Example 96 is suspended in dioxane (3 ml). To the suspension is added 4 N hydrogen chloride-dioxane solution (3 ml). The reaction solution is warmed to room temperature, and thereto is added methanol (2 ml), followed by stirring for 8 hours. The reaction solution is concentrated under reduced pressure, and the resulting residue is suspended in diethyl ether. The precipitates are collected by filtration to give the title compound (266 mg) as hydrochloride. The resulting hydrochloride is suspended in chloroform and thereto is added saturated aqueous sodium hydrogen carbonate solution. The precipitated solid is collected by filtration to give the title compound (88 mg).

APCI-MS M/Z: 483/485[M+H]$^+$

Examples 102-105

The corresponding starting compounds are treated in a similar manner to Example 100 or 101 to give the following compounds.

TABLE 26

| Ex. No. | Structure | Physicochemical Properties |
|---|---|---|
| 102 | 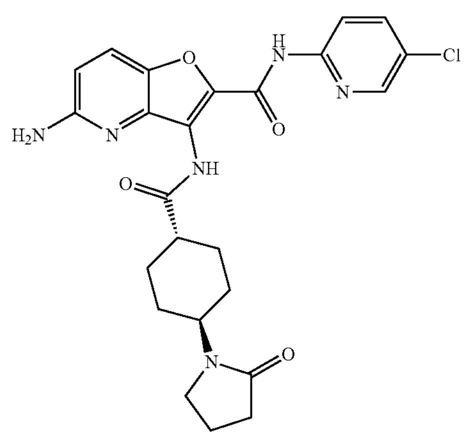 | APCI-MS M/Z: 497/499 [M + H]$^+$ |

TABLE 26-continued

| Ex. No. | Structure | Physicochemical Properties |
|---|---|---|
| 103 | 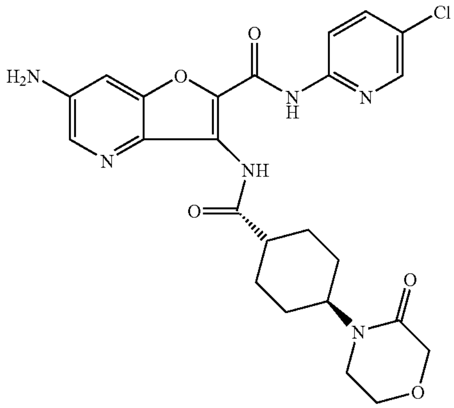 | APCI-MS M/Z: 513/515 [M + H]+ |
| 104 | 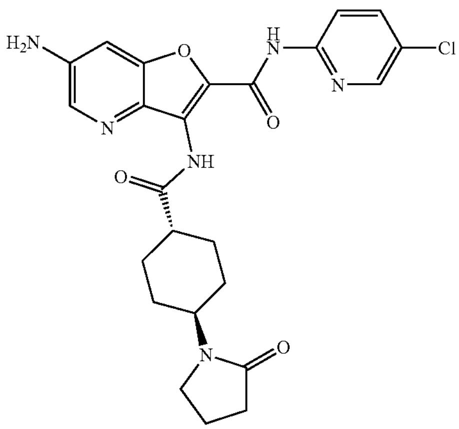 | APCI-MS M/Z: 497/499 [M + H]+ |
| 105 | 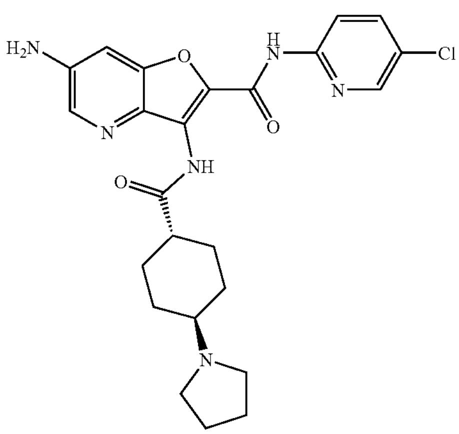 | ESI-MS M/Z: 483/485 [M + H]+ |

Example 106

N-(5-Chloropyridin-2-yl)-5-[(methylsulfonyl)amino]-3-({[trans-4-(3-oxomorpholin-4-yl)cyclohexyl]carbonyl}amino)furo[3,2-b]pyridine-2-carboxamide

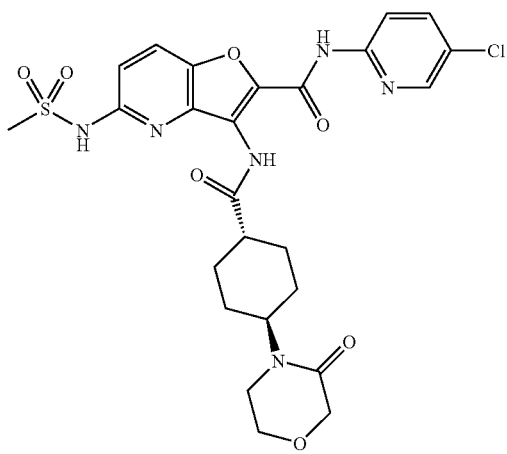

5-Amino-N-(5-chloropyridin-2-yl)-3-{[(trans-4-pyrrolidin-1-ylcyclohexyl)carbonyl]amino}furo[3,2-b]pyridine-2-carboxamide (110 mg) obtained in Example 101 is dissolved in pyridine (3 ml), and thereto is added methanesulfonyl chloride (46 µl) under ice-cooling. The mixture is stirred at room temperature for 3 hours. To the reaction solution is added saturated aqueous sodium hydrogen carbonate solution, and the mixture is extracted with chloroform. The organic layer is dried over sodium sulfate and the solvent is evaporated under reduced pressure. The resulting residue is purified by silica gel column chromatography (eluent: chloroform followed by chloroform/methanol=20/1). The resulting solid is suspended in diethyl ether, and collected by filtration to give the title compound (76 mg).

APCI-MS M/Z: 591/593[M+H]$^+$

Examples 107-114

The corresponding starting compounds are treated in a similar manner to Example 106 to give the following compounds.

TABLE 27

| Ex. No. | Structure | Physicochemical Properties |
|---|---|---|
| 107 | 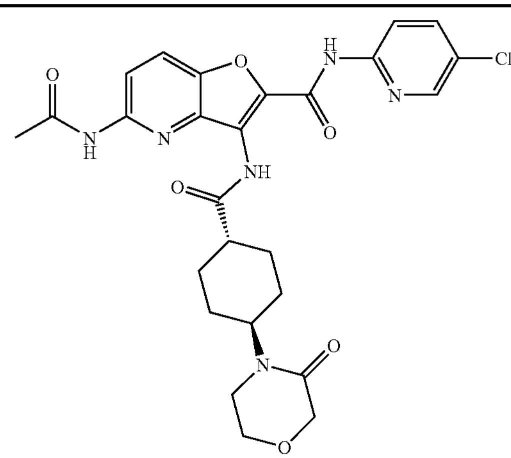 | APCI-MS M/Z: 555/557 [M + H]$^+$ |
| 108 | 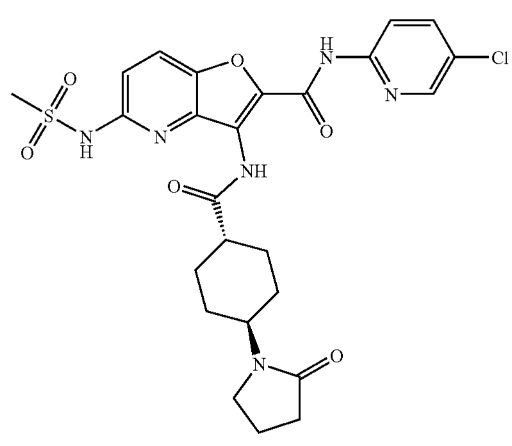 | APCI-MS M/Z: 575/577 [M + H]$^+$ |

TABLE 27-continued

| Ex. No. | Structure | Physicochemical Properties |
|---|---|---|
| 109 | 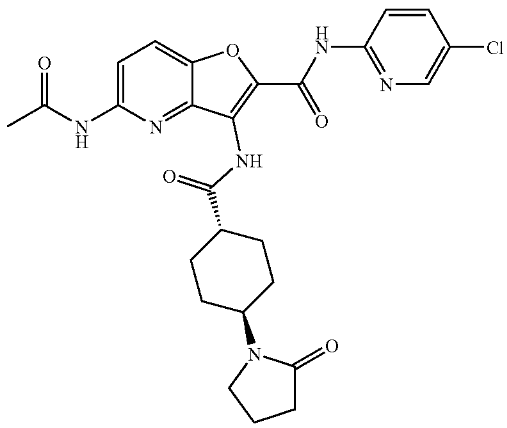 | APCI-MS M/Z: 539/541 [M + H]+ |
| 110 | 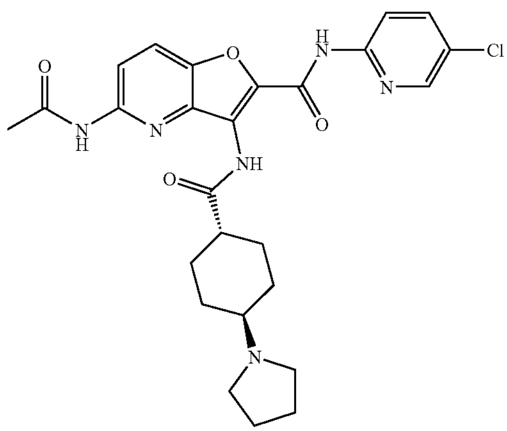 | APCI-MS M/Z: 525/527 [M + H]+ |

TABLE 28

| Ex. No. | Structure | Physicochemical Properties |
|---|---|---|
| 111 | 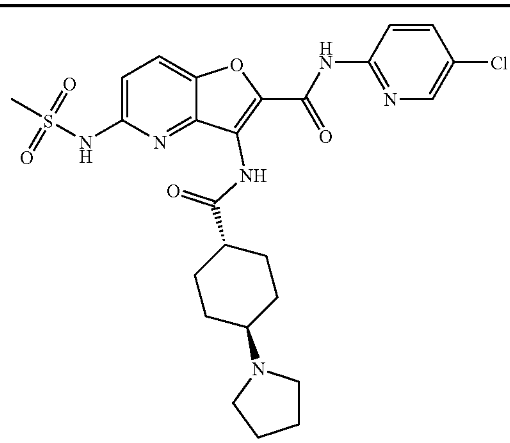 | APCI-MS M/Z: 561/563 [M + H]+ |

TABLE 28-continued

| Ex. No. | Structure | Physicochemical Properties |
|---------|-----------|---------------------------|
| 112 | 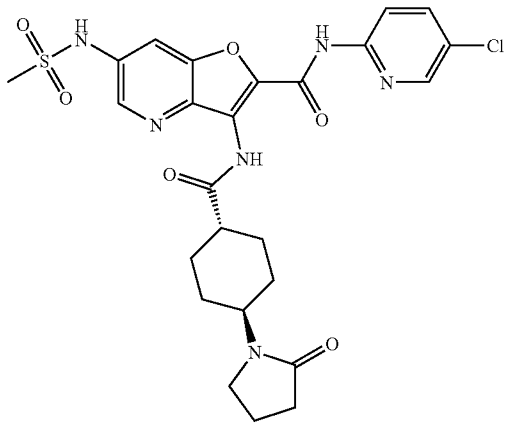 | APCI-MS M/Z: 573/575 [M − H]⁻ |
| 113 | 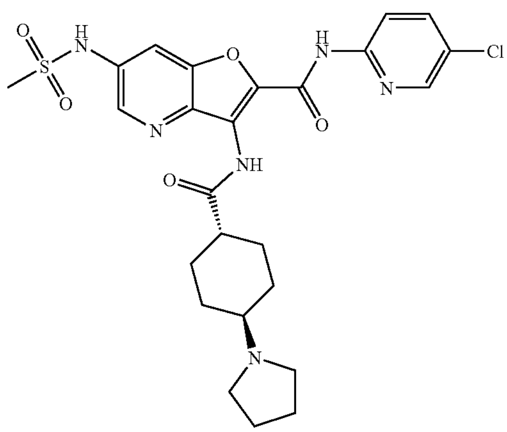 | APCI-MS M/Z: 561/563 [M + H]⁺ |
| 114 | 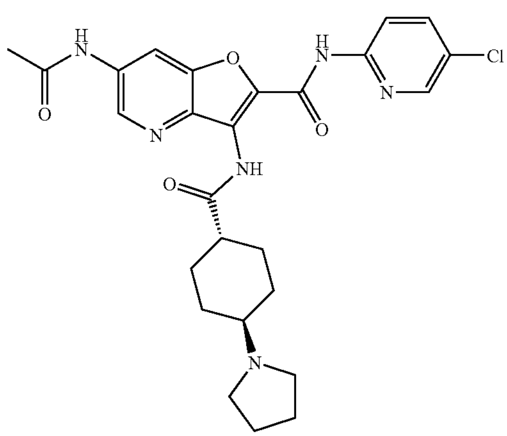 | APCI-MS M/Z: 525/527 [M + H]⁺ |

Example 115

N-(5-Chloropyridin-2-yl)-5-(hydroxymethyl)-3-({[trans-4-(3-oxomorpholin-4-yl)cyclohexyl]carbonyl}amino)furo[3,2-b]pyridine-2-carboxamide

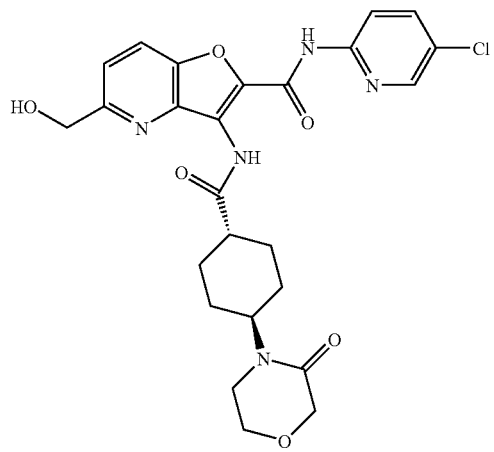

Methyl 2-{[(5-Chloropyridin-2-yl)amino]carbonyl}-3-({[trans-4-(3-oxomorpholin-4-yl)cyclohexyl]carbonyl}amino)furo[3,2-b]pyridine-5-carboxylate (300 mg) obtained in Example 39 is suspended in tetrahydrofuran (15 ml), and thereto is added lithium borohydride (24 mg) under ice-cooling, and the mixture is stirred at room temperature for 20 hours. To the reaction solution is poured 10% hydrochloric acid under ice-cooling, and the mixture is stirred at room temperature for 15 minutes. The reaction solution is alkalified with saturated aqueous sodium hydrogen carbonate solution, and then extracted with ethyl acetate. The organic layer is washed with saturated brine and dried over sodium sulfate, and the solvent is evaporated under reduced pressure. The resulting residue is purified by NH-silica gel column chromatography (eluent: ethyl acetate followed by ethyl acetate/methanol=10/1). The resulting solid is suspended in diethyl ether-n-hexane and collected by filtration to give the title compound (80 mg).

APCI-MS M/Z: 528/530[M+H]$^+$

Examples 116 and 117

The corresponding starting compounds are treated in a similar manner to Example 115 to give the following compounds.

TABLE 29

| Ex. No. | Structure | Physicochemical Properties |
|---|---|---|
| 116 | 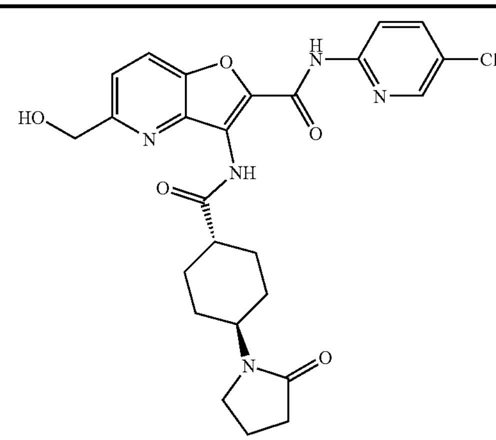 | APCI-MS M/Z: 512/514 [M + H]$^+$ |
| 117 | 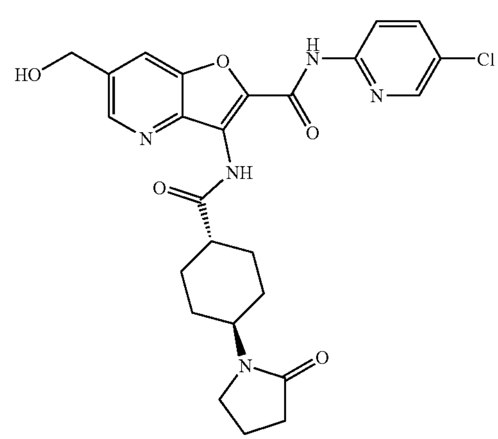 | APCI-MS M/Z: 512/514 [M + H]$^+$ |

Example 118 t-Butyl (trans-4-{[(2-{[(5-chloropyridin-2-yl)amino]-carbonyl}furo[3,2-b]pyridin-3-yl)amino]carbonyl}cyclohexyl)methylcarbamate

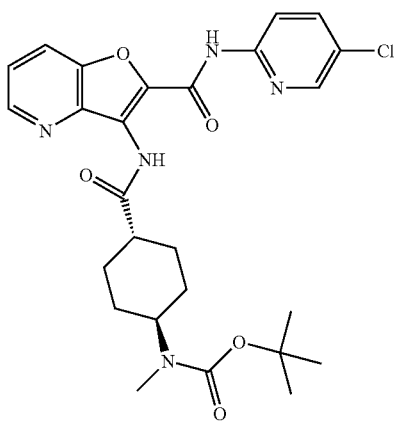

Trans-4-[(t-butoxycarbonyl)(methyl)amino]cyclohexanecarboxylic acid (1.30 g) obtained in Reference Example 12 is dissolved in chloroform (30 ml), and thereto is added pyridine (2.80 ml). After adding thionyl chloride (0.38 ml) dropwise under ice-cooling, the mixture is stirred at room temperature for 5 hours. To the resulting reaction solution are added successively 3-amino-N-(5-chloropyridin-2-yl)furo[3,2-b]pyridine-2-carboxamide (1.00 g) obtained in Reference Example 24 and pyridine (7.20 ml) under ice-cooling. The reaction solution is warmed to room temperature and stirred for 3 hours. To the reaction solution is poured saturated aqueous sodium hydrogen carbonate solution, and the mixture is extracted with chloroform. The organic layer is washed successively with water and saturated brine, and dried over sodium sulfate. The solvent is evaporated under reduced pressure, and the residue is purified by silica gel column chromatography (eluent: ethyl acetate) to give the title compound (1.71 g).

APCI-MS M/Z: 528/530[M+H]$^+$

Example 119

N-(5-Chloropyridin-2-yl)-3-({[trans-4-(methylamino)cyclohexyl]carbonyl}amino)furo[3,2-b]pyridine-2-carboxamide trihydrochloride

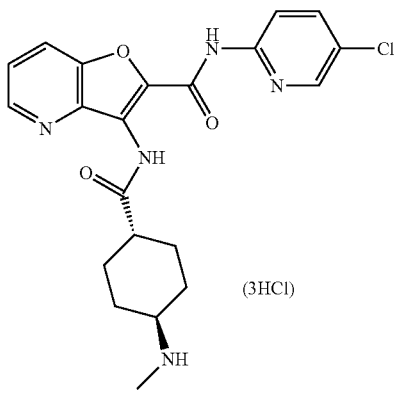

t-Butyl (trans-4-{[(2-{[(5-chloropyridin-2-yl)amino]carbonyl}-furo[3,2-b]pyridin-3-yl)amino]carbonyl}cyclohexyl)methylcarbamate (1.55 g) obtained in Example 118 is dissolved in dioxane (10 ml), and thereto is added 4N hydrogen chloride-dioxane solution (20 ml), and the mixture is stirred at room temperature for 12 hours. The reaction solution is concentrated under reduced pressure, and the residue is suspended in diethyl ether. The precipitates are collected by filtration and dried to give the title compound (1.49 g).

APCI-MS M/Z: 428/430[M+H]$^+$

Example 120 t-Butyl {3-[(trans-4-{[(2-{[(5-chloropyridin-2-yl)amino]-carbonyl}furo[3,2-b]pyridin-3-yl)amino]carbonyl}cyclohexyl)(methyl)amino]propyl}carbamate

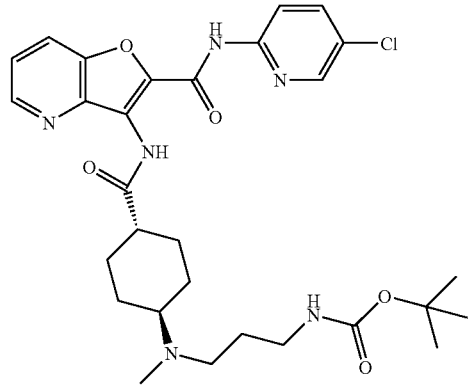

N-(5-Chloropyridin-2-yl)-3-({[trans-4-(methylamino)cyclohexyl]-carbonyl}amino)furo[3,2-b]pyridine-2-carboxamide trihydrochloride (300 mg) obtained in Example 119 is suspended in chloroform (7 ml). To the suspension are added 3-t-butoxycarbonylaminopropanal (208 mg), which can be prepared from 3-aminopropionaldehyde diethyl acetal in two steps according to the method described in a literature (Synthesis, 1994, 37) and triethylamine (334 µl) under ice-cooling, and the mixture is stirred for a few minutes. After addition of sodium triacetoxy borohydride (190 mg), the reaction solution is warmed to room temperature and stirred for 2 hours. To the reaction solution is poured saturated aqueous sodium hydrogen carbonate solution under ice-cooling, and the mixture is extracted with chloroform. The organic layer is washed successively with water and saturated brine, dried over sodium sulfate, and the solvent is evaporated under reduced pressure. The resulting residue is purified by NH-silica gel column chromatography (eluent: ethyl acetate followed by ethyl acetate/methanol=20/1) to give the title compound (291 mg).

APCI-MS M/Z: 585/587[M+H]$^+$

Example 121

3-[({Trans-4-[(3-aminopropyl)(methyl)amino]cyclohexyl}-carbonyl)amino]-N-(5-chloropyridin-2-yl)furo[3,2-b]pyridine-2-carboxamide

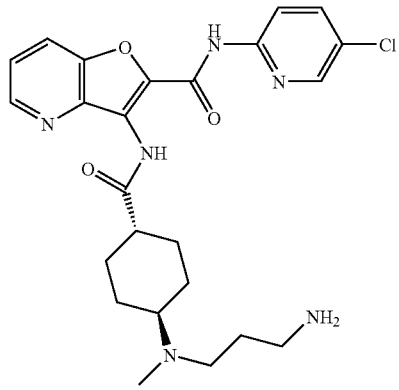

t-Butyl {3-[(trans-4-{[(2-{[(5-chloropyridin-2-yl)amino]carbonyl}-furo[3,2-b]pyridin-3-yl)amino]carbonyl}cyclohexyl)(methyl)amino]-propyl}carbamate (265 mg) obtained in Example 120 is dissolved in dioxane (3 ml), and thereto is added 4N hydrogen chloride-dioxane solution (6 ml), and the mixture is stirred at room temperature for 20 hours. The reaction solution is concentrated under reduced pressure, and the residue is suspended in diethyl ether. The precipitates are collected by filtration. The resulting solid is suspended in chloroform, and thereto is added saturated aqueous sodium hydrogen carbonate solution, and the organic layer is separated. The organic layer is washed with saturated brine, dried over sodium sulfate, and the solvent is evaporated under reduced pressure to give the title compound (206 mg).

APCI-MS M/Z: 485/487[M+H]+

Example 122

3-[({Trans-4-[[3-(acetylamino)propyl](methyl)amino]-cyclohexyl}carbonyl)amino]-N-(5-chloropyridin-2-yl)furo[3,2-b]pyridine-2-carboxamide

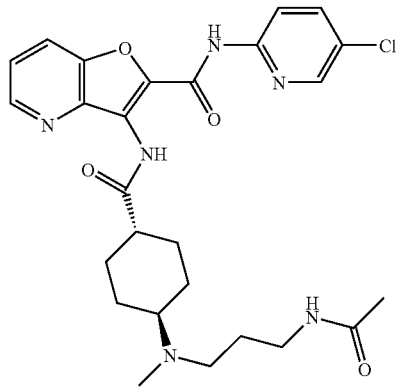

3-[({Trans-4-[(3-aminopropyl)(methyl)amino]cyclohexyl}-carbonyl)amino]-N-(5-chloropyridin-2-yl)furo[3,2-b]pyridine-2-carboxamide (113 mg) obtained in Example 121 and triethylamine (65 μl) are dissolved in chloroform (5 ml), and thereto is added acetyl chloride (25 μl) under ice-cooling. The mixture is warmed to room temperature and stirred for 1 hour. To the reaction solution is poured saturated aqueous sodium hydrogen carbonate solution, and the mixture is extracted with chloroform. The organic layer is washed successively with water and saturated brine, dried over sodium sulfate, and the solvent is evaporated under reduced pressure. The resulting residue is purified by NH-silica gel column chromatography (eluent: ethyl acetate followed by ethyl acetate/methanol=10/1). The resulting solid is suspended in n-hexane-diisopropyl ether, and collected by filtration to give the title compound (90 mg).

APCI-MS M/Z: 527/529[M+H]+

Example 123

6-(Acetyl)amino-N-(5-chloropyridin-2-yl)-3-({[trans-4-(3-oxomorpholin-4-yl)cyclohexyl]carbonyl}amino)furo[3,2-b]pyridine-2-carboxamide

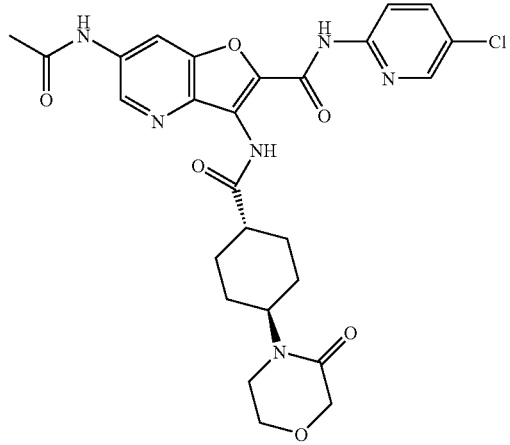

6-Amino-N-(5-chloropyridin-2-yl)-3-({[trans-4-(3-oxomorpholin-4-yl)cyclohexyl]carbonyl}amino)furo[3,2-b]pyridine-2-carboxamide (56 mg) obtained in Example 103 is treated in a similar manner to Example 122 to give the title compound (39 mg).

APCI-MS M/Z: 555/557[M+H]+

Example 124 t-Butyl 4-(trans-4-{[(2-{[(5-chloropyridin-2-yl)amino]-carbonyl}furo[3,2-b]pyridin-3-yl)amino]carbonyl}cyclohexyl)-3-oxopiperazine-1-carboxylate

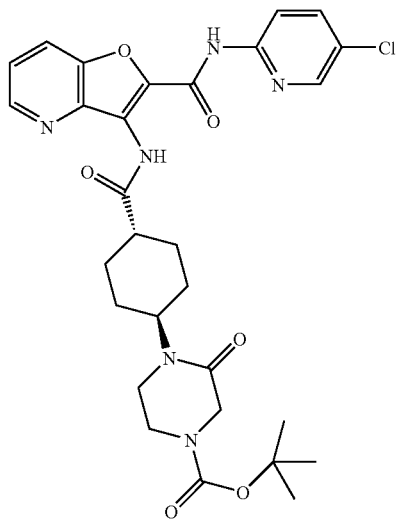

123

Trans-4-[4-(t-butoxycarbonyl)-2-oxopiperazin-1-yl]cyclohexanecarboxylic acid (370 mg) obtained in Reference Example 71 and 3-amino-N-(5-chloropyridin-2-yl)furo[3,2-b]pyridine-2-carboxamide (327 mg) obtained in Reference Example 24 are treated in a similar manner to Example 118 to give the title compound (151 mg).

APCI-MS M/Z: 597/599[M+H]⁺

Example 125

N-(5-Chloropyridin-2-yl)-3-({[trans-4-(2-oxopiperazin-1-yl)cyclohexyl]carbonyl}amino)furo[3,2-b]pyridine-2-carboxamide

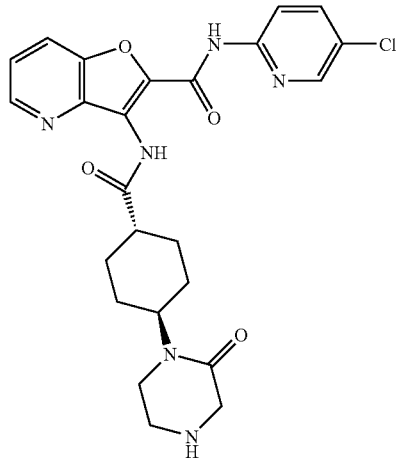

t-Butyl 4-(trans-4-{[(2-{[(5-chloropyridin-2-yl)amino]carbonyl}-furo[3,2-b]pyridin-3-yl)amino]carbonyl}cyclohexyl)-3-oxopiperazine-1-carboxylate (220 mg) obtained in Example 124 is treated in a similar manner to Example 121 to give the title compound (165 mg).

APCI-MS M/Z: 497/499[M+H]⁺

Example 126

N-(5-Chloropyridin-2-yl)-3-({[trans-4-(4-methyl-2-oxopiperazin-1-yl)cyclohexyl]carbonyl}amino)furo[3,2-b]pyridine-2-carboxamide

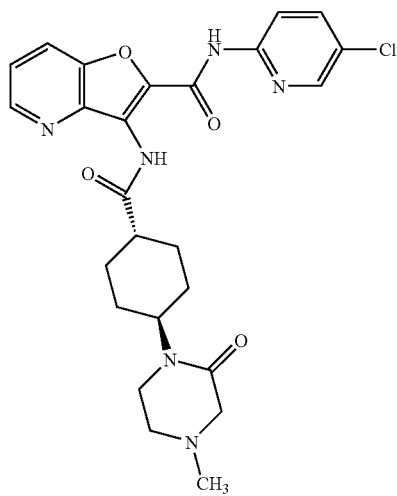

124

N-(5-Chloropyridin-2-yl)-3-({[trans-4-(2-oxopiperazin-1-yl)cyclohexyl]carbonyl}amino)furo[3,2-b]pyridine-2-carboxamide (60 mg) obtained in Example 125 and 35% aqueous formaldehyde solution (19 μl) are treated in a similar manner to Example 120 to give the title compound (46 mg).

APCI-MS M/Z: 511/513[M+H]⁺

Example 127

3-({[Trans-4-(4-acetyl-2-oxopiperazin-1-yl)cyclohexyl]-carbonyl}amino)-N-(5-chloropyridin-2-yl)furo[3,2-b]pyridine-2-carboxamide

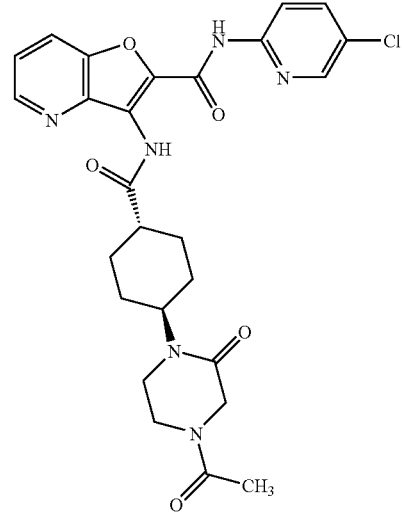

N-(5-Chloropyridin-2-yl)-3-({[trans-4-(2-oxopiperazin-1-yl)cyclohexyl]carbonyl}amino)furo[3,2-b]pyridine-2-carboxamide (50 mg) obtained in Example 125 and acetyl chloride (9 μl) are treated in a similar manner to Example 122 to give the title compound (41 mg).

APCI-MS M/Z: 539/541[M+H]⁺

Examples 128-138

The corresponding amino compounds and carboxylic acid compounds are treated in a similar manner to Example 2 to give the following compounds.

TABLE 30

| Ex. No. | Structure | Physicochemical Properties |
|---|---|---|
| 128 | 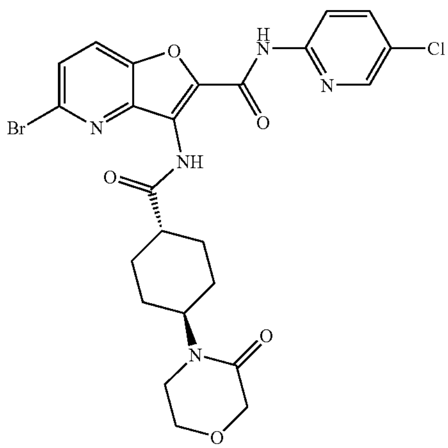 | APCI-MS M/Z: 576/578 [M + H]+ |
| 129 | 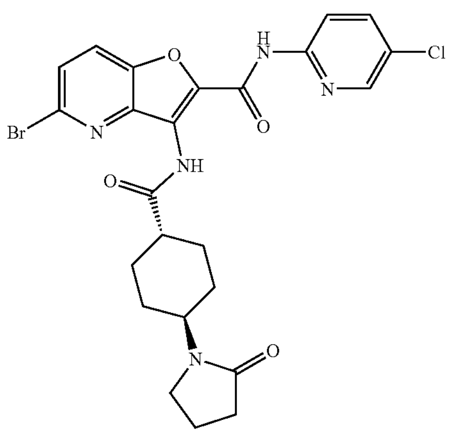 | APCI-MS M/Z: 560/562 [M + H]+ |
| 130 | 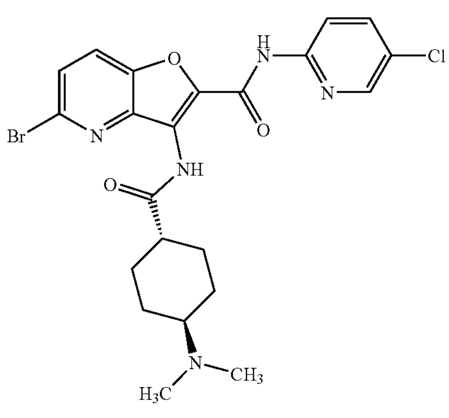 | APCI-MS M/Z: 520/522 [M + H]+ |

TABLE 30-continued

| Ex. No. | Structure | Physicochemical Properties |
|---|---|---|
| 131 | 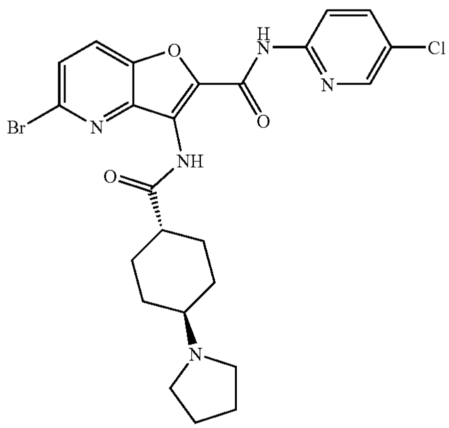 | APCI-MS M/Z: 546/548 [M + H]+ |

TABLE 31

| Ex. No. | Structure | Physicochemical Properties |
|---|---|---|
| 132 | 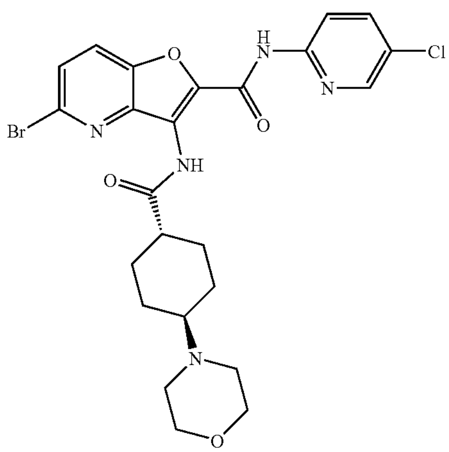 | APCI-MS M/Z: 562/564 [M + H]+ |
| 133 | 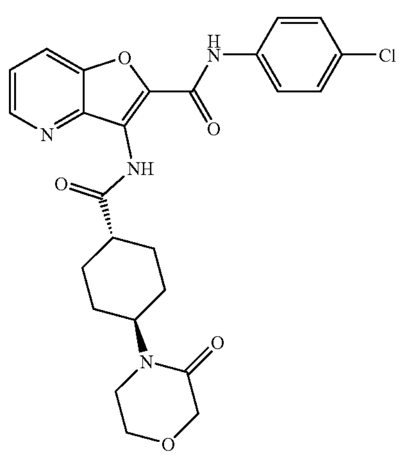 | APCI-MS M/Z: 497/499 [M + H]+ |

TABLE 31-continued

| Ex. No. | Structure | Physicochemical Properties |
|---------|-----------|----------------------------|
| 134 | 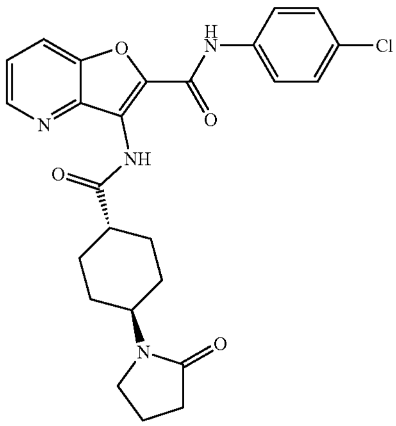 | APCI-MS M/Z: 481/483 [M + H]+ |
| 135 | 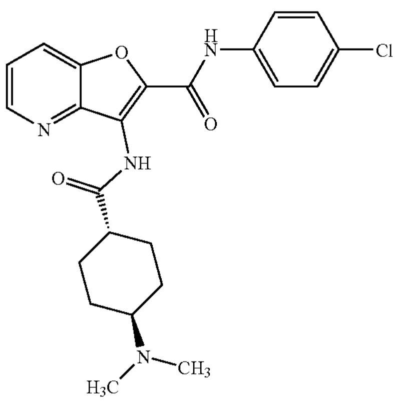 | APCI-MS M/Z: 441/443 [M + H]+ |

TABLE 32

| Ex. No. | Structure | Physicochemical Properties |
|---------|-----------|----------------------------|
| 136 | 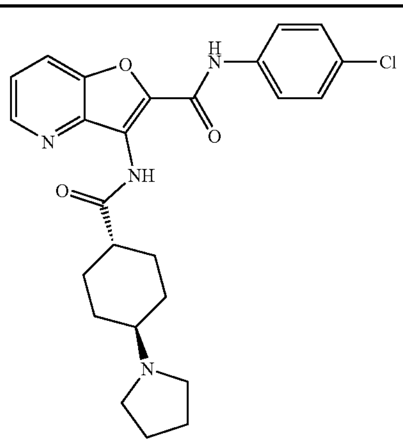 | APCI-MS M/Z: 467/469 [M + H]+ |

TABLE 32-continued
| Ex. No. | Structure | Physicochemical Properties |
|---|---|---|
| 137 | 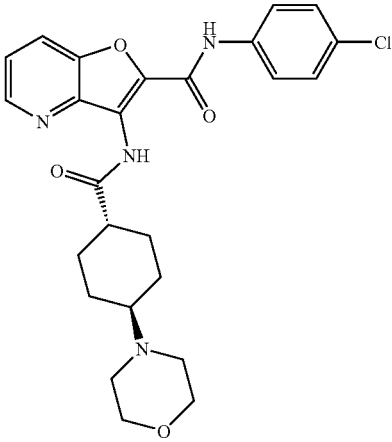 | APCI-MS M/Z: 483/485 [M + H]+ |
| 138 | 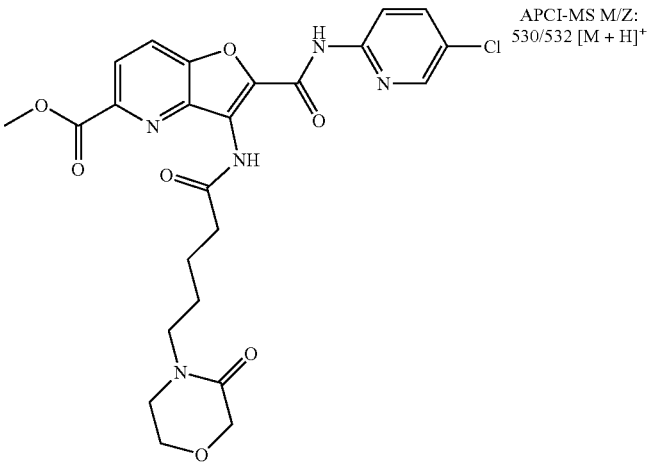 | APCI-MS M/Z: 530/532 [M + H]+ |

Example 139

2-{[(5-Chloropyridin-2-yl)amino]carbonyl}-3-{[5-(3-oxomorpholin-4-yl)pentanoyl]amino}furo[3,2-b]pyridine-5-carboxylic acid

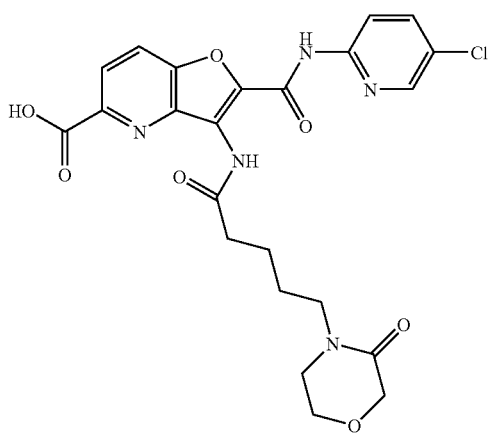

Methyl 2-{[(5-chloropyridin-2-yl)amino]carbonyl}-3-{[5-(3-oxomorpholin-4-yl)pentanoyl]amino}furo[3,2-b]pyridine-5-carboxylate (115 mg) obtained in Example 138 is treated in a similar manner to Example 79 to give the title compound (94 mg).

ESI-MS M/Z: 514/516[M−H]−

Example 140

$N^2$-(5-Chloropyridin-2-yl)-$N^5$-(methoxyethyl)-$N^5$-methyl-3-{[5-(3-oxomorpholin-4-yl)pentanoyl]amino}furo[3,2-b]pyridine-2,5-dicarboxamide

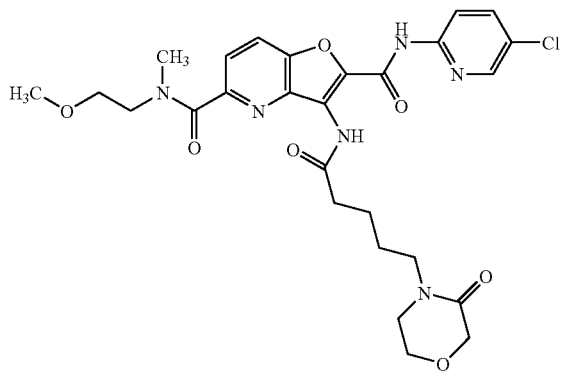

2-{[(5-Chloropyridin-2-yl)amino]carbonyl}-3-{[5-(3-oxomorpholin-4-yl)pentanoyl]amino}furo[3,2-b]pyridine-5-carboxylic acid (82 mg) obtained in Example 139 and N-(2-methoxyethyl)methylamine (28 mg) are treated in a similar manner to Example 85 to give the title compound (70 mg).

APCI-MS M/Z: 587/589[M+H]+

Example 141

N-(5-methylpyridine-2-yl)-3-({[trans-4-(3-oxomorpholin-4-yl)cyclohexyl]carbonyl}amino)furo[3,2-b]pyridine-2-carboxamide

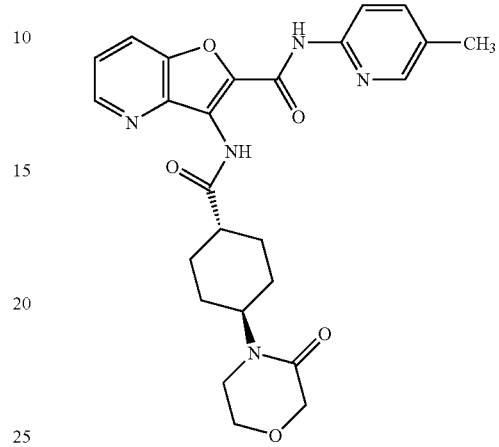

2-Amino-5-methylpyridine (81 mg) is dissolved in chloroform (5 ml). After adding 0.98 M trimethyl alminum-hexane solution (763 µl) under ice-cooling, the reaction solution is stirred under ice-cooling for 10 minutes, and then at room temperature for 0.5 hours. To the resulting reaction solution is added methyl 3-({[trans-4-(3-oxomorpholin-4-yl)cyclohexyl]carbonyl}amino)furo[3,2-b]pyridine-2-carboxylate (150 mg) obtained in Reference Example 79, and the mixture is stirred at room temperature for 2 hours and at 50° C. under heating for 5 hours. To the reaction solution is added 10% hydrochloric acid (3 ml) under ice-cooling, and the mixture is stirred at room temperature for 0.5 hours. The reaction solution is then neutralized by adding saturated aqueous sodium hydrogen carbonate solution, and extracted with chloroform. The organic layer is washed with saturated brine, dried over sodium sulfate, and the solvent is evaporated under reduced pressure. The residue is purified by NH-silica gel column chromatography (eluent: ethyl acetate followed by ethyl acetate/methanol=10/1). The resulting solid is suspended in diethyl ether, and collected by filtration to give the title compound (110 mg).

APCI-MS M/Z: 478[M+H]+

Examples 142-145
The corresponding esters and amino compounds are treated in a similar manner to Example 141 to give the following compounds.
TABLE 33
| Ex. No. | Structure | Physicochemical Properties |
|---|---|---|
| 142 | 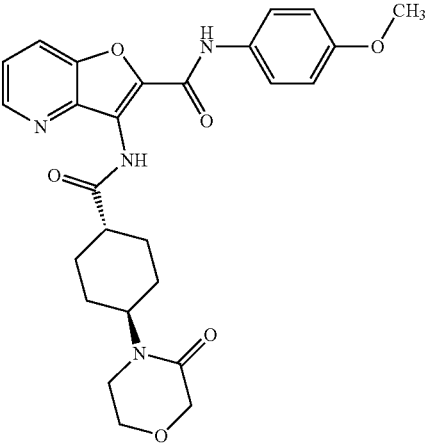 | APCI-MS M/Z: 493 [M + H]$^+$ |
| 143 | 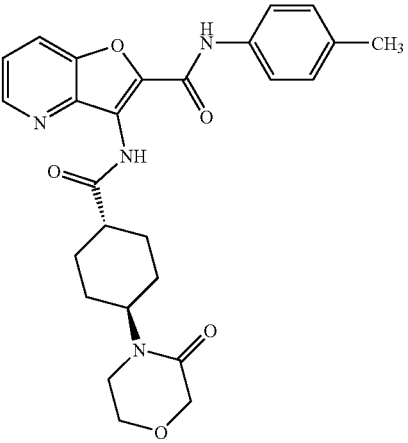 | APCI-MS M/Z: 477 [M + H]$^+$ |
| 144 | 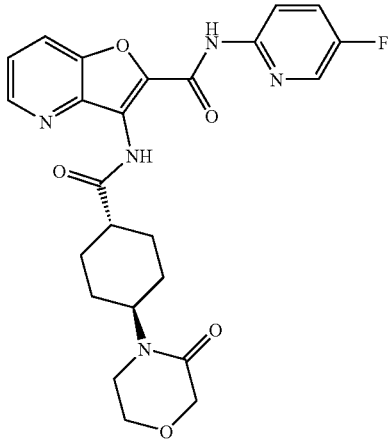 | APCI-MS M/Z: 482 [M + H]$^+$ |

TABLE 33-continued

| Ex. No. | Structure | Physicochemical Properties |
|---|---|---|
| 145 | 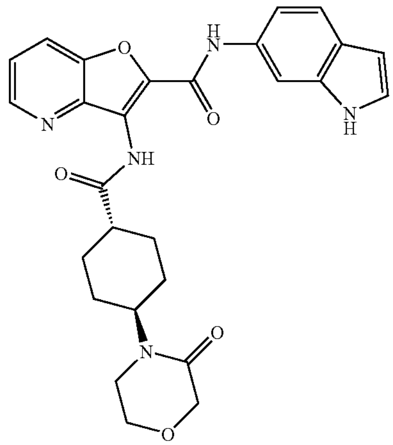 | APCI-MS M/Z: 502 [M + H]+ |

Examples 146-149

The corresponding carboxylic acids and amino compounds are treated in a similar manner to Example 1 or Example 2 to give the following compounds.

TABLE 34

| Ex. No. | Structure | Physicochemical Properties |
|---|---|---|
| 146 | 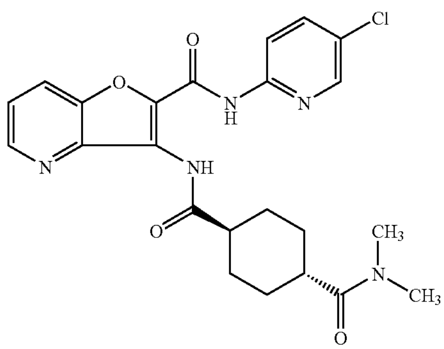 | APCI-MS M/Z: 470/472 [M + H]+ |
| 147 | 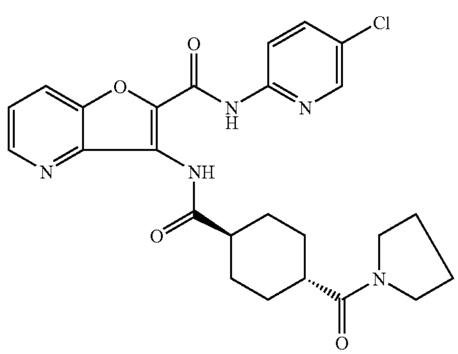 | APCI-MS M/Z: 496/498 [M + H]+ |

TABLE 34-continued
| Ex. No. | Structure | Physicochemical Properties |
|---|---|---|
| 148 | 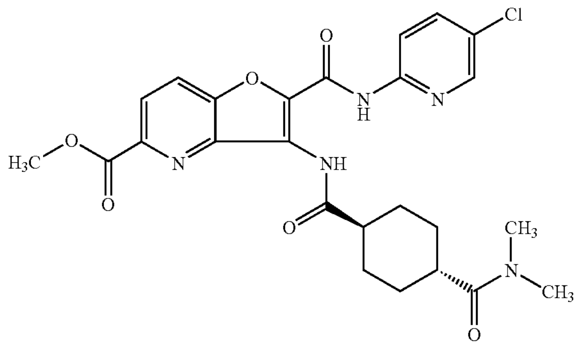 | APCI-MS M/Z: 528/530 [M + H]+ |
| 149 | 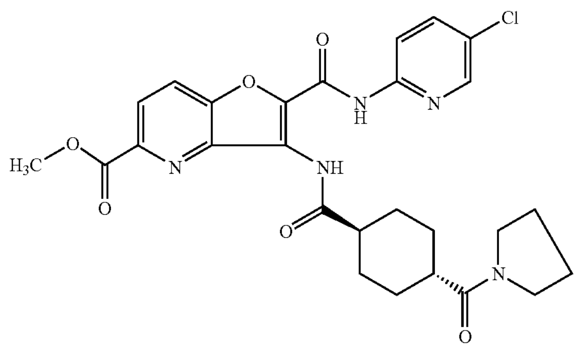 | APCI-MS M/Z: 554/556 [M + H]+ |
Examples 150, 151
The corresponding esters are treated in a similar manner to Example 79 to give the following compounds.
TABLE 35
| Ex. No. | Structure | Physicochemical Properties |
|---|---|---|
| 150 | 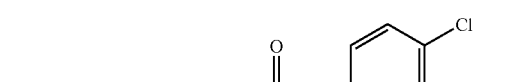 | ESI-MS M/Z: 511/513 [M + H]+ |

TABLE 35-continued

| Ex. No. | Structure | Physicochemical Properties |
|---|---|---|
| 151 | 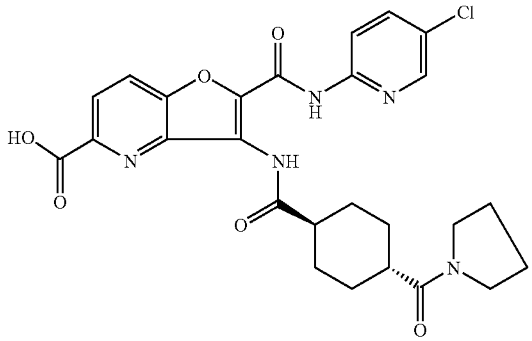 | ESI-MS M/Z: 537/539 [M + H]+ |

Examples 152, 153

The corresponding carboxylic acids and amino compounds are treated in a similar manner to Example 85 to give the following compounds.

TABLE 36

| Ex. No. | Structure | Physicochemical Properties |
|---|---|---|
| 152 | 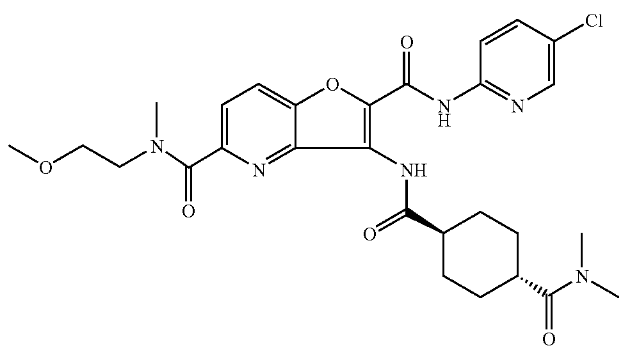 | APCI-MS M/Z: 585/587 [M + H]+ |
| 153 | 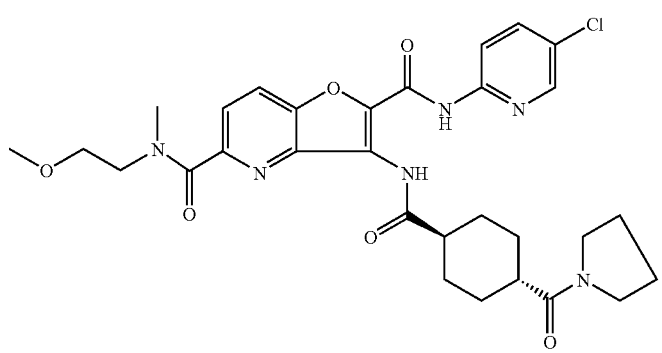 | APCI-MS M/Z: 611/613 [M + H]+ |

Example 154

N-(5-Chloropyridin-2-yl)-4-methoxy-3-{[(trans-4-pyrrolidin-1-ylcyclohexyl)carbonyl]amino}furo[3,2-c]pyridine-2-carboxamide

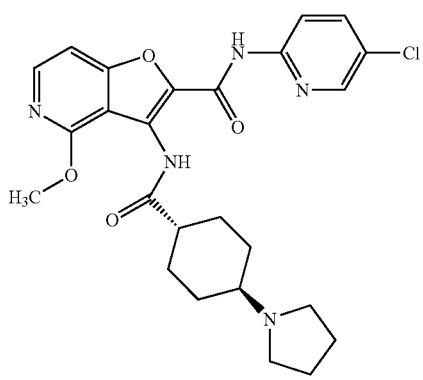

3-Amino-N-(5-chloropyridin-2-yl)-4-methoxyfuro[3,2-c]pyridine-2-carboxamide (82 mg) obtained in Reference Example 88 and trans-4-pyrrolidin-1-ylcyclohexanecarboxylic acid hydrochloride (106 mg) obtained in Reference Example 10 are treated in a similar manner to Example 2 to give the title compound (39 mg).

APCI-MS M/Z: 498/500[M+H]$^+$

Examples 155, 156

2-{[(5-Chloropyridin-2-yl)amino]carbonyl}-3-{[(trans-4-pyrrolidin-1-ylcyclohexyl)carbonyl]amino}furo[3,2-b]pyridine-5-carboxylic acid obtained in Example 81 and the corresponding amino compounds are treated in a similar manner to Example 85 to give the following compounds.

TABLE 37

| Ex. No. | Structure | Physicochemical Properties |
|---|---|---|
| 155 | 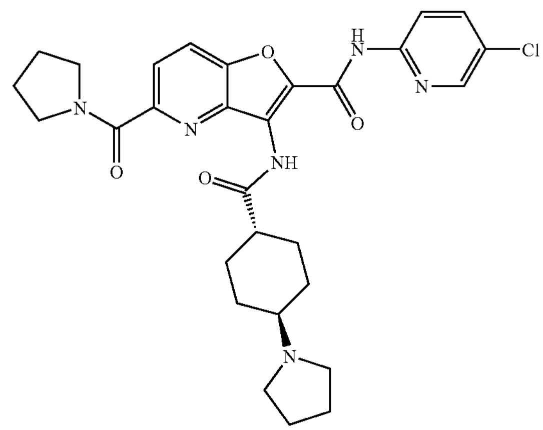 | APCI-MS M/Z: 565/567 [M + H]$^+$ |
| 156 | 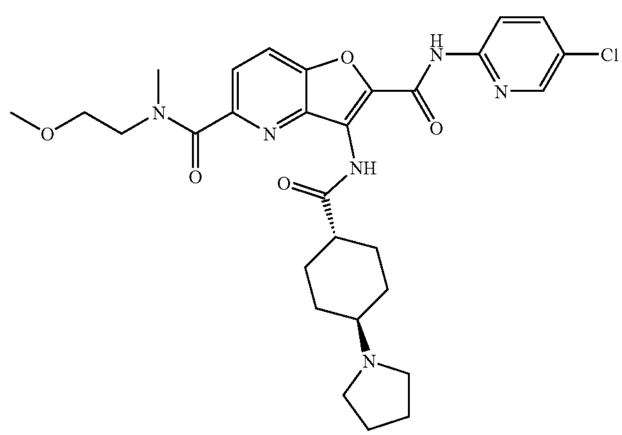 | APCI-MS M/Z: 538/540 [M + H]$^+$ |

145
Examples 157-185
The corresponding amino compounds and carboxylic acids obtained in Reference Examples are treated in a similar manner to Example 2 to give the following compounds.
TABLE 38
| Ex. No. | Structure | Physicochemical Properties |
|---|---|---|
| 157 | 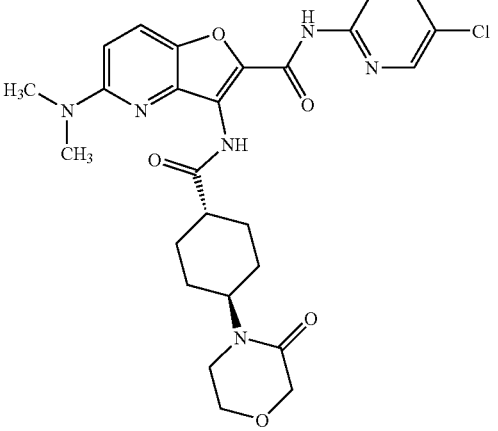 | APCI-MS M/Z: 541/543 [M + H]+ |
| 158 | 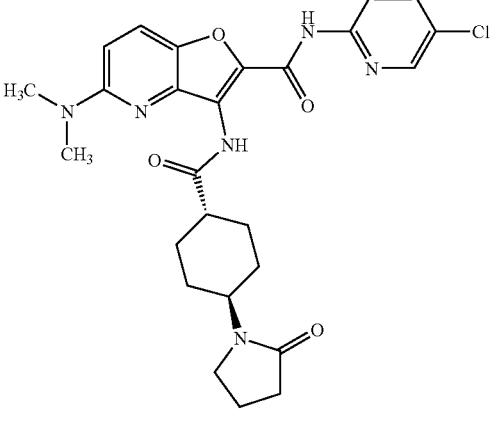 | APCI-MS M/Z: 525/527 [M + H]+ |
| 159 | 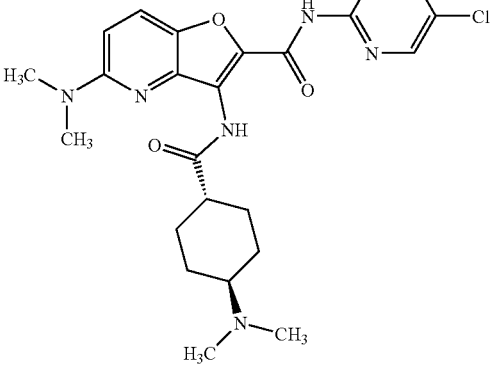 | APCI-MS M/Z: 485/487 [M + H]+ |

TABLE 38-continued

| Ex. No. | Structure | Physicochemical Properties |
|---|---|---|
| 160 | 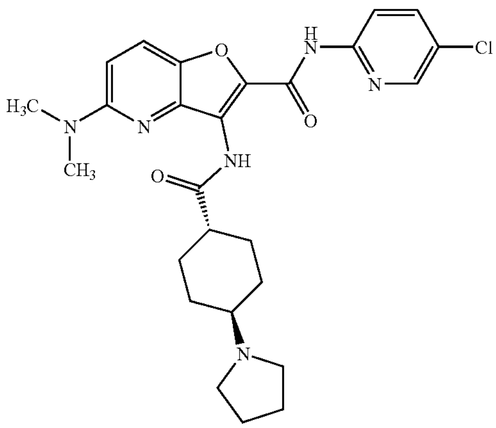 | APCI-MS M/Z: 511/513 [M + H]+ |

TABLE 39

| Ex. No. | Structure | Physicochemical Properties |
|---|---|---|
| 161 | 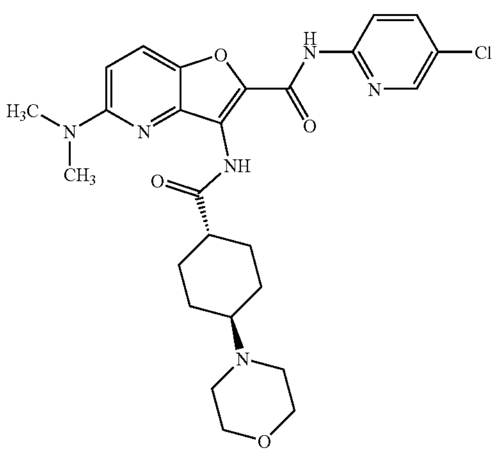 | APCI-MS M/Z: 527/529 [M + H]+ |
| 162 | 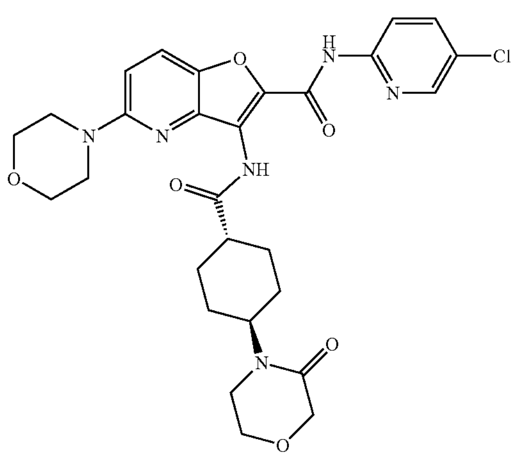 | APCI-MS M/Z: 583/585 [M + H]+ |

TABLE 39-continued

| Ex. No. | Structure | Physicochemical Properties |
|---|---|---|
| 163 | 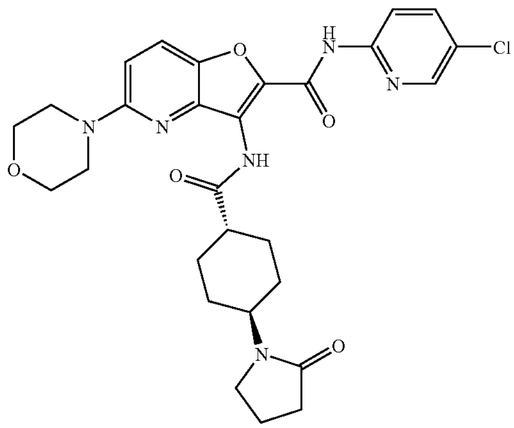 | APCI-MS M/Z: 567/569 [M + H]+ |
| 164 | 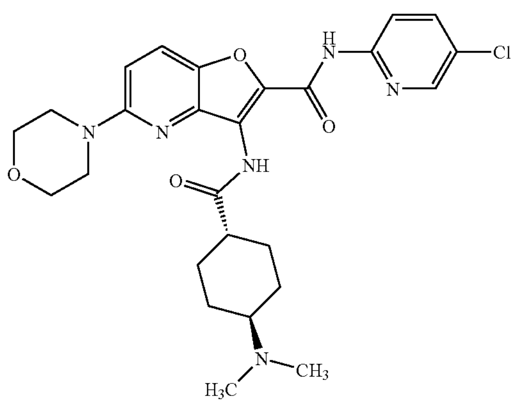 | APCI-MS M/Z: 527/529 [M + H]+ |

TABLE 40

| Ex. No. | Structure | Physicochemical Properties |
|---|---|---|
| 165 | 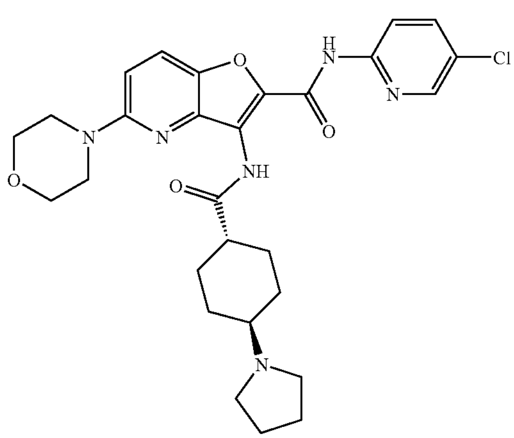 | APCI-MS M/Z: 553/555 [M + H]+ |

TABLE 40-continued

| Ex. No. | Structure | Physicochemical Properties |
|---|---|---|
| 166 | 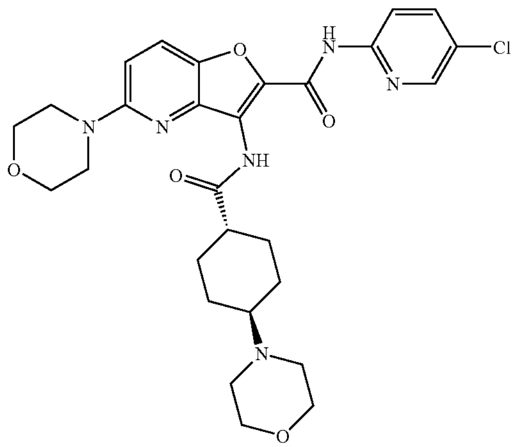 | APCI-MS M/Z: 569/571 [M + H]⁺ |
| 167 | 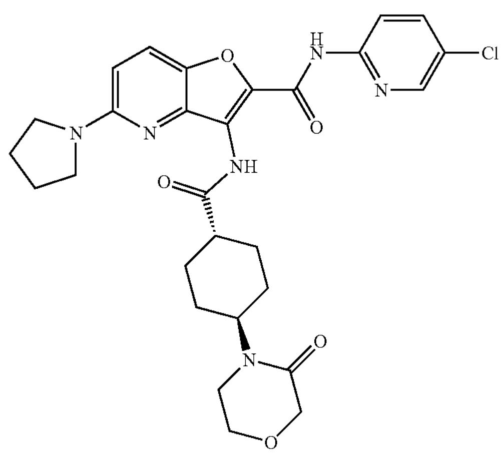 | APCI-MS M/Z: 567/569 [M + H]⁺ |
| 168 | 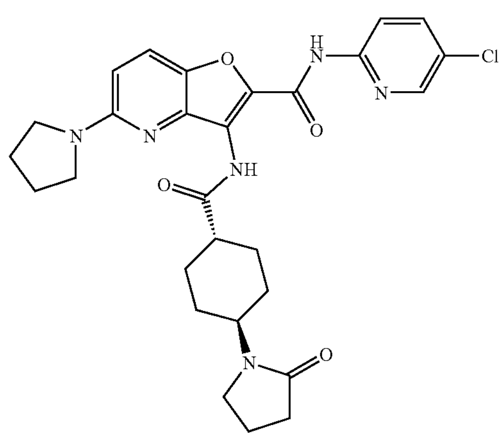 | APCI-MS M/Z: 551/553 [M + H]⁺ |

TABLE 41
| Ex. No. | Structure | Physicochemical Properties |
|---|---|---|
| 169 | 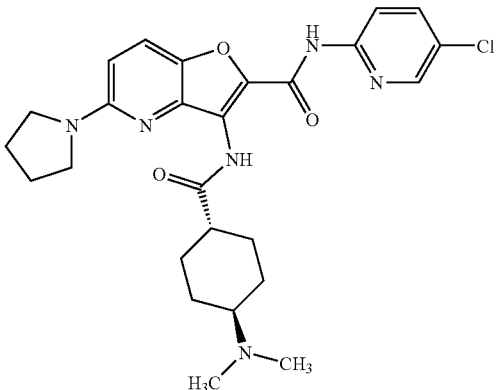 | APCI-MS M/Z: 511/513 [M + H]+ |
| 170 | 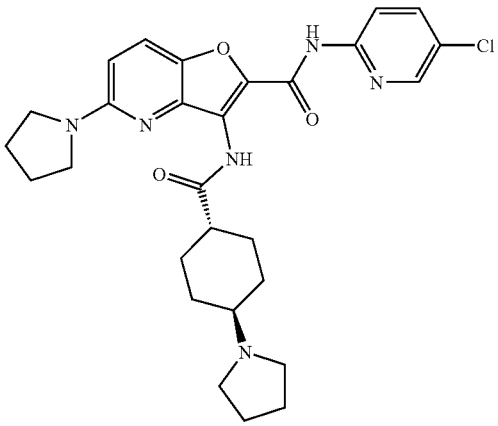 | APCI-MS M/Z: 537/539 [M + H]+ |
| 171 | 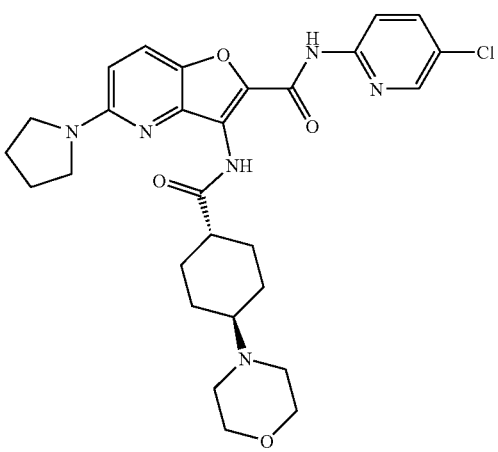 | APCI-MS M/Z: 553/555 [M + H]+ |

TABLE 41-continued
| Ex. No. | Structure | Physicochemical Properties |
|---|---|---|
| 172 | 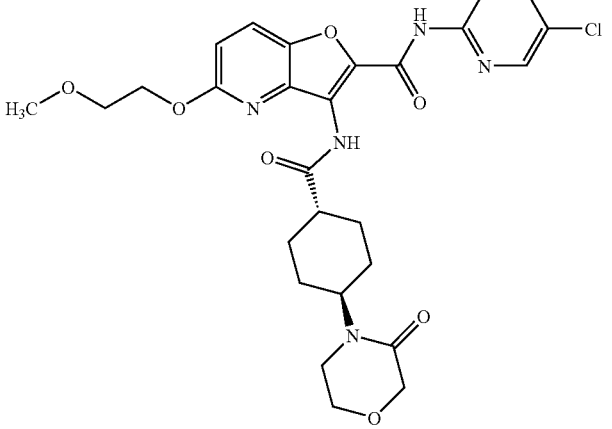 | APCI-MS M/Z: 572/574 [M + H]+ |
TABLE 42
| Ex. No. | Structure | Physicochemical Properties |
|---|---|---|
| 173 | 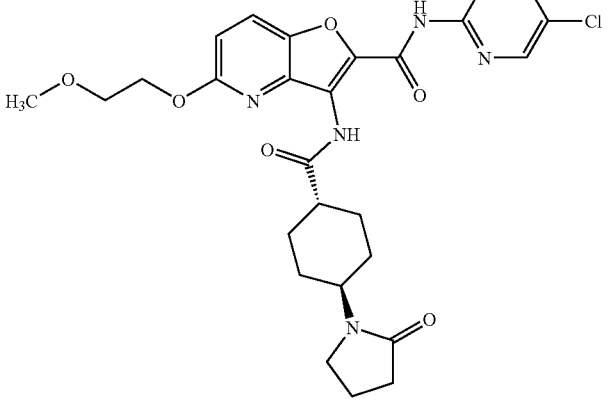 | APCI-MS M/Z: 566/568 [M + H]+ |
| 174 | 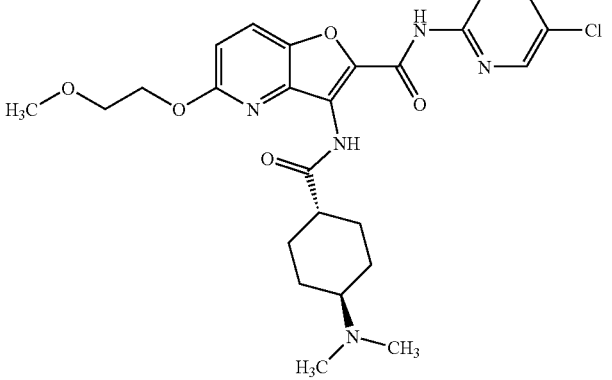 | APCI-MS M/Z: 516/518 [M + H]+ |

TABLE 42-continued
| Ex. No. | Structure | Physicochemical Properties |
|---|---|---|
| 175 | 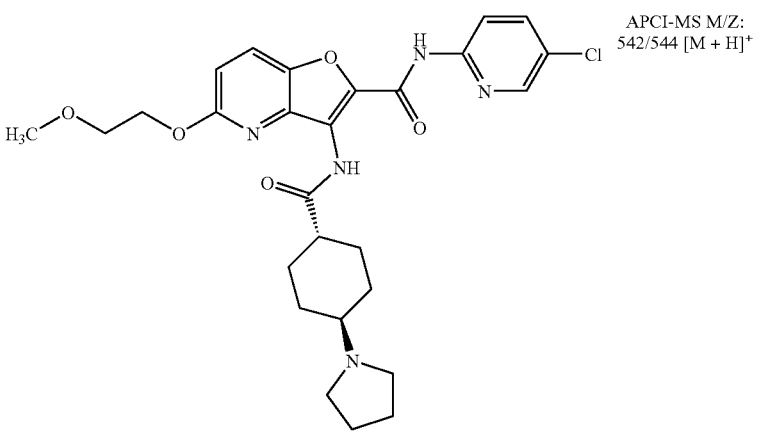 | APCI-MS M/Z: 542/544 [M + H]+ |
| 176 | 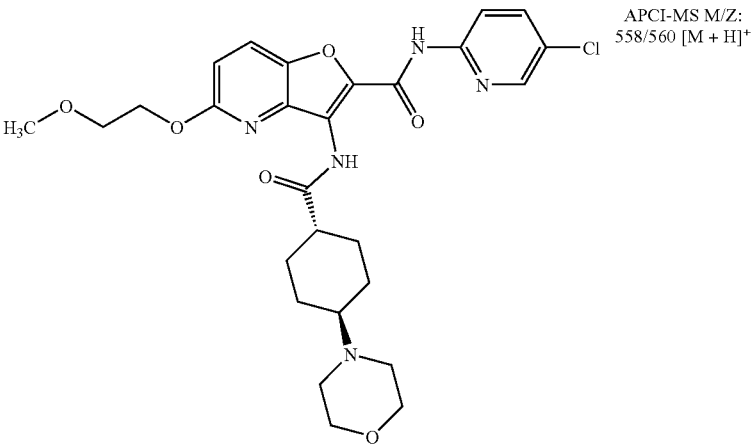 | APCI-MS M/Z: 558/560 [M + H]+ |
TABLE 43
| Ex. No. | Structure | Physicochemical Properties |
|---|---|---|
| 177 | 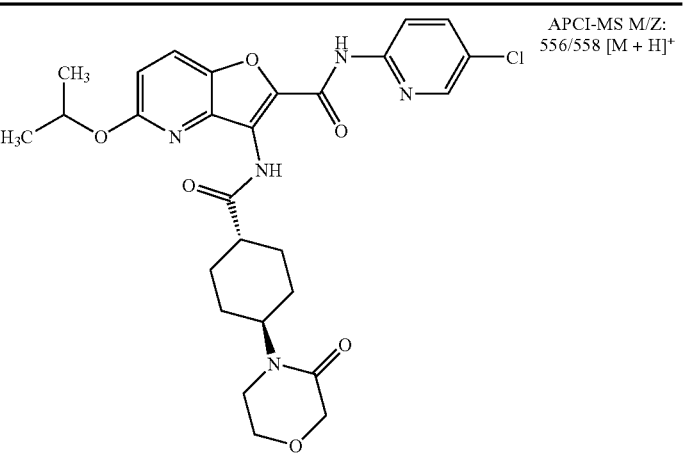 | APCI-MS M/Z: 556/558 [M + H]+ |

TABLE 43-continued

| Ex. No. | Structure | Physicochemical Properties |
|---|---|---|
| 178 | 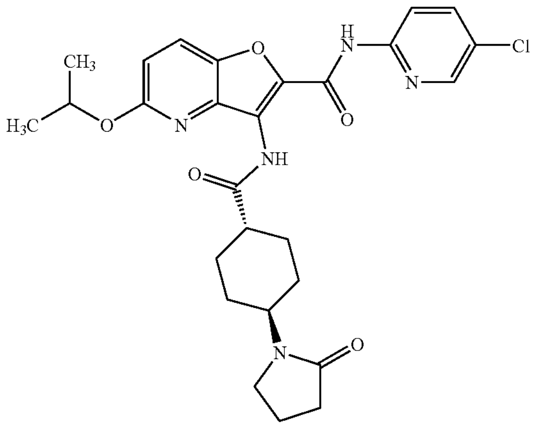 | APCI-MS M/Z: 540/542 [M + H]+ |
| 179 | 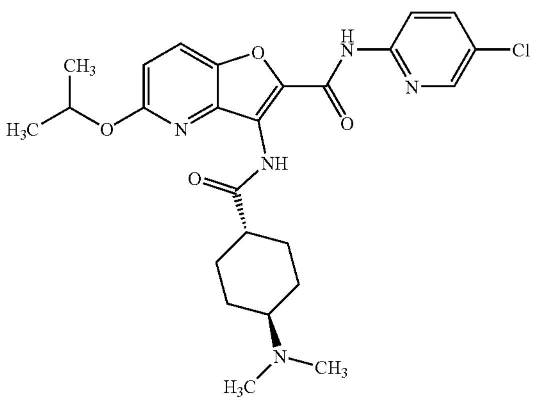 | APCI-MS M/Z: 500/502 [M + H]+ |
| 180 | 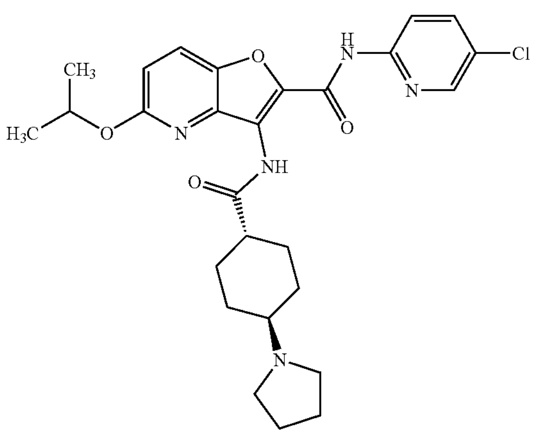 | APCI-MS M/Z: 526/528 [M + H]+ |

TABLE 44

| Ex. No. | Structure | Physicochemical Properties |
|---|---|---|
| 181 | 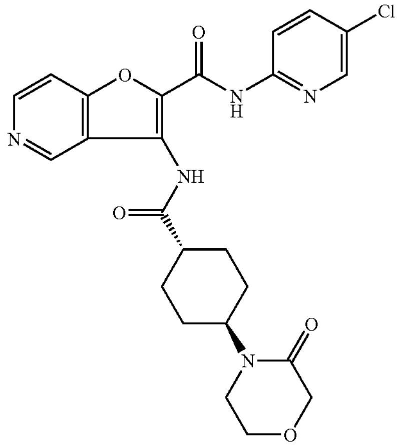 | APCI-MS M/Z: 498/500 [M + H]+ |
| 182 | 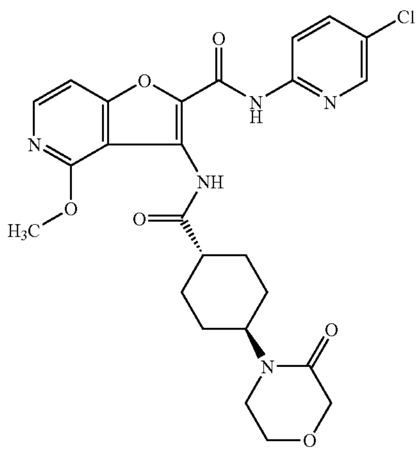 | APCI-MS M/Z: 528/530 [M + H]+ |
| 183 | 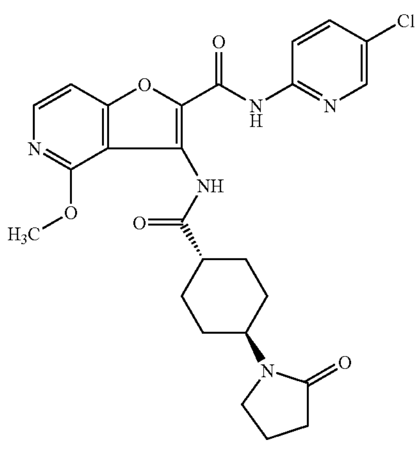 | APCI-MS M/Z: 512/514 [M + H]+ |

TABLE 44-continued

| Ex. No. | Structure | Physicochemical Properties |
|---|---|---|
| 184 | 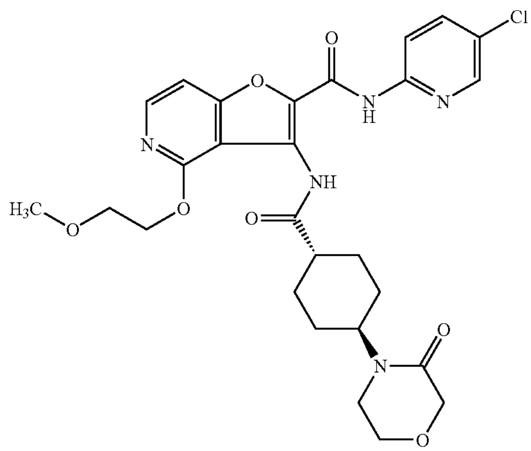 | APCI-MS M/Z: 572/574 [M + H]+ |

TABLE 45

| Ex. No. | Structure | Physicochemical Properties |
|---|---|---|
| 185 | 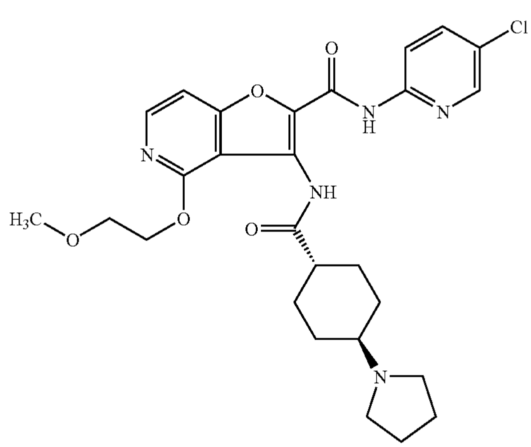 | APCI-MS M/Z: 542/544 [M + H]+ |

Examples 186-192

The corresponding esters and amino compounds are treated in a similar manner to Example 141 to give the following compounds.

TABLE 46

| Ex. No. | Structure | Physicochemical Properties |
|---|---|---|
| 186 | 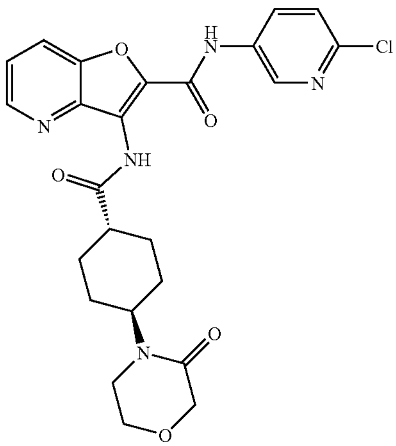 | APCI-MS M/Z: 498/500 [M + H]⁺ |
| 187 | 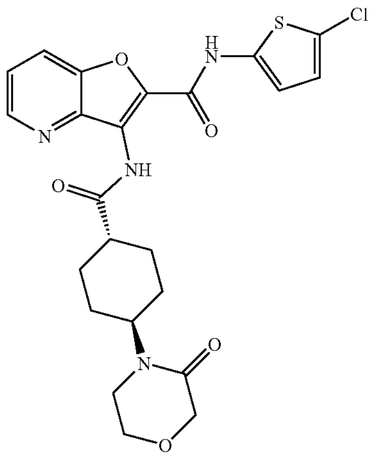 | APCI-MS M/Z: 503/505 [M + H]⁺ |
| 188 | 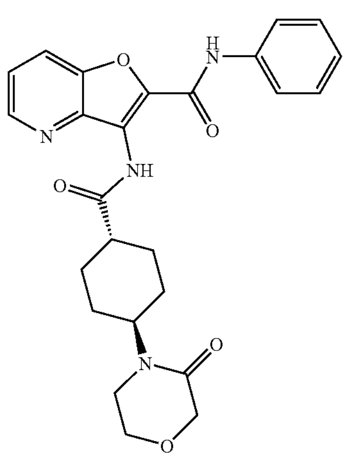 | APCI-MS M/Z: 463 [M + H]⁺ |

TABLE 46-continued

| Ex. No. | Structure | Physicochemical Properties |
|---|---|---|
| 189 | 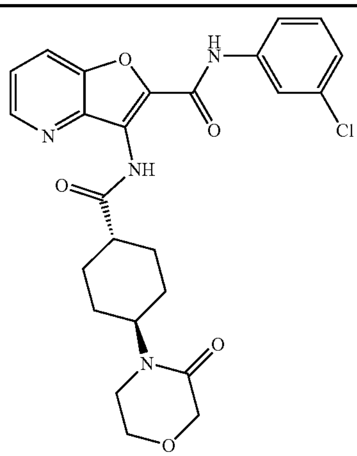 | APCI-MS M/Z: 497/499 [M + H]+ |

TABLE 47

| Ex. No. | Structure | Physicochemical Properties |
|---|---|---|
| 190 | 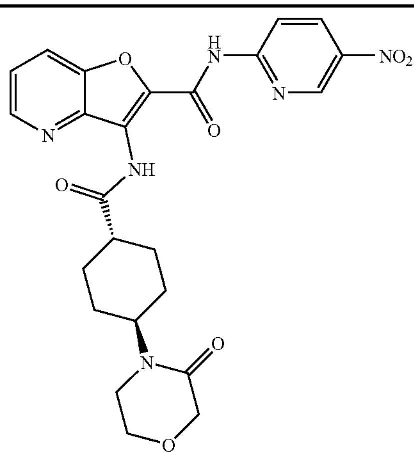 | APCI-MS M/Z: 509 [M + H]+ |
| 191 | 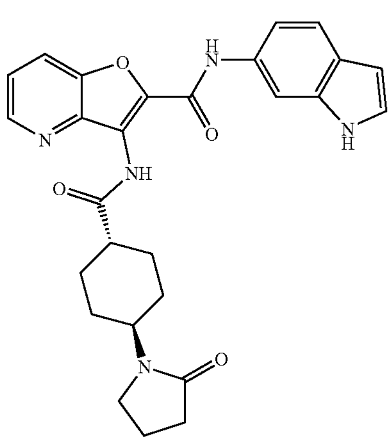 | APCI-MS M/Z: 486 [M + H]+ |

TABLE 47-continued

| Ex. No. | Structure | Physicochemical Properties |
|---|---|---|
| 192 | 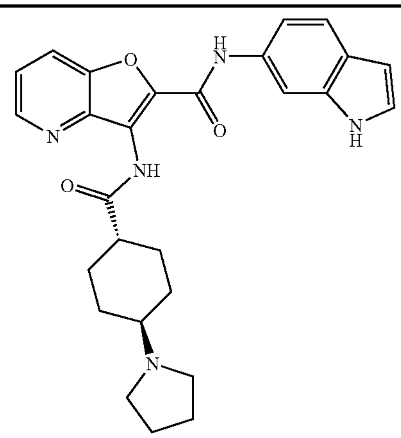 | APCI-MS M/Z: 472 [M + H]+ |

Examples 193-202

The corresponding amino compounds obtained in Reference Examples 24, 87, 90 and 91 and corresponding carboxylic acids are treated in a similar manner to Example 2 to give the following compounds.

TABLE 48

| Ex. No. | Structure | Physicochemical Properties |
|---|---|---|
| 193 | 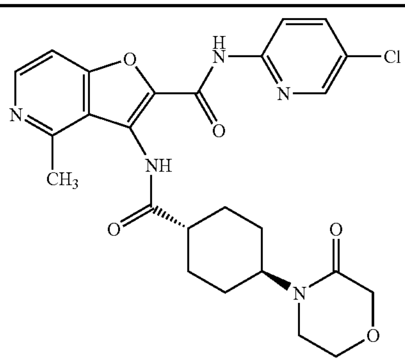 | APCI-MS M/Z: 512/514 [M + H]+ |
| 194 | 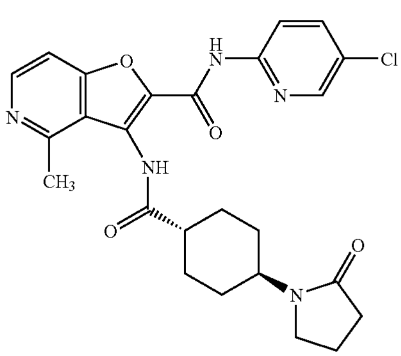 | APCI-MS M/Z: 496/498 [M + H]+ |

TABLE 48-continued

| Ex. No. | Structure | Physicochemical Properties |
|---|---|---|
| 195 | 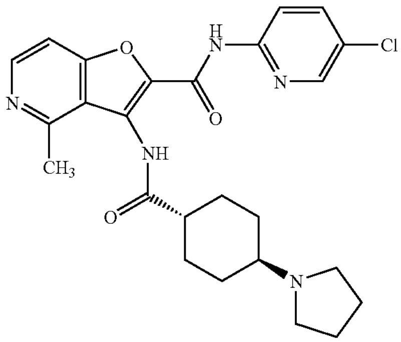 | APCI-MS M/Z: 482/484 [M + H]+ |
| 196 | 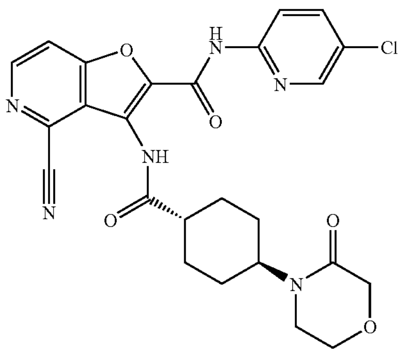 | APCI-MS M/Z: 523/525 [M + H]+ |

TABLE 49

| Ex. No. | Structure | Physicochemical Properties |
|---|---|---|
| 197 | 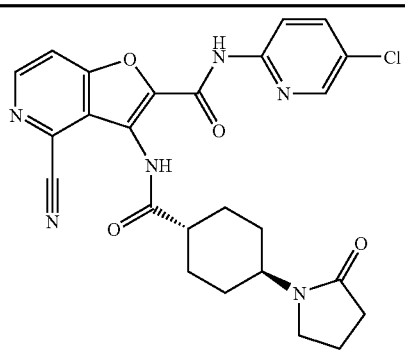 | APCI-MS M/Z: 507/509 [M + H]+ |
| 198 | 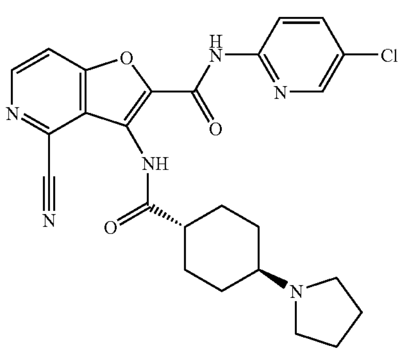 | APCI-MS M/Z: 493/495 [M + H]+ |

TABLE 49-continued

| Ex. No. | Structure | Physicochemical Properties |
|---|---|---|
| 199 | 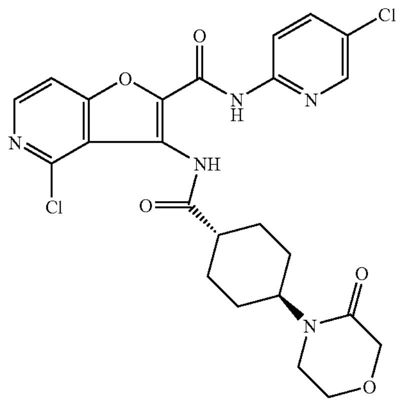 | APCI-MS M/Z: 532/534 [M + H]+ |
| 200 | 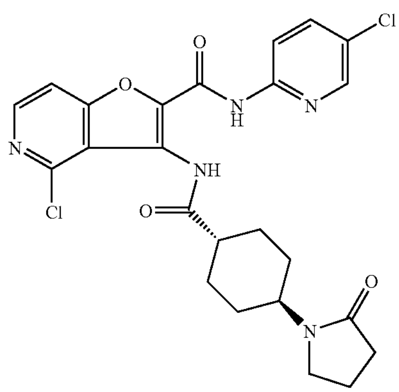 | APCI-MS M/Z: 516/518 [M + H]+ |

TABLE 50

| Ex. No. | Structure | Physicochemical Properties |
|---|---|---|
| 201 | 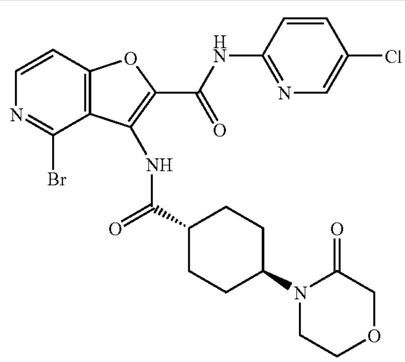 | APCI-MS M/Z: 576/578 [M + H]+ |

TABLE 50-continued

| Ex. No. | Structure | Physicochemical Properties |
|---|---|---|
| 202 | 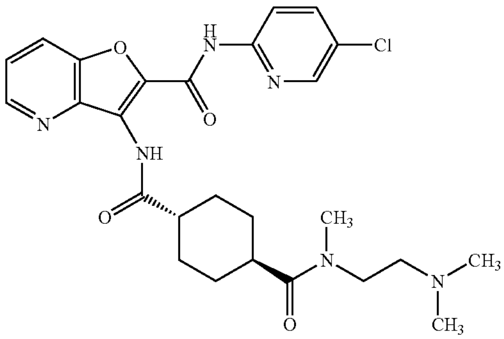 | APCI-MS M/Z: 527/529 [M + H]+ |

Examples 203, 204

The ester obtained in Reference Example 79 and amino compounds are treated in a similar manner to Example 141 to give the following compounds.

TABLE 51

| Ex. No. | Structure | Physicochemical Properties |
|---|---|---|
| 203 | 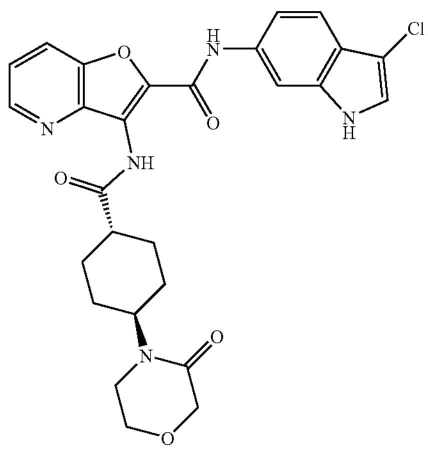 | APCI-MS M/Z: 536/538 [M + H]+ |
| 204 | 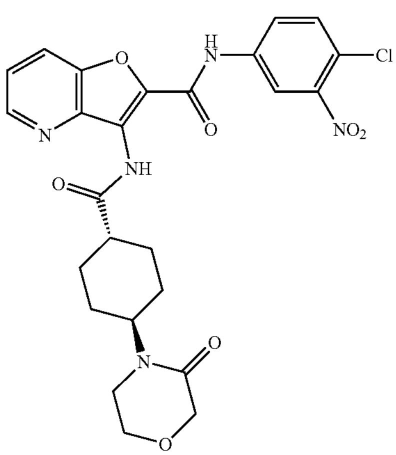 | ESI-MS M/Z: 540/542 [M − H]− |

Example 205

N-(3-Amino-4-chlorophenyl)-3-({[trans-4-(3-oxo-morpholin-4-yl)cyclohexyl]carbonyl}amino)furo[3,2-b]pyridine-2-carboxamide

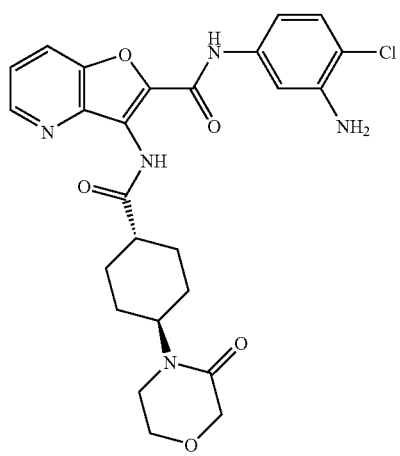

N-(4-Chloro-3-nitrophenyl)-3-({[trans-4-(3-oxomorphoin-4-yl)cyclohexyl]carbonyl}amino)furo[3,2-b]pyridine-2-carboxamide (50 mg) obtained in Example 204 is suspended in ethanol (3 ml), and thereto is added tin(II) chloride dihydrate (104 mg). The mixture is stirred at room temperature for 15 hours, followed by at 50° C. for 5 hours, and then at 70° C. for 7 hours. After allowing to cool, saturated aqueous sodium hydrogen carbonate solution and chloroform are poured to the reaction solution. The mixture is then stirred at room temperature vigorously. The organic layer is separated, dried over sodium sulfate, and evaporated under reduced pressure to remove the solvent. The residue is purified by silica gel column chromatography (eluent: chloroform followed by chloroform/methanol=10/1). The resulting solid is suspended in diethyl ether. The precipitates are collected by filtration to give the title compound (32 mg).

APCI-MS M/Z:512/514[M+H]$^+$

Examples 206-208

The amine compound obtained in Reference Example 125 and corresponding carboxylic acids are treated in a similar manner to Example 2 to give the following compound.

TABLE 52

| Ex. No. | Structure | Physicochemical Properties |
|---|---|---|
| 206 | 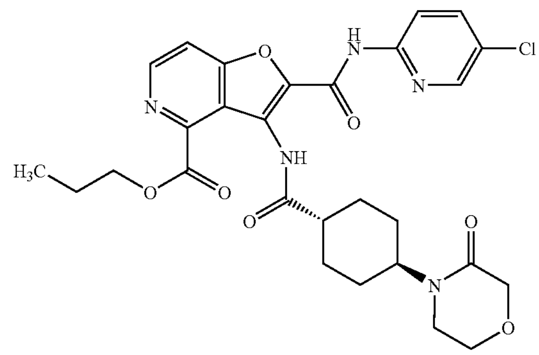 | APCI-MS M/Z: 584/586 [M + H]$^+$ |
| 207 | 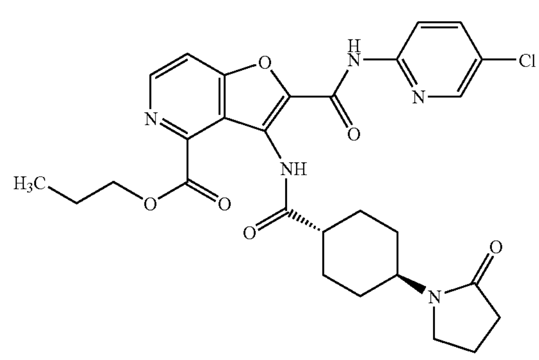 | APCI-MS M/Z: 568/570 [M + H]$^+$ |

TABLE 52-continued

| Ex. No. | Structure | Physicochemical Properties |
|---|---|---|
| 208 | 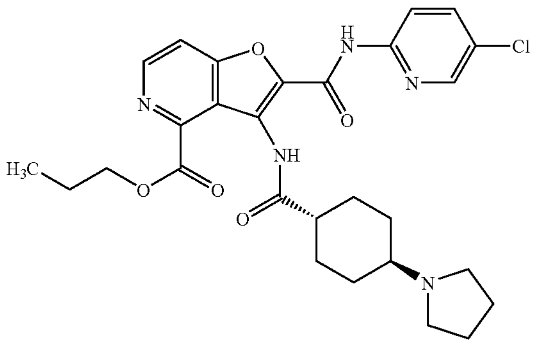 | APCI-MS M/Z: 554/556 [M + H]⁺ |

Examples 209-211

The compounds obtained in Examples 206-208 are treated in a similar manner to Example 79 to give the following compounds.

TABLE 53

| Ex. No. | Structure | Physicochemical Properties |
|---|---|---|
| 209 | 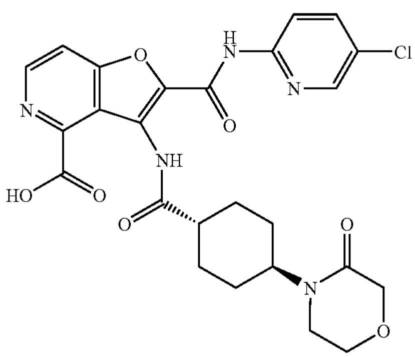 | ESI-MS M/Z: 540/542 [M − H]⁻ |
| 210 | 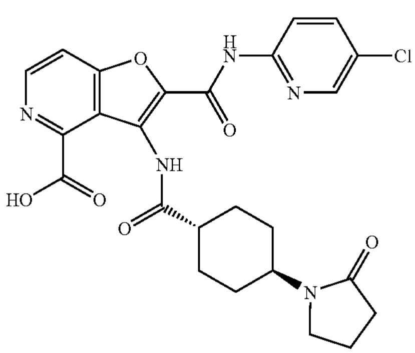 | ESI-MS M/Z: 524/526 [M − H]⁻ |

TABLE 53-continued

| Ex. No. | Structure | Physicochemical Properties |
|---|---|---|
| 211 | 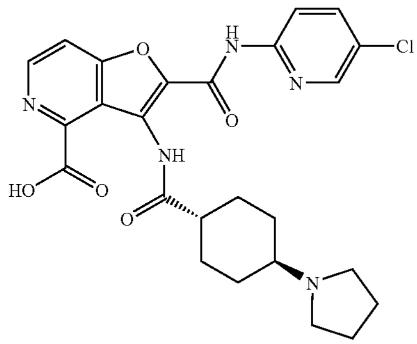 | ESI-MS M/Z: 510/512 [M − H]− |

Examples 212-214

The compounds obtained in Examples 209-211 are treated in a similar manner to Example 85 to give the following compounds.

TABLE 54

| Ex. No. | Structure | Physicochemical Properties |
|---|---|---|
| 212 | 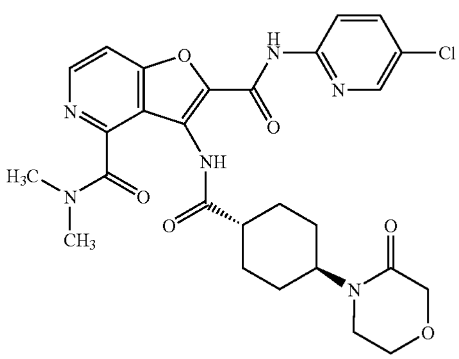 | APCI-MS M/Z: 569/571 [M + H]+ |
| 213 | 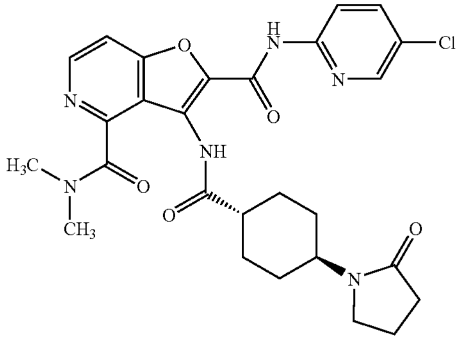 | APCI-MS M/Z: 553/555 [M + H]+ |

TABLE 54-continued

| Ex. No. | Structure | Physicochemical Properties |
|---|---|---|
| 214 | 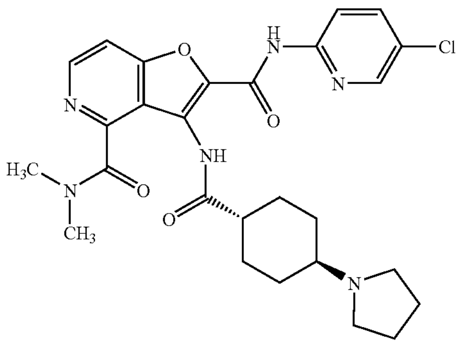 | APCI-MS M/Z: 539/541 [M + H]$^+$ |

Examples 215-355

In a similar manner to those described in the Examples above, the following compounds can be obtained.

TABLE 55

| Ex. No. | Structure |
|---|---|
| 215 | 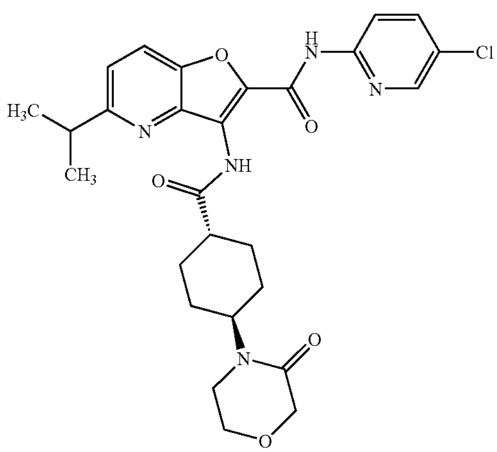 |
| 216 | 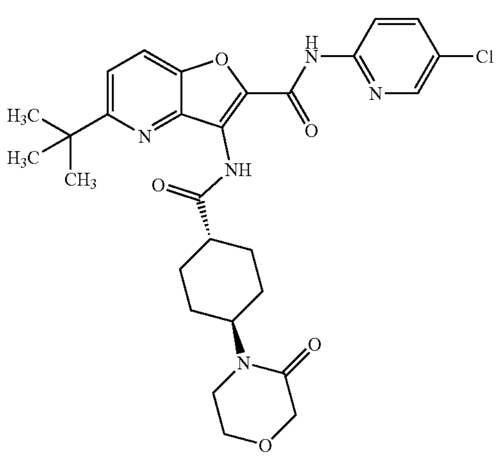 |

TABLE 55-continued
| Ex. No. | Structure |
|---|---|
| 217 | 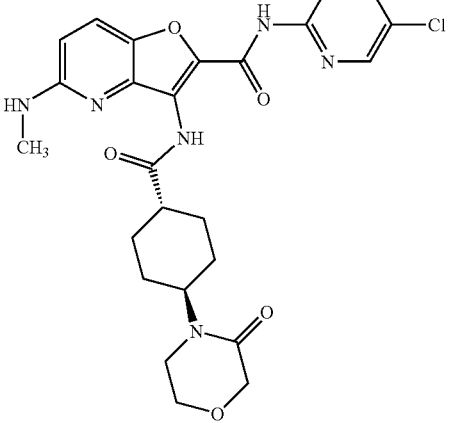 |
| 218 | 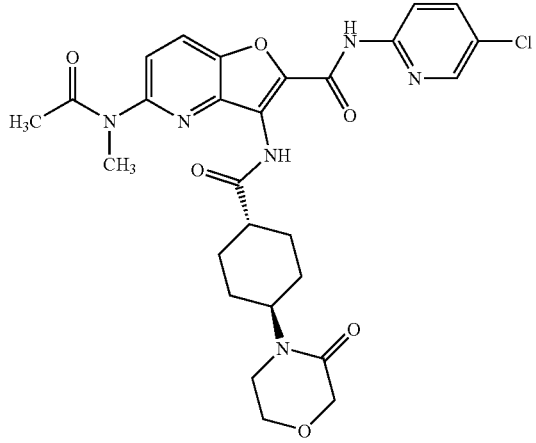 |
| 219 | 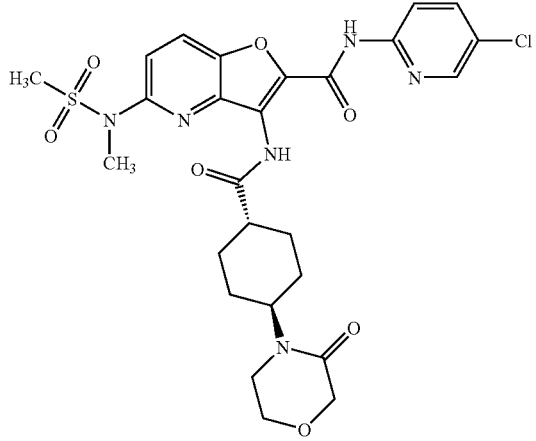 |

TABLE 55-continued
| Ex. No. | Structure |
| --- | --- |
| 220 | 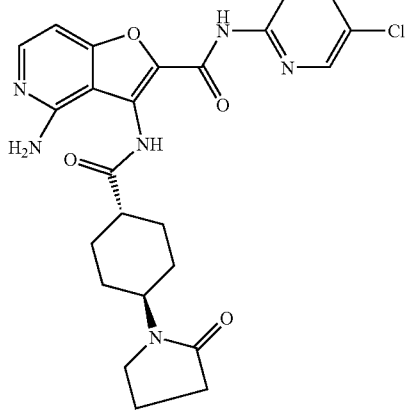 |
| 221 | 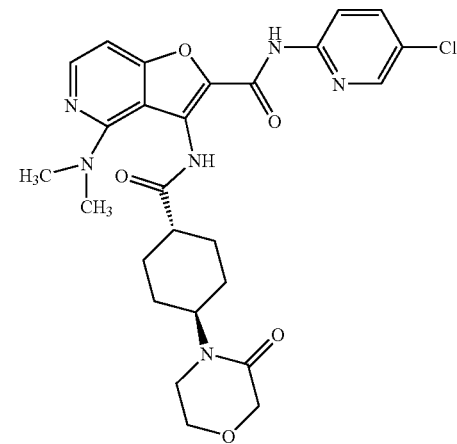 |
| 222 | 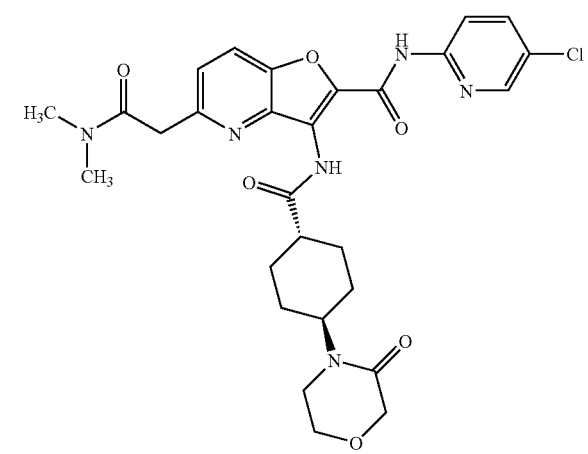 |

TABLE 56
| Ex. No. | Structure |
|---------|-----------|
| 223 | 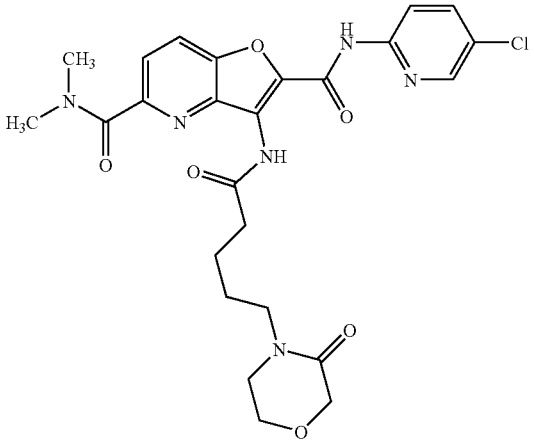 |
| 224 | 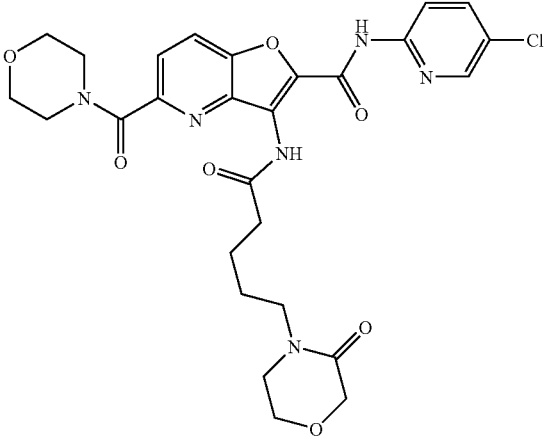 |
| 225 | 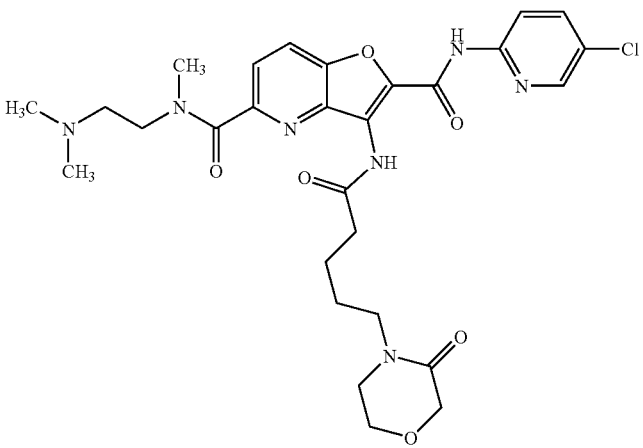 |

TABLE 56-continued

| Ex. No. | Structure |
| --- | --- |
| 226 | 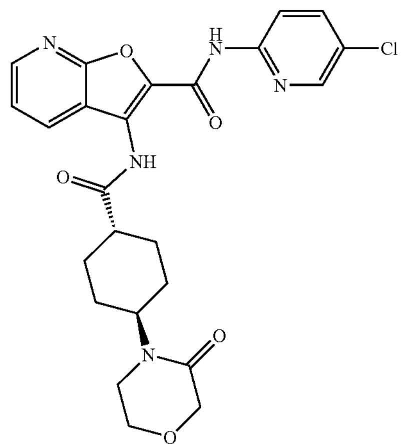 |

TABLE 57

| Ex. No. | Structure |
| --- | --- |
| 227 | 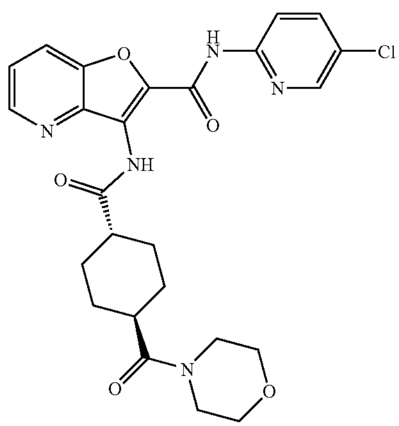 |
| 228 | 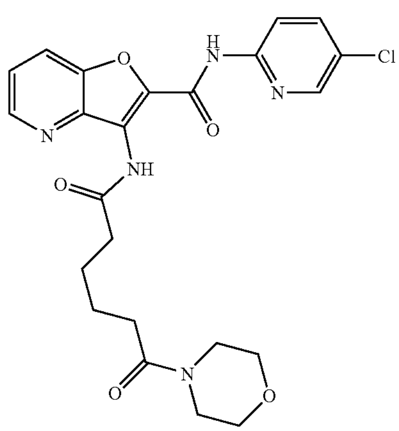 |

TABLE 57-continued

| Ex. No. | Structure |
| --- | --- |
| 229 | 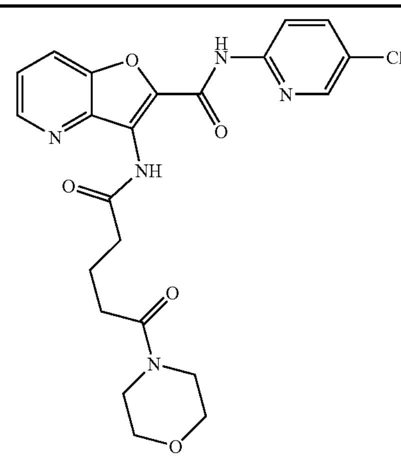 |
| 230 | 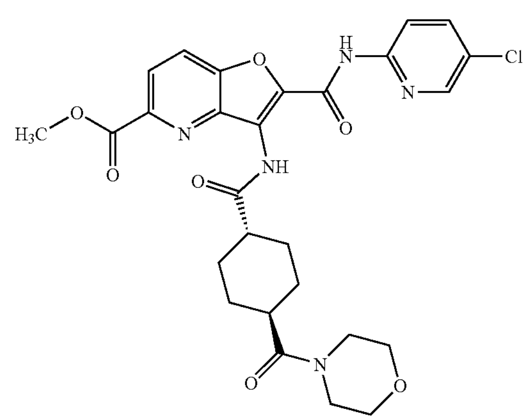 |

TABLE 57-continued

| Ex. No. | Structure |
|---|---|
| 231 | (structure) |
| 232 | (structure) |
| 233 | (structure) |
| 234 | (structure) |

TABLE 58

| Ex. No. | Structure |
|---|---|
| 235 | (structure) |

TABLE 58-continued

| Ex. No. | Structure |
|---|---|
| 236 | 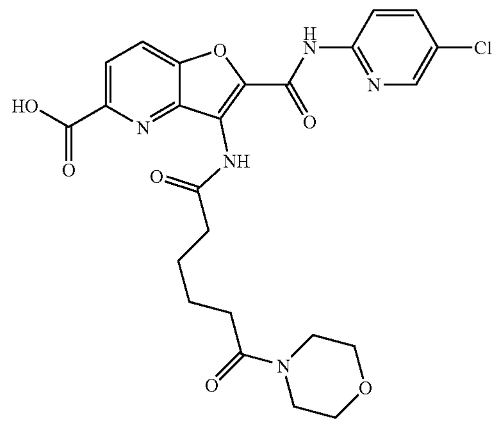 |
| 237 | 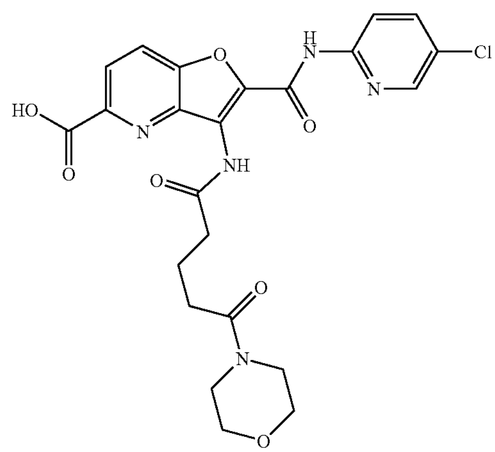 |
| 238 | 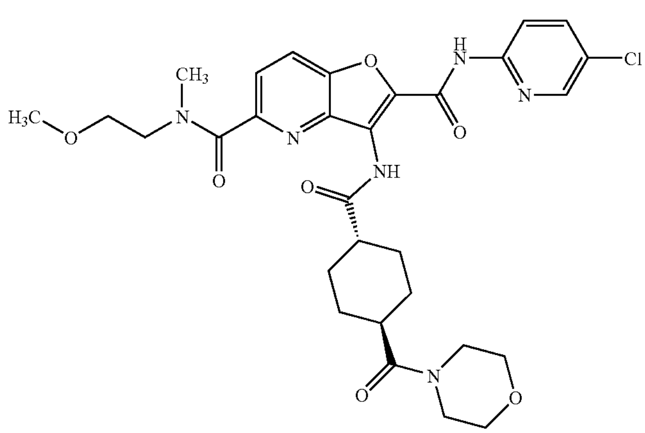 |

TABLE 58-continued

| Ex. No. | Structure |
|---------|-----------|
| 239 | 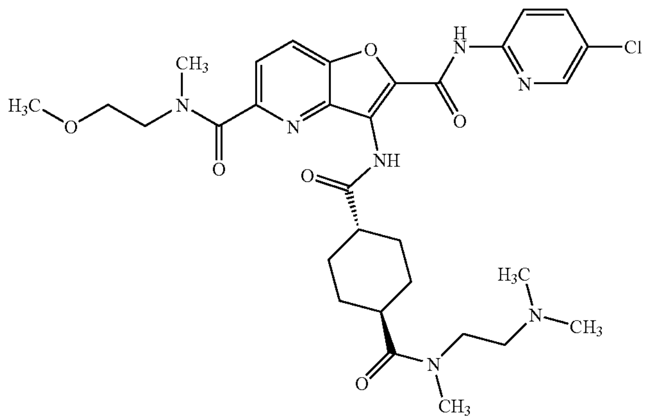 |
| 240 | 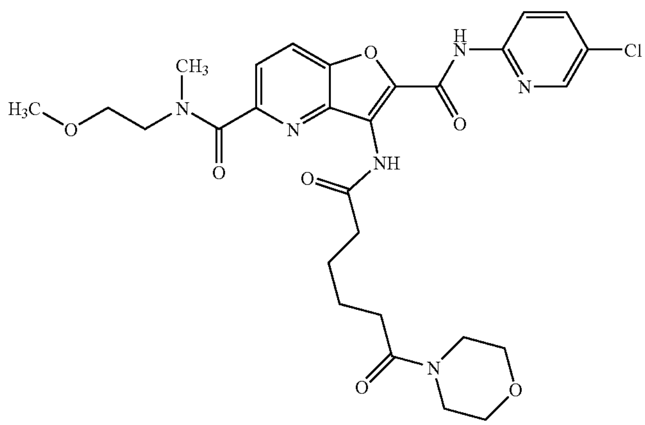 |
| 241 | 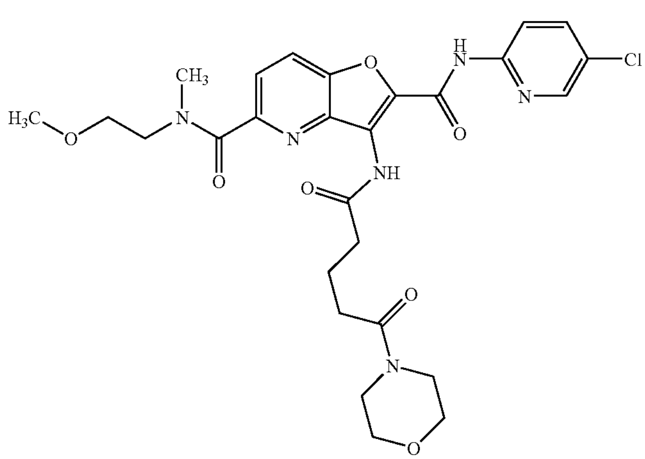 |

TABLE 58-continued

| Ex. No. | Structure |
|---|---|
| 242 | 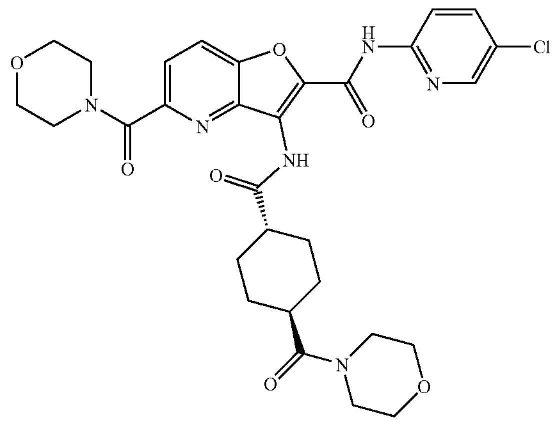 |

TABLE 59

| Ex. No. | Structure |
|---|---|
| 243 | 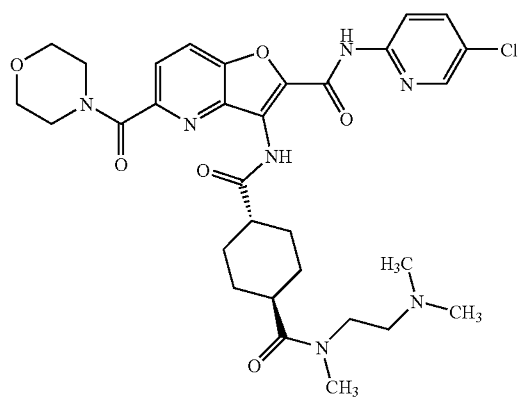 |
| 244 | 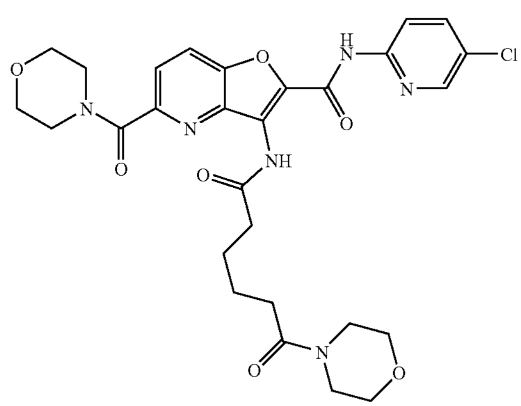 |

TABLE 59-continued

| Ex. No. | Structure |
|---|---|
| 245 | 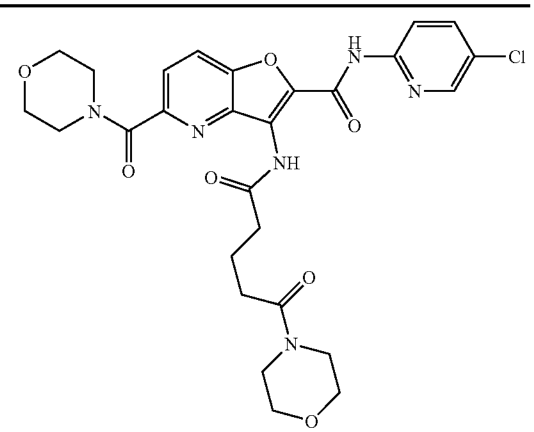 |
| 246 | 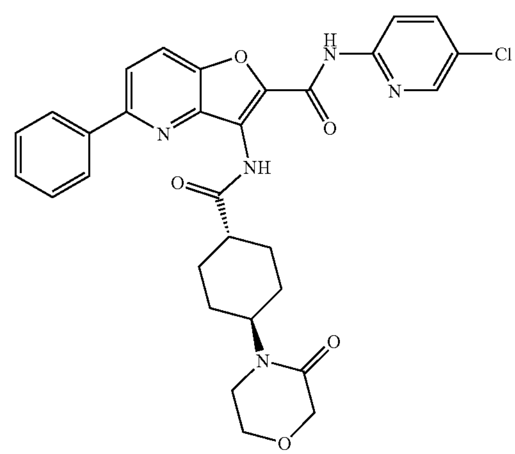 |

TABLE 59-continued

| Ex. No. | Structure |
|---|---|
| 247 | 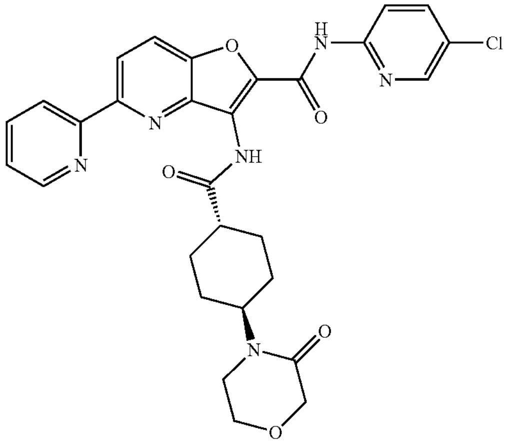 |
| 248 | 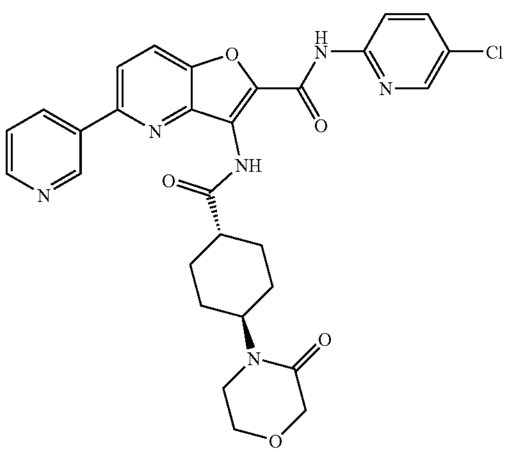 |
| 249 | 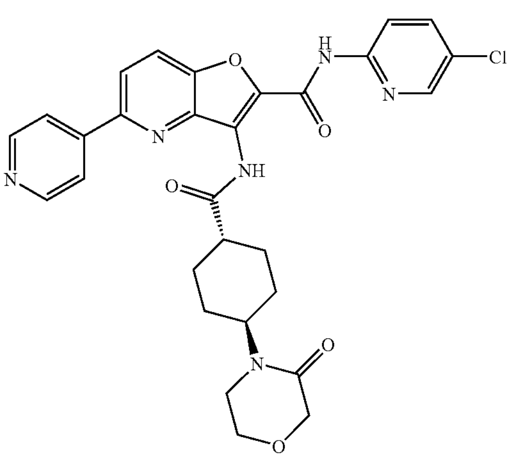 |

TABLE 59-continued

| Ex. No. | Structure |
|---|---|
| 250 | |

TABLE 60

| Ex. No. | Structure |
|---|---|
| 251 | 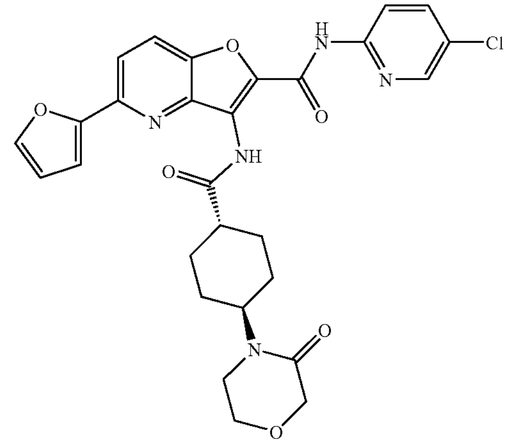 |
| 252 | 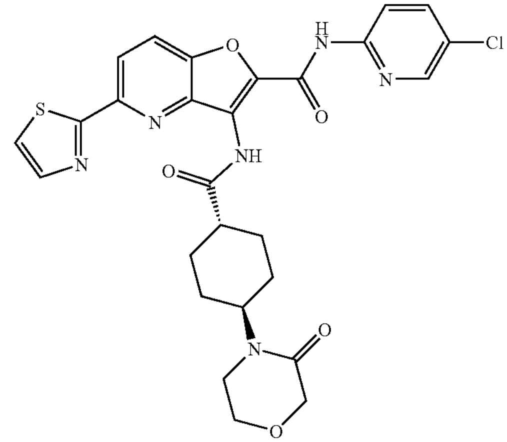 |

TABLE 60-continued

| Ex. No. | Structure |
|---|---|
| 253 | 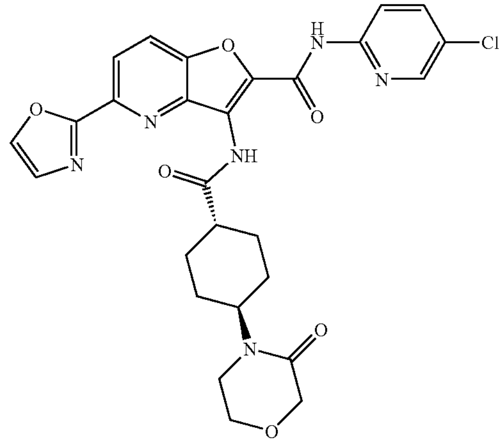 |
| 254 | 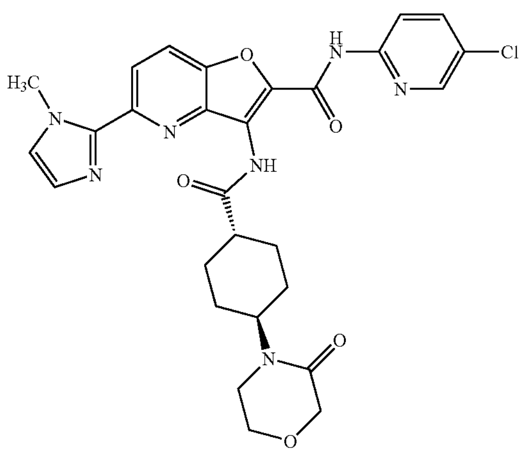 |
| 255 | 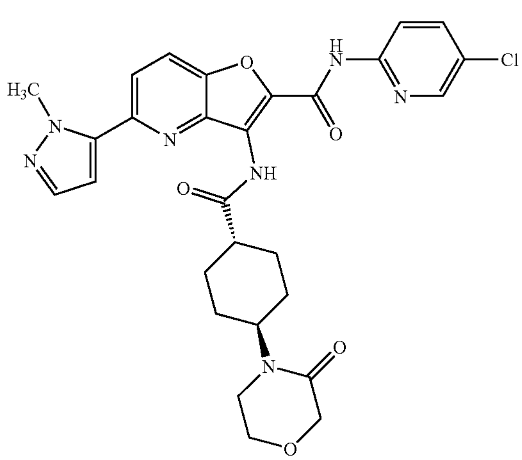 |
| 256 | |
| 257 | |
| 258 | |

TABLE 61

| Ex. No. | Structure |
|---|---|
| 259 | *furo[3,2-b]pyridine-2-carboxamide with N-(pyridin-4-yl), 3-NH-C(O)-cyclohexyl-(3-oxomorpholin-4-yl)* |
| 260 | *furo[3,2-c]pyridine-2-carboxamide with N-(6-chloropyridin-3-yl), 3-NH-C(O)-cyclohexyl-(3-oxomorpholin-4-yl)* |
| 261 | *furo[3,2-c]pyridine-2-carboxamide with N-(pyridin-4-yl), 3-NH-C(O)-cyclohexyl-(3-oxomorpholin-4-yl)* |

TABLE 61-continued

| Ex. No. | Structure |
|---|---|
| 262 | *furo[2,3-b]pyridine-2-carboxamide with N-(6-chloropyridin-3-yl), 3-NH-C(O)-cyclohexyl-(3-oxomorpholin-4-yl)* |
| 263 | *furo[2,3-b]pyridine-2-carboxamide with N-(pyridin-4-yl), 3-NH-C(O)-cyclohexyl-(3-oxomorpholin-4-yl)* |
| 264 | *5-(methoxycarbonyl)furo[3,2-b]pyridine-2-carboxamide with N-(6-chloropyridin-3-yl), 3-NH-C(O)-cyclohexyl-(3-oxomorpholin-4-yl)* |

TABLE 61-continued

| Ex. No. | Structure |
|---|---|
| 265 | *(structure)* |
| 266 | *(structure)* |

TABLE 62

| Ex. No. | Structure |
|---|---|
| 267 | *(structure)* |

TABLE 62-continued

| Ex. No. | Structure |
|---|---|
| 268 | *(structure)* |
| 269 | *(structure)* |
| 270 | *(structure)* |

TABLE 62-continued

| Ex. No. | Structure |
|---|---|
| 271 | (structure) |

TABLE 63

| Ex. No. | Structure |
|---|---|
| 272 | (structure) |
| 273 | (structure) |

TABLE 63-continued

| Ex. No. | Structure |
|---|---|
| 274 | (structure) |
| 275 | (structure) |
| 276 | (structure) |

TABLE 63-continued
| Ex. No. | Structure |
|---|---|
| 277 | 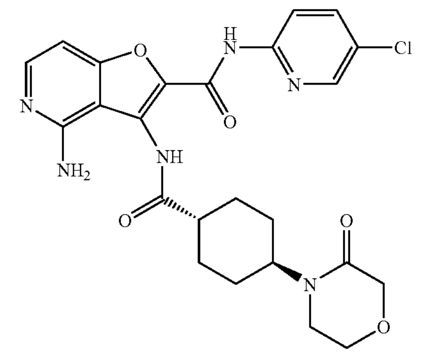 |
| 278 | 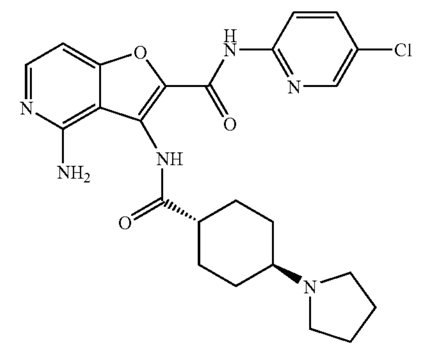 |
| 279 | 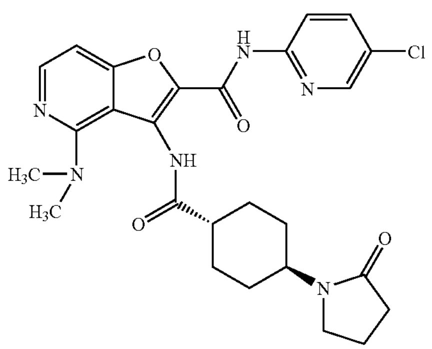 |
TABLE 64
| Ex. No. | Structure |
|---|---|
| 280 | 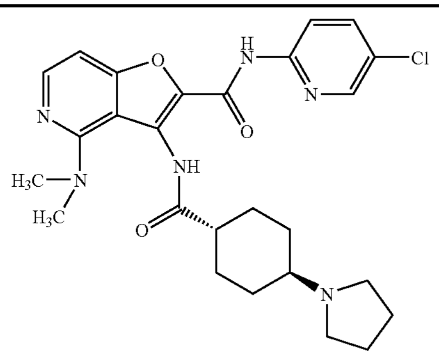 |
TABLE 64-continued
| Ex. No. | Structure |
|---|---|
| 281 | 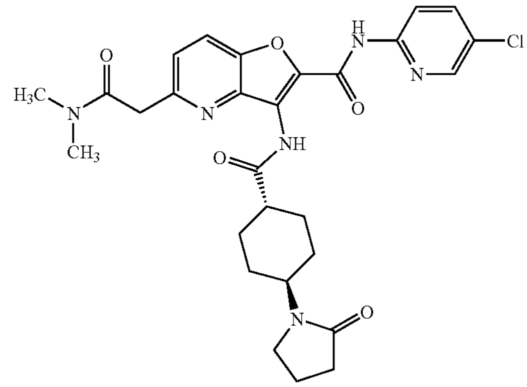 |
| 282 | 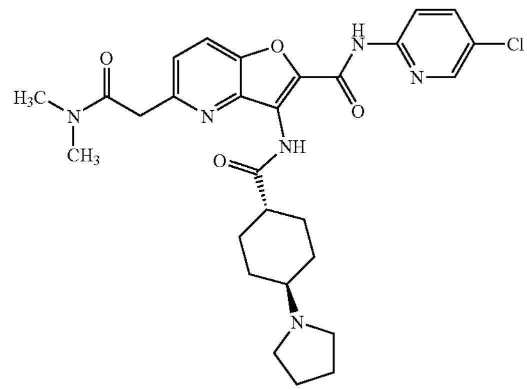 |
| 283 | 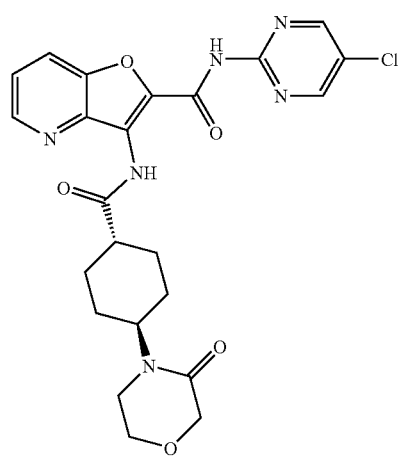 |

TABLE 64-continued
| Ex. No. | Structure |
|---|---|
| 284 | 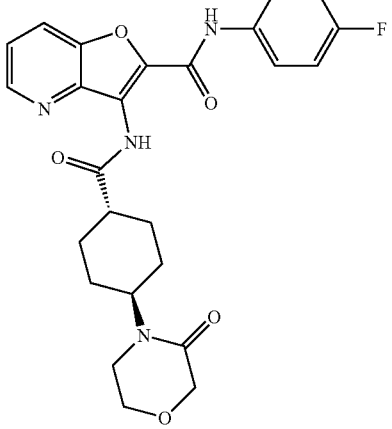 |
| 285 | 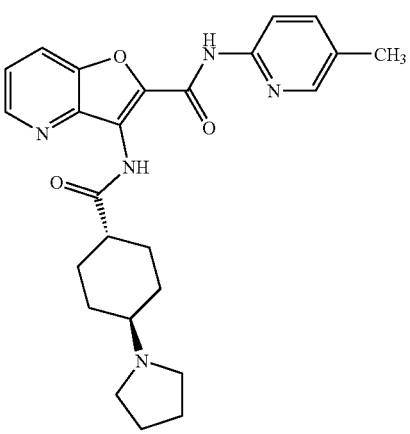 |
| 286 | 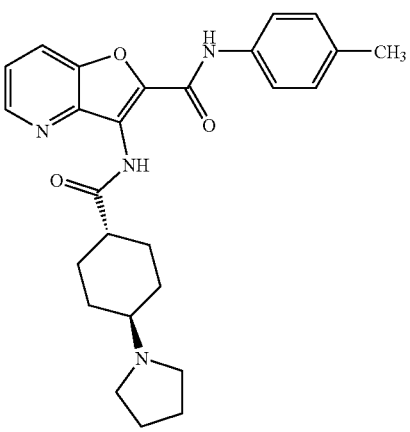 |
TABLE 64-continued
| Ex. No. | Structure |
|---|---|
| 287 | 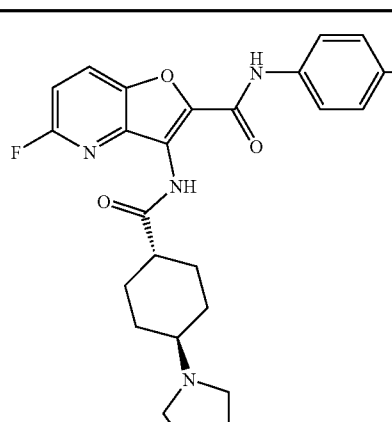 |
TABLE 65
| Ex. No. | Structure |
|---|---|
| 288 | 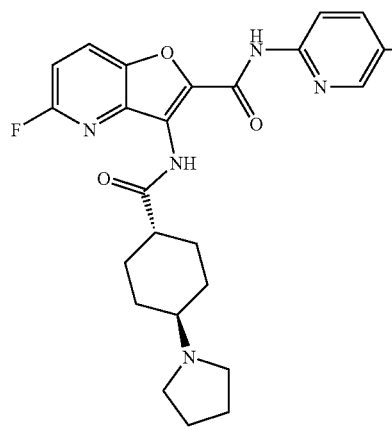 |
| 289 | 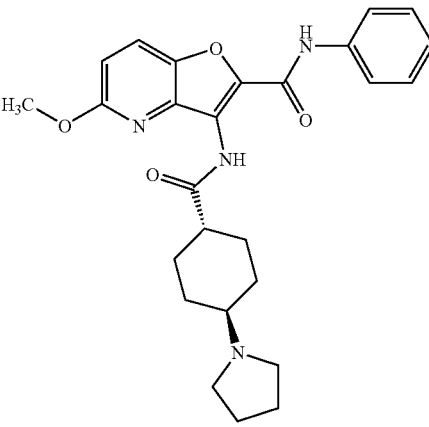 |

TABLE 65-continued

| Ex. No. | Structure |
|---|---|
| 290 | (5-methoxy-furo[3,2-b]pyridine-2-carboxylic acid (5-methyl-pyridin-2-yl)-amide, 3-position substituted with NH-C(O)-trans-cyclohexyl-pyrrolidin-1-yl) |
| 291 | (5-fluoro-furo[3,2-b]pyridine-2-carboxylic acid (4-methylphenyl)-amide, 3-position substituted with NH-C(O)-trans-cyclohexyl-(3-oxomorpholin-4-yl)) |
| 292 | (5-fluoro-furo[3,2-b]pyridine-2-carboxylic acid (5-methyl-pyridin-2-yl)-amide, 3-position substituted with NH-C(O)-trans-cyclohexyl-(3-oxomorpholin-4-yl)) |
| 293 | (5-methoxy-furo[3,2-b]pyridine-2-carboxylic acid (4-methylphenyl)-amide, 3-position substituted with NH-C(O)-trans-cyclohexyl-(3-oxomorpholin-4-yl)) |
| 294 | (5-methoxy-furo[3,2-b]pyridine-2-carboxylic acid (5-methyl-pyridin-2-yl)-amide, 3-position substituted with NH-C(O)-trans-cyclohexyl-(3-oxomorpholin-4-yl)) |
| 295 | (furo[3,2-b]pyridine-2-carboxylic acid (5-chloro-pyridin-2-yl)-amide, 3-position substituted with NH-C(O)-trans-cyclohexyl-C(O)-N(CH3)(CH2CH2OH)) |

TABLE 66
| Ex. No. | Structure |
|---------|-----------|
| 296 | 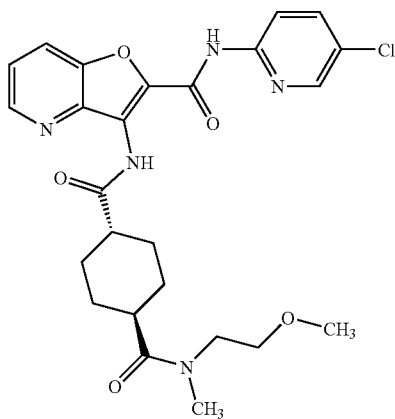 |
| 297 | 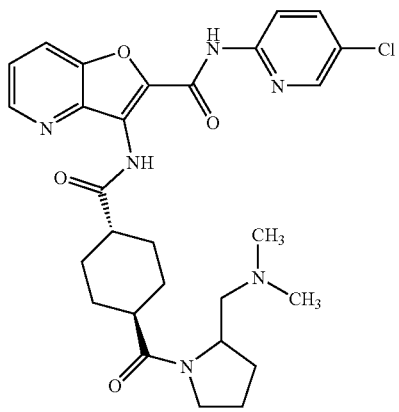 |
| 298 | 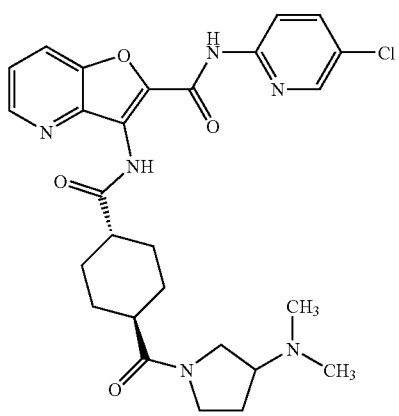 |
TABLE 66-continued
| Ex. No. | Structure |
|---------|-----------|
| 299 | 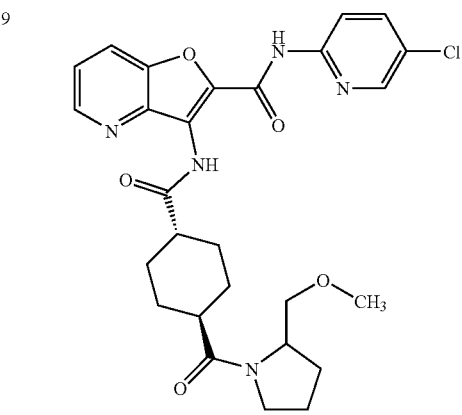 |
| 300 | 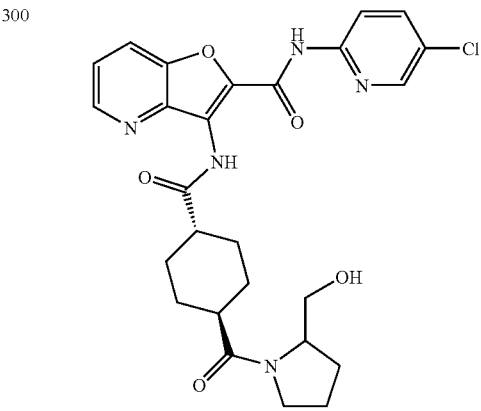 |
| 301 | 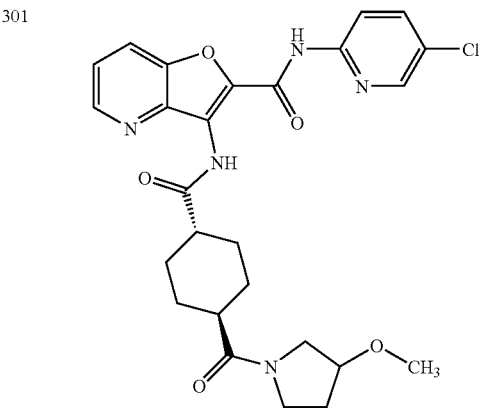 |

TABLE 66-continued

| Ex. No. | Structure |
|---|---|
| 302 | 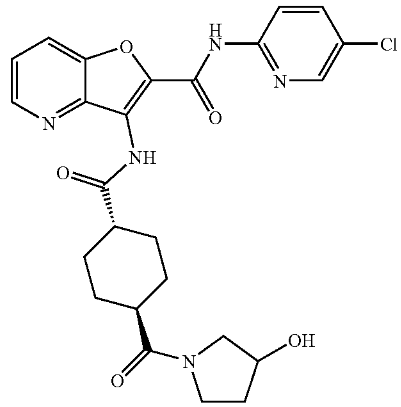 |
| 303 | 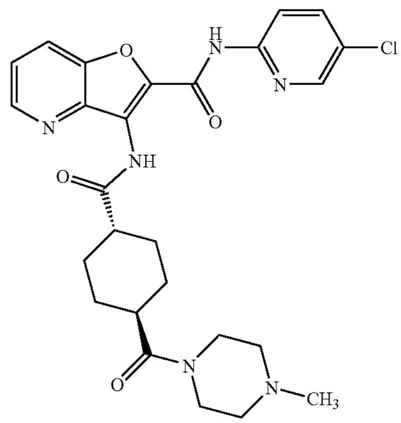 |

TABLE 67

| Ex. No. | Structure |
|---|---|
| 304 | 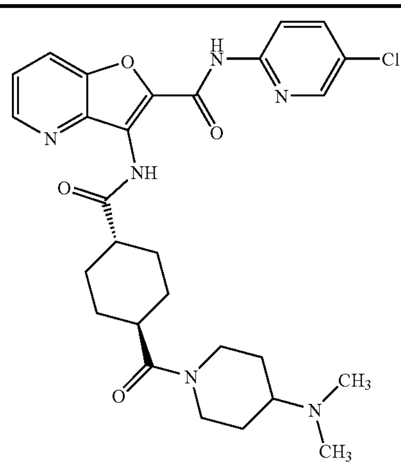 |

TABLE 67-continued

| Ex. No. | Structure |
|---|---|
| 305 | 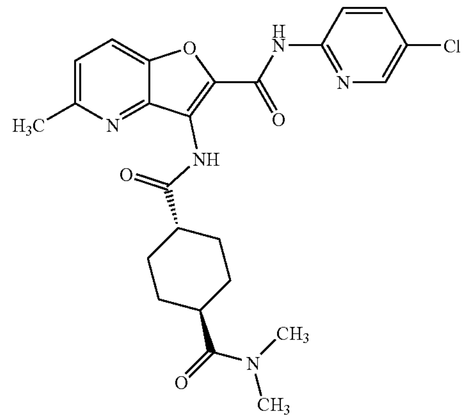 |
| 306 | 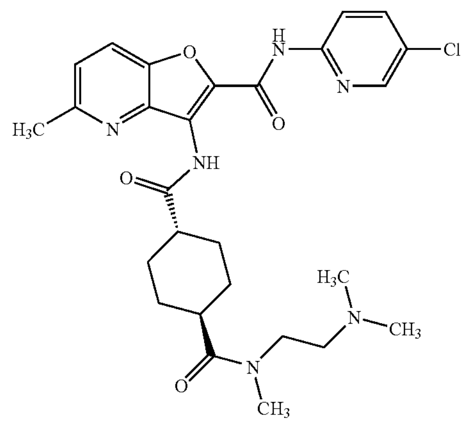 |
| 307 | 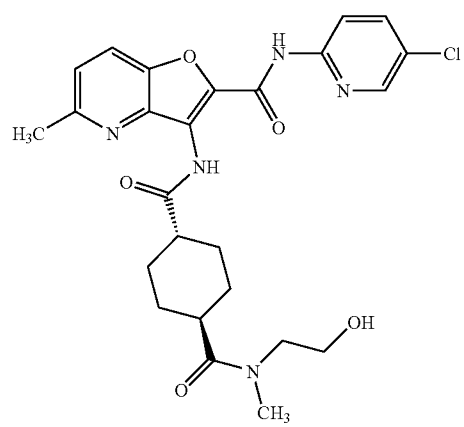 |

TABLE 67-continued
| Ex. No. | Structure |
|---|---|
| 308 | 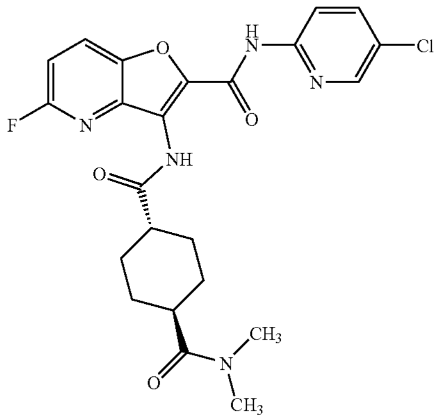 |
| 309 | 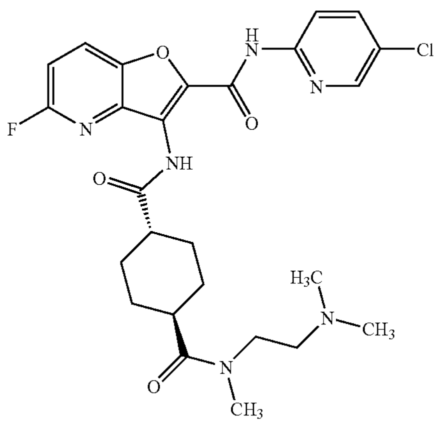 |
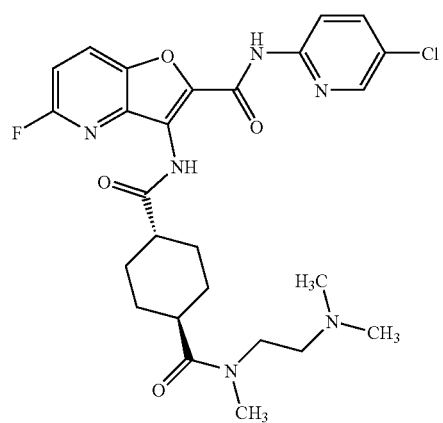
TABLE 67-continued
| Ex. No. | Structure |
|---|---|
| 311 | |
TABLE 68
| Ex. No. | Structure |
|---|---|
| 312 | 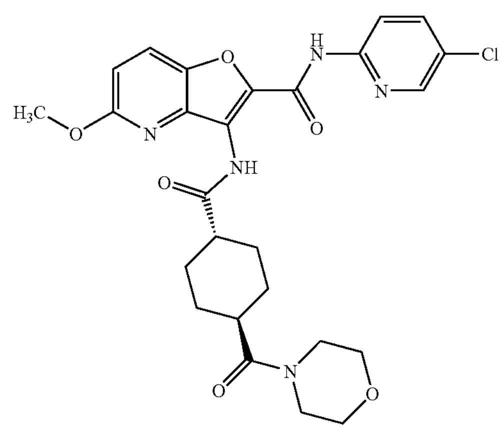 |
| 313 | 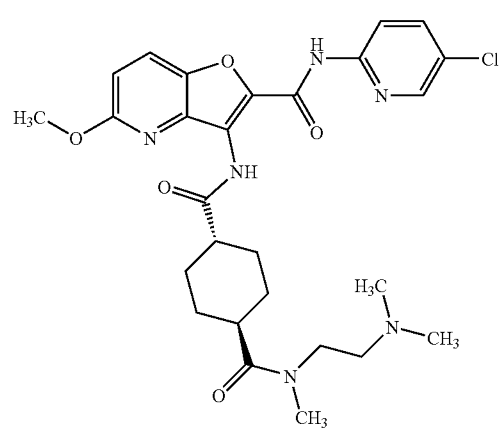 |
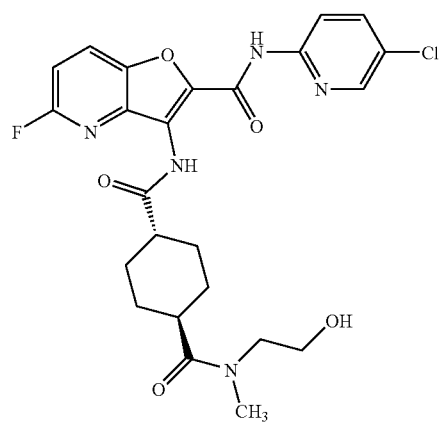
| 310 | |

TABLE 68-continued
| Ex. No. | Structure |
|---|---|
| 314 | 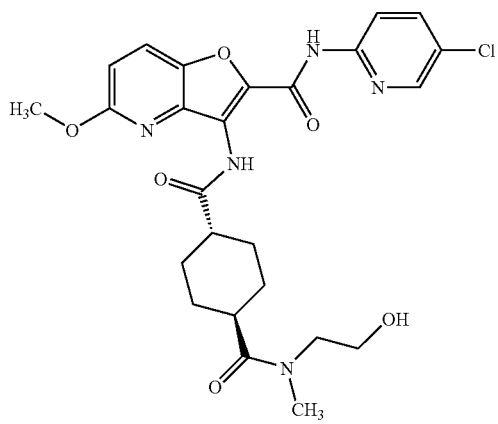 |
| 315 | 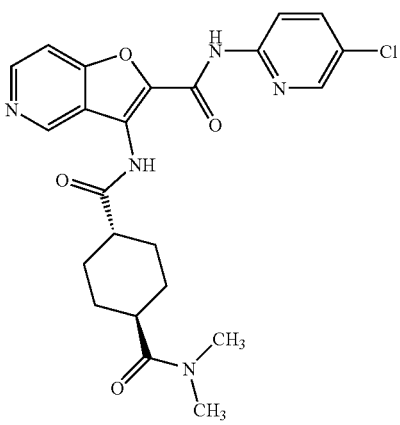 |
| 316 | 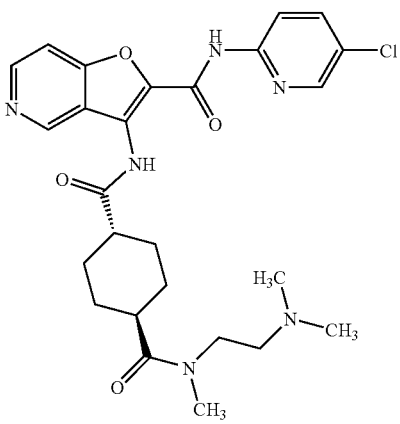 |
TABLE 68-continued
| Ex. No. | Structure |
|---|---|
| 317 | 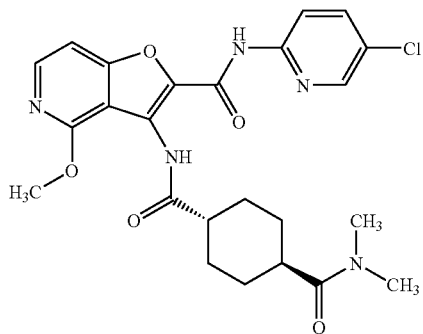 |
| 318 | 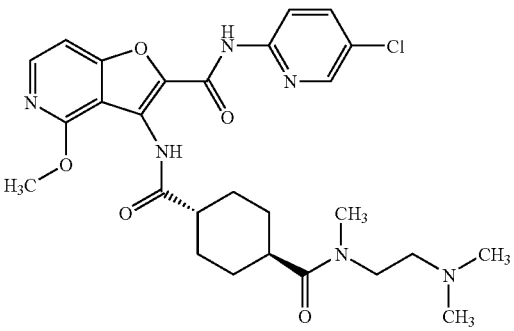 |
| 319 | 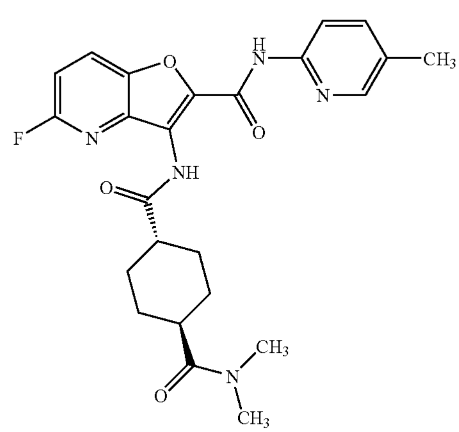 |

TABLE 69

| Ex. No. | Structure |
|---|---|
| 320 | 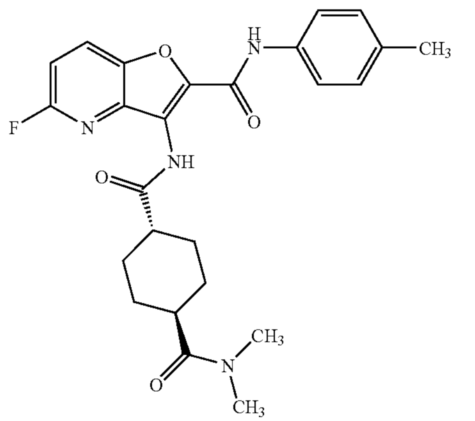 |
| 321 | 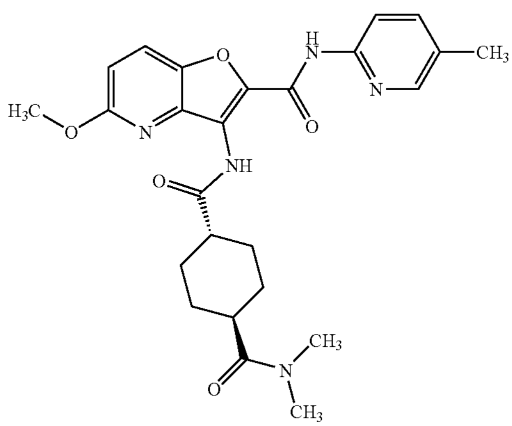 |
| 322 | 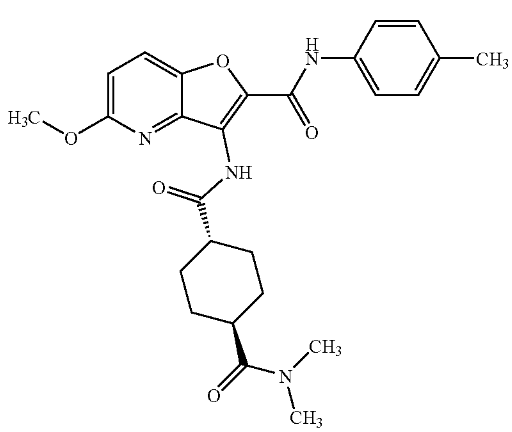 |

TABLE 69-continued

| Ex. No. | Structure |
|---|---|
| 323 | 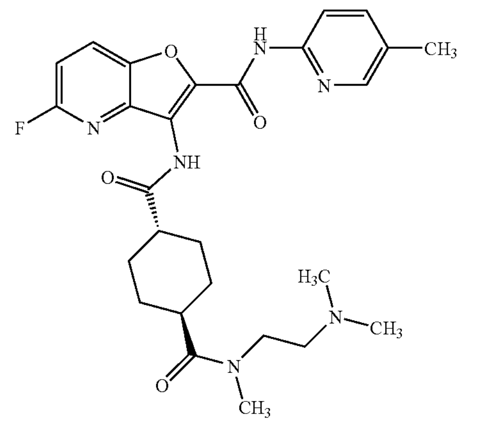 |
| 324 | 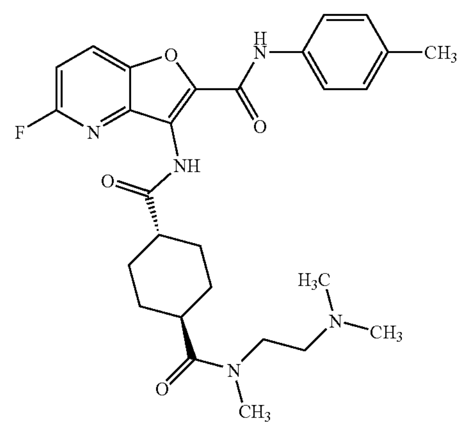 |
| 325 | 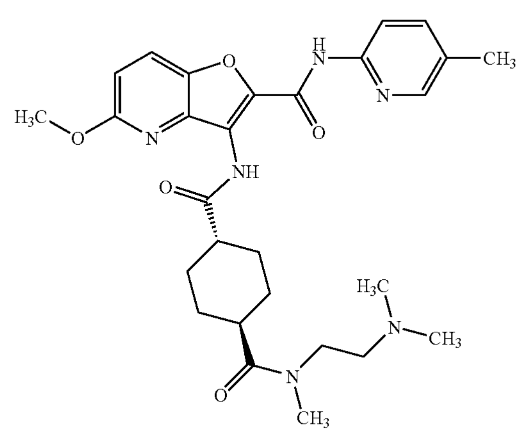 |

TABLE 69-continued

| Ex. No. | Structure |
|---|---|
| 326 | 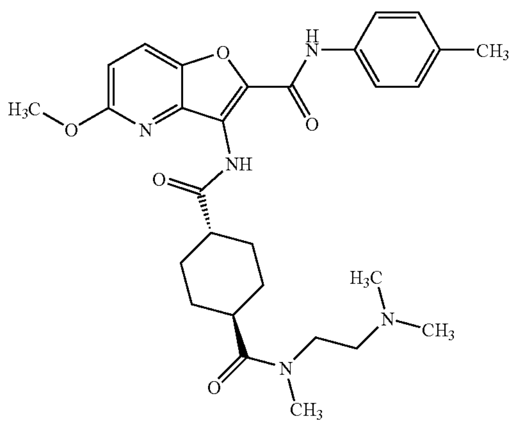 |
| 327 | 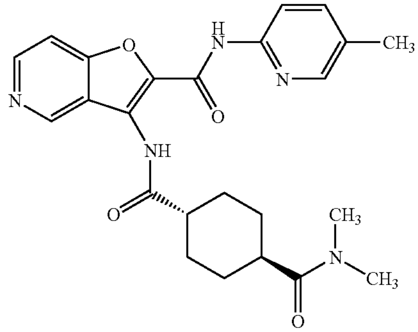 |

TABLE 70

| Ex. No. | Structure |
|---|---|
| 328 | 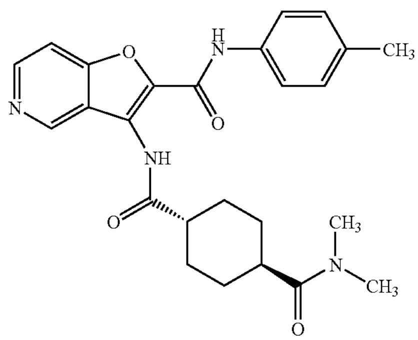 |

TABLE 70-continued

| Ex. No. | Structure |
|---|---|
| 329 | 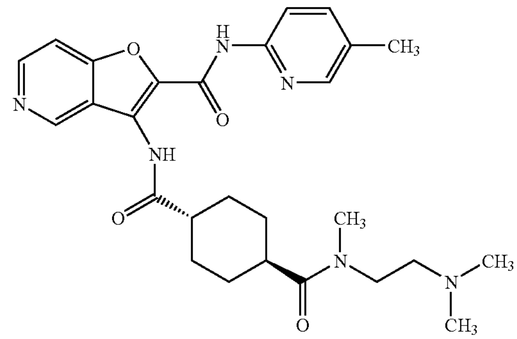 |
| 330 | 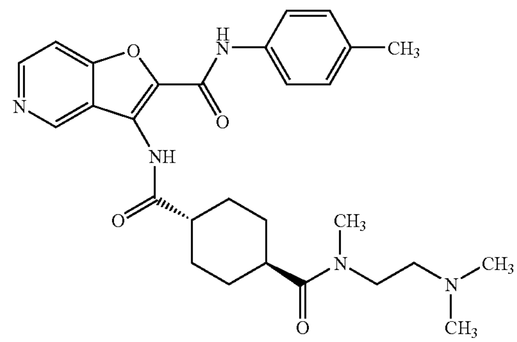 |
| 331 | 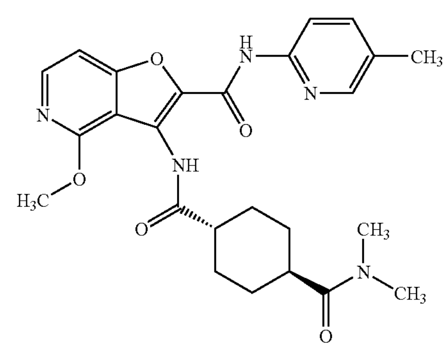 |
| 332 | 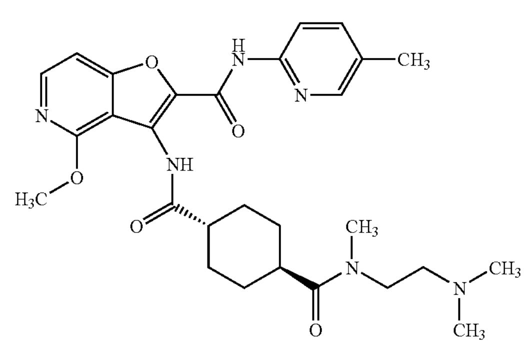 |

TABLE 70-continued
| Ex. No. | Structure |
|---|---|
| 333 | 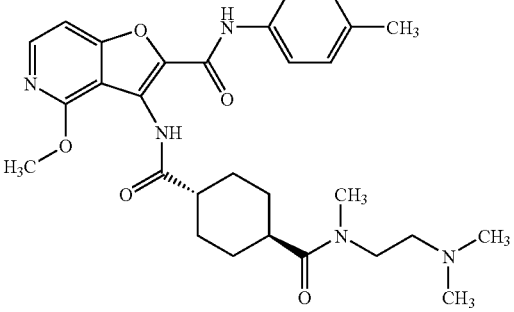 |
| 334 | 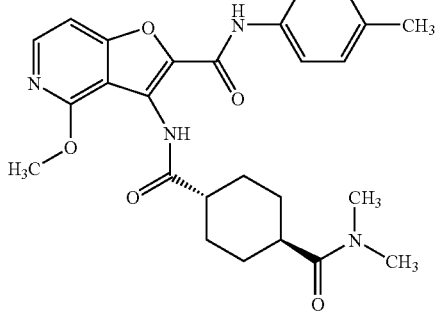 |
| 335 | 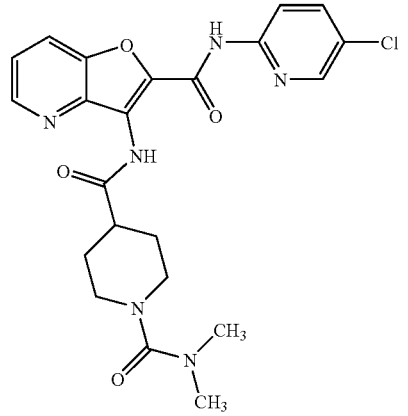 |
TABLE 71
| Ex. No. | Structure |
|---|---|
| 336 | 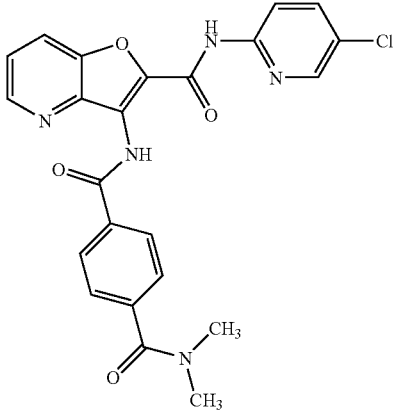 |
| 337 | 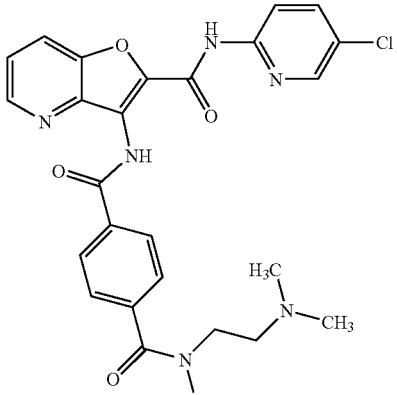 |
| 338 | 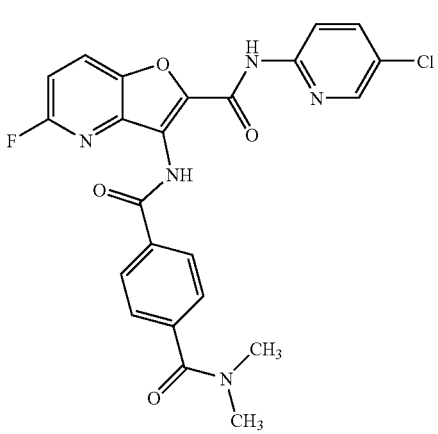 |

TABLE 71-continued
| Ex. No. | Structure |
|---|---|
| 339 | 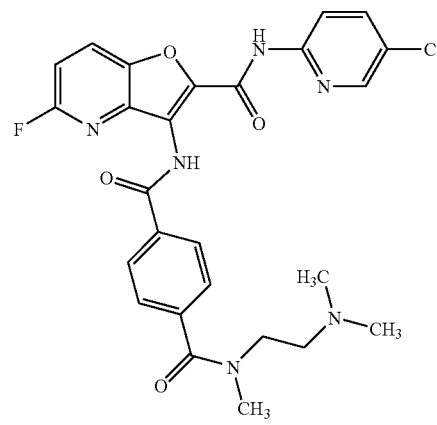 |
| 340 | 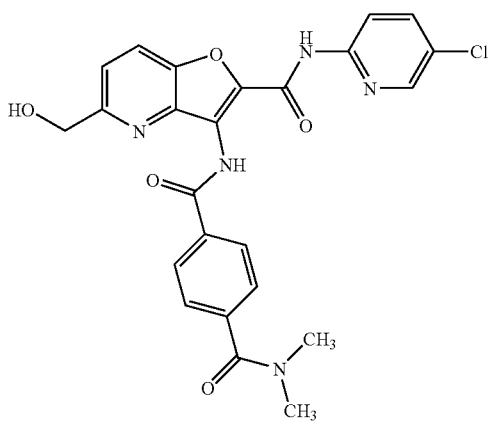 |
| 341 | 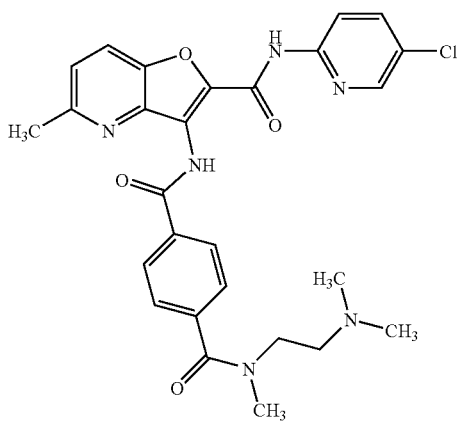 |
TABLE 71-continued
| Ex. No. | Structure |
|---|---|
| 342 | 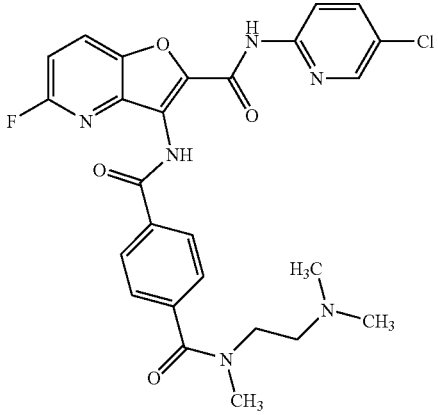 |
| 343 | 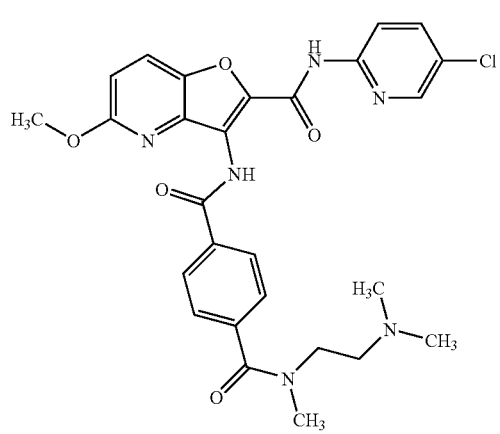 |
TABLE 72
| Ex. No. | Structure |
|---|---|
| 344 | 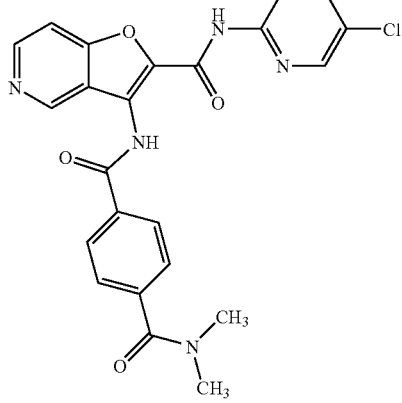 |

TABLE 72-continued
| Ex. No. | Structure |
|---|---|
| 345 | 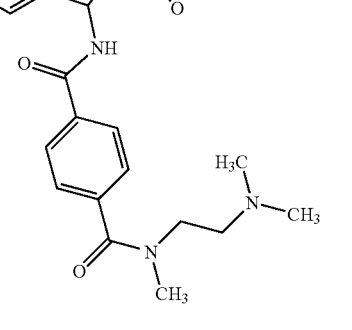 |
| 346 | 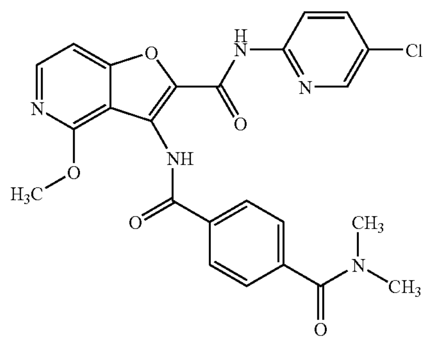 |
| 347 | 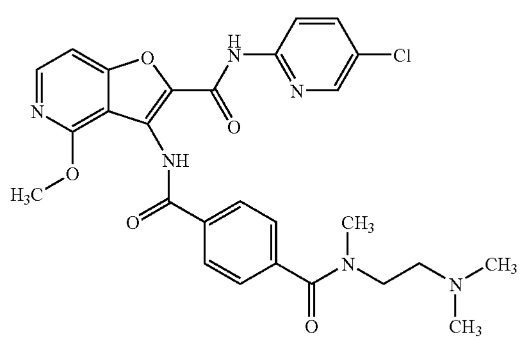 |
| 348 | 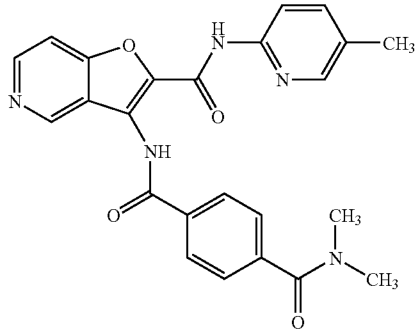 |
TABLE 72-continued
| Ex. No. | Structure |
|---|---|
| 349 | 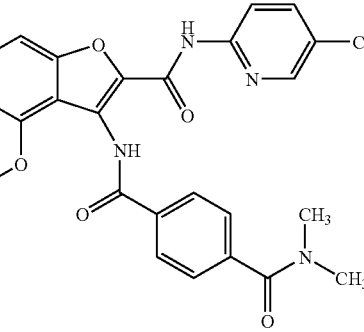 |
| 350 | |
| 351 | |
TABLE 73
| Ex. No. | Structure |
|---|---|
| 352 | 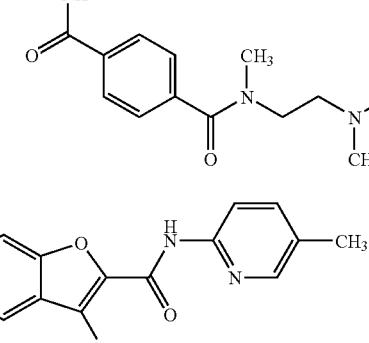 |

TABLE 73-continued

| Ex. No. | Structure |
|---|---|
| 352 | *(furo[3,2-c]pyridine-2-carboxamide with N-(4-methylphenyl) group and 3-NH-C(O)-C6H4-C(O)-N(CH3)-CH2CH2-N(CH3)2 substituent)* |
| 354 | *(4-methoxy furo[3,2-c]pyridine-2-carboxamide with N-(5-methylpyridin-2-yl) group and 3-NH-C(O)-C6H4-C(O)-N(CH3)-CH2CH2-N(CH3)2 substituent)* |
| 355 | *(4-methoxy furo[3,2-c]pyridine-2-carboxamide with N-(4-methylphenyl) group and 3-NH-C(O)-C6H4-C(O)-N(CH3)-CH2CH2-N(CH3)2 substituent)* |

Reference Example 1

Methyl trans-4-[(t-butoxycarbonyl)amino]-cyclohexanecarboxylate

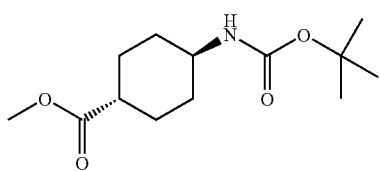

(1) Thionyl chloride (254 ml) is added dropwise to methanol (1500 ml) under cooling to −30° C. over a period of about an hour. After the addition, the reaction mixture is stirred at room temperature for 0.5 hours, and thereto is added trans-cyclohexane-1,4-dicarboxylic acid (500.0 g), and the mixture is stirred at room temperature for 17 hours. The reaction solution is concentrated under reduced pressure. The residue is diluted with chloroform, and washed with saturated aqueous sodium hydrogen carbonate solution and saturated brine. The organic layer is dried over sodium sulfate and evaporated to remove the solvent under reduced pressure. The resulting residue is crystallized from n-hexane. The product is collected by filtration and dried to give dimethyl trans-cyclohexane-1,4-dicarboxylate (545.0 g).

APCI-MS M/Z:201[M+H]$^+$.

(2) Dimethyl trans-cyclohexane-1,4-dicarboxylate (150.0 g) obtained in (1) above is dissolved in tetrahydrofuran (1500 ml), and to the solution is added dropwise a mixed solution of 28% sodium methoxide/methanol (149 g) and water (13.2 g) under ice-cooling. The reaction solution is warmed to room temperature, stirred for 3.5 hours, and thereto is poured n-hexane (1500 ml) and the mixture is filtered to collect the precipitates. The resulting solid is added to a mixture of conc. hydrochloric acid (50 ml), water (450 ml) and chloroform (1000 ml) under ice-cooling, and the mixture is stirred at room temperature for 20 minutes. The chloroform layer is separated and the aqueous layer is extracted with chloroform. The organic layers are combined, dried over sodium sulfate and evaporated to remove the solvent under reduced pressure. The resulting residue is crystallized from n-hexane, collected by filtration and dried to give trans-4-(methoxycarbonyl)cyclohexanecarboxylic acid (106.0 g).

ESI-MS M/Z: 185[M−H]$^-$.

(3) Trans-4-(methoxycarbonyl)cyclohexanecarboxylic acid (100.0 g) obtained in (2) above is dissolved in t-butanol (1000 ml), and thereto are added diphenylphosphoryl azide (155 g) and triethylamine (78.6 ml). The mixture is heated at about 60° C. for an hour and further heated under reflux for additional 17 hours. After allowing to cool, to the reaction solution is added ice-water, and the mixture is extracted with ethyl acetate. The organic layer is washed with saturated aqueous sodium hydrogen carbonate solution and saturated brine, dried over sodium sulfate and evaporated to remove the solvent under reduced pressure. The resulting residue is dissolved in methanol (250 ml), and thereto is added water (750 ml) and the mixture is stirred under ice-cooling. After 0.5 hours, the precipitates are collected by filtration, washed with water/methanol (3:1, 1000 ml) and n-hexane successively and dried to give the title compound (117.0 g).

APCI-MS M/Z: 275[M+H]$^+$.

Reference Example 2

Trans-4-(2-oxopyrrolidin-1-yl)cyclohexanecarboxylic acid

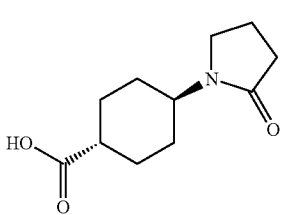

237

(1) Methyl trans-4-[(t-butoxycarbonyl)amino]-cyclohexanecarboxylate (234.0 g) obtained in Reference Example 1 is dissolved in dioxane (500 ml), and thereto is added 4 N hydrogen chloride/dioxane (500 ml), and the mixture is stirred at room temperature for 19 hours. The reaction solution is concentrated under reduced pressure, and the resulting residue is suspended in diethyl ether. The precipitates are collected by filtration to give methyl trans-4-aminocyclohexanecarboxylate hydrochloride (121.9 g).

APCI-MS M/Z: 158[M+H]$^+$.

(2) Methyl trans-4-aminocyclohexanecarboxylate hydrochloride (45.31 g) obtained in (1) above is suspended in dichloromethane (1000 ml), and thereto is added 4-chlorobutyryl chloride (31.5 ml) under ice-cooling, followed by dropwise addition of a solution of triethylamine (81.5 ml) in dichloromethane (80 ml). The reaction solution is warmed to room temperature, stirred for 3 hours and concentrated under reduced pressure. To the resulting residue are poured ethyl acetate and 5% hydrochloric acid, and the organic layer is separated, washed with saturated aqueous sodium hydrogen carbonate solution and saturated brine. The organic layer is dried over sodium sulfate and treated with activated carbon, and the filtrate is concentrated under reduced pressure. The resulting residue is suspended in diisopropyl ether. The precipitates are collected by filtration and dried to give methyl trans-4-[(4-chlorobutanoyl)amino]cyclohexanecarboxylate (38.81 g).

APCI-MS M/Z:262/264[M+H]$^+$.

(3) Sixty % sodium hydride in oil (9.60 g) is suspended in N,N-dimethylacetamide (500 ml), and to the mixture is added methyl trans-4-[(4-chlorobutanoyl)amino)]cyclohexanecarboxylate (52.32 g) obtained in (2) above in small portions under ice-cooling. The reaction solution is warmed to room temperature, stirred for 24 hours, and thereto are poured saturated aqueous ammonium chloride solution and ice-water. The reaction mixture is extracted with chloroform. The organic layer is washed with saturated brine, dried over magnesium sulfate and evaporated to remove the solvent under reduced pressure. The resulting residue is purified by silica gel column chromatography (eluent: ethyl acetate) and the residue is suspended in n-hexane/diisopropyl ether. The resulting crystals are collected by filtration and dried to give methyl trans-4-(2-oxopyrrolidin-1-yl)cyclohexanecarboxylate (39.20 g).

APCI-MS M/Z:226[M+H]$^+$.

(4) Methyl trans-4-(2-oxopyrrolidin-1-yl)cyclohexanecarboxylate (39.15 g) obtained in (3) above is dissolved in methanol (400 ml), and thereto is added 2 N aqueous sodium hydroxide solution (174 ml). The mixture is stirred at room temperature for 3 hours. The reaction solution is adjusted to pH 1-2 with 10% hydrochloric acid under ice-cooling, and saturated with sodium chloride, followed by extraction with chloroform. The organic layer is dried over sodium sulfate, and then evaporated to remove the solvent under reduced pressure. The resulting residue is suspended in a small amount of ethyl acetate, and diisopropyl ether is poured thereto. The resulting crystals are collected by filtration, washed with diisopropyl ether several times and dried to give the title compound (35.94 g).

ESI-MS M/Z:210[M−H]$^-$.

238

Reference Example 3

Trans-4-[acetyl(methyl)amino]cyclohexanecarboxylic acid

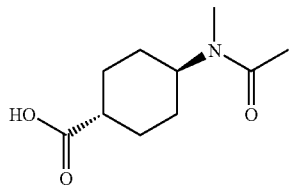

(1) Methyl trans-4-[(t-butoxycarbonyl)amino]cyclohexanecarboxylate (30.00 g) obtained in Reference Example 1 is dissolved in N,N-dimethylformamide (150 ml) and thereto is added 60% sodium hydride in oil (5.60 g) under ice-cooling. After stirring for 0.5 hours under the same cooling conditions, methyl iodide (14.5 ml) and methanol (0.15 ml) are added to the reaction solution successively. The reaction solution is warmed to room temperature and stirred for 4 hours. Under ice-cooling, to the reaction solution are poured saturated aqueous ammonium chloride solution and ice-water, and the mixture is extracted with ethyl acetate. The organic layer is washed with water and saturated brine successively, dried over sodium sulfate and evaporated to remove the solvent under reduced pressure. The resulting residue is purified by silica gel column chromatography (eluent: n-hexane/ethyl acetate=10/1, followed by 7/1) to give methyl trans-4-[(t-butoxycarbonyl)(methyl)amino)cyclohexanecarboxylate (26.33 g).

APCI-MS M/Z:272[M+H]$^+$.

(2) Methyl trans-4-[(t-butoxycarbonyl)(methyl)amino]cyclohexanecarboxylate (26.32 g) obtained in (1) above is dissolved in dioxane (100 ml), and thereto is added 4 N hydrogen chloride/dioxane solution (100 ml). The reaction solution is stirred at room temperature for 4 hours, and to the solution is poured diisopropyl ether (500 ml). The precipitates are collected by filtration, washed with diisopropyl ether and dried to give methyl trans-4-(methylamino)cyclohexanecarboxylate hydrochloride (19.01 g).

APCI-MS M/Z: 172[M+H]$^+$.

(3) Methyl trans-4-(methylamino)cyclohexanecarboxylate hydrochloride (18.93 g) obtained in (2) above is suspended in dichloromethane (400 ml), and to the solution is added acetyl chloride (8.42 ml) under ice-cooling, followed by dropwise addition of a solution of triethylamine (38.1 ml) in dichloromethane (40 ml). The reaction solution is warmed to room temperature and stirred for 2 hours. After adding 5% hydrochloric acid, the mixture is extracted with dichloromethane. The organic layer is washed with saturated brine, dried over sodium sulfate and evaporated to remove the solvent under reduced pressure. The resulting residue is purified by NH-silica gel column chromatography (eluent: ethyl acetate) to give methyl trans-4-[acetyl(methyl)amino]cyclohexanecarboxylate (19.05 g).

APCI-MS M/Z:214[M+H]$^+$.

(4) Methyl trans-4-[acetyl(methyl)amino]cyclohexanecarboxylate (19.00 g) obtained in (3) above is dissolved in methanol (200 ml), and thereto is added 2 N aqueous sodium hydroxide solution (60 ml). The mixture is then stirred at room temperature for 3 hours. Under ice-cooling, the reaction solution is adjusted to pH 1-2 by pouring 10% hydrochloric acid, saturated with sodium chloride, and then extracted with chloroform. The organic layer is dried over sodium sulfate, and evaporated to remove the solvent under reduced pressure. The resulting residue is suspended in a small amount of ethyl acetate, and to the mixture is poured diisopropyl ether. The crystals are collected by filtration, washed with diisopropyl ether several times and dried to give the title compound (16.31 g).

ESI-MS M/Z: 198[M−H]⁻.

Reference Example 4

Trans-4-(3-oxomorpholin-4-yl)cyclohexanecarboxylic acid

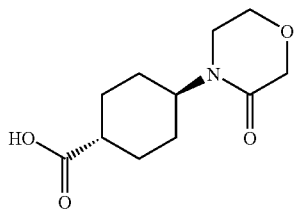

(1) Sixty % sodium hydride in oil (6.80 g) is suspended in N,N-dimethylacetamide (80 ml) and a solution of 2-(benzyloxy)ethanol (12.9 g) in N,N-dimethylacetamide (50 ml) is added dropwise to the mixture over 10 minutes under ice-cooling. After stirring at room temperature for 15 minutes, the reaction solution is cooled with ice, and thereto is added chloroacetic acid (8.13 g) in small portions. The mixture is then stirred at room temperature for 11 hours. The reaction solution is concentrated under reduced pressure, and to the resulting residue is added aqueous sodium hydrogen carbonate solution and the mixture is washed with diethyl ether. The aqueous layer is acidified with conc. hydrochloric acid, and then extracted with ethyl acetate. The organic layer is washed with saturated brine, dried over sodium sulfate and evaporated to remove solvent under reduced pressure to give [2-(benzyloxy)ethoxy]acetic acid (18.24 g).

ESI-MS M/Z:209[M−H]⁻.

(2) [(2-Benzyloxy)ethoxy]acetic acid (6.51 g) obtained in (1) above, methyl trans-4-aminocyclohexanecarboxylate hydrochloride (5.27 g) obtained in Reference Example 2(1) and 1-hydroxybenzotriazole (5.06 g) are dissolved in N,N-dimethylformamide (100 ml). To the mixture are added 1-ethyl-3-(3-dimethylaminopropyl)carbodiimide hydrochloride (7.10 g) and triethylamine (4.50 ml) successively under ice-cooling, and the mixture is stirred at room temperature for 3 days. The reaction solution is concentrated under reduced pressure, and to the resulting residue is added an aqueous sodium hydrogen carbonate solution, followed by extraction with ethyl acetate. The organic layer is washed with saturated brine, dried over sodium sulfate and evaporated to remove the solvent under reduced pressure. The resulting residue is purified by silica gel column chromatography (eluent: hexane/ethyl acetate=1:1 followed by ethyl acetate) to give methyl trans-4-({[2-(2-benzyloxy)ethoxy]acetyl}amino)cyclohexanecarboxylate (8.24 g).

APCI-MS M/Z:350[M+H]⁺.

(3) Methyl trans-4-({[2-(2-benzyloxy)ethoxy]acetyl}amino)cyclohexanecarboxylate (5.09 g) obtained in (2) above is dissolved in acetic acid (150 ml), and thereto is added 5% palladium carbon (1.01 g) and the mixture is stirred at room temperature for 2.4 hours under hydrogen atmosphere under normal pressure. The reaction solution is filtered to remove the catalyst, and the filtrate is concentrated under reduced pressure. The resulting residue is dissolved in chloroform, washed with saturated aqueous sodium hydrogen carbonate solution, dried over sodium sulfate and evaporated to remove the solvent to give methyl trans-4-{[(2-hydroxyethoxy)acetyl]amino}cyclohexanecarboxylate (3.32 g).

APCI-MS M/Z:260[M+H]⁺.

(4) Methyl trans-4-{[(2-hydroxyethoxy)acetyl]amino}cyclohexanecarboxylate (1.37 g) obtained in (3) above is dissolved in chloroform (15 ml), and thereto is added triethylamine (890 μl) under ice-cooling. Methanesulfonyl chloride (450 μl) is then added dropwise at the same temperature. The reaction solution is stirred for 3 hours under ice-cooling, diluted with water and extracted with chloroform. The organic layer is washed with saturated brine, dried over sodium sulfate and evaporated to remove the solvent under reduced pressure to give methyl trans-4-[({2-methylsulfonyl)oxy]ethoxy}acetyl)amino]-cyclohexanecarboxylate (1.83 g).

APCI-MS M/Z:338[M+H]⁺.

(5) Methyl trans-4-[({2-[(methylsulfonyl)oxy]ethoxy}acetyl)amino]-cyclohexanecarboxylate (1.08 g) obtained in (4) above is dissolved in N,N-dimethylacetamide (15 ml), and thereto is added 60% sodium hydride in oil (135 mg) under ice-cooling and the mixture is stirred at room temperature for 16 hours. The reaction solution is concentrated under reduced pressure, and to the resulting residue are added water and an excess sodium chloride, followed by extraction with chloroform. The organic layer is dried over sodium sulfate and evaporated to remove the solvent under reduced pressure. The resulting residue is purified by silica gel column chromatography (eluent: hexane/ethyl acetate=1:1 followed by ethyl acetate) to give methyl trans-4-(3-oxomorpholin-4-yl)cyclohexanecarboxylate (715 mg).

APCI-MS M/Z:242[M+H]⁺.

(6) Methyl trans-4-(3-oxomorpholin-4-yl)cyclohexanecarboxylate (500 mg) obtained in (5) above is treated in a similar manner to Reference Example 2(4) to give the title compound (322 mg).

ESI-MS M/Z:226[M−H]⁻.

Reference Example 5

Trans-4-(2-oxo-1,3-oxazolidin-3-yl)cyclohexanecarboxylic acid

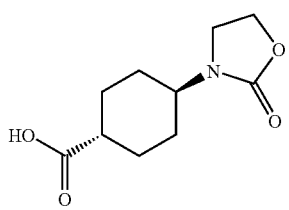

(1) Methyl trans-4-aminocyclohexanecarboxylate hydrochloride (5.00 g) obtained in Reference Example 2(1) is dissolved in chloroform (60 ml), and thereto is added triethylamine (11 ml) under ice-cooling, followed by dropwise addition of a solution of 2-chloroethyl chloroformate (3.3 ml) in chloroform (10 ml). After stirring at room temperature for 2.5 hours, to the reaction solution is added 5% hydrochloric acid and the mixture is extracted with chloroform. The organic layer is washed with saturated brine, dried over sodium sulfate, and then evaporated to remove the solvent under reduced pressure. The resulting residue is suspended in chloroform/diisopropyl ether. The precipitates are collected by filtration and dried to give methyl trans-4-{[(2-chloroethoxy)carbonyl]amino}cyclohexanecarboxylate (5.11 g).

APCI-MS M/Z:264/266[M+H]$^+$.

(2) Methyl trans-4-{[(2-chloroethoxy)carbonyl]amino}-cyclohexanecarboxylate (3.70 g) obtained in (1) above is dissolved in N,N-dimethylacetamide (50 ml), and thereto is added 60% sodium hydride in oil (630 mg) under ice-cooling. The mixture is then stirred at room temperature for 16.5 hours. To the reaction solution is added water, and the mixture is extracted with ethyl acetate. The organic layer is washed with water and saturated brine, and then dried over sodium sulfate. The solvent is removed by evaporation under reduced pressure and the resulting residue is purified by silica gel column chromatography (eluent: hexane/ethyl acetate=1/1, followed by ethyl acetate) to give methyl trans-4-(2-oxo-1,3-oxazolidin-3-yl)cyclohexanecarboxylate (1.83 g).

APCI-MS M/Z:228[M+H]$^+$.

(3) Methyl trans-4-(2-oxo-1,3-oxazolidin-3-yl)cyclohexanecarboxylate (1.84 g) obtained in (2) above is treated in a similar manner to Reference Example 2(4) to give the title compound (1.75 g).

ESI-MS M/Z:212[M−H]$^−$.

Reference Example 6

5-(2-Oxopyrrolidin-1-yl)pentanoic acid

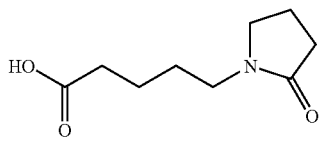

(1) 5-Aminovaleric acid (7.35 g) is dissolved in methanol (50 ml), and thereto is added dropwise thionyl chloride (4.9 ml) under ice-cooling. The reaction solution is then warmed to room temperature and stirred for 17 hours. The reaction solution is concentrated under reduced pressure. The resulting residue is suspended in diethyl ether and the precipitates are collected by filtration to give methyl 5-aminovalerate hydrochloride (9.93 g).

APCI-MS M/Z: 132[M+H]$^+$.

(2) Methyl 5-aminovalerate hydrochloride (1.68 g) obtained in (1) above is suspended in chloroform (20 ml), and to the suspension is added triethylamine (2.54 g) under ice-cooling, followed by dropwise addition of 4-chlorobutyryl chloride (1.55 g). The reaction solution is warmed to room temperature and stirred for 2 hours. Ice-water is poured to the reaction solution and the mixture is extracted with chloroform. The organic layer is washed with 10% hydrochloric acid, a saturated aqueous sodium hydrogen carbonate solution and saturated brine, and then dried over sodium sulfate. The solvent is evaporated under reduced pressure to give methyl 5-[(4-chlorobutanoyl)amino]-pentanoate (2.34 g).

APCI-MS M/Z:236/238[M+H]$^+$.

(3) Methyl 5-[(4-chlorobutanoyl)amino]pentanoate (2.33 g) obtained in (2) above is dissolved in N,N-dimethylacetamide (20 ml), and thereto is added 60% sodium hydride in oil (0.47 g) in small portions under ice-cooling. The reaction solution is warmed to room temperature, stirred for 20 hours and evaporated to remove the solvent under reduced pressure. The resulting residue is purified by silica gel column chromatography (eluent: chloroform followed by chloroform/ethyl acetate=20/1) to give methyl 5-(2-oxopyrrolidin-1-yl)pentanoate (2.15 g).

APCI-MS M/Z:200[M+H]$^+$.

(4) Methyl 5-(2-oxopyrrolidin-1-yl)pentanoate (1.00 g) obtained in (3) above is dissolved in methanol (20 ml), and thereto is added 4 N aqueous sodium hydroxide solution (2.5 ml). The reaction solution is warmed to room temperature and stirred for 18 hours. The reaction solution is washed with diethyl ether, and thereto is added 2 N hydrochloric acid (5.0 ml), followed by concentration under reduced pressure. The resulting residue is extracted with chloroform and dried over sodium sulfate. The solvent is evaporated under reduced pressure to give the title compound (0.90 g).

ESI-MS M/Z: 184[M−H]$^−$.

Reference Example 7

5-(3-Oxomorpholin-4-yl)pentanoic acid

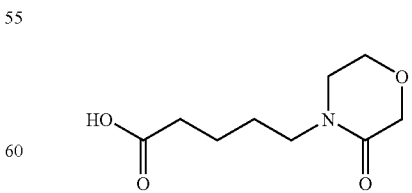

(1) Methyl 5-aminovalerate hydrochloride (3.35 g) obtained in Reference Example 6(1), [2-(benzyloxy)ethoxy]acetic acid (4.63 g) obtained in Reference Example 4(1) and 1-hydroxybenzotriazole (3.78 g) are dissolved in N,N-dimethylformamide (80 ml). To the mixture are added 1-ethyl-3-(3-dimethylaminopropyl)carbodiimide hydrochloride (5.37 g) and triethylamine (3.35 ml) successively under ice-cooling, and the mixture is stirred at room temperature for 2 days. The reaction solution is concentrated under reduced pressure, and the resulting residue is diluted with ice-water and extracted with ethyl acetate. The organic layer is washed with aqueous sodium hydrogen carbonate solution, water and saturated brine successively, dried over sodium sulfate and evaporated to remove the solvent under reduced pressure. The resulting residue is purified by silica gel column chromatography (eluent: hexane/ethyl acetate=1:1 followed by ethyl acetate) to give methyl 5-({[2-(benzyloxy)ethoxy]acetyl}amino)pentanoate (5.56 g).

APCI-MS M/Z:324[M+H]⁺.

(2) Methyl 5-({[2-(benzyloxy)ethoxy]acetyl}amino)pentanoate (5.54 g) obtained in (1) above is dissolved in tetrahydrofuran (60 ml), and thereto is added 20% palladium hydroxide on carbon (0.5 g). The mixture is then stirred for 4 hours at room temperature under hydrogen atmosphere under normal pressure. The reaction solution is filtered to remove the catalyst, and then the filtrate is concentrated under reduced pressure to give methyl 5-{[(2-hydroxyethoxy)acetyl]amino}pentanoate (3.76 g).

APCI-MS M/Z:234[M+H]⁺.

(3) Methyl 5-{[(2-hydroxyethoxy)acetyl]amino}pentanoate (1.17 g) obtained in (2) above is dissolved in chloroform (15 ml), and thereto is added triethylamine (0.84 ml) under ice-cooling. Methanesulfonyl chloride (0.43 ml) is then added dropwise to the mixture at the same temperature. The reaction solution is warmed to room temperature, stirred for 1 hour, and ice-water is poured thereto followed by extraction with chloroform. The organic layer is washed with saturated brine, dried over sodium sulfate and evaporated to remove the solvent under reduced pressure to give methyl 5-[({2-[(methylsulfonyl)oxy]ethoxy}-acetyl)amino]pentanoate (1.51 g).

APCI-MS M/Z:312[M+H]⁺.

(4) Methyl 5-[({2-[(methylsulfonyl)oxy]ethoxy}acetyl)amino]-pentanoate (1.48 g) obtained in (3) above is dissolved in N,N-dimethylacetamide (22 ml), and thereto is added 60% sodium hydride in oil (0.20 g) under ice-cooling. The mixture is then stirred at room temperature for 18 hours. Ice-water is poured to the reaction solution and the mixture is extracted with chloroform. The organic layer is washed with saturated brine, dried over sodium sulfate and the solvent is removed by evaporation under reduced pressure. The resulting residue is purified by silica gel column chromatography (eluent: hexane/ethyl acetate=1/1, followed by ethyl acetate) to give methyl 5-(3-oxomorpholin-4-yl)pentanoate (0.93 g).

APCI-MS M/Z:216[M+H]⁺.

(5) Methyl 5-(3-oxomorpholin-4-yl)pentanoate (500 mg) obtained in (4) above is dissolved in methanol (10 ml), and thereto is added an aqueous sodium hydroxide (0.40 g) solution (2 ml). The reaction solution is then warmed to room temperature and stirred for 17 hours. The reaction solution is concentrated under reduced pressure, neutralized with 2 N hydrochloric acid, and concentrated under reduced pressure. The resulting residue is extracted with chloroform, dried over sodium sulfate and evaporated to remove solvent under reduced pressure to give the title compound (0.35 g).

ESI-MS M/Z: 200[M−H]⁻.

Reference Example 8

Trans-4-(dimethylamino)cyclohexanecarboxylic acid hydrochloride

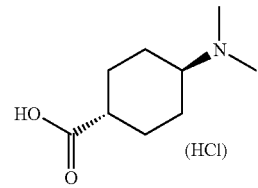

(1) Methyl trans-4-aminocyclohexanecarboxylate hydrochloride (93.0 g) obtained in Reference Example 2(1) is dissolved in methanol (1000 ml), and thereto are added 35% aqueous formaldehyde solution (95.4 ml), sodium acetate (39.4 g) and 10% palladium/carbon (10 g). The mixture is then stirred at room temperature for 3.5 hours under atmospheric hydrogen pressure. The insoluble materials are removed by filtration, and the filtrate is concentrated under reduced pressure. To the resulting residue is poured 20% aqueous potassium carbonate solution (500 ml), and the mixture is extracted with chloroform. The organic layer is dried over sodium sulfate and potassium carbonate, and evaporated to remove the solvent under reduced pressure. The resulting residue is purified by NH-silica gel column chromatography (eluent: n-hexane/ethyl acetate=2/1) to give methyl trans-4-dimethylaminocyclohexanecarboxylate (87.3 g).

APCI-MS M/Z: 186[M+H]⁺.

(2) Methyl trans-4-(dimethylamino)cyclohexanecarboxylate (27.6 g) obtained in (1) above is dissolved in dioxane (300 ml) and water (100 ml), and thereto is added 6 N hydrochloric acid (50 ml). The mixture is heated under reflux for 4 hours. To the mixture is supplied additional 6 N hydrochloric acid (50 ml), and the reaction mixture is heated under reflux for another one hour. The reaction solution is concentrated under reduced pressure, and subjected to azeotropic distillation with toluene. The resulting residue is suspended in diisopropyl ether. The precipitates are collected by filtration, washed with diisopropyl ether and dried to give the title compound (27.5 g).

APCI-MS M/Z: 172[M+H]⁺.

Reference Example 9

Trans-4-[(dimethylamino)methyl]cyclohexanecarboxylic acid hydrochloride

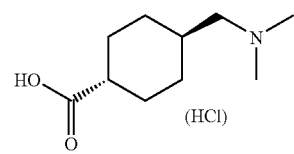

(1) Trans-4-(aminomethyl)cyclohexanecarboxylic acid (6.29 g) is suspended in methanol (32 ml) and thereto is added dropwise thionyl chloride (6 ml) under ice-cooling. The reaction solution is warmed to room temperature, stirred overnight and concentrated under reduced pressure to dryness to give methyl trans-4-(aminomethyl)cyclohexanecarboxylate hydrochloride (8.69 g).

APCI-MS M/Z: 172[M+H]$^+$.

(2) Methyl trans-4-(aminomethyl)cyclohexanecarboxylate hydrochloride (8.69 g) obtained in (1) above is suspended in dichloromethane (400 ml), and thereto is added triethylamine (11.2 ml). The mixture is then stirred at room temperature for several minutes, and thereto are added 35% aqueous formaldehyde solution (15.9 ml) and sodium triacetoxyborohydride (25.43 g) under ice-cooling. The reaction solution is warmed to room temperature and stirred for 2 hours. Saturated aqueous sodium hydrogen carbonate solution is poured to the solution, and the mixture is extracted with chloroform. The organic layer is washed with water and saturated brine successively, dried over sodium sulfate. The solvent is evaporated under reduced pressure to give methyl trans-4-[(dimethylamino)methyl)cyclohexanecarboxylate (7.42 g).

APCI-MS M/Z:200[M+H]$^+$.

(3) Methyl trans-4-[(dimethylamino)methyl]cyclohexanecarboxylate (7.41 g) obtained in (2) above is dissolved in dioxane (140 ml), and thereto is added 2 N hydrochloric acid (70 ml). The mixture is then heated under reflux for 3 hours. After allowing to cool, the reaction solution is concentrated under reduced pressure. The resulting residue is subjected to azeotropic distillation with toluene, and the resulting product is dried to give the title compound (8.45 g).

APCI-MS M/Z:186[M+H]$^+$.

Reference Example 10

Trans-4-pyrrolidin-1-ylcyclohexanecarboxylic acid hydrochloride

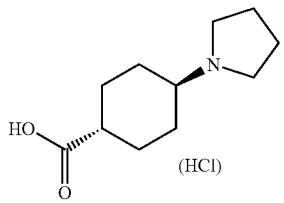

(1) Methyl trans-4-aminocyclohexanecarboxylate hydrochloride (10 g) obtained in Reference Example 2(1), 1,4-diiodobutane (19.2 g) and sodium carbonate (16.4 g) are suspended in a mixture of tetrahydrofuran (300 ml) and N,N-dimethyl acetamide (60 ml), and the mixture is stirred at 70° C. for 20 hours. The reaction solution is concentrated under reduced pressure. The residue is dissolved in ethyl acetate/water and the organic layer is separated. The organic layer is washed with water and saturated brine, dried over sodium sulfate and evaporated to remove the solvent under reduced pressure. The resulting residue is purified by NH-silica gel column chromatography (eluent: ethyl acetate/hexane=1/5) to give methyl trans-4-pyrrolidin-1-ylcyclohexanecarboxylate (10.9 g).

APCI-MS M/Z:212[M+H]$^+$.

(2) To a solution of methyl trans-4-pyrrolidin-1-ylcyclohexanecarboxylate (10.9 g) obtained in (1) above in dioxane (150 ml), 2 N hydrochloric acid (80 ml) is added and the mixture is stirred at 110° C. for 3 hours while evaporating methanol. The reaction solution is concentrated under reduced pressure. The resulting residue is suspended in diethyl ether and collected by filtration to give the title compound (11.1 g).

APCI-MS M/Z: 198[M+H]$^+$.

Reference Example 11

Trans-4-morpholin-4-ylcyclohexanecarboxylic acid hydrochloride

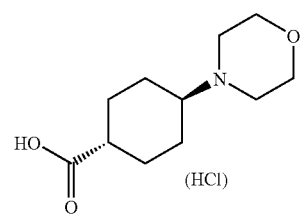

(1) Methyl trans-4-aminocyclohexanecarboxylate hydrochloride (47.5 g) obtained in Reference Example 2(1), bis(2-chloroethyl)ether (34.5 ml), sodium carbonate (77.9 g) and sodium iodide (88 g) are suspended in a mixture of tetrahydrofuran (1400 ml) and N,N-dimethylacetamide (280 ml). The mixture is then heated under reflux for 18 hours. Bis(2-chloroethyl)ether (23 ml) and sodium iodide (22 g) are added to the reaction solution and the mixture is refluxed for additional 6 hours. The reaction solution is concentrated under reduced pressure. The residue is dissolved in ethyl acetate/water and the organic layer is separated. The organic layer is washed with water and saturated brine, dried over sodium sulfate and evaporated to remove the solvent under reduced pressure. The resulting residue is purified by NH-silica gel column chromatography (eluent: ethyl acetate/hexane=1/30, subsequently by ethyl acetate/hexane=1/5 followed by 1/3) to give methyl trans-4-morpholin-4-ylcyclohexanecarboxylate (53.9 g).

APCI-MS M/Z:228[M+H]$^+$.

(2) To a solution of methyl trans-4-morpholin-4-ylcyclohexanecarboxylate (53.8 g) obtained in (1) above in dioxane (750 ml) is added 2 N hydrochloric acid (400 ml), and the mixture is stirred at 110° C. for 4 hours while evaporating methanol. The reaction solution is concentrated. The resulting residue is suspended in diethyl ether, and collected by filtration to give the title compound (54.8 g).

APCI-MS M/Z:214[M+H]$^+$.

Reference Example 12

Trans-4-[(t-butoxycarbonyl)(methyl)amino]-cyclohexanecarboxylic acid

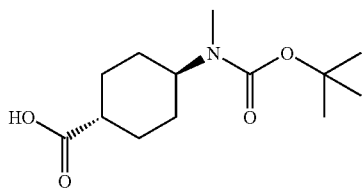

Methyl trans-4-[(t-butoxycarbonyl)(methyl)amino]cyclohexanecarboxylate (44.78 g) obtained in Reference Example 3(1) is dissolved in methanol (300 ml), and thereto is added 2 N aqueous sodium hydroxide solution (100 ml). The mixture is then stirred at room temperature for 6 hours. The reaction solution is concentrated under reduced pressure. To the residue are added ice-water, ethyl acetate and 10% hydrochloric acid under ice-cooling, and the mixture is extracted with ethyl acetate. The organic layer is washed with water and saturated brine successively, dried over sodium sulfate and evaporated to remove the solvent under reduced pressure. The resulting residue is suspended in a small amount of ethyl acetate, and n-hexane is poured to the mixture. The resulting crystals are collected by filtration, washed with n-hexane/diisopropyl ether several times and dried to give the title compound (39.20 g).

ESI-MS M/Z:256[M−H]$^-$

Reference Example 13

[Trans-4-(dimethylamino)cyclohexyl]acetic acid hydrochloride

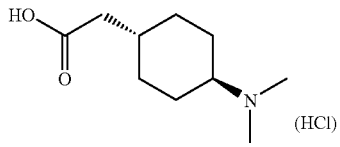

(1) Potassium hydroxide (12.8 g) is dissolved in water (30 ml) and thereto is added diethyl ether (45 ml). To the resulting mixture is added N-nitroso-N-methylurea (5.07 g) under ice-cooling. The reaction solution is stirred for 10 minutes under the same cooling conditions, and the organic layer is separated and dried over potassium hydroxide to give a solution of diazomethane in diethyl ether.

Under argon atmosphere, trans-4-[(t-butoxycarbonyl) amino]-cyclohexanecarboxylic acid (3.0 g) obtained in Reference Example 12 is suspended in diethyl ether (40 ml), and thereto is added triethylamine (1.89 ml) at −10° C., followed by dropwise addition of isobutyl chloroformate (1.75 ml). The reaction solution is stirred at −10° C. for 30 minutes, and the solution of diazomethane in diethyl ether is added dropwise to the reaction solution at −10° C. The reaction solution is then warmed to room temperature and stirred for 15 hours. Under ice-cooling, 10% aqueous citric acid solution is poured to the solution, and the organic layer is separated. The organic layer is washed with saturated aqueous sodium hydrogen carbonate solution, water and saturated brine, dried over sodium sulfate and evaporated to remove the solvent under reduced pressure. The resulting residue is purified by silica gel column chromatography (eluent: ethyl acetate/hexane=1/3, followed by ethyl acetate/hexane=1/2) to give t-butyl [trans-4-(2-diazoacetyl)cyclohexyl]carbamate (1.86 g).

APCI-MS M/Z:285[M+NH$_4$]$^+$.

(2) t-Butyl [trans-4-(2-diazoacetyl)cyclohexyl]carbamate (1.62 g) obtained in (1) above is dissolved in methanol (30 ml) in a light resistant reaction vessel under argon atmosphere, and the mixture is cooled to −25° C. To the reaction solution is added a solution of silver benzoate (153 mg) in triethylamine (2.4 ml), and the mixture is warmed to room temperature and stirred for 3 hours. The reaction solution is concentrated under reduced pressure. The resulting residue is dissolved in ethyl acetate and washed with saturated aqueous sodium hydrogen carbonate solution, saturated aqueous ammonium chloride solution and saturated brine successively. The mixture is dried over sodium sulfate and evaporated to remove the solvent to give methyl {trans-[4-(N-t-butoxycarbonyl)amino]cyclohexyl}acetate (1.25 g).

APCI-MS M/Z:289[M+NH$_4$]$^+$.

(3) To a solution of methyl {trans-[4-(N-t-butoxycarbonyl)amino]-cyclohexyl}acetate (1.23 g) obtained in (2) above in 1,4-dioxane (8 ml) is added 4 N hydrogen chloride/dioxane solution (8 ml), and the mixture is stirred at room temperature for 5 hours. The reaction solution is concentrated to dryness under reduced pressure to give methyl (trans-4-aminocyclohexyl)acetate hydrochloride (898 mg).

APCI-MS M/Z: 172[M+H]$^+$.

(4) Under ice-cooling, triethylamine (1.2 ml) is added to a suspension of methyl (trans-4-aminocyclohexyl)acetate hydrochloride (895 mg) obtained in (3) above in dichloromethane (30 ml), and the mixture is stirred. Thirty five % aqueous formaldehyde solution (1.71 ml) and sodium triacetoxy borohydride (2.74 g) are then successively added under ice-cooling. The reaction solution is warmed to room temperature and stirred for 6 hours. Saturated aqueous sodium hydrogen carbonate solution is poured under ice-cooling and the mixture is extracted with chloroform. The organic layer is washed with saturated brine and dried over sodium sulfate. The solvent is removed by evaporation under reduced pressure to give methyl [trans-4-(dimethylamino)cyclohexyl]acetate (771 mg).

APCI-MS M/Z:200[M+H]$^+$.

(5) To a solution of methyl [trans-4-(dimethylamino)cyclohexyl]-acetate (760 mg) obtained in (4) above in dioxane (25 ml), 1 N hydrochloric acid (15 ml) is added and the mixture is heated under reflux for 3 hours. The reaction solution is concentrated under reduced pressure, and the resulting residue is suspended in diethyl ether. The precipitates are collected by filtration and dried to give the title compound (795 mg).

APCI-MS M/Z: 186[M+H]$^+$.

Reference Example 14

Ethyl piperidin-4-ylacetate hydrochloride

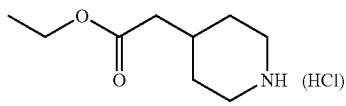

Ethyl (pyridin-4-yl)acetate (50.00 g) is dissolved in acetic acid (500 ml), and thereto is added platinum oxide (3.44 g). The mixture is shaken at room temperature for 20 hours under 55 psi hydrogen atmosphere. The insoluble materials are removed by filtration and the filtrate is concentrated under reduced pressure. The resulting residue is dissolved in dioxane (200 ml), and thereto is added 4 N hydrogen chloride/dioxane (400 ml). The mixture is then evaporated to remove the solvent under reduced pressure. The resulting residue is suspended in diethyl ether/diisopropyl ether, and the precipitates are collected by filtration. The resultant is washed with diisopropyl ether, and dried to give the title compound (61.80 g).

APCI-MS M/Z: 172[M+H]$^+$.

Reference Example 15

(1-Isopropylpiperidin-4-yl)acetic acid hydrochloride

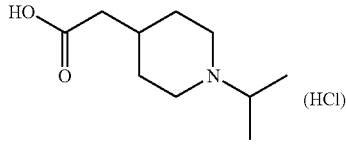

(1) Ethyl (piperidin-4-yl)acetate hydrochloride (11.12 g) obtained in Reference Example 14 is dissolved in ethanol (150 ml), and thereto are added 2-iodepropane (6.4 ml) and potassium carbonate (22.2 g). The mixture is then heated under reflux overnight. The insoluble materials are removed by filtration and the filtrate is concentrated under reduced pressure. The residue is diluted with chloroform, washed with water and saturated brine successively, dried over sodium sulfate and evaporated to remove solvent under reduced pressure. The resulting residue is purified by NH-silica gel column chromatography (eluent: n-hexane/ethyl acetate=10/1) to give ethyl (1-isopropylpiperidin-4-yl)acetate (9.87 g).

APCI-MS M/Z:214[M+H]$^+$.

(2) To ethyl (1-isopropylpiperidin-4-yl)acetate (9.77 g) obtained in (1) above, water (33 ml) and conc. hydrochloric acid (66 ml) are added and the mixture is heated under reflux for 24 hours. The reaction solution is concentrated under reduced pressure and the residue is subjected to azeotropic distillation with toluene. The resulting residue is collected by filtration, washed with diisopropyl ether and then, dried to give the title compound (9.76 g).

APCI-MS M/Z: 186[M+H]$^+$.

Reference Example 16

1-Isopropylpiperidine-4-carboxylic acid hydrochloride

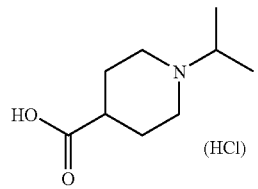

Ethyl piperidine-4-carboxylate is treated in a similar manner to Reference Example 15 to give the title compound.

APCI-MS M/Z: 172[M+H]$^+$.

Reference Example 17

1-Pyridin-4-ylpiperidin-4-carboxylic acid

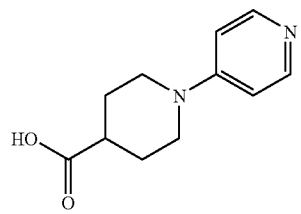

4-Chloropyridine hydrochloride (9.55 g) and triethylamine (26.0 ml) are dissolved in ethanol (10 ml) and water (30 ml), and thereto is added ethyl isonicotinate (10.00 g). The reaction solution is then heated at 150° C. for 96 hours in a sealed tube. After allowing to cool, ethanol is added to the reaction solution and the insoluble materials are removed by filtration. The filtrate is concentrated under reduced pressure, and the resulting residue is suspended in chloroform. The precipitates are collected by filtration and recrystallized from water/N,N-dimethylformamide to give the title compound (10.34 g).

APCI-MS M/Z:207[M+H]$^+$.

Reference Example 18

Trans-4-(4-oxo-1,3-oxazolidin-3-yl)cyclohexanecarboxylic acid

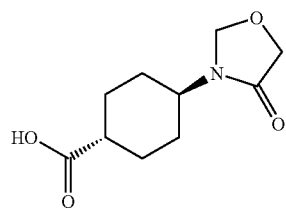

(1) 1-Ethyl-3-(3-dimethylaminopropyl)carbodiimide hydrochloride (742 mg) and 1-hydroxybenzotriazole (523 mg) are added to a solution of methyl trans-4-aminocyclohexanecarboxylate hydrochloride (500 mg) obtained in Reference Example 2(1), triethylamine (540 µl) and glycolic acid (295 mg) in N,N-dimethylformamide (10 ml) under ice-cooling. The mixture is then stirred at room temperature for 15 hours. The reaction solution is concentrated, and saturated aqueous sodium hydrogen carbonate solution is poured thereto followed by extraction with chloroform. The organic layer is dried over sodium sulfate and evaporated to remove the solvent under reduced pressure. The resulting residue is purified by silica gel column chromatography (eluent: chloroform to methanol/chloroform=1/20) to give methyl trans-4-(glycoloylamino)cyclohexanecarboxylate (602 mg).

APCI-MS M/Z: 216 [M+H]$^+$.

(2) Methyl trans-4-(glycoloylamino)cyclohexanecarboxylate (280 mg) obtained in (1) above, paraformaldehyde (280 mg) and para-toluenesulfonic acid monohydrate (45 mg) are added to toluene (5 ml) and the mixture is stirred at 100° C. for 4 hours. After cooling, saturated aqueous sodium hydrogen carbonate solution is poured to the reaction solution and the mixture is extracted with ethyl acetate. The organic layer is washed with water and saturated brine, dried over sodium sulfate and evaporated to remove solvent under reduced pressure. The resulting residue is purified by silica gel column chromatography (eluent: ethyl acetate/hexane=1/1 to ethyl acetate) to give methyl trans-4-(4-oxo-1,3-oxazolidin-3-yl)cyclohexanecarboxylate (190 mg).

APCI-MS M/Z:228[M+H]$^+$.

(3) To a solution of methyl trans-4-(4-oxo-1,3-oxazolidin-3-yl)cyclohexanecarboxylate (330 mg) obtained in (2) above in methanol (5 ml), 1 N aqueous sodium hydroxide solution (2.9 ml) is added. The mixture is then stirred at room temperature for 3 hours. The reaction solution is concentrated, acidified with 2 N hydrochloric acid, and thereto is added sodium chloride followed by extraction with chloroform. The organic layer is dried over sodium sulfate and evaporated to remove the solvent under reduced pressure. The resulting residue is suspended in diethyl ether and collected by filtration to give the title compound (288 mg).

ESI-MS M/Z: 212[M−H]$^−$.

Reference Example 19

Trans-4-(4-oxo-1,3-oxazinan-3-yl)cyclohexanecarboxylic acid

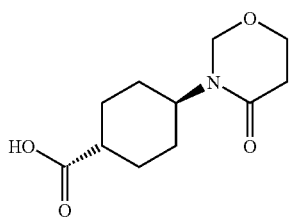

(1) To a solution of methyl trans-4-aminocyclohexanecarboxylate hydrochloride (1.0 g) obtained in Reference Example 2(1), triethylamine (1.1 ml), 30% aqueous 3-hydroxypropionic acid solution (1.86 ml) in N,N-dimethylformamide (15 ml) are added 1-ethyl-3-(3-dimethylaminopropyl)carbodiimide hydrochloride (1.19 g) and 1-hydroxybenzotriazole (837 mg) under ice-cooling. The mixture is then stirred at room temperature for 20 hours. The reaction solution is concentrated and saturated aqueous sodium hydrogen carbonate solution is poured to the residue, followed by extraction with chloroform. The organic layer is dried over sodium sulfate and evaporated to remove the solvent. The resulting residue is purified by silica gel column chromatography (eluent: ethyl acetate) to give methyl trans-4-[(3-hydroxypropanoyl)amino]cyclohexanecarboxylate (534 mg).

APCI-MS M/Z: 230[M+H]$^+$.

(2) Methyl trans-4-[(3-hydroxypropanoyl)amino]-cyclohexanecarboxylate (530 mg) obtained in (1) above, paraformaldehyde (530 mg) and paratoluenesulfonic acid monohydrate (85 mg) are added to toluene (10 ml), and the mixture is stirred at 100° C. for 4 hours. After cooling, saturated aqueous sodium hydrogen carbonate solution and ethyl acetate are poured to the mixture, and the insoluble materials are separated by filtration. The organic layer of the filtrate is separated and the aqueous layer is extracted with ethyl acetate. The organic layers are combined, washed with water and saturated brine, dried over sodium sulfate and evaporated under reduced pressure to remove the solvent. The resulting residue is purified by silica gel column chromatography (eluent: ethyl acetate) to give methyl trans-4-(4-oxo-1,3-oxazinan-3-yl)cyclohexanecarboxylate (306 mg).

APCI-MS M/Z:242[M+H]$^+$.

(3) To a solution of methyl trans-4-(4-oxo-1,3-oxazinan-3-yl)cyclohexanecarboxylate (300 mg) obtained in (2) above in methanol (5 ml), 1 N aqueous sodium hydroxide solution (2.5 ml) is added. The mixture is then stirred at room temperature for 4 hours. The reaction solution is concentrated and acidified with 2 N hydrochloric acid, and thereto is added sodium chloride, followed by extraction with chloroform. The organic layer is dried over sodium sulfate and evaporated to remove the solvent under reduced pressure. The resulting residue is suspended in diethyl ether and collected by filtration to give the title compound (252 mg).

ESI-MS M/Z:226[M−H]$^−$.

Reference Example 20

Trans-4-(1,1-dioxidoisothiazolidin-2-yl)cyclohexanecarboxylic acid

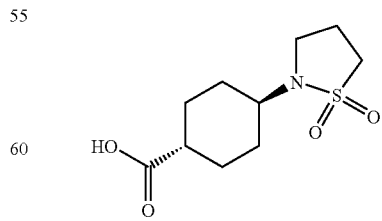

(1) Methyl trans-4-aminocyclohexanecarboxylate hydrochloride (4.08 g) obtained in Reference Example 2(1) is suspended in chloroform (50 ml), and thereto is added triethylamine (8.8 ml) under ice-cooling. Subsequently, a solution of 3-chloropropanesulfonyl chloride (3.35 ml) in chloroform (20 ml) is added dropwise over 20 minutes under the same temperature. After stirring for 2 hours at room temperature, 5% hydrochloric acid is added to the reaction solution and the mixture is extracted with chloroform. The organic layer is washed with saturated brine, dried over sodium sulfate and evaporated to remove the solvent under reduced pressure. The resulting residue is suspended in diisopropylamine, and filtered to collect precipitates to give methyl trans-4-{[(3-chloropropyl)sulfonyl]amino}cyclohexanecarboxylate (6.14 g).

APCI-MS M/Z:315/317[M+H]$^+$.

(2) Methyl trans-4-{[(3-chloropropyl)sulfonyl]amino}-cyclohexanecarboxylate (3.08 g) obtained in (1) above is dissolved in tetrahydrofuran (40 ml), and a solution of potassium tert-butoxide (1.35 g) in tetrahydrofuran (20 ml) is added dropwise over 10 minutes under ice-cooling. After stirring for 3.5 hours at room temperature, additional potassium tert-butoxide (370 mg) is added under ice-cooling and the mixture is stirred overnight at room temperature. The reaction solution is poured into 5% hydrochloric acid (100 ml), and the aqueous layer is saturated with excess sodium chloride, followed by extraction with chloroform. The organic layer is dried over sodium sulfate and evaporated to remove the solvent under reduced pressure. The resulting residue is purified by silica gel column chromatography (eluent: n-hexane/ethyl acetate=1/2, followed by ethyl acetate) to give methyl trans-4-(1,1-dioxidoisothiazolidin-2-yl)cyclohexanecarboxylate (1.42 g, APCI-MS M/Z:279[M+NH$_4$]$^+$) and the title compound (0.56 g).

ESI-MS M/Z:246[M–H]$^-$.

Reference Example 21

2-Chloro-N-(5-chloropyridin-2-yl)acetamide

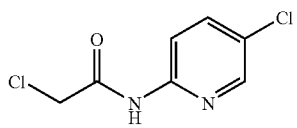

Chloroacetyl chloride (95.5 ml) is dissolved in dichloromethane (500 ml), and thereto is added dropwise a suspension of 2-amino-5-chloropyridine (128.6 g) and triethylamine (169 ml) in dichloromethane (1000 ml) under ice-cooling. The reaction solution is warmed to room temperature and stirred for 0.5 hours. The reaction solution is concentrated under reduced pressure, and thereto is poured ice-water, followed by extraction with ethyl acetate. The organic layer is washed with saturated brine, dried over sodium sulfate and treated with activated charcoal. After filtration to remove insoluble materials, the filtrate is concentrated under reduced pressure and the resulting residue is suspended in diisopropyl ether. The precipitates are collected by filtration, washed with diisopropyl ether and dried to give the title compound (153.4 g).

APCI-MS M/Z:205/207[M+H]$^+$.

Reference Example 22

N-(5-Chloropyridin-2-yl)-2-hydroxyacetamide

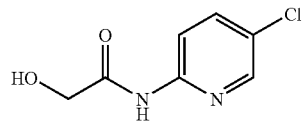

(1) 2-Chloro-N-(5-chloropyridin-2-yl)acetamide (30.68 g) obtained in Reference Example 21 is dissolved in N,N-dimethylformamide (500 ml), and thereto is added sodium acetate (24.55 g). The mixture is then stirred at 60° C. for 5 hours. The reaction solution is diluted with ethyl acetate, and washed with water and saturated brine successively. The solution is dried over magnesium sulfate, treated with activated charcoal, and the filtrate is concentrated under reduced pressure. The resulting residue is suspended in n-hexane and the crystals are collected by filtration. The crystals are washed with n-hexane and dried to give 2-[(5-chloropyridin-2-yl)amino]-2-oxoethyl acetate (30.58 g).

APCI-MS M/Z:229/231[M+H]$^+$.

(2) 2-[(5-Chloropyridin-2-yl)amino]-2-oxoethylacetate (30.36 g) obtained in (1) above is suspended in methanol (1200 ml) and thereto is added potassium carbonate (22.0 g) under ice-cooling. The reaction solution is warmed to room temperature, stirred for 0.5 hours and concentrated under reduced pressure. To the resulting residue are poured ethyl acetate (1500 ml) and ice-water (1000 ml), followed by extraction with ethyl acetate. The organic layer is washed with saturated brine, dried over sodium sulfate and evaporated to remove the solvent under reduced pressure. The resulting residue is suspended in a small amount of ethyl acetate, and thereto is poured diisopropyl ether. The precipitated crystals are collected by filtration, washed with diisopropyl ether and dried to give the title compound (22.85 g).

APCI-MS M/Z: 187/189[M+H]$^+$.

Reference Example 23

N-(5-chloropyridin-2-yl)-2-[(2-cyanopyridin-3-yl)oxy]acetamide

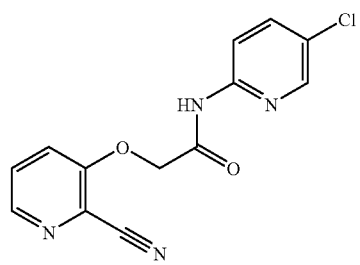

2-Cyano-3-hydroxypyridine (35.0 g) obtained according to the method described in a literature (Synthesis 1983, 316) is dissolved in acetone (800 ml), and thereto are added 2-chloro-N-(5-chloropyridin-2-yl)acetamide (62.6 g) obtained in Reference Example 21, potassium carbonate (60.0 g) and sodium iodide (45.8 g). The mixture is then heated under reflux for 2 hours. After allowing to cool, water and ethyl acetate are poured to the reaction mixture, and the insoluble materials are removed by filtration. The organic layer is then separated. The aqueous layer is extracted with ethyl acetate and the organic layers are combined, washed with saturated brine and dried over sodium sulfate. The solvent is removed by evaporation under reduced pressure and the resulting residue is suspended in diethyl ether. The precipitates are collected by filtration to give the title compound (80.3 g).

APCI-MS M/Z:289/291[M+H]$^+$.

Reference Example 24

3-Amino-N-(5-chloropyridin-2-yl)furo[3,2-b]pyridine-2-carboxamide

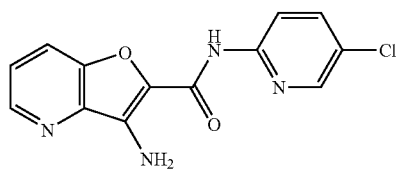

N-(5-Chloropyridin-2-yl)-2-[(2-cyanopyridin-3-yl)oxy]acetamide (80.0 g) obtained in Reference Example 23 is dissolved in N,N-dimethylacetamide (700 ml), and thereto is added sodium carbonate (35.2 g). The mixture is then stirred at 100° C. for 10 hours. After allowing to cool, the reaction solution is concentrated to reduce the volume by 1/3 under reduced pressure. After pouring ice-water, the precipitates are collected by filtration. The resulting solid is suspended in ethyl acetate and collected by filtration. The resultant is washed with chloroform and diethyl ether successively and dried to give the title compound (48.5 g).

APCI-MS M/Z:289/291[M+H]$^+$.

Reference Example 25

4-Chloronicotinonitrile

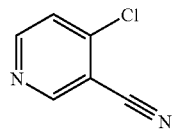

(1) To a solution of diisopropylamine (20.0 g) in tetrahydrofuran (200 ml) is added dropwise 1.6 M n-butyllithium/n-hexane solution under ice-cooling. The mixture is then stirred for 30 minutes under the same cooling conditions. The reaction mixture is cooled with dry ice-acetone, and thereto is added dropwise a solution of 4-chloropyridine (20.4 g) in tetrahydrofuran (100 ml). The mixture is then stirred for 20 minutes under the same cooling conditions. The resulting reaction solution is poured in crushed dry ice in a portion and then warmed to room temperature. The reaction solution is cooled with ice and basified by addition of sodium hydroxide, followed by concentration under reduced pressure. The resulting residue is dissolved in water and washed with dichloromethane. The aqueous layer is cooled with ice and acidified with conc. hydrochloric acid. The precipitates are collected by filtration and dried to give 4-chloronicotinic acid hydrochloride (21.4 g).

(2) 4-Chloronicotinic acid hydrochloride (500 mg) obtained in (1) above is dissolved in thionyl chloride (6 ml), and thereto is added N,N-dimethylformamide (1 drop). The reaction solution is then heated under reflux for 12 hours. After allowing to cool, the reaction solution is concentrated to dryness under reduced pressure. The resulting residue is suspended in dichloromethane (10 ml), and thereto are added ammonium chloride (152 mg) and triethylamine (1.8 ml) under ice-cooling. The mixture is then stirred for 2 hours under the same cooling conditions. To the reaction solution, saturated aqueous sodium hydrogen carbonate solution and sodium chloride are added, and the mixture is extracted with chloroform. The organic layer is dried over sodium sulfate and evaporated the solvent under reduced pressure. Purification by silica gel column chromatography (eluent: chloroform, followed by chloroform/methanol=20/1 to 10/1) gives 4-chloronicotinamide (211 mg).

APCI-MS M/Z: 157/159[M+H]$^+$.

(3) 4-Chloronicotinamide (210 mg) obtained in (2) above is suspended in phosphoryl chloride (7 ml) and the mixture heated at 100° C. for 2 hours. After allowing to cool, the reaction solution is concentrated under reduced pressure. To the resulting residue are poured saturated aqueous sodium hydrogen carbonate solution and chloroform under ice-cooling. The mixture is then warmed to room temperature and stirred for 1 hour. The organic layer is separated, washed with saturated brine, dried over sodium sulfate and the solvent is removed by evaporation under reduced pressure. The resulting residue is purified by silica gel column chromatography (eluent: chloroform followed by chloroform/methanol=20/1) to give the title compound (115 mg).

$^1$H-NMR(CDCl$_3$,300 MHz): δ:8.86(1H,d,J=0.4 Hz), 8.71 (1H,d,J=5.4 Hz), 7.51(1H,dd,J=5.4,0.4 Hz).

Reference Example 26

N-(5-Chloropyridin-2-yl)-2-[(3-cyanopyridin-4-yl)oxy]acetamide

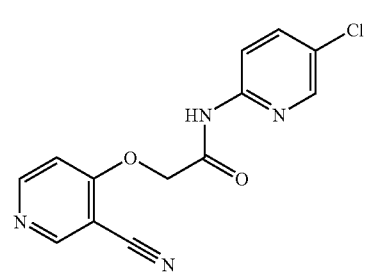

N-(5-Chloropyridin-2-yl)-2-hydroxyacetamide (142 mg) obtained in Reference Example 22 is dissolved in N,N-dimethylformamide (3 ml), and thereto is added 60% sodium hydride in oil (61 mg) under ice-cooling. The reaction solution is warmed to room temperature, stirred for 15 minute and cooled again with ice, followed by addition of a solution of 4-chloronicotinonitrile (105 mg) obtained in Reference Example 25 in N,N-dimethylformamide (1 ml). The reaction solution is stirred at room temperature for 1 hour, and thereto is poured water under ice-cooling, followed by extraction with ethyl acetate. The organic layer is washed with water and saturated brine, dried over sodium sulfate, and evaporated to remove the solvent under reduced pressure. The resulting residue is suspended in n-hexane/diisopropyl ether, collected by filtration and dried to give the title compound (200 mg).

APCI-MS M/Z:289/291[M+H]$^+$.

Reference Example 27

3-Amino-N-(5-chloropyridin-2-yl)furo[3,2-c]pyridine-2-carboxamide

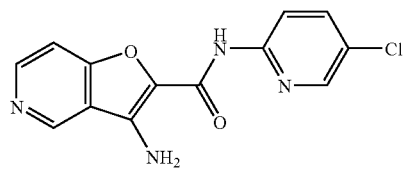

N-(5-Chloropyridin-2-yl)-2-[(3-cyanopyridin-4-yl)oxy] acetamide (195 mg) obtained in Reference Example 26 is dissolved in N,N-dimethylacetamide (5 ml), and thereto is added sodium carbonate (86 mg). The mixture is then stirred at 100° C. for 3 hours. After allowing to cool, the reaction solution is concentrated under reduced pressure, and ice-water is poured to the resulting residue. The precipitates are collected by filtration, washed with water followed and then with diethyl ether to give the title compound (171 mg).

APCI-MS M/Z:289/291[M+H]$^+$.

Reference Example 28

N-(5-Chloropyridin-2-yl)-2-[(4-cyanopyridin-3-yl)oxy]acetamide

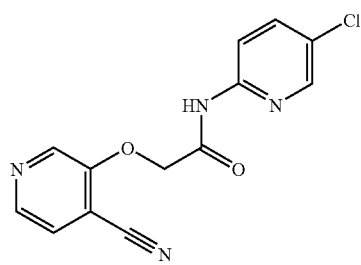

(1) Ethyl 3-aminoisonicotinate (5.55 g) is suspended in water (70 ml), and thereto added conc. sulfuric acid (4.0 ml). The reaction solution is cooled with ice, and a solution of sodium nitrite (2.79 g) in water (30 ml) is added dropwise thereto. The reaction solution is stirred under the same cooling conditions for 20 minutes and then at 90° C. for 80 minutes. The reaction solution is diluted with water (100 ml) and the solution is adjusted to pH 8 to 9 by addition of saturated aqueous sodium hydrogen carbonate solution, followed by extraction with chloroform. The organic layer is dried over sodium sulfate and evaporated to remove the solvent under reduced pressure. The resulting residue is purified by silica gel column chromatography (eluent: n-hexane/ethyl acetate=5/1) to give ethyl 3-hydroxyisonicotinate (2.64 g).

APCI-MS M/Z: 168[M+H]$^+$.

(2) Ethyl 3-hydroxyisonicotinate (1.60 g) obtained in (1) above is dissolved in ethanol (30 ml), and ammonia gas is bubbled therein under ice-cooling. To the reaction solution is added tetrahydrofuran (50 ml), and additional ammonia gas is bubbled in the mixture. The reaction solution is warmed to room temperature and stirred for 3 hours. The bubbling of ammonia gas is stopped and the mixture is stirred at room temperature for 2.5 days. The reaction solution is concentrated to dryness under reduced pressure to give 3-hydroxyisonicotinamide (1.35 g).

ESI-MS M/Z: 137[M−H]$^−$.

(3) Pyridine (1.20 ml) is added dropwise to a solution of trifluoroacetic anhydride (3.10 g) in dichloromethane (30 ml) and a suspension of 3-hydroxyisoniconamide (683 mg) obtained in (2) above in dichloromethane (10 ml) is added thereto in small portions under ice-cooling. The reaction solution is warmed to room temperature, stirred for 13 hours and then, and thereto are added water and saturated aqueous sodium hydrogen carbonate solution. The aqueous layer is separated and concentrated to dryness under reduced pressure to give crude 3-hydroxyisonicotinonitrile. Then, the resulting crude product is suspended in acetone (50 ml), and thereto are added 2-chloro-N-(5-chloropyridin-2-yl)acetamide (1.08 g) obtained in Reference Example 21, cesium carbonate (3.03 g) and sodium iodide (0.78 g), and the mixture is heated under reflux for 19 hours. After allowing to cool, water, tetrahydrofuran and ethyl acetate are poured to the mixture and the insoluble materials are removed by filtration. The organic layer is separated, dried over magnesium sulfate, and evaporated to remove the solvent under reduced pressure. The resulting residue is purified by silica gel column chromatography (eluent: n-hexane/ethyl acetate=1/1, followed by 1/2) to give the title compound (87 mg).

APCI-MS M/Z:289/291[M+H]$^+$.

Reference Example 29

3-Amino-N-(5-chloropyridin-2-yl)furo[2,3-c]pyridine-2-carboxamide

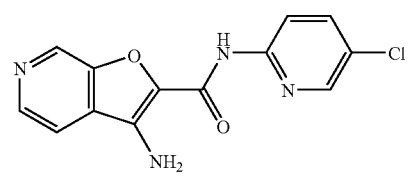

N-(5-Chloropyridin-2-yl)-2-[(4-cyanopyridin-3-yl)oxy] acetamide (82 mg) obtained in Reference Example 28 is dissolved in N,N-dimethylacetamide (5 ml), and thereto is added sodium carbonate (39 mg). The mixture is then stirred at 100° C. for 3 hours. After allowing to cool, the reaction solution is diluted with water. The precipitates are collected by filtration, washed with water and dried to give the title compound (47 mg).

APCI-MS M/Z:289/291[M+H]$^+$.

Reference Example 30

N-(5-Chloropyridin-2-yl)-2-[(3-cyanopyridin-2-yl)oxy]acetamide

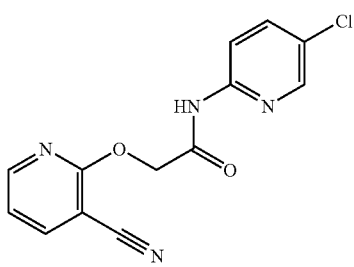

N-(5-Chloropyridin-2-yl)-2-hydroxyacetamide (187 mg) obtained in Reference Example 22 is dissolved in N,N-dimethylformamide (3 ml) and thereto is added 60% sodium hydride in oil (80 mg). The reaction solution is stirred for 15 minutes, and thereto is added 2-chloronicotinonitrile (139 mg). The reaction solution is stirred at room temperature for 1 hour, and thereto are added saturated aqueous ammonium chloride solution and water successively under ice-cooling. The precipitates are collected by filtration, washed with water and diisopropyl ether successively, and dried to give the title compound (212 mg).

APCI-MS M/Z:289/291[M+H]$^+$.

Reference Example 31

3-Amino-N-(5-chloropyridin-2-yl)furo[2,3-b]-pyridin-2-carboxamide

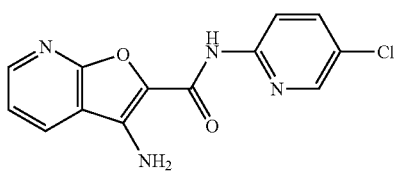

N-(5-Chloropyridin-2-yl)-2-[(3-cyanopyridin-2-yl)oxy]acetamide (209 mg) obtained in Reference Example 30 is dissolved in N,N-dimethylacetamide (3 ml), and thereto is added sodium carbonate (92 mg). The mixture is then stirred at 100° C. overnight. Additional sodium carbonate (90 mg) is added to the mixture and the mixture is again stirred at 100° C. overnight. After allowing to cool, ice-water is poured to the reaction solution. The precipitates are collected by filtration, dissolved in chloroform/methanol and dried over sodium sulfate. The solvent is evaporated under reduced pressure and the resulting residue is suspended in n-hexane/ethyl acetate. The precipitates are collected by filtration to give the title compound (111 mg).

APCI-MS M/Z:289/291[M+H]$^+$.

Reference Example 32

3-Chloropyrazine-2-carbonitrile

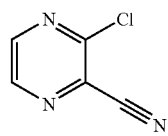

Pyrazine-2-carbonitrile (26.36 g) is dissolved in toluene (187 ml)/N,N-dimethylformamide (19 ml), and thereto is added dropwise sulfuryl chloride (135 g) under ice-cooling. After completion of addition, the reaction solution is warmed to room temperature gradually and stirred overnight. The toluene layer is separated and the residual red oil is extracted with diethyl ether. The organic layers are combined, cooled with ice, and after pouring thereto ice-water, neutralized by adding saturated aqueous sodium hydrogen carbonate solution. The organic layer is separated, and aqueous layer is extracted with diethyl ether. The organic layers are combined, washed with water, dried over sodium sulfate and evaporated to remove the solvent under reduced pressure. The resulting residue is purified by silica gel column chromatography (eluent: n-hexane/ethyl acetate=4/1) to give the title compound (16.58 g).

$^1$H-NMR(CDCl$_3$,300 MHz) δ:8.66(1H,d,J=2.4 Hz), 8.61 (1H,d,J=2.4 Hz).

Reference Example 33

N-(5-Chloropyridin-2-yl)-2-[(3-cyanopyrazin-2-yl)oxy]acetamide

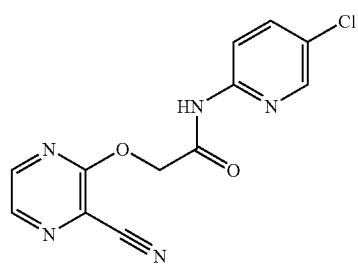

N-(5-Chloropyridin-2-yl)-2-hydroxyacetamide (1.34 g) obtained in Reference Example 22 is dissolved in N,N-dimethylformamide (15 ml), and thereto is added 60% sodium hydride in oil (574 mg). The reaction solution is stirred at room temperature for 15 minutes, cooled again with ice, and a solution of 3-chloropyrazine-2-carbonitrile (1.0 g) obtained in Reference Example 32 in N,N-dimethylformamide (5 ml) is added. The reaction solution is stirred at room temperature for 1 hour, and thereto is poured water under ice-cooling, followed by extraction with ethyl acetate. The organic layer is washed with water and saturated brine, dried over sodium sulfate and evaporated to remove the solvent under reduced pressure. The resulting residue is suspended in n-hexane-diisopropyl ether. The precipitates are collected by filtration and dried to give the title compound (1.92 g).

APCI-MS M/Z:290/292[M+H]$^+$.

Reference Example 34

7-Amino-N-(5-chloropyridin-2-yl)furo[2,3-b]pyrazine-6-carboxamide

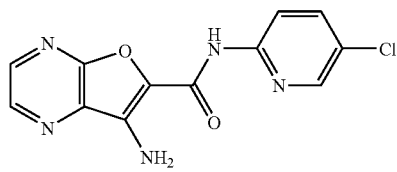

N-(5-Chloropyridin-2-yl)-2-[(3-cyanopyrazin-2-yl)oxy] acetamide (1.90 g) obtained in Reference Example 33 is dissolved in N,N-dimethylacetamide (20 ml), and thereto is added sodium carbonate (834 mg) and the mixture is stirred at 100° C. for 3 days. After allowing to cool, the reaction solution is concentrated under reduced pressure and water is poured to the residue. The precipitates are collected by filtration, washed with diethyl ether and dry to give the title compound (0.38 g).

APCI-MS M/Z:290/292[M+H]$^+$.

Reference Example 35

Methyl 5-hydroxypyridine-2-carboxylate 1-oxide

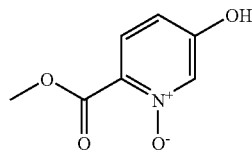

To a suspension of methyl 5-hydroxypyridin-2-carboxylate (5.30 g) in dichloromethane (75 ml), m-chloroperbenzoic acid (>65%, 11.0 g) is added under ice-cooling, and the mixture is stirred at room temperature for 5 hours. The reaction solution is concentrated under reduced pressure. The residue is suspended in ethyl acetate and collected by filtration to give the title compound (4.62 g). Mother liquor is concentrated under reduced pressure and the resulting residue is purified by silica gel column chromatography (eluent: chloroform to methanol/chloroform=1/5). The resulting solid is suspended in ethyl acetate/diethyl ether and collected by filtration to give the title compound (0.68 g).

APCI-MS M/Z: 170[M+H]$^+$.

Reference Example 36

Methyl 6-cyano-5-hydroxypyridine-2-carboxylate

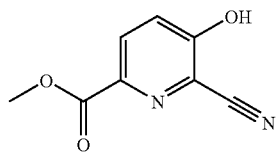

Methyl 5-hydroxypyridine-2-carboxylate 1-oxide (5.18 g) obtained in Reference Example 35, sodium cyanide (4.50 g) and triethylamine (29.9 ml) are added to N,N-dimethylformamide (55 ml), and thereto is added chlorotrimethylsilane (19.4 ml) over 20 minutes. The mixture is then stirred at 80° C. for 28 hours. The reaction solution is cooled to room temperature, filtered to remove the insoluble materials and the filtrate is concentrated under reduced pressure. Methanol (150 ml) is added to the residue, and the mixture is stirred at room temperature for 30 minutes and evaporated to remove the solvent under reduced pressure. The residue is purified by silica gel column chromatography (eluent: chloroform to methanol/chloroform=1/5). The resulting solid is suspended in diethyl ether and collected by filtration to give the title compound (4.66 g).

ESI-MS M/Z: 177[M−H]$^−$.

Reference Examples 37-43

The corresponding starting compounds are treated in a similar manner to Reference Example 35 to give the following compounds.

TABLE 74

| Ref. Ex. No. | Structure | Physicochemical Properties |
|---|---|---|
| 37 | ![structure] | ESI-MS M/Z: 124 [M − H]$^−$ |
| 38 | ![structure] | ESI-MS M/Z: 144/146 [M − H]$^−$ |
| 39 | ![structure] | APCI-MS M/Z: 130 [M + H]$^+$ |

TABLE 74-continued

| Ref. Ex. No. | Structure | Physicochemical Properties |
|---|---|---|
| 40 | 2-methoxy-5-hydroxypyridine N-oxide | APCI-MS M/Z: 142 [M + H]⁺ |
| 41 | 2-cyano-5-hydroxypyridine N-oxide | ESI-MS M/Z: 135 [M − H]⁻ |
| 42 | 3-chloro-5-hydroxypyridine N-oxide | ESI-MS M/Z: 144/146 [M − H]⁻ |
| 43 | methyl 5-hydroxynicotinate N-oxide | ESI-MS M/Z: 168 [M − H]⁻ |

Reference Examples 44-50

The corresponding starting compounds are treated in a similar manner to Reference Example 36 to give the following compounds.

TABLE 75

| Ref. Ex. No. | Structure | Physicochemical Properties |
|---|---|---|
| 44 | 6-methyl-3-hydroxy-2-cyanopyridine | ESI-MS M/Z: 133 [M − H]⁻ |
| 45 | 6-chloro-3-hydroxy-2-cyanopyridine | ESI-MS M/Z: 153/155 [M − H]⁻ |
| 46 | 6-fluoro-3-hydroxy-2-cyanopyridine | ESI-MS M/Z: 137 [M − H]⁻ |
| 47 | 6-methoxy-3-hydroxy-2-cyanopyridine | APCI-MS M/Z: 151 [M + H]⁺ |
| 48 | 3-hydroxy-2,6-dicyanopyridine | ESI-MS M/Z: 144 [M − H]⁻ |
| 49 | 5-chloro-3-hydroxy-2-cyanopyridine | ESI-MS M/Z: 153/155 [M − H]⁻ |
| 50 | methyl 5-hydroxy-6-cyanonicotinate | APCI-MS M/Z: 179 [M + H]⁺ |

Reference Examples 51-58

The corresponding starting compounds are treated in a similar manner to Reference 23 to give the following compounds.

TABLE 76

| Ref. Ex. No. | Structure | Physicochemical Properties |
|---|---|---|
| 51 | 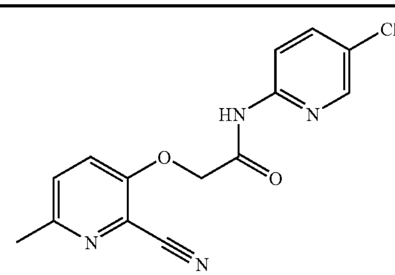 | APCI-MS M/Z: 303/305 [M + H]⁺ |

TABLE 76-continued
| Ref. Ex. No. | Structure | Physicochemical Properties |
| --- | --- | --- |
| 52 | 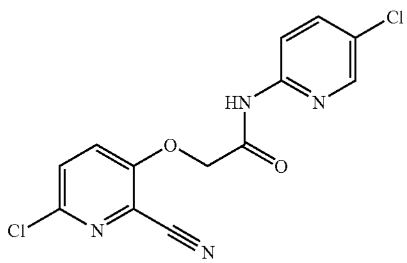 | APCI-MS M/Z: 323/325 [M + H]+ |
| 53 | 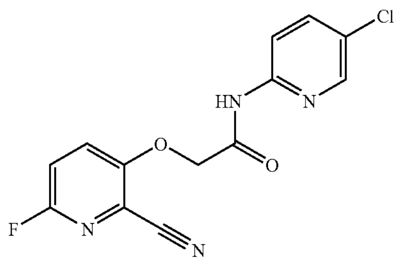 | APCI-MS M/Z: 307/309 [M + H]+ |
| 54 | 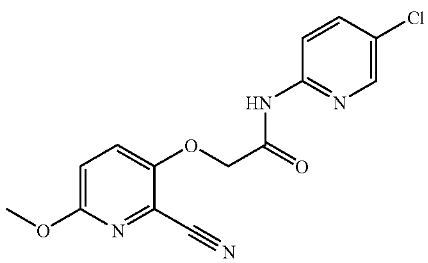 | APCI-MS M/Z: 319/321 [M + H]+ |
| 55 | 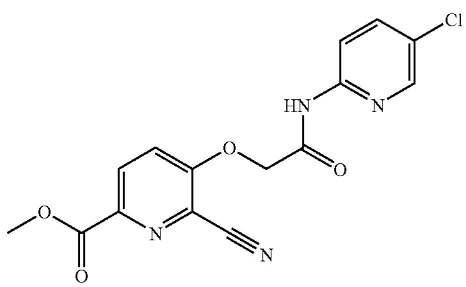 | APCI-MS M/Z: 347/349 [M + H]+ |
TABLE 77
| Ref. Ex. No. | Structure | Physicochemical Properties |
| --- | --- | --- |
| 56 | 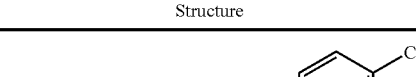 | APCI-MS M/Z: 314/316 [M + H]+ |

TABLE 77-continued

| Ref. Ex. No. | Structure | Physicochemical Properties |
|---|---|---|
| 57 | 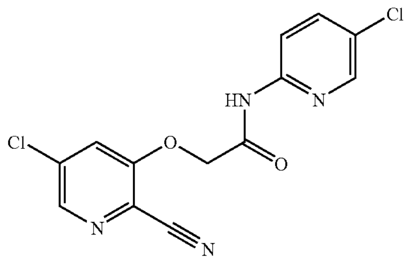 | APCI-MS M/Z: 323/325 [M + H]$^+$ |
| 58 | 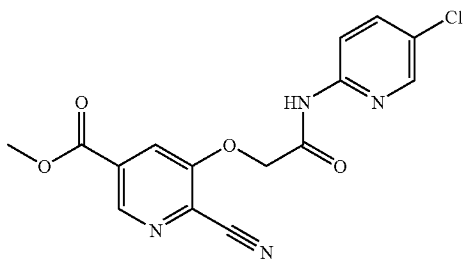 | APCI-MS M/Z: 347/349 [M + H]$^+$ |

Reference Examples 59-66

The corresponding starting compounds are treated in a similar manner to Reference Example 24 to give the following compounds.

TABLE 78

| Ref. Ex. No. | Structure | Physicochemical Properties |
|---|---|---|
| 59 | 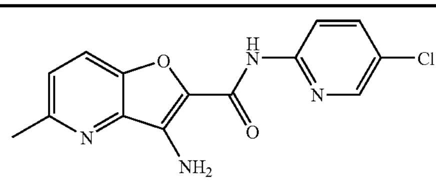 | APCI-MS M/Z: 303/305 [M + H]$^+$ |
| 60 | 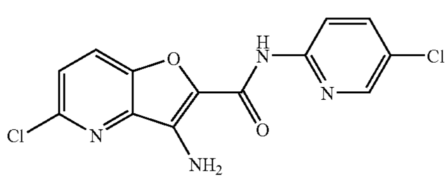 | APCI-MS M/Z: 323/325 [M + H]$^+$ |
| 61 | 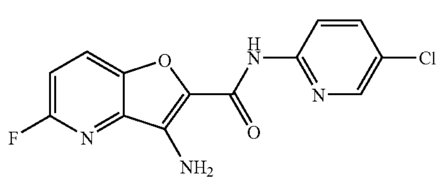 | APCI-MS M/Z: 307 [M + H]$^+$ |
| 62 | 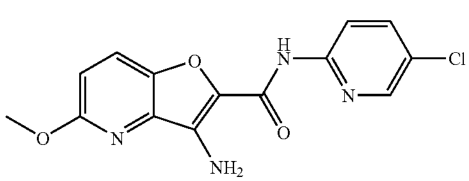 | APCI-MS M/Z: 319/321 [M + H]$^+$ |

TABLE 78-continued

| Ref. Ex. No. | Structure | Physicochemical Properties |
|---|---|---|
| 63 | 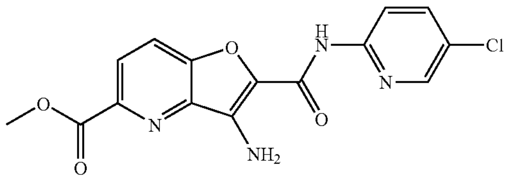 | APCI-MS M/Z: 347/349 [M + H]+ |
| 64 | 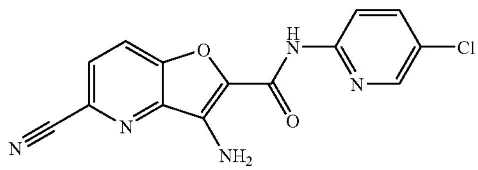 | APCI-MS M/Z: 314/316 [M + H]+ |
| 65 | 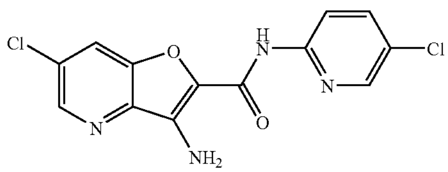 | APCI-MS M/Z: 323/325 [M + H]+ |
| 66 | 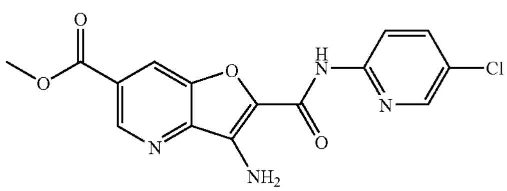 | APCI-MS M/Z: 347/349 [M + H]+ |

Reference Example 67

3-Amino-2-{[(5-chloropyridin-2-yl)amino]-carbonyl}furo[3,2-b]pyridine-5-carboxylic acid

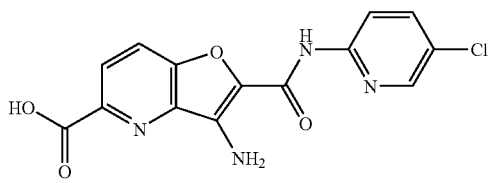

Methyl 3-amino-2-{[(5-chloropyridin-2-yl)amino]carbonyl}furo[3,2-b]pyridine-5-carboxylate (800 mg) obtained in Reference Example 63 is suspended in tetrahydrofuran/methanol (3:1, 40 ml), and thereto is added 1 N aqueous sodium hydroxide solution (11.5 ml). The mixture is then stirred at room temperature for 2 days. The reaction solution is neutralized with 1 N hydrochloric acid (11.5 ml) and diluted with water. The precipitated solid is collected by filtration and dried to give the title compound (615 mg).

ESI-MS M/Z:331/333[M−H]−.

Reference Example 68

The corresponding starting compounds are treated in a similar manner to Reference Example 67 to give the following compounds.

TABLE 79

| Ref. Ex. No. | Structure | Physicochemical Properties |
|---|---|---|
| 68 | 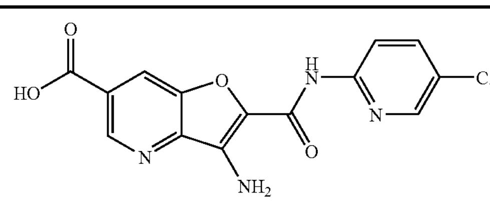 | ESI-MS M/Z: 331/333 [M − H]− |

Reference Example 69

3-Amino-$N^2$-(5-chloropyridin-2-yl)-$N^5$,$N^5$-dimethyl-furo[3,2-b]pyridine-2,5-dicarboxamide

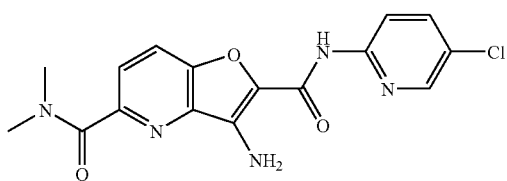

3-Amino-2-{[(5-chloropyridin-2-yl)amino]carbonyl}furo[3,2-b]-pyridine-5-carboxylic acid (605 mg) obtained in Reference Example 67 is suspended in N,N-dimethylformamide (10 ml), and thereto are added dimethylamine hydrochloride (297 mg), 1-hydroxybenzotriazole (492 mg), 1-ethyl-3-(3-dimethylaminopropyl)carbodiimide hydrochloride (698 mg) and triethylamine (634 µl) successively. The mixture is then stirred at room temperature for 24 hours. The reaction solution is concentrated under reduced pressure. To the resulting residue, saturated aqueous sodium hydrogen carbonate solution and water are poured. The precipitated solid is collected by filtration, washed with water and diethyl ether and dried to give the title compound (621 mg).

APCI-MS M/Z:360/362[M+H]$^+$.

Reference Example 70

The corresponding starting compounds are treated in a similar manner to Reference Example 69 to give the following compound.

TABLE 80

| Ref. Ex. No. | Structure | Physicochemical Properties |
| --- | --- | --- |
| 70 | 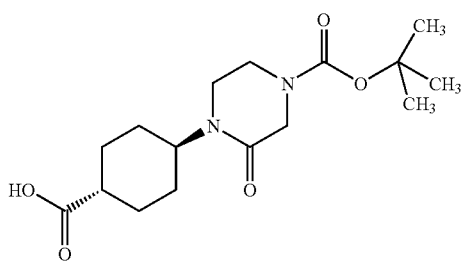 | APCI-MS M/Z: 360/362 [M + H]$^+$ |

Reference Example 71

Trans-4-[4-(t-butoxycarbonyl)-2-oxopiperazin-1-yl]cyclohexanecarboxylic acid (1) Methyl trans-4-aminocyclohexanecarboxylate hydrochloride (1.22 g) obtained in Reference Example 2(1) is suspended in dichloromethane (10 ml), and thereto is added triethylamine (1.76 ml) and the mixture is stirred for several minutes. After a solution of t-butyl (2-oxoethyl)carbamate (1.00 g) in dichloromethane (5 ml) and sodium triacetoxy borohydride (1.46 g) are added successively under ice-cooling, the reaction solution is warmed to the room temperature and stirred for 15 hours. Saturated aqueous sodium hydrogen carbonate solution is poured to the reaction solution, and the mixture is extracted with chloroform. The organic layer is dried over sodium sulfate and evaporated to remove the solvent under reduced pressure. A portion (1.71 g) of the resulting residue (2.33 g) is purified by silica gel column chromatography (eluent: chloroform/methanol=10/1) to give methyl trans-4-({2-[(t-butoxycarbonyl)amino]ethyl}amino)cyclohexanecarboxylate (793 mg).

APCI-MS M/Z:301[M+H]$^+$.

(2) Methyl trans-4-({2-[(t-butoxycarbonyl)amino]ethyl}amino)cyclohexanecarboxylate (785 mg) obtained in Reference Example 71 (1) is dissolved in chloroform (8 ml), and thereto are added triethylamine (1.82 ml) and chloroacetyl chloride (249 µl) under ice-cooling. The mixture is then stirred at room temperature for 2 hours. The reaction solution is cooled with ice again, and chloroacetyl chloride (62 µl) is supplied thereto. The mixture is stirred at room temperature for 1 hour. To the reaction solution, saturated aqueous sodium hydrogen carbonate solution is poured and the mixture is extracted with chloroform. The organic layer is washed with water and saturated brine successively, dried over sodium sulfate and evaporated to remove the solvent under reduced pressure. The resulting residue is purified by silica gel column chromatography (eluent: n-hexane/ethyl acetate=2/1, followed by 1/1) to give methyl trans-4-[{2-[(t-butoxycarbonyl)amino]ethyl}-(chloroacetyl)amino]cyclohexanecarboxylate (568 mg).

APCI-MS M/Z:377/379[M+H]$^+$.

(3) Methyl trans-4-[{2-[(t-butoxycarbonyl)amino]ethyl}-(chloroacetyl)amino]cyclohexanecarboxylate (560 mg) obtained in Reference Example 71(2) is dissolved in N,N-dimethylacetamide (5 ml), and 60% sodium hydride in oil (119 mg) is added thereto under ice-cooling. The reaction solution is then stirred for 0.5 hours under the same cooling conditions. Saturated aqueous ammonium chloride solution and water are poured to the reaction solution successively under ice-cooling, and the mixture is extracted with ethyl acetate. The organic layer is washed with water and saturated brine successively, dried over sodium sulfate and evaporated to remove the solvent under reduced pressure. The resulting residue is purified by silica gel column chromatography (eluent: n-hexane/ethyl acetate=1/1) to give t-butyl 4-[trans-4-(methoxycarbonyl)cyclohexyl]-3-oxopiperazine-1-carboxylate (302 mg).

APCI-MS M/Z:341[M+H]$^+$.

(4) t-Butyl 4-[trans-4-(methoxycarbonyl)cyclohexyl]-3-oxopiperazine-1-carboxylate (385 mg) obtained in Reference Example 71 (3) is dissolved in methanol (8 ml), and thereto is added 1 N aqueous sodium hydroxide solution (3.4 ml) under ice-cooling. The reaction solution is stirred at room temperature for 20 hours and concentrated under reduced pressure. Water and chloroform are poured to the residue, and aqueous layer is acidified by addition of 2 N hydrochloric acid. The organic layer is separated, washed with saturated brine and dried over sodium sulfate. The solvent is removed by evaporation under reduced pressure to give the title compound (375 mg).

ESI-MS M/Z:325[M−H]$^-$.

Reference Example 72

2-[(6-Bromo-2-cyanopyridin-3-yl)oxy]-N-(5-chloropyridin-2-yl)acetamide

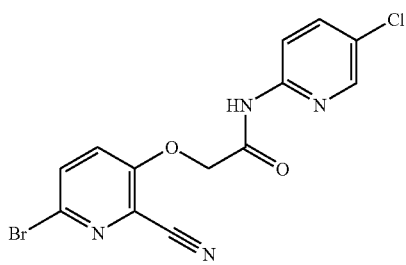

(1) 2-Cyano-3-hydroxypyridine (3.00 g) is dissolved in acetonitrile/water (5:1, 90 ml), and N-bromosuccinic imide (5.34 g) is added thereto in small portions under ice-cooling. The mixture is then stirred for 2 hours under the same cooling conditions. The reaction solution is diluted with ethyl acetate, washed with water and saturated brine successively and dried over sodium sulfate. The solvent is removed by evaporation under reduced pressure to give crude 6-bromo-3-hydroxypyridine-2-carbonitrile (6.26 g).

ESI-MS M/Z:197/199[M−H]$^-$.

(2) 6-Bromo-3-hydroxypyridine-2-carbonitrile (6.20 g) obtained in Reference Example 72(1) is treated in a similar manner to Reference Example 23 to give the title compound (4.36 g).

APCI-MS M/Z:367/369[M+H]$^+$.

Reference Example 73

3-Amino-5-bromo-N-(5-chloropyridin-2-yl)-furo[3,2-b]pyridine-2-carboxamide

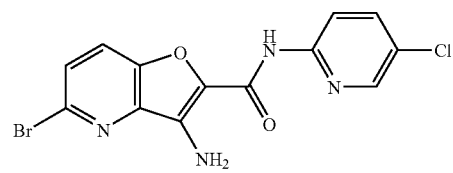

2-[(6-Bromo-2-cyanopyridin-3-yl)oxy]-N-(5-chloropyridin-2-yl)acetamide (4.00 g) obtained in Reference Example 72 is treated in a similar manner to Reference Example 24 to give the title compound (2.96 g).

APCI-MS M/Z:367/369[M+H]$^+$.

Reference Example 74

2-Chloro-N-(4-chlorophenyl)acetamide

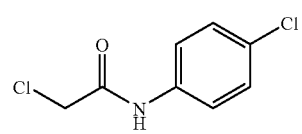

5-Chloroaniline (7.03 g) is treated in a similar manner to Reference Example 21 to give the title compound (10.18 g).

APCI-MS M/Z:204/206[M+H]$^+$.

Reference Example 75

N-(4-Chlorophenyl)-2-[(2-cyanopyridin-3-yl)oxy]acetamide

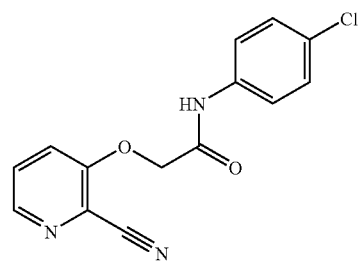

2-Cyano-3-hydroxypyridine (2.00 g) and 2-chloro-N-(4-chlorophenyl)acetamide (3.75 g) obtained in Reference Example 74 are treated in a similar manner to Reference Example 23 to give the title compound (4.58 g).

APCI-MS M/Z:288/290[M+H]$^+$.

Reference Example 76

3-Amino-N-(4-chlorophenyl)furo[3,2-b]pyridin-2-carboxamide

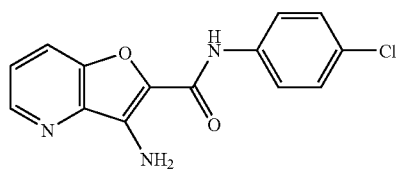

N-(4-Chlorophenyl)-2-[(2-cyanopyridin-3-yl)oxy]acetamide (4.50 g) obtained in Reference Example 75 is treated in a similar manner to Reference Example 24 to give the title compound (2.98 g).

APCI-MS M/Z: 288/290[M+H]$^+$.

Reference Example 77

Methyl [(2-cyanopyridin-3-yl)oxy]acetate

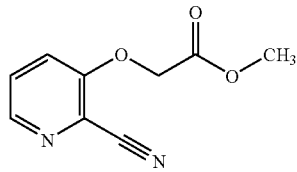

2-Cyano-3-hydroxypyridine (5.00 g) is dissolved in acetone (50 ml), and thereto are added methyl bromoacetate (7.0 g) and potassium carbonate (6.3 g). The mixture is heated under reflux for 1.5 hours. After allowing to cool, ice-water is poured to the reaction solution and extracted with ethyl acetate. The organic layer is washed with saturated brine, dried over sodium sulfate and evaporated to remove the solvent under reduced pressure. The resulting residue is suspended in diethyl ether/n-hexane and the solid is collected by filtration to give the title compound (7.91 g).

APCI-MS M/Z: 193[M+H]$^+$.

Reference Example 78

Methyl 3-aminofuro[3,2-b]pyridine-2-carboxylate

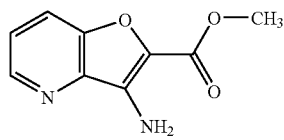

Methyl [(2-cyanopyridin-3-yl)oxy]acetate (4.00 g) obtained in Reference Example 77 is dissolved in tetrahydrofuran (100 ml), and 60% sodium hydride in oil (1.53 g) is added in small portions under ice-cooling. The reaction solution is warmed to room temperature and stirred for 1 hour. The reaction solution is poured to aqueous ammonium chloride/citric acid solution under ice-cooling, followed by extraction with ethyl acetate. The organic layer is washed with saturated brine, dried over sodium sulfate and evaporated to remove the solvent under reduced pressure. The resulting residue is suspended in n-hexane and the solid is collected by filtration to give the title compound (2.96 g).

APCI-MS M/Z: 193[M+H]$^+$.

Reference Example 79

Methyl 3-({[trans-4-(3-oxomorpholin-4-yl)cyclohexyl]carbonyl}amino)furo[3,2-b]pyridine-2-carboxylate

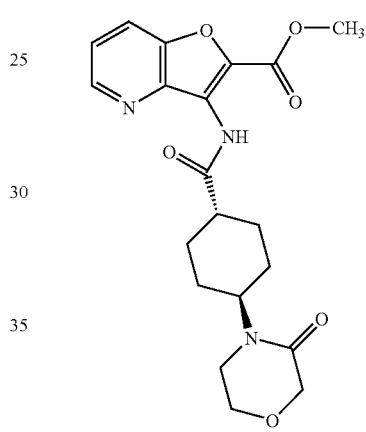

Trans-4-(3-oxomorpholin-4-yl)cyclohexanecarboxylic acid (3.55 g) obtained in Reference Example 4 is dissolved in thionyl chloride (20 ml). The mixture is then stirred at room temperature for 15 hours. The reaction solution is concentrated under reduced pressure, and the residue is subjected to azeotropic distillation with toluene and dissolved in chloroform (25 ml). Under ice-cooling, methyl 3-aminofuro[3,2-b]-pyridine-2-carboxylate (2.00 g) obtained in Reference Example 78 and pyridine (1.68 ml) are added in this order, and the reaction solution is warmed to room temperature and stirred for 5 hours. Saturated aqueous sodium hydrogen carbonate solution is poured to the reaction solution under ice-cooling and the mixture is extracted with chloroform. The organic layer is washed with water and saturated brine successively, dried over sodium sulfate and evaporated to remove the solvent under reduced pressure. The residue is purified by NH-silica gel column chromatography (eluent: ethyl acetate, followed by ethyl acetate/methanol=5/1). The resulting solid is suspended in diethyl ether/n-hexane and collected by filtration to give the title compound (3.54 g).

APCI-MS M/Z: 402[M+H]$^+$.

Reference Example 80

Trans-4-[(dimethylamino)carbonyl]cyclohexanecarboxylic acid

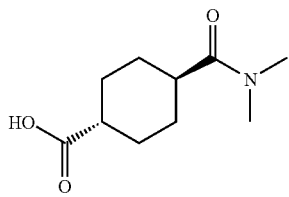

(1) Trans-4-(methoxycarbonyl)cyclohexanecarboxylic acid (20.0 g) obtained in Reference Example 1(2) is dissolved in chloroform (200 ml), and thereto are added dimethylamine hydrochloride (10.5 g), 1-ethyl-3-(3-dimethylaminopropyl) carbodiimide hydrochloride (24.7 g) and triethylamine (26.0 g) under ice-cooling. The mixture is then stirred at room temperature for 17 hours. Ice-water is poured to the reaction solution and the mixture is extracted with chloroform. The organic layer is washed with 10% hydrochloric acid, saturated aqueous sodium hydrogen carbonate solution and saturated brine successively and dried over sodium sulfate. The solvent is concentrated under reduced pressure and the resulting residue is purified by silica gel column chromatography (eluent: chloroform, followed by chloroform/methanol= 20/1) to give methyl trans-4-[(dimethylamino)carbonyl]-cyclohexanecarboxylate (20.1 g).

APCI-MS M/Z:214[M+H]$^+$.

(2) Methyl trans-4-[(dimethylamino)carbonyl]cyclohexanecarboxylate (20.0 g) obtained in Reference Example 80(1) is dissolved in methanol (100 ml), and thereto is added a solution of sodium hydroxide (7.50 g) in water (40 ml). The mixture is then stirred at room temperature for 18 hours. The reaction solution is concentrated under reduced pressure, and the residue is diluted with ice-water and washed with diethyl ether. The resulting aqueous layer is acidified with 10% hydrochloric acid and extracted twice with chloroform. The organic layer is washed with saturated brine and dried over sodium sulfate. The solvent is concentrated under reduced pressure. The resulting residue is suspended in n-hexane and collected by filtration to give the title compound (15.7 g).

ESI-MS M/Z: 198[M−H]$^-$.

Reference Example 81

Trans-4-(pyrrolidin-1-ylcarbonyl)cyclohexanecarboxylic acid

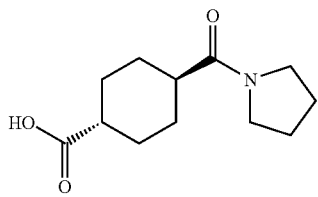

(1) Trans-4-(methoxycarbonyl)cyclohexanecarboxylic acid (20.0 g) obtained in Reference Example 1(2) is dissolved in chloroform (200 ml), and thereto are added pyrrolidine (9.2 g), 1-ethyl-3-(3-dimethylaminopropyl)carbodiimide hydrochloride (24.7 g) and triethylamine (13.6 g) under ice-cooling. The mixture is then stirred at room temperature for 17 hours. Ice-water is poured to the reaction solution and the mixture is extracted with chloroform. The organic layer is washed with 10% hydrochloric acid, saturated aqueous sodium hydrogen carbonate solution and saturated brine successively, and dried over sodium sulfate. The solvent is concentrated under reduced pressure. The resulting residue is purified by silica gel column chromatography (eluent: chloroform, followed by chloroform/methanol=20/1) to give methyl trans-4-(pyrrolidin-1-ylcarbonyl)cyclohexanecarboxylate (11.8 g).

APCI-MS M/Z:240[M+H]$^+$.

(2) Methyl trans-4-(pyrrolidin-1-ylcarbonyl)cyclohexanecarboxylate (11.7 g) obtained in Reference Example 81(1) is dissolved in methanol (50 ml), and thereto is added a solution of sodium hydroxide (3.95 g) in water (20 ml). The mixture is then stirred at room temperature for 18 hours. The reaction solution is concentrated under reduced pressure. The residue is diluted with ice-water and washed with diethyl ether. The resulting aqueous layer is acidified with 10% hydrochloric acid and extracted twice chloroform. The organic layer is washed with saturated brine and dried over sodium sulfate. The solvent is concentrated under reduced pressure. The resulting residue is suspended in n-hexane and collected by filtration to give the title compound (10.1 g).

ESI-MS M/Z:224[M−H]$^-$.

Reference Example 82

Trans-4-(morpholin-4-ylcarbonyl)cyclohexanecarboxylic acid

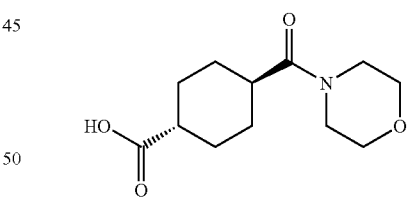

(1) Trans-4-(methoxycarbonyl)cyclohexanecarboxylic acid (800 mg) obtained in Reference Example 1(2) is dissolved in chloroform (30 ml), and thereto are added morpholine (560 mg), 1-ethyl-3-(3-dimethylaminopropyl)carbodiimide hydrochloride (1.24 g) and triethylamine (650 mg) under ice-cooling. The mixture is then stirred at room temperature for 19 hours. Ice-water is poured to the reaction solution and the mixture is extracted with chloroform. The organic layer is washed with 10% hydrochloric acid, saturated aqueous sodium hydrogen carbonate solution and saturated brine successively and dried over sodium sulfate. The solvent is concentrated under reduced pressure. The resulting residue is purified by silica gel column chromatography (eluent: chloroform, followed by chloroform/methanol=30/1) to give methyl trans-4-(morpholin-4-ylcarbonyl)cyclohexanecarboxylate (897 mg).

APCI-MS M/Z:256[M+H]$^+$.

(2) Methyl trans-4-(morpholin-4-ylcarbonyl)cyclohexanecarboxylate (860 mg) obtained in Reference Example 82(1) is dissolved in methanol (40 ml), and thereto is added 4 N aqueous sodium hydroxide solution (1.68 ml). The mixture is then stirred at room temperature for 18 hours. The reaction solution is concentrated under reduced pressure. The residue is diluted with ice-water, neutralized with 10% hydrochloric acid and extracted with chloroform. The organic layer is dried over sodium sulfate and the solvent is concentrated under reduced pressure to give title compound (638 mg).

ESI-MS M/Z:240[M−H]$^−$.

Reference Example 83

Trans-4-{[[2-(dimethylamino)ethyl](methyl)amino]carbonyl}cyclohexanecarboxylic acid

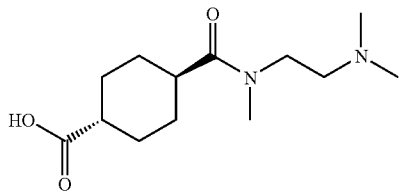

(1) Trans-4-(methoxycarbonyl)cyclohexanecarboxylic acid (8.84 g) obtained in Reference Example 1(2) is dissolved in chloroform (100 ml), and thereto are added 1-hydroxybenzotriazole (7.14 g), 1-ethyl-3-(3-dimethylaminopropyl)carbodiimide hydrochloride (10.00 g) and N,N,N'-trimethylethylenediamine (5.33 g) under ice-cooling. The mixture is then stirred at room temperature for 4 hours. Saturated aqueous sodium hydrogen carbonate solution is poured to the reaction solution and the mixture is extracted with chloroform. The organic layer is washed with saturated brine and dried over sodium sulfate. The solvent is concentrated under reduced pressure. The resulting residue is purified by silica gel column chromatography (eluent: chloroform/methanol/28% ammonia water=200/10/1) to give methyl trans-4-{[[2-(dimethylamino)ethyl](methyl)amino]carbonyl}-cyclohexanecarboxylate (11.98 g).

APCI-MS M/Z:271[M+H]$^+$.

(2) Methyl trans-4-{[[2-(dimethylamino) ethyl](methyl)amino]-carbonyl}cyclohexanecarboxylate (6.32 g) obtained in Reference Example 83(1) is dissolved in methanol (20 ml), and thereto is added 1 N aqueous sodium hydroxide solution (25 ml). The mixture is stirred at room temperature for 3 hours. To the reaction solution is added 1 N hydrochloric acid (25 ml) and the reaction solution is concentrated under reduced pressure. The residue is lyophilized to give the crude title compound which contains equimolar sodium chloride (6.71 g).

APCI-MS M/Z:257[M+H]$^+$.

Reference Example 84

6-Morpholin-4-yl-6-oxohexanoic acid

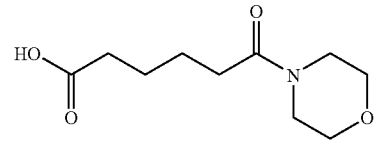

(1) Monomethyl adipate (3.20 g) is dissolved in chloroform (70 ml), and thereto are added morpholine (2.61 g), 1-ethyl-3-(3-dimethylaminopropyl)carbodiimide hydrochloride (5.75 g) and triethylamine (3.04 g) under ice-cooling. The mixture is then stirred at room temperature for 19 hours. Ice-water is added to the reaction solution and the mixture is extracted with chloroform. The organic layer is washed with 10% hydrochloric acid, saturated aqueous sodium hydrogen carbonate solution and saturated brine successively and dried over sodium sulfate. The solvent is removed by evaporation under reduced pressure to give methyl 6-morpholin-4-yl-6-oxohexanoate (4.63 g).

APCI-MS M/Z:230[M+H]$^+$.

(2) Methyl 6-morpholin-4-yl-6-oxohexanoate (4.60 g) obtained in Reference Example 84(1) is dissolved in methanol (20 ml), and thereto is added a solution of sodium hydroxide (1.61 g) in water (8 ml). The mixture is stirred at room temperature for 19 hours. The reaction solution is concentrated under reduced pressure and the residue is neutralized with 2 N hydrochloric acid. The residue is concentrated under reduced pressure and extracted with chloroform. The organic layer is dried over sodium sulfate and the solvent is concentrated under reduced pressure to give the title compound (4.11 g).

ESI-MS M/Z:214[M−H]$^−$.

Reference Example 85

5-Morpholin-4-yl-5-oxopentanoate

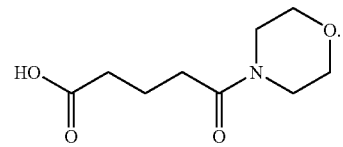

Glutaric anhydride (1.14 g) is dissolved in tetrahydrofuran (20 ml), and thereto added morpholine (0.87 g). The mixture is then stirred at room temperature for 19 hours. The reaction solution is concentrated under reduced pressure, and the residue is diluted with chloroform and washed with 10% hydrochloric acid. The organic layer is dried over sodium sulfate and evaporated to remove the solvent under reduced pressure to give the title compound (1.05 g).

ESI-MS M/Z:200[M−H]$^−$.

Reference Example 86

N-(5-Chloropyridin-2-yl)-2-[(2-bromo-3-cyanopyridin-4-yl)oxy]acetamide

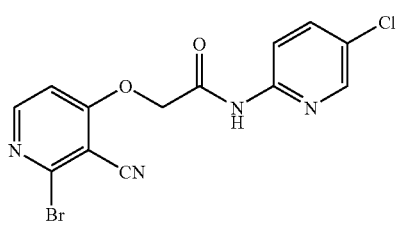

(1) 2-Bromo-3-cyano-4(1H)pyridone (literature as reference: M. Mittelback et al., Arch. Pharm., 1985, 318, 481-486) (837 mg) is suspended in acetone (30 ml), and thereto are added potassium carbonate (853 mg), 2-chloro-N-(5-chloropyridin-2-yl)acetamide (1.22 g) obtained in Reference Example 21 and sodium iodide (900 mg). The mixture is heated under reflux for 2 hours and 20 minutes. After potassium carbonate (150 mg), 2-chloro-N-(5-chloropyridin-2-yl)acetamide (221 mg) obtained in Reference Example 21 and sodium iodide (162 mg) are further added, the reaction mixture is heated under reflux for additional 45 minutes. The reaction solution is allowed to cool to room temperature and poured to water. The precipitated solid is collected by filtration. The resulting solid is dissolved in tetrahydrofuran, dried over sodium sulfate and evaporated to remove the solvent under reduced pressure. The resulting residue is purified by silica gel column chromatography (eluent: chloroform/methanol=50/1 followed by 30/1 and then 9/1) and suspended in chloroform/diisopropyl ether. The precipitates are collected by filtration to give the title compound (669 mg).

APCI-MS M/Z:367/369[M+H]$^+$.

Reference Example 87

3-Amino-4-bromo-N-(5-chloropyridin-2-yl)furo[3,2-c]pyridine-2-carboxamide

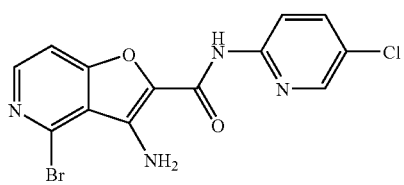

N-(5-Chloropyridin-2-yl)-2-[(2-bromo-3-cyanopyridin-4-yl)oxy]acetamide (429 mg) obtained in Reference Example 86 is treated in a similar manner to Reference Example 24 to give the title compound (260 mg).

APCI-MS M/Z:367/369[M+H]$^+$.

Reference Example 88

3-Amino-4-methoxy-N-(5-chloropyridin-2-yl)furo[3,2-c]pyridine-2-carboxamide

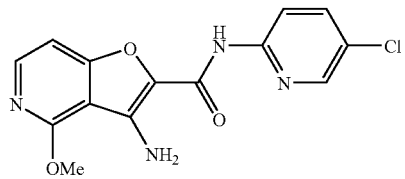

3-Amino-4-bromo-N-(5-chloropyridin-2-yl)furo[3,2-c]pyridine-2-carboxamide (125 mg) obtained in Reference Example 87 is suspended in N,N-dimethylformamide (2 ml), and thereto are added methanol (200 μl) and 60% sodium hydride in oil (69 mg) under ice-cooling. The mixture is stirred at room temperature for 3.5 hours. To the reaction solution, aqueous citric acid solution is added and the precipitated solid is collected by filtration to give the title compound (82 mg).

APCI-MS M/Z:319/321 [M+H]$^+$.

Reference Example 89

3-Amino-N-(5-chloropyridin-2-yl)-4-(2-methoxyethoxy)furo[3,2-c]pyridin-2-carboxamide

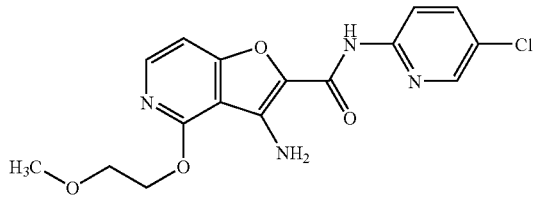

3-Amino-4-bromo-N-(5-chloropyridin-2-yl)furo[3,2-c]pyridine-2-carboxamide (508 mg) obtained in Reference Example 87 is suspended in N,N-dimethylformamide (10 ml) and thereto are added 2-methoxyethanol (2 ml) and 60% sodium hydride in oil (280 mg) under ice-cooling. The mixture is stirred at room temperature for 20 hours and the reaction solution is added to an aqueous citric acid solution. The precipitated solid is collected by filtration, washed with water and ethanol, and dried under reduced pressure to give the title compound (377 mg).

APCI-MS M/Z:363/365[M+H]$^+$.

Reference Example 90

3-Amino-N-(5-chloropyridin-2-yl)-4-methylfuro[3,2-c]pyridine-2-carboxamide

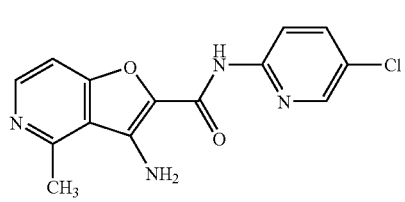

3-Amino-4-bromo-N-(5-chloropyridin-2-yl)furo[3,2-c]pyridine-2-carboxamide (1.09 g) obtained in Reference Example 87 is suspended in 10% aqueous 1,4-dioxane (30 ml), and thereto are added trimethylboroxine (0.57 ml) and potassium carbonate (1.67 g) at room temperature. The reaction solution is degassed and displaced with argon, and thereto is added tetrakis(triphenylphosphine)palladium (0) (416 mg). The mixture is further degassed and displaced with argon, and stirred at 110° C. for 21 hours. After adding water, the reaction solution is extracted with chloroform containing a slight amount of methanol. The organic layer is dried over sodium sulfate, and evaporated to remove the solvent under reduced pressure. The residue is purified by NH-silica gel column chromatography (eluent: n-hexane/ethyl acetate=3/1, followed by 1/1) to give the title compound (775 mg).

APCI-MS M/Z:303/305[M+H]$^+$.

Reference Example 91

3-Amino-N-(5-chloropyridin-2-yl)-4-cyanofuro[3,2-c]pyridine-2-carboxamide

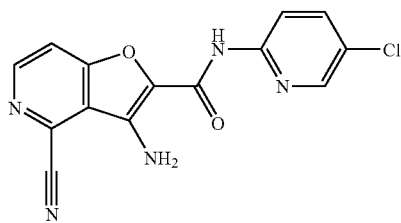

A suspension of 3-amino-4-bromo-N-(5-chloropyridin-2-yl)furo[3,2-c]pyridine-2-carboxamide (103 mg) obtained in Reference Example 87 and zinc cyanide (24 mg) in N,N-dimethylformamide (6 ml) is degassed and displaced with argon, and thereto is added tetrakis(triphenylphosphine)palladium (0) (23 mg). The mixture is again degassed and displaced with argon again, and stirred at 80° C. for 4 days. To the reaction solution are added water and chloroform, and the insoluble materials are removed by filtration. The organic layer is separated and dried over sodium sulfate. The solvent is removed by evaporation under reduced pressure. The residue is purified by silica gel column chromatography (eluent: n-hexane/ethyl acetate=70/30, followed by 40/60) to give the title compound (21 mg).

APCI-MS M/Z:314/316[M+H]$^+$.

Reference Example 92

3-(Benzyloxy)-6-bromopyridine-2-carbonitrile

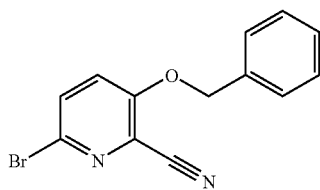

6-Bromo-3-hydroxypyridine-2-carbonitrile (53.8 g) obtained in Reference Example 72(1) is dissolved in acetone (550 ml), and thereto are added benzyl bromide (35.6 ml) and potassium carbonate (43.1 g). The mixture is then heated under reflux for 4 hours. After allowing to cool, water (600 ml) is added to the reaction solution, and the mixture is extracted with ethyl acetate. The aqueous layer is extracted with ethyl acetate once, and combined with the previous organic layer. The solution is washed with saturated brine and dried over sodium sulfate. The solvent is removed by evaporation under reduced pressure and the residue is purified by silica gel column chromatography (eluent: n-hexane/ethyl acetate=5/1, followed by 3/1). The resulting residue is suspended in diethyl ether/n-hexane and the solid is collected by filtration to give the title compound (24.1 g).

APCI-MS M/Z:289/291[M+H]$^+$.

Reference Example 93

3-(Benzyloxy)-6-(dimethylamino)pyridine-2-carbonitrile

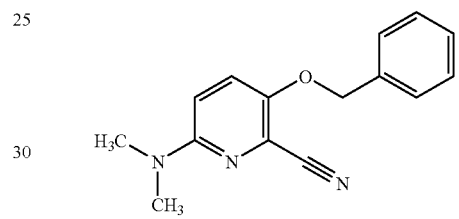

3-(Benzyloxy)-6-bromopyridine-2-carbonitrile (2.50 g) obtained in Reference Example 92 is added to toluene (25 ml), and thereto are added 2 mol/l dimethylamine/tetrahydrofuran solution (8.65 ml), tripotassium phosphate (2.75 g), tris(dibenzylideneacetone)dipalladium (0) (158 mg) and 2-(dicyclohexylphosphino)biphenyl (243 mg). The reaction solution is heated in a sealed tube at 80° C. for 24 hours, and 2 mol/l dimethylamine-tetrahydrofuran solution (8.65 ml), tripotassium phosphate (1.38 g), tris(dibenzylideneacetone)dipalladium (0) (79 mg) and 2-(dicyclohexylphosphino)biphenyl (122 mg) are added thereto, followed by heating in a sealed tube at 80° C. for additional 24 hours. After allowing to cool, water is poured to the reaction solution and the mixture is extracted with ethyl acetate. The organic layer is washed with saturated brine and dried over sodium sulfate. The solvent is evaporated under reduced pressure, and the residue is purified by silica gel column chromatography (eluent: n-hexane/chloroform=1/2) to give the title compound (1.29 g).

APCI-MS M/Z:254[M+H]$^+$.

Reference Example 94

3-(Benzyloxy)-6-(methylamino)pyridine-2-carbonitrile

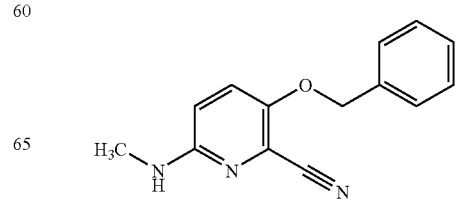

3-(Benzyloxy)-6-bromopyridine-2-carbonitrile (2.00 g) obtained in Reference Example 92 and 2 mol/l methylamine/tetrahydrofuran solution (26.0 ml) are treated in a similar manner to Reference Example 93 to give the title compound (0.34 g).

APCI-MS M/Z:240[M+H]⁺.

Reference Example 95 t-Butyl [5-(benzyloxy)-6-cyanopyridin-2-yl]methyl carbamate

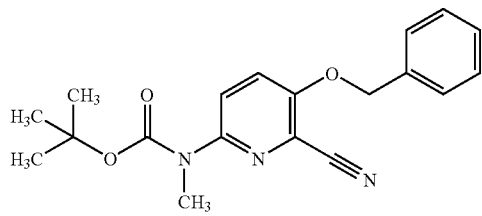

3-(Benzyloxy)-6-(methylamino)pyridine-2-carbonitrile (335 mg) obtained in Reference Example 94 is dissolved in chloroform (7 ml), and thereto are added di-t-butyl dicarbonate (321 mg) and 4-dimethylaminopyridine (34 mg) under ice-cooling. The mixture is stirred at room temperature for 2 hours, followed by at 50° C. for 2 hours. Di-t-butyl dicarbonate (321 mg) and 4-dimethylaminopyridine (17 mg) are added to the reaction solution, and the mixture is heated under reflux for 5 hours. Further, di-t-butyl dicarbonate (642 mg) and 4-dimethylaminopyridine (137 mg) are added to the reaction mixture and the mixture is stirred at 60° C. for 15 hours. After adding di-t-butyl dicarbonate (920 mg) and 4-dimethylaminopyridine (171 mg), the mixture is heated under reflux for 10 hours. The reaction solution is allowed to cool, and thereto poured water, followed by extraction with chloroform. The organic layer is washed with saturated brine and dried over sodium sulfate. The solvent is removed by evaporation under reduced pressure. The residue is purified by silica gel column chromatography (eluent: n-hexane/ethyl acetate=5/1, followed by 2/1) to give the title compound (156 mg).

APCI-MS M/Z:340[M+H]⁺.

Reference Example 96

3-(Benzyloxy)-6-morpholin-4-ylpyridine-2-carbonitrile

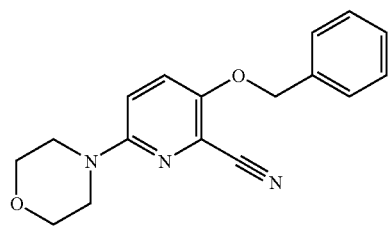

3-(Benzyloxy)-6-bromopyridine-2-carbonitrile (1.00 g) obtained in Reference Example 92 is added to toluene (10 ml), and thereto are added morpholine (362 µl), tripotassium phosphate (1.03 g), tris(dibenzylideneacetone)dipalladium (0) (63 mg) and 2-(dicyclohexylphosphino)biphenyl (97 mg). The reaction solution is stirred at 80° C. for 24 hours under argon atmosphere, and thereto are added morpholine (362 µl), tripotassium phosphate (1.03 g), tris(dibenzylideneacetone)dipalladium (0) (63 mg) and 2-(dicyclohexylphosphino)biphenyl (97 mg). The mixture is stirred at 80° C. for 24 hours. After allowing to cool, water is poured to the reaction solution and the mixture is extracted with ethyl acetate. The organic layer is washed with saturated brine and dried over sodium sulfate. The solvent is removed by evaporation under reduced pressure. The residue is purified by silica gel column chromatography (eluent: n-hexane/ethyl acetate=2/1) to give the title compound (0.62 g).

APCI-MS M/Z:296[M+H]⁺.

Reference Example 97

3-(Benzyloxy)-6-pyrrolidin-1-yl pyridine-2-carbonitrile

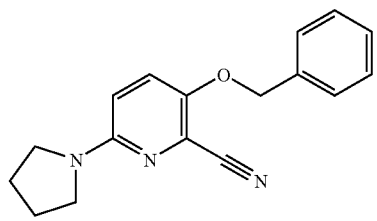

3-(Benzyloxy)-6-bromopyridine-2-carbonitrile (2.00 g) obtained in Reference Example 92 and pyrrolidine (3.46 ml) are treated in a similar manner to Reference Example 96 to give the title compound (1.30 g).

APCI-MS M/Z:280[M+H]⁺.

Reference Example 98

3-(Benzyloxy)-6-(2-methoxyethoxy)pyridine-2-carbonitrile

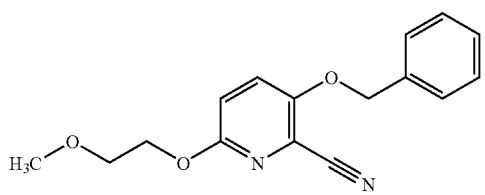

3-(Benzyloxy)-6-bromopyridine-2-carbonitrile (100 mg) obtained in Reference Example 92 is added to toluene (2 ml), and thereto are added cesium carbonate (169 mg), palladium acetate (II) (1.6 mg), 2-(di-t-butylphosphino)-1,1'-binaphthyl (racemate) (3.4 mg) and 2-methoxyethanol (55 µl). The mixture is stirred at 70° C. for 24 hours. After allowing to cool, water is poured to the reaction solution and the mixture is extracted with ethyl acetate. The organic layer is washed with saturated brine and dried over sodium sulfate. The solvent is removed by evaporation under reduced pressure. The residue is purified by silica gel column chromatography (eluent: n-hexane/ethyl acetate=3/1 followed by 2/1) to give the title compound (84 mg).

APCI-MS M/Z:285[M+H]$^+$.

Reference Example 99

3-(Benzyloxy)-6-isopropoxypyridine-2-carbonitrile

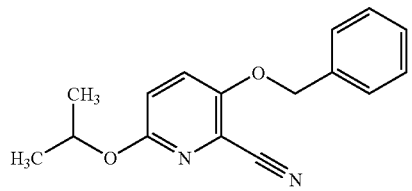

3-(Benzyloxy)-6-bromopyridine-2-carbonitrile (2.00 g) obtained in Reference Example 92 and 2-propanol (3.96 ml) are treated in a similar manner to Reference Example 98 to give the title compound (1.53 g).

APCI-MS M/Z:269[M+H]$^+$.

Reference Example 100

6-(Dimethylamino)-3-hydroxypyridine-2-carbonitrile

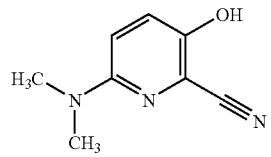

3-(Benzyloxy)-6-(dimethylamino)pyridine-2-carbonitrile (1.28 g) obtained in Reference Example 93 is dissolved in ethanol (50 ml), and thereto is added 20% palladium hydroxide/carbon (0.13 g). The mixture is stirred at room temperature for 2 hours under hydrogen atmosphere under normal pressure. The catalyst is removed by filtration. The filtrate is concentrated under reduced pressure and dried to give the title compound (0.88 g).

APCI-MS M/Z: 164[M+H]$^+$.

Reference Examples 101-105

The corresponding starting compounds are treated in a similar manner to Reference Example 100 to give the following compounds.

TABLE 81

| Ref. Ex. No. | Structure | Physicochemical Properties |
|---|---|---|
| 101 | 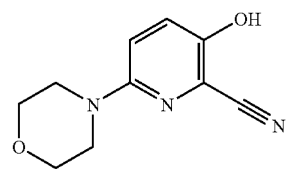 | APCI-MS M/Z: 206 [M + H]$^+$ |
| 102 | 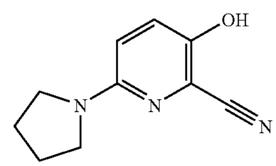 | APCI-MS M/Z: 190 [M + H]$^+$ |
| 103 | 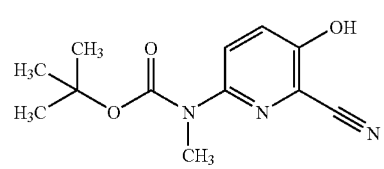 | APCI-MS M/Z: 250 [M + H]$^+$ |
| 104 | 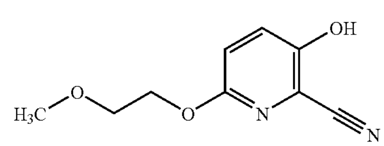 | APCI-MS M/Z: 195 [M + H]$^+$ |

TABLE 81-continued

| Ref. Ex. No. | Structure | Physicochemical Properties |
|---|---|---|
| 105 | (structure) | APCI-MS M/Z: 179 [M + H]+ |

Reference Examples 106-111

The corresponding starting compounds are treated in a similar manner to Reference Example 23 to give the following compounds.

TABLE 82

| Ref. Ex. No. | Structure | Physicochemical Properties |
|---|---|---|
| 106 | (structure) | APCI-MS M/Z: 332/334 [M + H]+ |
| 107 | (structure) | APCI-MS M/Z: 374/376 [M + H]+ |
| 108 | (structure) | APCI-MS M/Z: 358/360 [M + H]+ |
| 109 | (structure) | APCI-MS M/Z: 418/420 [M + H]+ |

TABLE 82-continued

| Ref. Ex. No. | Structure | Physicochemical Properties |
|---|---|---|
| 110 | 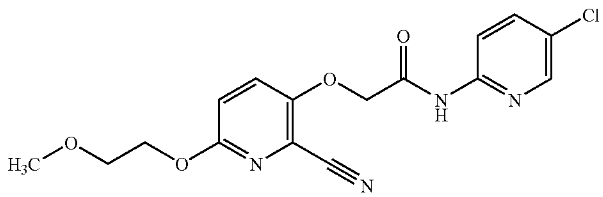 | APCI-MS M/Z: 363/365 [M + H]+ |
| 111 | 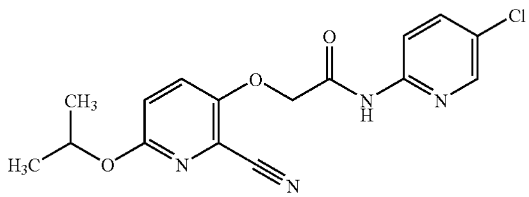 | APCI-MS M/Z: 347/349 [M + H]+ |

Reference Example 112

3-Amino-N-(5-chloropyridin-2-yl)-5-(dimethylamino) furo[3,2-b]pyridine-2-carboxamide

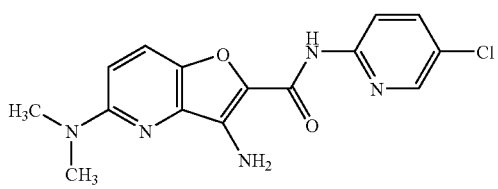

N-(5-Chloropyridin-2-yl)-2-{[2-cyano-6-(dimethylamino)pyridin-3-yl]oxy}acetamide (1.59 g) obtained in Reference Example 106 is suspended in t-butanol (50 ml), and thereto is added potassium t-butoxide (54 mg). The mixture is heated under reflux for 2 hours. After allowing to cool, water is poured to the reaction solution and the precipitated solid is collected by filtration. The resulting solid is washed with diethyl ether and dried to give the title compound (1.16 g).
APCI-MS M/Z:332/334[M+H]+.

Reference Examples 113-117

The corresponding starting compounds are treated in a similar manner to Reference Example 112 to give the following compounds.

TABLE 83

| Ref. Ex. No. | Structure | Physicochemical Properties |
|---|---|---|
| 113 | 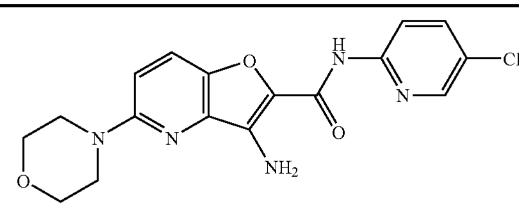 | APCI-MS M/Z: 374/376 [M + H]+ |
| 114 | 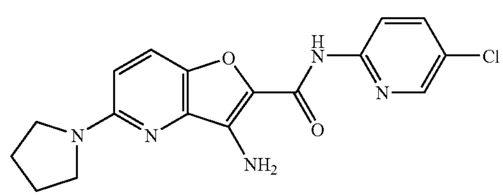 | APCI-MS M/Z: 358/360 [M + H]+ |

TABLE 83-continued

| Ref. Ex. No. | Structure | Physicochemical Properties |
|---|---|---|
| 115 | 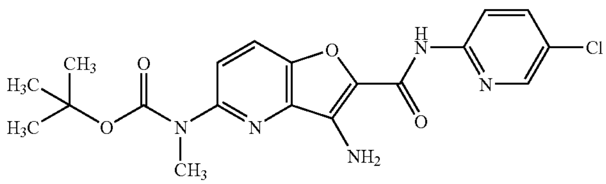 | APCI-MS M/Z: 418/420 [M + H]⁺ |
| 116 | 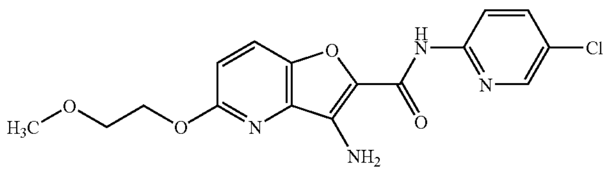 | APCI-MS M/Z: 363/365 [M + H]⁺ |
| 117 | 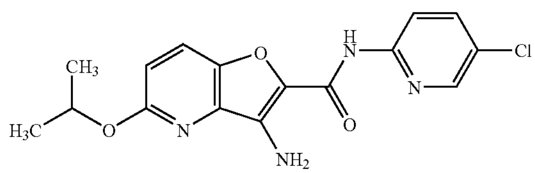 | APCI-MS M/Z: 347/349 [M + H]⁺ |

Reference Examples 118 and 119

The corresponding carboxylic acid and methyl 3-aminofuro[3,2-b]pyridine-2-carboxylate obtained in Reference Example 78 are treated in a similar manner to Reference Example 79 to give the following compounds.

TABLE 84

| Ref. Ex. No. | Structure | Physicochemical Properties |
|---|---|---|
| 118 | 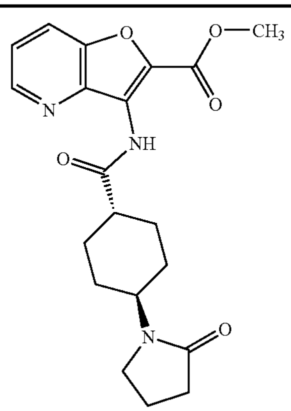 | APCI-MS M/Z: 386 [M + H]⁺ |

TABLE 84-continued

| Ref. Ex. No. | Structure | Physicochemical Properties |
|---|---|---|
| 119 | 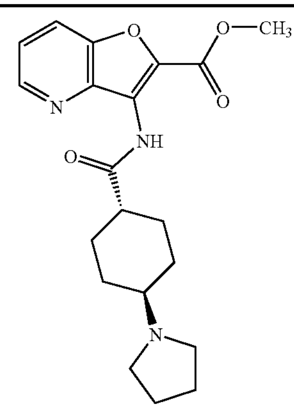 | APCI-MS M/Z: 372 [M + H]⁺ |

Reference Example 120

3-Amino-4-chloro-N-(5-chloropyridin-2-yl)furo[3,2-c]pyridine-2-carboxamide

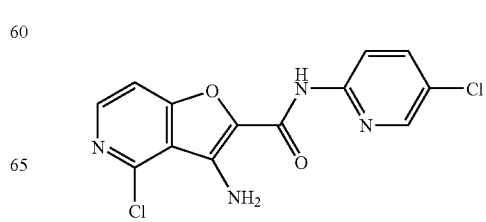

(1) 2-Chloro-4-methoxy-3-carbonitrile known in a literature (reference: M. Mittelback et al., Arch. Pharm., 1985, 318, 481-486) is demethylated with 25% hydrogen bromide/acetic acid to give 2-chloro-3-cyano-4(1H)-pyridone as a crude solid.

ESI-MS M/Z:153/155[M−H]−

(2) 2-Chloro-3-cyano-4(1H)-pyridone obtained in (1) above is treated in a similar manner to Reference Example 23 to give N-(5-chloropyridin-2-yl)-2-[(2-chloro-3-cyanopyridin-4-yl)oxy]acetamide as a crude solid.

APCI-MS M/Z:323/325[M+H]+

(3) N-(5-Chloropyridin-2-yl)-2-[(2-chloro-3-cyanopyridin-4-yl)oxy]acetamide obtained in (2) above is treated in a similar manner to Referance Example 112 to give the title compound as a crude solid.

APCI-MS M/Z:323/325[M+H]+

Reference Example 121

4-(Benzyloxy)-2-bromopyridine-3-carbonitrile

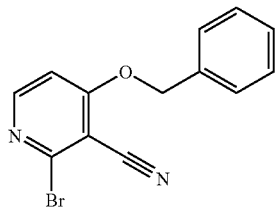

2-Bromo-3-cyano-4(1H)-pyridone is treated in a similar manner to Reference Example 92 to give the title compound.
APCI-MS M/Z: 289/291[M+H]+

Reference Example 122

4-(Benzyloxy)-2-(propoxycarbonyl)pyridine-3-carbonitrile

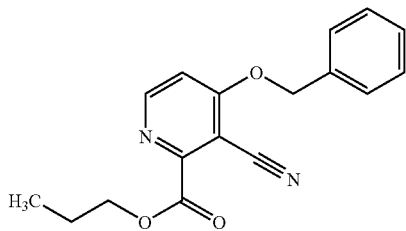

4-(Benzyloxy)-2-bromopyridine-3-carbonitrile (500 mg) obtained in Reference Example 121 is dissolved in N,N-dimethylformamide (10 ml) and thereto are added 1-propanol (20 ml) and triethylamine (410 μl) at room temperature, and the mixture is displaced with argon. To the reaction solution, 1,3-bis(diphenylphosphino)propane (114 mg) and palladium acetate (62 mg) are added, and the mixture is degassed and displaced with carbon monoxide. The mixture is stirred at 90° C. for 19.5 hours under carbon monoxide atmosphere, and the reaction solution is diluted with water and extracted with chloroform. The organic layer is dried over sodium sulfate and the solvent is evaporated under reduced pressure. The obtained residue is purified by silica gel column chromatography (eluent: n-hexane/ethyl acetate=4/1 followed by 1/1) to give the title compound (200 mg).

APCI-MS M/Z:297[M+H]+

Reference Example 123

4-Hydroxy-2-(propoxycarbonyl)pyridine-3-carbonitrile

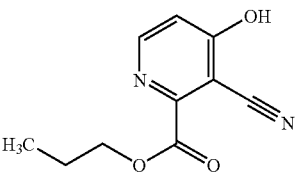

4-(Benzyloxy)-2-(propoxycarbonyl)pyridine-3-carbonitrile (199 mg) obtained in Reference Example 122 is treated in a similar manner to Reference Example 100 to give the title compound (149 mg).
APCI-MS M/Z:207[M+H]+

Reference Example 124

N-(5-Chloropyridin-2-yl)-2-[(2-propoxycarbonyl-3-cyanopyridin-4-yl)oxy]acetamide

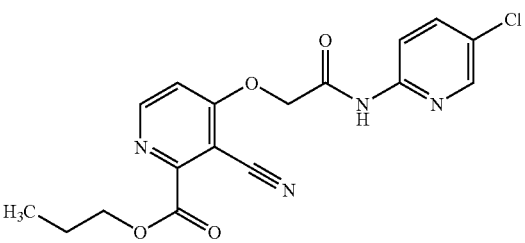

4-Hydroxy-2-(propoxycarbonyl)pyridine-3-carbonitrile (145 mg) obtained in Reference Example 123 is treated in a similar manner to Reference Example 23 to give the title compound (67.3 mg).
APCI-MS M/Z:375/377[M+H]+

Reference Example 125

3-Amino-N-(5-chloropyridin-2-yl)-4-(propoxycarbonyl)furo[3,2-c]pyridine-2-carboxamide

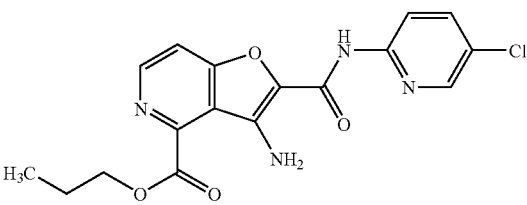

N-(5-Chloropyridin-2-yl)-2-[(2-propoxycarbonyl-3-cyanopyridin-4-yl)oxy]acetamide (65 mg) obtained in Reference Example 124 is treated in a similar manner to Reference Example 112 to give the title compound (68 mg).

APCI-MS M/Z: 375/377[M+H]$^+$

Experimental Example 1

Inhibitory Effect on Activated Blood Coagulation Factor X

A substrate solution was prepared by dissolving chromogenic substrate S-2222 at the concentration of 0.625 mM (final concentration 0.5 mM) in 100 mM Tris buffer (pH 8.4) containing 200 mM sodium chloride and 0.1% bovine serum albumin, and a test compound solution was prepared by dissolving a test compound in a buffer containing 10% dimethyl sulfoxide. The test compound solution (25 μl) was added to the substrate solution (200 μl). In the control group, 25 μl of the buffer containing 10% dimethyl sulfoxide was used instead of the test compound solution.

After pre-warming at 37° C. for 3 minutes, 25 μl of human FXa (Enzyme Research Laboratories, Inc.) dissolved at 0.5 U/ml in a buffer was added to the reaction mixture (final concentration of FXa: 0.05 U/ml) to initiate the reaction. During a 5-minute reaction at 37° C., the absorbance at 405 nm was monitored continuously on a 96 well microplate reader (Spectra MAX250, Molecular Devices) and the increase of absorbance was used as an index of FXa activity. In order to evaluate FXa inhibitory activity of a test compound, the 50% inhibitory concentration of the test compound for FXa activity compared to the control group (IC$_{50}$ value) was calculated using analytic soft (GraphPad Prism, GraphPad Software, Inc.). An example in the results is shown in Table 85 below.

TABLE 85

| Example | IC$_{50}$ (nM) |
|---------|----------------|
| 36      | 10.8           |

The compounds of the present invention showed the 50% inhibitory concentration (IC$_{50}$ value) of less than 1 μM, and the preferred compounds among them showed the IC$_{50}$ value of less than 20 nM. Thus, the present compounds were revealed to have excellent inhibitory effect on activated blood coagulation factor X.

INDUSTRIAL APPLICABILITY

The compound of the formula (I) or a pharmaceutically acceptable salt thereof is less toxic and safe, and has an excellent inhibitory effect on activated blood coagulation factor X. Accordingly, the said compound (I) is useful as a medicament for prevention and treatment of diseases caused by thrombus or embolus.

The invention claimed is:
1. A condensed furan compound of the formula (I):

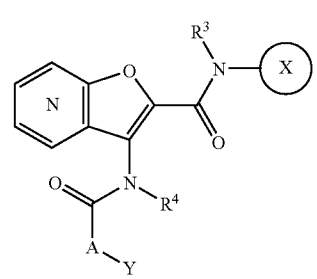

wherein, Ring:

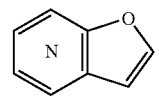

is
Ring X is:

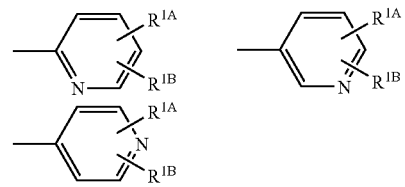

Y is an optionally substituted amino; an optionally substituted cycloalkyl; an optional substituted aryl; an optionally substituted saturated heterocyclic group; or an optionally substituted unsaturated heterocyclic group;

A is a single bond; an alkylene optionally substituted by oxo; an alkenylene; an alkenylidene; or an oxygen atom;

R$^{1A}$, R$^{1B}$ are the same or different and each is hydrogen; a halogen; an alkyl; a haloalkyl; an alkoxy; cyano; nitro; or an optionally substituted amino;

R$^{2A}$, R$^{2B}$ are the same or different and each is hydrogen; a halogen; an optionally substituted alkyl; an optionally substituted alkoxy; an optionally substituted amino; nitro; cyano; hydroxy; carboxy; an optionally substituted alkoxycarbonyl; an optionally substituted carbamoyl; a carbonyl substituted by an optionally substituted saturated heterocyclic group; an optionally substituted saturated heterocyclic group; aryl; or an optionally substituted unsaturated heterocyclic group;

R$^3$ is hydrogen or an alkyl; and
R$^4$ is hydrogen or an alkyl,
or a pharmaceutically acceptable salt thereof.

2. The condensed furan compound according to claim 1, wherein Y is an optionally substituted cycloalkyl or an optionally substituted saturated heterocyclic group,
or a pharmaceutically acceptable salt thereof.

3. The condensed furan compound according to claim 1, wherein the substituent in the definition of "optionally substituted cycloalkyl" for Y is a group selected from an optionally substituted alkyl; an optionally substituted carbamoyl; a carbonyl substituted by an optionally substituted saturated heterocyclic group; an optionally substituted amino; and an optionally substituted saturated heterocyclic group, or a pharmaceutically acceptable salt thereof.

4. The condensed furan compound according to claim 1, wherein the substituent in the definition of "optionally substituted cycloalkyl" for Y is a group selected from: (1) an amino optionally substituted by a group selected from an optionally substituted acyl, an alkoxycarbonyl and an optionally substituted alkyl; (2) an aminoalkyl optionally substituted by a group selected from an optionally substituted acyl and an optionally substituted alkyl; (3) a carbamoyl optionally substituted by an optionally substituted alkyl; (4) a carbonyl substituted by a saturated heterocyclic group; and (5) an optionally substituted saturated heterocyclic group, or a pharmaceutically acceptable salt thereof.

5. The condensed furan compound according to claim 3 or 4, wherein the saturated heterocyclic group is a 4- to 7-membered saturated heterocyclic group containing 1 to 4 hetero atoms selected from the group consisting of nitrogen atom, oxygen atom and sulfur atom, or a pharmaceutically acceptable salt thereof.

6. The condensed furan compound according to claim 3, wherein the saturated heterocyclic group is a group selected from imidazolidinyl, pyrazolidinyl, piperidyl, piperidino, piperazinyl, morpholinyl, morpholino, thiomorphohnyl, thiomorpholino, homopiperazinyl, homopiperidyl, homopiperidino and pyrrolidinyl, or a pharmaceutically acceptable salt thereof.

7. The condensed fin-an compound according to claim 1, wherein the substituent in the definition of "optionally substituted cycloalkyl" for Y is: (1) an amino optionally substituted by a group selected from acyl, alkoxycarbonyl, alkyl, aminoalkyl, alkyl-substituted aminoalkyl, alkoxycarbonylaminoalkyl and acylarninoalkyl; (2) an alkyl substituted by amino optionally substituted by alkyl; (3) a carbamoyl optionally mono- or di-substituted by alkyl or aminoalkyl which may be substituted by alkyl or aminoalkyl which may be substituted by alkyl; (4) a group selected from pyrrolidinylcarbonyl, piperidylcarbonyl, piperazinylcarbonyl, morpholinocarbonyl, homopiperidinylcarbonyl and homopiperazinylcarbonyl; or (5) a saturated heterocyclic group selected from pyrrolidinyl optionally substituted by oxo, piperidyl optionally substituted by oxo, piperazinyl optionally substituted by oxo, morpholino optionally substituted by oxo, homopiperidinyl optionally substituted by oxo, and homopiperazinyl optionally substituted by oxo, or a pharmaceutically acceptable salt thereof.

8. The condensed fin-an compound according to claim 1, wherein the substituent in the definition of "optionally substituted cycloalkyl" for Y is pyrrolidinyl optionally substituted by oxo; morpholino optionally substituted by oxo; dialkylcarbamoyl; pyrrolidinylcarbonyl; amino that is di-substituted by alkyl and acylaminoalkyl; or dialkylamino, or a pharmaceutically acceptable salt thereof.

9. The condensed furan compound according to claim 1, wherein Y is an aryl or unsaturated heterocyclic group substituted by an optionally substituted carbamoyl, or a pharmaceutically acceptable salt thereof.

10. The condensed furan compound according to claim 1, wherein A is a single bond or methylene, or a pharmaceutically acceptable salt thereof.

11. The condensed furan compound according to claim 1, wherein A is a single bond or methylene, and Y is an unsaturated heterocyclic group or a saturated heterocyclic group optionally substituted by alkyl, or a pharmaceutically acceptable salt thereof.

12. The condensed furan compound according to claim 1, wherein A is tetramethylene, and Y is an optionally substituted saturated heterocyclic group, or a pharmaceutically acceptable salt thereof.

13. The condensed furan compound according to claim 1, wherein $R^{1A}$, $R^{1B}$ are the same or different and each is hydrogen, a halogen or an alkyl, or a pharmaceutically acceptable salt thereof.

14. The condensed furan compound according to claim 1, wherein $R^{2A}$, $R^{2B}$ are the same or different and each is hydrogen; a halogen; an optionally substituted alkyl; an optionally substituted alkoxy; an optionally substituted amino; cyano; carboxy; an alkoxycarbonyl; an optionally substituted carbamoyl; a carbonyl substituted by saturated heterocyclic group; or a saturated heterocyclic group, or a pharmaceutically acceptable salt thereof.

15. The condensed furan compound according to claim 14, wherein the saturated heterocyclic group is a 4- to 7-membered saturated heterocyclic group containing 1 to 4 hetero atoms selected from the group consisting of nitrogen atom, oxygen atom and sulfur atom, or a pharmaceutically acceptable salt thereof.

16. The condensed furan compound according to claim 1, wherein $R^{2A}$, $R^{2B}$ are the same or different and each is hydrogen, fluoro, chioro, bromo, methyl, hydroxymethyl, methoxy, amino, methylsulfonylamino, acetylamino, t-butoxycarbonylamino, dimethylamino, cyano, carboxy, methoxycarbonyl, ethoxycarbonyl, methoxy, ethoxy, isopropoxy, methoxyethoxy, dimethylcarbamoyl, N-methyl-N-(2-methoxyethyl) carbamoyl, pyrrolidinyl, pyrrolidinylcarbonyl, morpholinocarbonyl or morpholino, or a pharmaceutically acceptable salt thereof.

17. The condensed furan compound according to claim 1, wherein $R^3$ is hydrogen, or a pharmaceutically acceptable salt thereof.

18. The condensed furan compound according to claim 1, wherein $R^4$ is hydrogen, or a pharmaceutically acceptable salt thereof.

19. The condensed furan compound according to claim 1, wherein Ring X is

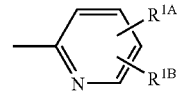

wherein $R^{1A}$ and $R^{1B}$ are as defined in claim 1, or a pharmaceutically acceptable salt thereof.

20. The condensed furan compound according to claim 1, which is selected from the following compounds:
(1) N-(5-chloropyridin-2-yl)-3- {[(trans-4-pyrrolidin-1-ylcyclohexyl)carbonyl]aznino}furo[3,2-c]pyridine-2-carboxaxnide,
(2) N-(5-chloropyridin-2-yl)-4-(2-methoxyethoxy)-3-{[(trans-4-pyrrolidin-1-ylcyclohexyl)carbonyl]amino}furo[3,2-c]pyridine-2-carboxamide,
(3) N-(5-chloropyridin-2-yl)-4-(2-methoxyethoxy)-3-({[trans-4-(3-oxomorpholin-4-yl)cyclohexyl]carbonyl}amino)furo[3,2-c]pyridine-2-carboxamide,
(4) N-(5-chloropyridin-2-yl)-4-methoxy-3-{[(trans-4-pyrrolidin-1-ylcyclohexyl)carbonyl]amino}furo[3,2-c]pyridine-2-carboxamide,
(5) N-(5-chloropyridin-2-yl)-3-({[trans-4-(3-oxomorpholin-4-yl)cyclohexyl]carbonyl}amino)furo[3,2-c]pyridine-2-carbamide, (6) N-(5-chloropyridin-2-yl)-4-methoxy-3-({[trans-4-(3-oxomorpholin-4-yl)cyclohexyl]carbonyl}amino)furo[3,2-c]pyridine-2-carboxamide, (7) N-(5-chloropyridin-2-yl)-4-cyano-3 -{[(trans-4-pyrrolidin- 1-ylcyclohexyl)carbonyl]amino}furo[3,2-c]pyridine-2-carboxamide, (8) N-(5-chloropyridin-2-yl)-4-methyl-3-({[trans-4-(3 -oxomorpholin-4-yl)cyclohexyl]carbonyl}amino)furo[3,2-c]pyridine-2-carboxaxnide, (9) N-(5-chloropyridin-2-yl)-4-cyano-3 -({[trans-4-(3-oxomorpholin-4-yl)cyclohexyl]carbonyl}amino)furo[3,2-c]pyridine-2-carboxamide,

(10) N-(5-chloropyridin-2-yl)-4-methyl-3-({[trans-4-(2-oxopyrrolidin-1-yl)cyclohyexyl]carbonyl}amino)furo[3,2-c]pyridine-2-carboxamide,

(11) 4-chloro-N-(5-chloropyridin-2-yl)-3-({[trans-4-(3-oxomorpholin-4-yl)cyclohexyl]carbonyl}amino)furo[3,2-c]pyridine-2-carboxamide, and

(12) N-(5-chloropyridin-2-yl)-4-methyl-3- {[(trans-4-pyrrolidin- 1-ylcyclohexyl)carbonyl]amino }furo[3,2-c]pyridine-2-carboxamide, or a pharmaceutically acceptable salt thereof.

* * * * *

UNITED STATES PATENT AND TRADEMARK OFFICE
CERTIFICATE OF CORRECTION

PATENT NO. : 7,514,449 B2  Page 1 of 1
APPLICATION NO. : 10/540878
DATED : April 7, 2009
INVENTOR(S) : Takayuki Kawaguchi et al.

It is certified that error appears in the above-identified patent and that said Letters Patent is hereby corrected as shown below:

\*\* Claim 1, column 298, line 25, the following formula was omitted after the word "is":

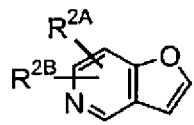

\*\*

Signed and Sealed this

First Day of September, 2009

David J. Kappos
*Director of the United States Patent and Trademark Office*